(12) United States Patent
Thurman et al.

(10) Patent No.: US 8,840,868 B2
(45) Date of Patent: Sep. 23, 2014

(54) NON-INVASIVE DETECTION OF COMPLEMENT-MEDIATED INFLAMMATION USING CR2-TARGETED NANOPARTICLES

(75) Inventors: Joshua M. Thurman, Greenwood Village, CO (US); Natalie Serkova, Denver, CO (US); Conrad Stoldt, Denver, CO (US); Brian Larsen, Denver, CO (US); V. Michael Holers, Denver, CO (US)

(73) Assignee: The Regents of the University of Colorado, a body corporate, Boulder, CO (US)

( * ) Notice: Subject to any disclaimer, the term of this patent is extended or adjusted under 35 U.S.C. 154(b) by 26 days.

(21) Appl. No.: 13/148,028

(22) PCT Filed: Feb. 4, 2010

(86) PCT No.: PCT/US2010/023201
§ 371 (c)(1),
(2), (4) Date: Aug. 4, 2011

(87) PCT Pub. No.: WO2010/091183
PCT Pub. Date: Aug. 12, 2010

(65) Prior Publication Data
US 2011/0286938 A1     Nov. 24, 2011

Related U.S. Application Data

(60) Provisional application No. 61/149,975, filed on Feb. 4, 2009.

(51) Int. Cl.
| | |
|---|---|
| A61K 49/00 | (2006.01) |
| A61B 5/055 | (2006.01) |
| B82Y 5/00 | (2011.01) |
| A61K 49/18 | (2006.01) |
| A61K 49/16 | (2006.01) |

(52) U.S. Cl.
CPC ............. *A61K 49/1812* (2013.01); *B82Y 5/00* (2013.01); *A61K 49/1863* (2013.01); *A61K 49/1866* (2013.01); *A61K 49/1875* (2013.01); *A61K 49/1887* (2013.01); *A61K 49/16* (2013.01)
USPC .......................... 424/9.323; 424/9.1; 424/9.32

(58) Field of Classification Search
None
See application file for complete search history.

(56) References Cited

U.S. PATENT DOCUMENTS

| | | |
|---|---|---|
| 6,589,506 B2 | 7/2003 | Cremillieux |
| 6,599,498 B1 | 7/2003 | Groman |
| 6,690,962 B2 | 2/2004 | Schmitz |
| 2008/0268061 A1* | 10/2008 | Jordan et al. ................. 424/490 |
| 2009/0004113 A1 | 1/2009 | Wolf |

FOREIGN PATENT DOCUMENTS

WO    WO 2004045520 A2 *   6/2004

OTHER PUBLICATIONS

Schwab et al. "Complement activated C4d immunoreactive oligodendrocytes delineate small cortical plaques in multiple sclerosis" Experimental Nuerology 174, 81-89 (2002).*
T.Y. Tang et al., Comparison of the Inflammatory Burden of Truly Asymptomatic Carotid Atheroma with Atherosclerotic Plaques in Patients with Asymptomatic Carotid Stenosis Undergoing Coronary Artery Bypass Grafting: An Ultrasmall Superparamagnetic Iron Oxide Enhanced Magnetic Resonance Study, Eur J Vasc Endovasc Surg. 2008, vol. 35, No. 4, pp. 392-398.
Karin Muller et al., Effect of ultrasmall superparamagnetic iron oxide nanoparticles (Ferumoxtran-10) on human monocyte-macrophages in vitro, Biomaterials, 2007, vol. 28, No. 9, pp. 1629-1642.
Joanne B. Morris et al., p38 MAPK Inhibition Reduces Aortic Ultrasmall Superparamagnetic Iron Oxide Uptake in a Mouse Model of Atherosclerosis: MRI Assessment; Arterioscler Thromb Vasc Boil. 2008, vol. 28, No. 2, pp. 265-271.
Martin Rausch et al., Dynamic Patterns of USPIO Enhancement Can Be Observed in Macrophages After Ischemic Brain Damage, Magnetic Resonance in Medicine, 2001, vol. 46, No. 5, pp. 1018-1022.
Korean Intellectual Property Office, International Search Report for PCT Application No. PCT/US2010/023201, mailed Jan. 5, 2011, 6 pages.
Korean Intellectual Property Office, Written Opinion of the International Searching Authority for International Application No. PCT/US2010/023201, mailed Jan. 5, 2011, 4 pages.
Jepsen et al., "Enhancing effect of autologous human erythrocytes on generation of C3 cleavage products beyond iC3b.", *Complement*, 5:120-129, 1988.
Kao et al., "Erythrocyte C3d and C4d for monitoring disease activity in systemic lupus erythematosus.", *Arthritis and Rheumatism*, 62:837-844, 2010.
Thurman et al., "Lack of a functional alternative complement pathway ameliorates ischemic acute renal failure in mice.", *The Journal of Immunology*, 170:1517-1523, 2003.
Weissleder et al., "Ultrasmall superparamagnetic iron oxide: characterization of a new class of contrast agents for MR imaging." *Radiology*, 175:489-493, 1990.

(Continued)

*Primary Examiner* — Daniel E Kolker
*Assistant Examiner* — James Rogers
(74) *Attorney, Agent, or Firm* — Kilpatrick Townsend & Stockton LLP

(57) ABSTRACT

Methods of non-invasive imaging of complement-mediated inflammation are provided. Compositions including CR-targeted ultrasmall superparamagnetic nanoparticles or aggregates thereof for use with those methods are also provided.

7 Claims, 8 Drawing Sheets

(56) References Cited

OTHER PUBLICATIONS

Hauger et al., "MR imaging of intrarenal macrophage infiltration in an experimental model of nephrotic syndrome. Magnetic resonance in medicine.", *Official Journal of the Society of Magnetic Resonance in Medicine / Society of Magnetic Resonance in Medicine*, 41:156-162, 1999.

Hauger et al., "Nephrotoxic nephritis and obstructive nephropathy: evaluation with MR imaging enhanced with ultrasmall superparamagnetic iron oxide-preliminary findings in a rat model.", *Radiology*, 217:819-826, 2000.

Jo et al., "Detection of inflammation following renal ischemia by magnetic resonance imaging.", *Kidney International*, 64:43-51, 2003.

Hauger et al., "USPIO-enhanced MR imaging of macrophage infiltration in native and transplanted kidneys: initial results in humans." *European Radiology*, 17:2898-2907, 2007.

Denis et al., "Imaging inflammation of the pancreatic islets in type 1 diabetes.", *Proceedings of the National Academy of Sciences of the United States of America*, 101:12634-12639, 2004.

Turvey et al., "Noninvasive imaging of pancreatic inflammation and its reversal in type 1 diabetes.", *The Journal of Clinical Investigation*, 115:2454-2461, 2005.

Bajaj, Sangeeta et al., "Serial renal biopsy in systemic lupus erythematosus," The Journal of Rheumatology (2000) 27:12, pp. 2822-2826.

Sargsysn, Siranush A. et al., "Detection of glomerular complement C3 fragments by magnetic resonance imaging in murine lupus nephritis," Kidney International (2012)81:152-159.

Serkova, Natalie J. et al., "Renal inflammation: targeted iron oxide nanoparticles for molecular MR imaging in mice[1]," Radiology 255(2):517-526, May 2010.

* cited by examiner

SEQUENCE LISTING

<160> NUMBER OF SEQ ID NOS: 30

<210> SEQ ID NO 1
<211> LENGTH: 1087
<212> TYPE: PRT
<213> ORGANISM: Homo sapiens

<400> SEQUENCE: 1

-continued

```
Met Gly Ala Ala Gly Leu Leu Gly Val Phe Leu Ala Leu Val Ala Pro
 1               5                  10                 15

Gly Val Leu Gly Ile Ser Cys Gly Ser Pro Pro Ile Leu Asn Gly
             20                  25                  30

Arg Ile Ser Tyr Tyr Ser Thr Pro Ile Ala Val Gly Thr Val Ile Arg
             35                  40                  45

Tyr Ser Cys Ser Gly Thr Phe Arg Leu Ile Gly Glu Lys Ser Leu Leu
         50                  55                  60

Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
             100                 105                 110

Ser Val Thr Phe Ala Cys Lys Thr Asn Phe Ser Met Asn Gly Asn Lys
             115                 120                 125

Ser Val Trp Cys Gln Ala Asn Asn Met Trp Gly Pro Thr Arg Leu Pro
             130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                 165                 170                 175

Leu Ser Val Thr Tyr Ser Cys Glu Ser Gly Tyr Leu Leu Val Gly Glu
             180                 185                 190

Lys Ile Ile Asn Cys Leu Ser Ser Gly Lys Trp Ser Ala Val Pro Pro
             195                 200                 205

Thr Cys Glu Glu Ala Arg Cys Lys Ser Leu Gly Arg Phe Pro Asn Gly
     210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                 245                 250                 255

Val Ile Ala Gly Gln Gly Val Ala Trp Thr Lys Met Pro Val Cys Glu
             260                 265                 270

Glu Ile Phe Cys Pro Ser Pro Pro Ile Leu Asn Gly Arg His Ile
             275                 280                 285

Gly Asn Ser Leu Ala Asn Val Ser Tyr Gly Ser Ile Val Thr Tyr Thr
     290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
             325                 330                 335

Gly Pro Ala Pro Arg Cys Glu Leu Ser Thr Ser Ala Val Gln Cys Pro
             340                 345                 350

His Pro Gln Ile Leu Arg Gly Arg Met Val Ser Gly Gln Lys Asp Arg
             355                 360                 365

Tyr Thr Tyr Asn Asp Thr Val Ile Phe Ala Cys Met Phe Gly Phe Thr
     370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                 405                 410                 415

Leu Asn Gly Gln Lys Glu Asp Arg His Met Val Arg Phe Asp Pro Gly
```

```
                420             425             430
Thr Ser Ile Lys Tyr Ser Cys Asn Pro Gly Tyr Val Leu Val Gly Glu
            435             440             445
Glu Ser Ile Gln Cys Thr Ser Glu Gly Val Trp Thr Pro Pro Val Pro
450             455             460
Gln Cys Lys Val Ala Ala Cys Glu Ala Thr Gly Arg Gln Leu Leu Thr
465             470             475             480
Lys Pro Gln His Gln Phe Val Arg Pro Asp Val Asn Ser Ser Cys Gly
            485             490             495
Glu Gly Tyr Lys Leu Ser Gly Ser Val Tyr Gln Glu Cys Gln Gly Thr
            500             505             510
Ile Pro Trp Phe Met Glu Ile Arg Leu Cys Lys Glu Ile Thr Cys Pro
            515             520             525
Pro Pro Pro Val Ile Tyr Asn Gly Ala His Thr Gly Ser Ser Leu Glu
            530             535             540
Asp Phe Pro Tyr Gly Thr Thr Val Thr Tyr Thr Cys Asn Pro Gly Pro
545             550             555             560
Glu Arg Gly Val Glu Phe Ser Leu Ile Gly Glu Ser Thr Ile Arg Cys
            565             570             575
Thr Ser Asn Asp Gln Glu Arg Gly Thr Trp Ser Gly Pro Ala Pro Leu
            580             585             590
Cys Lys Leu Ser Leu Leu Ala Val Gln Cys Ser His Val His Ile Ala
            595             600             605
Asn Gly Tyr Lys Ile Ser Gly Lys Glu Ala Pro Tyr Phe Tyr Asn Asp
            610             615             620
Thr Val Thr Phe Lys Cys Tyr Ser Gly Phe Thr Leu Lys Gly Ser Ser
625             630             635             640
Gln Ile Arg Cys Lys Arg Asp Asn Thr Trp Asp Pro Glu Ile Pro Val
            645             650             655
Cys Glu Lys Gly Cys Gln Pro Pro Gly Leu His His Gly Arg His
            660             665             670
Thr Gly Gly Asn Thr Val Phe Phe Val Ser Gly Met Thr Val Asp Tyr
            675             680             685
Thr Cys Asp Pro Gly Tyr Leu Leu Val Gly Asn Lys Ser Ile His Cys
            690             695             700
Met Pro Ser Gly Asn Trp Ser Pro Ser Ala Pro Arg Cys Glu Glu Thr
705             710             715             720
Cys Gln His Val Arg Gln Ser Leu Gln Glu Leu Pro Ala Gly Ser Arg
            725             730             735
Val Glu Leu Val Asn Thr Ser Cys Gln Asp Gly Tyr Gln Leu Thr Gly
            740             745             750
His Ala Tyr Gln Met Cys Gln Asp Ala Glu Asn Gly Ile Trp Phe Lys
            755             760             765
Lys Ile Pro Leu Cys Lys Val Ile His Cys His Pro Pro Pro Val Ile
            770             775             780
Val Asn Gly Lys His Thr Gly Met Met Ala Glu Asn Phe Leu Tyr Gly
785             790             795             800
Asn Glu Val Ser Tyr Glu Cys Asp Gln Gly Phe Tyr Leu Leu Gly Glu
            805             810             815
Lys Asn Cys Ser Ala Glu Val Ile Leu Lys Ala Trp Ile Leu Glu Arg
            820             825             830
Ala Phe Pro Gln Cys Leu Arg Ser Leu Cys Pro Asn Pro Glu Val Lys
            835             840             845
```

His Gly Tyr Lys Leu Asn Lys Thr His Ser Ala Tyr Ser His Asn Asp
        850                 855                 860

Ile Val Tyr Val Asp Cys Asn Pro Gly Phe Ile Met Asn Gly Ser Arg
865                 870                 875                 880

Val Ile Arg Cys His Thr Asp Asn Thr Trp Val Pro Gly Val Pro Thr
                885                 890                 895

Cys Ile Lys Lys Ala Phe Ile Gly Cys Pro Pro Pro Lys Thr Pro
            900                 905                 910

Asn Gly Asn His Thr Gly Gly Asn Ile Ala Arg Phe Ser Pro Gly Met
            915                 920                 925

Ser Ile Leu Tyr Ser Cys Asp Gln Gly Tyr Leu Val Val Gly Glu Pro
        930                 935                 940

Leu Leu Leu Cys Thr His Glu Gly Thr Trp Ser Gln Pro Ala Pro His
945                 950                 955                 960

Cys Lys Glu Val Asn Cys Ser Ser Pro Ala Asp Met Asp Gly Ile Gln
                965                 970                 975

Lys Gly Leu Glu Pro Arg Lys Met Tyr Gln Tyr Gly Ala Val Val Thr
            980                 985                 990

Leu Glu Cys Glu Asp Gly Tyr Met Leu Glu Gly Ser Pro Gln Ser Gln
        995                 1000                1005

Cys Gln Ser Asp His Gln Trp Asn Pro Pro Leu Ala Val Cys Arg
    1010                1015                1020

Ser Arg Ser Leu Ala Pro Val Leu Cys Gly Ile Ala Ala Gly Leu
    1025                1030                1035

Ile Leu Leu Thr Phe Leu Ile Val Ile Thr Leu Tyr Val Ile Ser
    1040                1045                1050

Lys His Arg Glu Arg Asn Tyr Tyr Thr Asp Thr Ser Gln Lys Glu
    1055                1060                1065

Ala Phe His Leu Glu Ala Arg Glu Val Tyr Ser Val Asp Pro Tyr
    1070                1075                1080

Asn Pro Ala Ser
    1085

<210> SEQ ID NO 2
<211> LENGTH: 1025
<212> TYPE: PRT
<213> ORGANISM: Mus musculus

<400> SEQUENCE: 2

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu

-continued

```
            115                 120                 125
Met Trp Gly Pro Thr Ala Leu Pro Val Cys Glu Ser Asp Phe Pro Leu
130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
                180                 185                 190

Gly Asp Trp Asp Gly Val Ile Pro Thr Cys Lys Glu Ala Gln Cys Glu
                195                 200                 205

His Pro Gly Lys Phe Pro Asn Gly Gln Val Lys Glu Pro Leu Ser Leu
210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Ile Leu Cys Pro Pro Pro Pro
                260                 265                 270

Pro Val Arg Asn Gly Ser His Thr Gly Ser Phe Ser Glu Asn Val Pro
            275                 280                 285

Tyr Gly Ser Thr Val Thr Tyr Thr Cys Asp Pro Ser Pro Glu Lys Gly
290                 295                 300

Val Ser Phe Thr Leu Ile Gly Glu Lys Thr Ile Asn Cys Thr Thr Gly
305                 310                 315                 320

Ser Gln Lys Thr Gly Ile Trp Ser Gly Pro Ala Pro Tyr Cys Val Leu
                325                 330                 335

Ser Thr Ser Ala Val Leu Cys Leu Gln Pro Lys Ile Lys Arg Gly Gln
            340                 345                 350

Ile Leu Ser Ile Leu Lys Asp Ser Tyr Ser Tyr Asn Asp Thr Val Ala
            355                 360                 365

Phe Ser Cys Glu Pro Gly Phe Thr Leu Lys Gly Asn Arg Ser Ile Arg
370                 375                 380

Cys Asn Ala His Gly Thr Trp Glu Pro Pro Val Pro Val Cys Glu Lys
385                 390                 395                 400

Gly Cys Gln Ala Pro Lys Ile Ile Asn Gly Gln Lys Glu Asp Ser
                405                 410                 415

Tyr Leu Leu Asn Phe Asp Pro Gly Thr Ser Ile Arg Tyr Ser Cys Asp
                420                 425                 430

Pro Gly Tyr Leu Leu Val Gly Glu Asp Thr Ile His Cys Thr Pro Glu
            435                 440                 445

Gly Lys Trp Thr Pro Ile Thr Pro Gln Cys Thr Val Ala Glu Cys Lys
            450                 455                 460

Pro Val Gly Pro His Leu Phe Lys Arg Pro Gln Asn Gln Phe Ile Arg
465                 470                 475                 480

Thr Ala Val Asn Ser Ser Cys Asp Glu Gly Phe Gln Leu Ser Glu Ser
                485                 490                 495

Ala Tyr Gln Leu Cys Gln Gly Thr Ile Pro Trp Phe Ile Glu Ile Arg
            500                 505                 510

Leu Cys Lys Glu Ile Thr Cys Pro Pro Pro Val Ile His Asn Gly
            515                 520                 525

Thr His Thr Trp Ser Ser Ser Glu Asp Val Pro Tyr Gly Thr Val Val
            530                 535                 540
```

```
Thr Tyr Met Cys Tyr Pro Gly Pro Glu Glu Gly Val Lys Phe Lys Leu
545                 550                 555                 560

Ile Gly Glu Gln Thr Ile His Cys Thr Ser Asp Ser Arg Gly Arg Gly
            565                 570                 575

Ser Trp Ser Ser Pro Ala Pro Leu Cys Lys Leu Ser Leu Pro Ala Val
        580                 585                 590

Gln Cys Thr Asp Val His Val Glu Asn Gly Val Lys Leu Thr Asp Asn
    595                 600                 605

Lys Ala Pro Tyr Phe Tyr Asn Asp Ser Val Met Phe Lys Cys Asp Asp
610                 615                 620

Gly Tyr Ile Leu Ser Gly Ser Ser Gln Ile Arg Cys Lys Ala Asn Asn
625                 630                 635                 640

Thr Trp Asp Pro Glu Lys Pro Leu Cys Lys Lys Glu Gly Cys Glu Pro
                645                 650                 655

Met Arg Val His Gly Leu Pro Asp Asp Ser His Ile Lys Leu Val Lys
            660                 665                 670

Arg Thr Cys Gln Asn Gly Tyr Gln Leu Thr Gly Tyr Thr Tyr Glu Lys
        675                 680                 685

Cys Gln Asn Ala Glu Asn Gly Thr Trp Phe Lys Lys Ile Glu Val Cys
    690                 695                 700

Thr Val Ile Leu Cys Gln Pro Pro Lys Leu Ala Asn Gly Gly His
705                 710                 715                 720

Thr Gly Met Met Ala Lys His Phe Leu Tyr Gly Asn Glu Val Ser Tyr
                725                 730                 735

Glu Cys Asp Glu Gly Phe Tyr Leu Leu Gly Glu Lys Ser Leu Gln Cys
            740                 745                 750

Val Asn Asp Ser Lys Gly His Gly Ser Trp Ser Gly Pro Pro Pro Gln
        755                 760                 765

Cys Leu Gln Ser Ser Pro Leu Thr His Cys Pro Asp Pro Glu Val Lys
    770                 775                 780

His Gly Tyr Lys Leu Asn Lys Thr His Ser Ala Phe Ser His Asn Asp
785                 790                 795                 800

Ile Val His Phe Val Cys Asn Gln Gly Phe Ile Met Asn Gly Ser His
                805                 810                 815

Leu Ile Arg Cys His Thr Asn Asn Thr Trp Leu Pro Gly Val Pro Thr
            820                 825                 830

Cys Ile Arg Lys Ala Ser Leu Gly Cys Gln Ser Pro Ser Thr Ile Pro
        835                 840                 845

Asn Gly Asn His Thr Gly Gly Ser Ile Ala Arg Phe Pro Pro Gly Met
    850                 855                 860

Ser Val Met Tyr Ser Cys Tyr Gln Gly Phe Leu Met Ala Gly Glu Ala
865                 870                 875                 880

Arg Leu Ile Cys Thr His Glu Gly Thr Trp Ser Gln Pro Pro Pro Phe
                885                 890                 895

Cys Lys Glu Val Asn Cys Ser Phe Pro Glu Asp Thr Asn Gly Ile Gln
            900                 905                 910

Lys Gly Phe Gln Pro Gly Lys Thr Tyr Arg Phe Gly Ala Thr Val Thr
        915                 920                 925

Leu Glu Cys Glu Asp Gly Tyr Thr Leu Glu Gly Ser Pro Gln Ser Gln
    930                 935                 940

Cys Gln Asp Asp Ser Gln Trp Asn Pro Pro Leu Ala Leu Cys Lys Tyr
945                 950                 955                 960
```

-continued

```
Arg Arg Trp Ser Thr Ile Pro Leu Ile Cys Gly Ile Ser Val Gly Ser
                965                 970                 975

Ala Leu Ile Ile Leu Met Ser Val Gly Phe Cys Met Ile Leu Lys His
            980                 985                 990

Arg Glu Ser Asn Tyr Tyr Thr Lys Thr Arg Pro Lys Glu Gly Ala Leu
        995                 1000                1005

His Leu Glu Thr Arg Glu Val Tyr Ser Ile Asp Pro Tyr Asn Pro
    1010                1015                1020

Ala Ser
    1025

<210> SEQ ID NO 3
<211> LENGTH: 951
<212> TYPE: PRT
<213> ORGANISM: Artificial Sequence
<220> FEATURE:
<223> OTHER INFORMATION: Synthetic polypeptide sequence of extracellular
      domain of human CR2 protein

<400> SEQUENCE: 3

Ile Ser Cys Gly Ser Pro Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
        35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
    130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Glu Ile Phe Cys
                245                 250                 255

Pro Ser Pro Pro Pro Ile Leu Asn Gly Arg His Ile Gly Asn Ser Leu
            260                 265                 270

Ala Asn Val Ser Tyr Gly Ser Ile Val Thr Tyr Thr Cys Asp Pro Asp
        275                 280                 285
```

```
Pro Glu Glu Gly Val Asn Phe Ile Leu Ile Gly Ser Thr Leu Arg
    290                 295                 300

Cys Thr Val Asp Ser Gln Lys Thr Gly Thr Trp Ser Gly Ala Pro
305                 310                 315                 320

Arg Cys Glu Leu Ser Thr Ser Ala Val Gln Cys Pro His Pro Gln Ile
                325                 330                 335

Leu Arg Gly Arg Met Val Ser Gly Gln Lys Asp Arg Tyr Thr Tyr Asn
                340                 345                 350

Asp Thr Val Ile Phe Ala Cys Met Phe Gly Phe Thr Leu Lys Gly Ser
            355                 360                 365

Lys Gln Ile Arg Cys Asn Ala Gln Gly Thr Trp Glu Pro Ser Ala Pro
    370                 375                 380

Val Cys Glu Lys Glu Cys Gln Ala Pro Pro Asn Ile Leu Asn Gly Gln
385                 390                 395                 400

Lys Glu Asp Arg His Met Val Arg Phe Asp Pro Gly Thr Ser Ile Lys
                405                 410                 415

Tyr Ser Cys Asn Pro Gly Tyr Val Leu Val Gly Glu Glu Ser Ile Gln
                420                 425                 430

Cys Thr Ser Glu Gly Val Trp Thr Pro Pro Val Pro Gln Cys Lys Val
            435                 440                 445

Ala Ala Cys Glu Ala Thr Gly Arg Gln Leu Leu Thr Lys Pro Gln His
    450                 455                 460

Gln Phe Val Arg Pro Asp Val Asn Ser Ser Cys Gly Glu Gly Tyr Lys
465                 470                 475                 480

Leu Ser Gly Ser Val Tyr Gln Glu Cys Gln Gly Thr Ile Pro Trp Phe
                485                 490                 495

Met Glu Ile Arg Leu Cys Lys Glu Ile Thr Cys Pro Pro Pro Val
                500                 505                 510

Ile Tyr Asn Gly Ala His Thr Gly Ser Ser Leu Glu Asp Phe Pro Tyr
        515                 520                 525

Gly Thr Thr Val Thr Tyr Thr Cys Asn Pro Gly Pro Glu Arg Gly Val
    530                 535                 540

Glu Phe Ser Leu Ile Gly Glu Ser Thr Ile Arg Cys Thr Ser Asn Asp
545                 550                 555                 560

Gln Glu Arg Gly Thr Trp Ser Gly Pro Ala Pro Leu Cys Lys Leu Ser
                565                 570                 575

Leu Leu Ala Val Gln Cys Ser His Val His Ile Ala Asn Gly Tyr Lys
            580                 585                 590

Ile Ser Gly Lys Glu Ala Pro Tyr Phe Tyr Asn Asp Thr Val Thr Phe
    595                 600                 605

Lys Cys Tyr Ser Gly Phe Thr Leu Lys Gly Ser Ser Gln Ile Arg Cys
610                 615                 620

Lys Ala Asp Asn Thr Trp Asp Pro Glu Ile Pro Val Cys Glu Lys Glu
625                 630                 635                 640

Thr Cys Gln His Val Arg Gln Ser Leu Gln Glu Leu Pro Ala Gly Ser
                645                 650                 655

Arg Val Glu Leu Val Asn Thr Ser Cys Gln Asp Gly Tyr Gln Leu Thr
                660                 665                 670

Gly His Ala Tyr Gln Met Cys Gln Asp Ala Glu Asn Gly Ile Trp Phe
            675                 680                 685

Lys Lys Ile Pro Leu Cys Lys Val Ile His Cys His Pro Pro Pro Val
    690                 695                 700
```

Ile Val Asn Gly Lys His Thr Gly Met Met Ala Glu Asn Phe Leu Tyr
705                 710                 715                 720

Gly Asn Glu Val Ser Tyr Glu Cys Asp Gln Gly Phe Tyr Leu Leu Gly
            725                 730                 735

Glu Lys Lys Leu Gln Cys Arg Ser Asp Ser Lys Gly His Gly Ser Trp
            740                 745                 750

Ser Gly Pro Ser Pro Gln Cys Leu Arg Ser Pro Val Thr Arg Cys
            755                 760                 765

Pro Asn Pro Glu Val Lys His Gly Tyr Lys Leu Asn Lys Thr His Ser
770                 775                 780

Ala Tyr Ser His Asn Asp Ile Val Tyr Val Asp Cys Asn Pro Gly Phe
785                 790                 795                 800

Ile Met Asn Gly Ser Arg Val Ile Arg Cys His Thr Asp Asn Thr Trp
            805                 810                 815

Val Pro Gly Val Pro Thr Cys Ile Lys Lys Ala Phe Ile Gly Cys Pro
            820                 825                 830

Pro Pro Pro Lys Thr Pro Asn Gly Asn His Thr Gly Gly Asn Ile Ala
            835                 840                 845

Arg Phe Ser Pro Gly Met Ser Ile Leu Tyr Ser Cys Asp Gln Gly Tyr
850                 855                 860

Leu Leu Val Gly Glu Ala Leu Leu Cys Thr His Glu Gly Thr Trp
865                 870                 875                 880

Ser Gln Pro Ala Pro His Cys Lys Glu Val Asn Cys Ser Ser Pro Ala
            885                 890                 895

Asp Met Asp Gly Ile Gln Lys Gly Leu Glu Pro Arg Lys Met Tyr Gln
            900                 905                 910

Tyr Gly Ala Val Val Thr Leu Glu Cys Glu Asp Gly Tyr Met Leu Glu
            915                 920                 925

Gly Ser Pro Gln Ser Gln Cys Gln Ser Asp His Gln Trp Asn Pro Pro
            930                 935                 940

Leu Ala Val Cys Arg Ser Arg
945                 950

<210> SEQ ID NO 4
<211> LENGTH: 952
<212> TYPE: PRT
<213> ORGANISM: Artificial Sequence
<220> FEATURE:
<223> OTHER INFORMATION: Synthetic polypeptide sequence of extracellular
      domain of mouse CR2 protein

<400> SEQUENCE: 4

Ile Ser Cys Asp Pro Pro Glu Val Lys Asn Ala Arg Lys Pro Tyr
1               5                   10                  15

Tyr Ser Leu Pro Ile Val Pro Gly Thr Val Leu Arg Tyr Thr Cys Ser
            20                  25                  30

Pro Ser Tyr Arg Leu Ile Gly Glu Lys Ala Ile Phe Cys Ile Ser Glu
            35                  40                  45

Asn Gln Val His Ala Thr Trp Asp Lys Ala Pro Pro Ile Cys Glu Ser
        50                  55                  60

Val Asn Lys Thr Ile Ser Cys Ser Asp Pro Ile Val Pro Gly Gly Phe
65                  70                  75                  80

Met Asn Lys Gly Ser Lys Ala Pro Phe Arg His Gly Asp Ser Val Thr
                85                  90                  95

Phe Thr Cys Lys Ala Asn Phe Thr Met Lys Gly Ser Lys Thr Val Trp
            100                 105                 110

-continued

Cys Gln Ala Asn Glu Met Trp Gly Pro Thr Ala Leu Pro Val Cys Glu
            115                 120                 125

Ser Asp Phe Pro Leu Glu Cys Pro Ser Leu Pro Thr Ile His Asn Gly
    130                 135                 140

His His Thr Gly Gln His Val Asp Gln Phe Val Ala Gly Leu Ser Val
145                 150                 155                 160

Thr Tyr Ser Cys Glu Pro Gly Tyr Leu Leu Thr Gly Lys Lys Thr Ile
                165                 170                 175

Lys Cys Leu Ser Ser Gly Asp Trp Asp Gly Val Ile Pro Thr Cys Lys
                180                 185                 190

Glu Ala Gln Cys Glu His Pro Gly Lys Phe Pro Asn Gly Gln Val Lys
                195                 200                 205

Glu Pro Leu Ser Leu Gln Val Gly Thr Thr Val Tyr Phe Ser Cys Asn
    210                 215                 220

Glu Gly Tyr Gln Leu Gln Gly Gln Pro Ser Ser Gln Cys Val Ile Val
225                 230                 235                 240

Glu Gln Lys Ala Ile Trp Thr Lys Lys Pro Val Cys Lys Glu Ile Leu
                245                 250                 255

Cys Pro Pro Pro Pro Val Arg Asn Gly Ser His Thr Gly Ser Phe
                260                 265                 270

Ser Glu Asn Val Pro Tyr Gly Ser Thr Val Thr Tyr Thr Cys Asp Pro
    275                 280                 285

Ser Pro Glu Lys Gly Val Ser Phe Thr Leu Ile Gly Glu Lys Thr Ile
    290                 295                 300

Asn Cys Thr Thr Gly Ser Gln Lys Thr Gly Ile Trp Ser Gly Pro Ala
305                 310                 315                 320

Pro Tyr Cys Val Leu Ser Thr Ser Ala Val Leu Cys Leu Gln Pro Lys
                325                 330                 335

Ile Lys Arg Gly Gln Ile Leu Ser Ile Leu Lys Asp Ser Tyr Ser Tyr
                340                 345                 350

Asn Asp Thr Val Ala Phe Ser Cys Glu Pro Gly Phe Thr Leu Lys Gly
    355                 360                 365

Asn Arg Ser Ile Arg Cys Asn Ala His Gly Thr Trp Glu Pro Pro Val
    370                 375                 380

Pro Val Cys Glu Lys Gly Cys Gln Ala Pro Lys Ile Ile Asn Gly
385                 390                 395                 400

Gln Lys Glu Asp Ser Tyr Leu Leu Asn Phe Asp Pro Gly Thr Ser Ile
                405                 410                 415

Arg Tyr Ser Cys Asp Pro Gly Tyr Leu Leu Val Gly Glu Asp Thr Ile
                420                 425                 430

His Cys Thr Pro Glu Gly Lys Trp Thr Pro Ile Thr Pro Gln Cys Thr
                435                 440                 445

Val Ala Glu Cys Lys Pro Val Gly Pro His Leu Phe Lys Arg Pro Gln
    450                 455                 460

Asn Gln Phe Ile Arg Thr Ala Val Asn Ser Ser Cys Asp Glu Gly Phe
465                 470                 475                 480

Gln Leu Ser Glu Ser Ala Tyr Gln Leu Cys Gln Gly Thr Ile Pro Trp
                485                 490                 495

Phe Ile Glu Ile Arg Leu Cys Lys Glu Ile Thr Cys Pro Pro Pro
                500                 505                 510

Val Ile His Asn Gly Thr His Thr Trp Ser Ser Ser Glu Asp Val Pro
                515                 520                 525

```
Tyr Gly Thr Val Val Thr Tyr Met Cys Tyr Pro Gly Pro Glu Glu Gly
    530                 535                 540

Val Lys Phe Lys Leu Ile Gly Glu Gln Thr Ile His Cys Thr Ser Asp
545                 550                 555                 560

Ser Arg Gly Arg Gly Ser Trp Ser Ser Pro Ala Pro Leu Cys Lys Leu
                565                 570                 575

Ser Leu Pro Ala Val Gln Cys Thr Asp Val His Val Glu Asn Gly Val
            580                 585                 590

Lys Leu Thr Asp Asn Lys Ala Pro Tyr Phe Tyr Asn Asp Ser Val Met
        595                 600                 605

Phe Lys Cys Asp Asp Gly Tyr Ile Leu Ser Gly Ser Ser Gln Ile Arg
    610                 615                 620

Cys Lys Ala Asn Asn Thr Trp Asp Pro Glu Lys Pro Leu Cys Lys Lys
625                 630                 635                 640

Glu Gly Cys Glu Pro Met Arg Val His Gly Leu Pro Asp Asp Ser His
                645                 650                 655

Ile Lys Leu Val Lys Arg Thr Cys Gln Asn Gly Tyr Gln Leu Thr Gly
            660                 665                 670

Tyr Thr Tyr Glu Lys Cys Gln Asn Ala Glu Asn Gly Thr Trp Phe Lys
        675                 680                 685

Lys Ile Glu Val Cys Thr Val Ile Leu Cys Gln Pro Pro Lys Ile
    690                 695                 700

Ala Asn Gly Gly His Thr Gly Met Met Ala Lys His Phe Leu Tyr Gly
705                 710                 715                 720

Asn Glu Val Ser Tyr Glu Cys Asp Glu Gly Phe Tyr Leu Leu Gly Glu
                725                 730                 735

Lys Ser Leu Gln Cys Val Asn Asp Ser Lys Gly His Gly Ser Trp Ser
            740                 745                 750

Gly Pro Pro Pro Gln Cys Leu Gln Ser Ser Pro Leu Thr His Cys Pro
        755                 760                 765

Asp Pro Glu Val Lys His Gly Tyr Lys Leu Asn Lys Thr His Ser Ala
    770                 775                 780

Phe Ser His Asn Asp Ile Val His Phe Val Cys Asn Gln Gly Phe Ile
785                 790                 795                 800

Met Asn Gly Ser His Leu Ile Arg Cys His Thr Asn Asn Thr Trp Leu
                805                 810                 815

Pro Gly Val Pro Thr Cys Ile Arg Lys Ala Ser Leu Gly Cys Gln Ser
            820                 825                 830

Pro Ser Thr Ile Pro Asn Gly Asn His Thr Gly Gly Ser Ile Ala Arg
        835                 840                 845

Phe Pro Pro Gly Met Ser Val Met Tyr Ser Cys Tyr Gln Gly Phe Leu
    850                 855                 860

Met Ala Gly Glu Ala Arg Leu Ile Cys Thr His Glu Gly Thr Trp Ser
865                 870                 875                 880

Gln Pro Pro Pro Phe Cys Lys Glu Val Asn Cys Ser Phe Pro Glu Asp
                885                 890                 895

Thr Asn Gly Ile Gln Lys Gly Phe Gln Pro Gly Lys Thr Tyr Arg Phe
            900                 905                 910

Gly Ala Thr Val Thr Leu Glu Cys Glu Asp Gly Tyr Thr Leu Glu Gly
        915                 920                 925

Ser Pro Gln Ser Gln Cys Gln Asp Asp Ser Gln Trp Asn Pro Pro Leu
    930                 935                 940

Ala Leu Cys Lys Tyr Arg Arg Trp
```

<210> SEQ ID NO 5
<211> LENGTH: 504
<212> TYPE: PRT
<213> ORGANISM: Artificial Sequence
<220> FEATURE:
<223> OTHER INFORMATION: Synthetic polypeptide sequence of SCRs 1 to 8
of human CR2 protein

<400> SEQUENCE: 5

```
Ile Ser Cys Gly Ser Pro Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
        35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
            100                 105                 110

Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
    130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Glu Ile Phe Cys
                245                 250                 255

Pro Ser Pro Pro Pro Ile Leu Asn Gly Arg His Ile Gly Asn Ser Leu
            260                 265                 270

Ala Asn Val Ser Tyr Gly Ser Ile Val Thr Tyr Thr Cys Asp Pro Asp
        275                 280                 285

Pro Glu Glu Gly Val Asn Phe Ile Leu Ile Gly Glu Ser Thr Leu Arg
    290                 295                 300

Cys Thr Val Asp Ser Gln Lys Thr Gly Thr Trp Ser Gly Pro Ala Pro
305                 310                 315                 320

Arg Cys Glu Leu Ser Thr Ser Ala Val Gln Cys Pro His Pro Gln Ile
                325                 330                 335

Leu Arg Gly Arg Met Val Ser Gly Gln Lys Asp Arg Tyr Thr Tyr Asn
            340                 345                 350
```

```
Asp Thr Val Ile Phe Ala Cys Met Phe Gly Phe Thr Leu Lys Gly Ser
            355                 360                 365

Lys Gln Ile Arg Cys Asn Ala Gln Gly Thr Trp Glu Pro Ser Ala Pro
370                 375                 380

Val Cys Glu Lys Glu Cys Gln Ala Pro Pro Asn Ile Leu Asn Gly Gln
385                 390                 395                 400

Lys Glu Asp Arg His Met Val Arg Phe Asp Pro Gly Thr Ser Ile Lys
                405                 410                 415

Tyr Ser Cys Asn Pro Gly Tyr Val Leu Val Gly Glu Ser Ile Gln
            420                 425                 430

Cys Thr Ser Glu Gly Val Trp Thr Pro Pro Val Pro Gln Cys Lys Val
        435                 440                 445

Ala Ala Cys Glu Ala Thr Gly Arg Gln Leu Leu Thr Lys Pro Gln His
    450                 455                 460

Gln Phe Val Arg Pro Asp Val Asn Ser Ser Cys Gly Glu Gly Tyr Lys
465                 470                 475                 480

Leu Ser Gly Ser Val Tyr Gln Glu Cys Gln Gly Thr Ile Pro Trp Phe
                485                 490                 495

Met Glu Ile Arg Leu Cys Lys Glu
            500

<210> SEQ ID NO 6
<211> LENGTH: 505
<212> TYPE: PRT
<213> ORGANISM: Artificial Sequence
<220> FEATURE:
<223> OTHER INFORMATION: Synthetic polypeptide sequence of SCRs 1 to 8
      of mouse CR2 protein

<400> SEQUENCE: 6

Ile Ser Cys Asp Pro Pro Pro Glu Val Lys Asn Ala Arg Lys Pro Tyr
1               5                   10                  15

Tyr Ser Leu Pro Ile Val Pro Gly Thr Val Leu Arg Tyr Thr Cys Ser
            20                  25                  30

Pro Ser Tyr Arg Leu Ile Gly Glu Lys Ala Ile Phe Cys Ile Ser Glu
        35                  40                  45

Asn Gln Val His Ala Thr Trp Asp Lys Ala Pro Pro Ile Cys Glu Ser
50                  55                  60

Val Asn Lys Thr Ile Ser Cys Ser Asp Pro Ile Val Pro Gly Gly Phe
65                  70                  75                  80

Met Asn Lys Gly Ser Lys Ala Pro Phe Arg His Gly Asp Ser Val Thr
                85                  90                  95

Phe Thr Cys Lys Ala Asn Phe Thr Met Lys Gly Ser Lys Thr Val Trp
            100                 105                 110

Cys Gln Ala Asn Glu Met Trp Gly Pro Thr Ala Leu Pro Val Cys Glu
        115                 120                 125

Ser Asp Phe Pro Leu Glu Cys Pro Ser Leu Pro Thr Ile His Asn Gly
    130                 135                 140

His His Thr Gly Gln His Val Asp Gln Phe Val Ala Gly Leu Ser Val
145                 150                 155                 160

Thr Tyr Ser Cys Glu Pro Gly Tyr Leu Leu Thr Gly Lys Lys Thr Ile
                165                 170                 175

Lys Cys Leu Ser Ser Gly Asp Trp Asp Gly Val Ile Pro Thr Cys Lys
            180                 185                 190

Glu Ala Gln Cys Glu His Pro Gly Lys Phe Pro Asn Gly Gln Val Lys
        195                 200                 205
```

```
Glu Pro Leu Ser Leu Gln Val Gly Thr Thr Val Tyr Phe Ser Cys Asn
    210                 215                 220

Glu Gly Tyr Gln Leu Gln Gly Gln Pro Ser Ser Gln Cys Val Ile Val
225                 230                 235                 240

Glu Gln Lys Ala Ile Trp Thr Lys Lys Pro Val Cys Lys Glu Ile Leu
                245                 250                 255

Cys Pro Pro Pro Pro Val Arg Asn Gly Ser His Thr Gly Ser Phe
                260                 265                 270

Ser Glu Asn Val Pro Tyr Gly Ser Thr Val Thr Tyr Thr Cys Asp Pro
        275                 280                 285

Ser Pro Glu Lys Gly Val Ser Phe Thr Leu Ile Gly Glu Lys Thr Ile
    290                 295                 300

Asn Cys Thr Thr Gly Ser Gln Lys Thr Gly Ile Trp Ser Gly Pro Ala
305                 310                 315                 320

Pro Tyr Cys Val Leu Ser Thr Ser Ala Val Leu Cys Leu Gln Pro Lys
                325                 330                 335

Ile Lys Arg Gly Gln Ile Leu Ser Ile Leu Lys Asp Ser Tyr Ser Tyr
                340                 345                 350

Asn Asp Thr Val Ala Phe Ser Cys Glu Pro Gly Phe Thr Leu Lys Gly
            355                 360                 365

Asn Arg Ser Ile Arg Cys Asn Ala His Gly Thr Trp Glu Pro Pro Val
370                 375                 380

Pro Val Cys Glu Lys Gly Cys Gln Ala Pro Lys Ile Ile Asn Gly
385                 390                 395                 400

Gln Lys Glu Asp Ser Tyr Leu Leu Asn Phe Asp Pro Gly Thr Ser Ile
                405                 410                 415

Arg Tyr Ser Cys Asp Pro Gly Tyr Leu Leu Val Gly Leu Asp Thr Ile
                420                 425                 430

His Cys Thr Pro Glu Gly Lys Trp Thr Pro Ile Thr Pro Gln Cys Thr
            435                 440                 445

Val Ala Glu Cys Lys Pro Val Gly Pro His Leu Phe Lys Arg Pro Gln
    450                 455                 460

Asn Gln Phe Ile Arg Thr Ala Val Asn Ser Ser Cys Asp Glu Gly Phe
465                 470                 475                 480

Gln Leu Ser Glu Ser Ala Tyr Gln Leu Cys Gln Gly Thr Ile Pro Trp
                485                 490                 495

Phe Ile Glu Ile Arg Leu Cys Lys Glu
                500                 505

<210> SEQ ID NO 7
<211> LENGTH: 128
<212> TYPE: PRT
<213> ORGANISM: Artificial Sequence
<220> FEATURE:
<223> OTHER INFORMATION: Synthetic polypeptide sequence of SCRs 1 and 2
      of human CR2 protein

<400> SEQUENCE: 7

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
            35                  40                  45

Asp Lys Val Asp Gly Thr Trp Asp Lys Pro Ala Pro Lys Cys Glu Tyr
```

```
                50                  55                  60
Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
            115                 120                 125
```

<210> SEQ ID NO 8
<211> LENGTH: 129
<212> TYPE: PRT
<213> ORGANISM: Artificial Sequence
<220> FEATURE:
<223> OTHER INFORMATION: Synthetic polypeptide sequence of SCRs 1 and 2
      of mouse CR2 protein

<400> SEQUENCE: 8

```
Ile Ser Cys Asp Pro Pro Glu Val Lys Asn Ala Arg Lys Pro Tyr
 1               5                  10                  15

Tyr Ser Leu Pro Ile Val Pro Gly Thr Val Leu Arg Tyr Thr Cys Ser
                 20                  25                  30

Pro Ser Tyr Arg Leu Ile Gly Glu Lys Ala Ile Phe Cys Ile Ser Glu
                 35                  40                  45

Asn Gln Val His Ala Thr Trp Asp Lys Ala Pro Pro Ile Cys Glu Ser
             50                  55                  60

Val Asn Lys Thr Ile Ser Cys Ser Asp Pro Ile Val Pro Gly Gly Phe
 65                  70                  75                  80

Met Asn Lys Gly Ser Lys Ala Pro Phe Arg His Gly Asp Ser Val Thr
                 85                  90                  95

Phe Thr Cys Lys Ala Asn Phe Thr Met Lys Gly Ser Lys Thr Val Trp
                100                 105                 110

Cys Gln Ala Asn Glu Met Trp Gly Pro Thr Ala Leu Pro Val Cys Glu
            115                 120                 125

Ser
```

<210> SEQ ID NO 9
<211> LENGTH: 375
<212> TYPE: PRT
<213> ORGANISM: Artificial Sequence
<220> FEATURE:
<223> OTHER INFORMATION: Synthetic polypeptide sequence of SCRs 1 and 2
      of human CR2 protein fused to Fc domain of mouse IgG1

<400> SEQUENCE: 9

```
Ile Ser Cys Gly Ser Pro Pro Ile Leu Asn Gly Arg Ile Ser Tyr
 1               5                  10                  15

Tyr Ser Thr Pro Ile Ala Val Gly Thr Val Ile Arg Tyr Ser Cys Ser
                 20                  25                  30

Gly Thr Phe Arg Leu Ile Gly Glu Lys Ser Leu Leu Cys Ile Thr Lys
                 35                  40                  45

Asp Lys Val Asp Gly Thr Trp Asp Lys Pro Ala Pro Lys Cys Glu Tyr
             50                  55                  60

Phe Asn Lys Tyr Ser Ser Cys Pro Glu Pro Ile Val Pro Gly Gly Tyr
 65                  70                  75                  80

Lys Ile Arg Gly Ser Thr Pro Tyr Arg His Gly Asp Ser Val Thr Phe
                 85                  90                  95
```

```
Ala Cys Lys Thr Asn Phe Ser Met Asn Gly Asn Lys Ser Val Trp Cys
            100                 105                 110
Gln Ala Asn Asn Met Trp Gly Pro Thr Arg Leu Pro Thr Cys Val Ser
        115                 120                 125
Val Phe Pro Leu Glu Gly Ser Ile Glu Gly Arg Gly Gly Ser Glu Leu
    130                 135                 140
Ala Asp Pro Glu Val Pro Arg Asp Cys Gly Cys Lys Pro Cys Ile Cys
145                 150                 155                 160
Thr Val Pro Glu Val Ser Ser Val Phe Ile Phe Pro Pro Lys Pro Lys
                165                 170                 175
Asp Val Leu Thr Ile Thr Leu Thr Pro Lys Val Thr Cys Val Val Val
            180                 185                 190
Asp Ile Ser Lys Asp Asp Pro Glu Val Gln Phe Ser Trp Phe Val Asp
        195                 200                 205
Asp Val Glu Val His Thr Ala Gln Thr Gln Pro Arg Glu Glu Gln Phe
    210                 215                 220
Asn Ser Thr Phe Arg Ser Val Ser Glu Leu Pro Ile Met His Gln Asp
225                 230                 235                 240
Trp Leu Asn Gly Lys Glu Phe Lys Cys Arg Val Asn Ser Ala Ala Phe
                245                 250                 255
Pro Ala Pro Ile Glu Lys Thr Ile Ser Lys Thr Lys Gly Arg Pro Lys
            260                 265                 270
Ala Pro Gln Leu Tyr Thr Ile Pro Pro Pro Lys Glu Gln Met Ala Lys
        275                 280                 285
Asp Lys Val Ser Leu Thr Cys Met Ile Thr Asp Phe Phe Pro Glu Asp
    290                 295                 300
Ile Thr Val Glu Trp Gln Trp Asn Gly Gln Pro Ala Glu Asn Tyr Lys
305                 310                 315                 320
Asn Thr Gln Pro Ile Met Asn Thr Asn Glu Ser Tyr Phe Val Tyr Ser
                325                 330                 335
Lys Leu Asn Val Gln Lys Ser Asn Trp Glu Ala Gly Asn Thr Phe Thr
            340                 345                 350
Cys Ser Val Leu His Glu Gly Leu His Asn His Thr Glu Lys Ser
        355                 360                 365
Leu Ser His Ser Pro Gly Lys
    370                 375

<210> SEQ ID NO 10
<211> LENGTH: 302
<212> TYPE: PRT
<213> ORGANISM: Homo sapiens

<400> SEQUENCE: 10

His Leu Ile Val Thr Pro Ser Gly Cys Gly Glu Gln Asn Met Ile Gly
1               5                   10                  15
Met Thr Pro Thr Val Ile Ala Val His Tyr Leu Asp Glu Thr Glu Gln
            20                  25                  30
Trp Glu Lys Phe Gly Leu Glu Lys Arg Gln Gly Ala Leu Glu Leu Ile
        35                  40                  45
Lys Lys Gly Tyr Thr Gln Gln Leu Ala Phe Arg Gln Pro Ser Ser Ala
    50                  55                  60
Phe Ala Ala Phe Val Lys Arg Ala Pro Ser Thr Trp Leu Thr Ala Tyr
65                  70                  75                  80
Val Val Lys Val Phe Ser Leu Ala Val Asn Leu Ile Ala Ile Asp Ser
```

```
                    85                  90                  95
Gln Val Leu Cys Gly Ala Val Lys Trp Leu Ile Leu Glu Lys Gln Lys
            100                 105                 110

Pro Asp Gly Val Phe Gln Glu Asp Ala Pro Val Ile His Gln Glu Met
            115                 120                 125

Ile Gly Gly Leu Arg Asn Asn Asn Glu Lys Asp Met Ala Leu Thr Ala
            130                 135                 140

Phe Val Leu Ile Ser Leu Gln Glu Ala Lys Asp Ile Cys Glu Glu Gln
145                 150                 155                 160

Val Asn Ser Leu Pro Gly Ser Ile Thr Lys Ala Gly Asp Phe Leu Glu
            165                 170                 175

Ala Asn Tyr Met Asn Leu Gln Arg Ser Tyr Thr Val Ala Ile Ala Gly
            180                 185                 190

Tyr Ala Leu Ala Gln Met Gly Arg Leu Lys Gly Pro Leu Leu Asn Lys
            195                 200                 205

Phe Leu Thr Thr Ala Lys Asp Lys Asn Arg Trp Glu Asp Pro Gly Lys
            210                 215                 220

Gln Leu Tyr Asn Val Glu Ala Thr Ser Tyr Ala Leu Leu Ala Leu Leu
225                 230                 235                 240

Gln Leu Lys Asp Phe Asp Phe Val Pro Pro Val Val Arg Trp Leu Asn
            245                 250                 255

Glu Gln Arg Tyr Tyr Gly Gly Gly Tyr Gly Ser Thr Gln Ala Thr Phe
            260                 265                 270

Met Val Phe Gln Ala Leu Ala Gln Tyr Gln Lys Asp Ala Pro Asp His
            275                 280                 285

Gln Glu Leu Asn Leu Asp Val Ser Leu Gln Leu Pro Ser Arg
            290                 295                 300

<210> SEQ ID NO 11
<211> LENGTH: 349
<212> TYPE: PRT
<213> ORGANISM: Homo sapiens

<400> SEQUENCE: 11

Glu Gly Val Gln Lys Glu Asp Ile Pro Pro Ala Asp Leu Ser Asp Gln
1               5                   10                  15

Val Pro Asp Thr Glu Ser Glu Thr Arg Ile Leu Leu Gln Gly Thr Pro
            20                  25                  30

Val Ala Gln Met Thr Glu Asp Ala Val Asp Ala Glu Arg Leu Lys His
            35                  40                  45

Leu Ile Val Thr Pro Ser Gly Cys Gly Glu Gln Asn Met Ile Gly Met
50                  55                  60

Thr Pro Thr Val Ile Ala Val His Tyr Leu Asp Glu Thr Glu Gln Trp
65                  70                  75                  80

Glu Lys Phe Gly Leu Glu Lys Arg Gln Gly Ala Leu Glu Leu Ile Lys
            85                  90                  95

Lys Gly Tyr Thr Gln Gln Leu Ala Phe Arg Gln Pro Ser Ser Ala Phe
            100                 105                 110

Ala Ala Phe Val Lys Arg Ala Pro Ser Thr Trp Leu Thr Ala Tyr Val
            115                 120                 125

Val Lys Val Phe Ser Leu Ala Val Asn Leu Ile Ala Ile Asp Ser Gln
            130                 135                 140

Val Leu Cys Gly Ala Val Lys Trp Leu Ile Leu Glu Lys Gln Lys Pro
145                 150                 155                 160
```

```
Asp Gly Val Phe Gln Glu Asp Ala Pro Val Ile His Gln Glu Met Ile
                165                 170                 175

Gly Gly Leu Arg Asn Asn Asn Glu Lys Asp Met Ala Leu Thr Ala Phe
            180                 185                 190

Val Leu Ile Ser Leu Gln Glu Ala Lys Asp Ile Cys Glu Glu Gln Val
        195                 200                 205

Asn Ser Leu Pro Gly Ser Ile Thr Lys Ala Gly Asp Phe Leu Glu Ala
    210                 215                 220

Asn Tyr Met Asn Leu Gln Arg Ser Tyr Thr Val Ala Ile Ala Gly Tyr
225                 230                 235                 240

Ala Leu Ala Gln Met Gly Arg Leu Lys Gly Pro Leu Leu Asn Lys Phe
                245                 250                 255

Leu Thr Thr Ala Lys Asp Lys Asn Arg Trp Glu Asp Pro Gly Lys Gln
            260                 265                 270

Leu Tyr Asn Val Glu Ala Thr Ser Tyr Ala Leu Leu Ala Leu Leu Gln
        275                 280                 285

Leu Lys Asp Phe Asp Phe Val Pro Pro Val Val Arg Trp Leu Asn Glu
    290                 295                 300

Gln Arg Tyr Tyr Gly Gly Gly Tyr Gly Ser Thr Gln Ala Thr Phe Met
305                 310                 315                 320

Val Phe Gln Ala Leu Ala Gln Tyr Gln Lys Asp Ala Pro Asp His Gln
                325                 330                 335

Glu Leu Asn Leu Asp Val Ser Leu Gln Leu Pro Ser Arg
            340                 345

<210> SEQ ID NO 12
<211> LENGTH: 349
<212> TYPE: PRT
<213> ORGANISM: Homo sapiens

<400> SEQUENCE: 12

Glu Gly Val Gln Lys Glu Asp Ile Pro Pro Ala Asp Leu Ser Asp Gln
1               5                   10                  15

Val Pro Asp Thr Glu Ser Glu Thr Arg Ile Leu Leu Gln Gly Thr Pro
            20                  25                  30

Val Ala Gln Met Thr Glu Asp Ala Val Asp Ala Glu Arg Leu Lys His
        35                  40                  45

Leu Ile Val Thr Pro Ser Gly Cys Gly Glu Gln Asn Met Ile Gly Met
    50                  55                  60

Thr Pro Thr Val Ile Ala Val His Tyr Leu Asp Glu Thr Glu Gln Trp
65                  70                  75                  80

Glu Lys Phe Gly Leu Glu Lys Arg Gln Gly Ala Leu Glu Leu Ile Lys
                85                  90                  95

Lys Gly Tyr Thr Gln Gln Leu Ala Phe Arg Gln Pro Ser Ser Ala Phe
            100                 105                 110

Ala Ala Phe Val Lys Arg Ala Pro Ser Thr Trp Leu Thr Ala Tyr Val
        115                 120                 125

Val Lys Val Phe Ser Leu Ala Val Asn Leu Ile Ala Ile Asp Ser Gln
    130                 135                 140

Val Leu Cys Gly Ala Val Lys Trp Leu Ile Leu Glu Lys Gln Lys Pro
145                 150                 155                 160

Asp Gly Val Phe Gln Glu Asp Ala Pro Val Ile His Gln Glu Met Ile
                165                 170                 175

Gly Gly Leu Arg Asn Asn Asn Glu Lys Asp Met Ala Leu Thr Ala Phe
            180                 185                 190
```

```
Val Leu Ile Ser Leu Gln Glu Ala Lys Asp Ile Cys Glu Glu Gln Val
            195                 200                 205

Asn Ser Leu Pro Gly Ser Ile Thr Lys Ala Gly Asp Phe Leu Glu Ala
    210                 215                 220

Asn Tyr Met Asn Leu Gln Arg Ser Tyr Thr Val Ala Ile Ala Gly Tyr
225                 230                 235                 240

Ala Leu Ala Gln Met Gly Arg Leu Lys Gly Pro Leu Leu Asn Lys Phe
            245                 250                 255

Leu Thr Thr Ala Lys Asp Lys Asn Arg Trp Glu Asp Pro Gly Lys Gln
            260                 265                 270

Leu Tyr Asn Val Glu Ala Thr Ser Tyr Ala Leu Leu Ala Leu Leu Gln
            275                 280                 285

Leu Lys Asp Phe Asp Phe Val Pro Pro Val Val Arg Trp Leu Asn Glu
            290                 295                 300

Gln Arg Tyr Tyr Gly Gly Gly Tyr Gly Ser Thr Gln Ala Thr Phe Met
305                 310                 315                 320

Val Phe Gln Ala Leu Ala Gln Tyr Gln Lys Asp Ala Pro Asp His Gln
            325                 330                 335

Glu Leu Asn Leu Asp Val Ser Leu Gln Leu Pro Ser Arg
            340                 345
```

<210> SEQ ID NO 13
<211> LENGTH: 915
<212> TYPE: PRT
<213> ORGANISM: Homo sapiens

<400> SEQUENCE: 13

```
Ser Asn Leu Asp Glu Asp Ile Ile Ala Glu Glu Asn Ile Val Ser Arg
1               5                   10                  15

Ser Glu Phe Pro Glu Ser Trp Leu Trp Asn Val Glu Asp Leu Lys Glu
            20                  25                  30

Pro Pro Lys Asn Gly Ile Ser Thr Lys Leu Met Asn Ile Phe Leu Lys
            35                  40                  45

Asp Ser Ile Thr Thr Trp Glu Ile Leu Ala Val Ser Met Ser Asp Lys
50                  55                  60

Lys Gly Ile Cys Val Ala Asp Pro Phe Glu Val Thr Val Met Gln Asp
65                  70                  75                  80

Phe Phe Ile Asp Leu Arg Leu Pro Tyr Ser Val Val Arg Asn Glu Gln
            85                  90                  95

Val Glu Ile Arg Ala Val Leu Tyr Asn Tyr Arg Gln Asn Gln Glu Leu
            100                 105                 110

Lys Val Arg Val Glu Leu Leu His Asn Pro Ala Phe Cys Ser Leu Ala
            115                 120                 125

Thr Thr Lys Arg Arg His Gln Gln Thr Val Thr Ile Pro Pro Lys Ser
            130                 135                 140

Ser Leu Ser Val Pro Tyr Val Ile Val Pro Leu Lys Thr Gly Leu Gln
145                 150                 155                 160

Glu Val Glu Val Lys Ala Ala Val Tyr His His Phe Ile Ser Asp Gly
            165                 170                 175

Val Arg Lys Ser Leu Lys Val Val Pro Glu Gly Ile Arg Met Asn Lys
            180                 185                 190

Thr Val Ala Val Arg Thr Leu Asp Pro Glu Arg Leu Gly Arg Glu Gly
            195                 200                 205

Val Gln Lys Glu Asp Ile Pro Pro Ala Asp Leu Ser Asp Gln Val Pro
```

-continued

```
                210                 215                 220
Asp Thr Glu Ser Glu Thr Arg Ile Leu Leu Gln Gly Thr Pro Val Ala
225                 230                 235                 240

Gln Met Thr Glu Asp Ala Val Asp Ala Glu Arg Leu Lys His Leu Ile
                245                 250                 255

Val Thr Pro Ser Gly Cys Gly Glu Gln Asn Met Ile Gly Met Thr Pro
                260                 265                 270

Thr Val Ile Ala Val His Tyr Leu Asp Glu Thr Glu Gln Trp Glu Lys
                275                 280                 285

Phe Gly Leu Glu Lys Arg Gln Gly Ala Leu Glu Leu Ile Lys Lys Gly
290                 295                 300

Tyr Thr Gln Gln Leu Ala Phe Arg Gln Pro Ser Ser Ala Phe Ala Ala
305                 310                 315                 320

Phe Val Lys Arg Ala Pro Ser Thr Trp Leu Thr Ala Tyr Val Val Lys
                325                 330                 335

Val Phe Ser Leu Ala Val Asn Leu Ile Ala Ile Asp Ser Gln Val Leu
                340                 345                 350

Cys Gly Ala Val Lys Trp Leu Ile Leu Glu Lys Gln Lys Pro Asp Gly
                355                 360                 365

Val Phe Gln Glu Asp Ala Pro Val Ile His Gln Glu Met Ile Gly Gly
                370                 375                 380

Leu Arg Asn Asn Asn Glu Lys Asp Met Ala Leu Thr Ala Phe Val Leu
385                 390                 395                 400

Ile Ser Leu Gln Glu Ala Lys Asp Ile Cys Glu Glu Gln Val Asn Ser
                405                 410                 415

Leu Pro Gly Ser Ile Thr Lys Ala Gly Asp Phe Leu Glu Ala Asn Tyr
                420                 425                 430

Met Asn Leu Gln Arg Ser Tyr Thr Val Ala Ile Ala Gly Tyr Ala Leu
                435                 440                 445

Ala Gln Met Gly Arg Leu Lys Gly Pro Leu Leu Asn Lys Phe Leu Thr
450                 455                 460

Thr Ala Lys Asp Lys Asn Arg Trp Glu Asp Pro Gly Lys Gln Leu Tyr
465                 470                 475                 480

Asn Val Glu Ala Thr Ser Tyr Ala Leu Leu Ala Leu Leu Gln Leu Lys
                485                 490                 495

Asp Phe Asp Phe Val Pro Pro Val Val Arg Trp Leu Asn Glu Gln Arg
                500                 505                 510

Tyr Tyr Gly Gly Gly Tyr Gly Ser Thr Gln Ala Thr Phe Met Val Phe
                515                 520                 525

Gln Ala Leu Ala Gln Tyr Gln Lys Asp Ala Pro Asp His Gln Glu Leu
530                 535                 540

Asn Leu Asp Val Ser Leu Gln Leu Pro Ser Arg Ser Ser Lys Ile Thr
545                 550                 555                 560

His Arg Ile His Trp Glu Ser Ala Ser Leu Leu Arg Ser Glu Glu Thr
                565                 570                 575

Lys Glu Asn Glu Gly Phe Thr Val Thr Ala Glu Gly Lys Gly Gln Gly
                580                 585                 590

Thr Leu Ser Val Val Thr Met Tyr His Ala Lys Ala Lys Asp Gln Leu
                595                 600                 605

Thr Cys Asn Lys Phe Asp Leu Lys Val Thr Ile Lys Pro Ala Pro Glu
                610                 615                 620

Thr Glu Lys Arg Pro Gln Asp Ala Lys Asn Thr Met Ile Leu Glu Ile
625                 630                 635                 640
```

```
Cys Thr Arg Tyr Arg Gly Asp Gln Asp Ala Thr Met Ser Ile Leu Asp
                645                 650                 655

Ile Ser Met Met Thr Gly Phe Ala Pro Asp Thr Asp Leu Lys Gln
        660                 665                 670

Leu Ala Asn Gly Val Asp Arg Tyr Ile Ser Lys Tyr Glu Leu Asp Lys
            675                 680                 685

Ala Phe Ser Asp Arg Asn Thr Leu Ile Ile Tyr Leu Asp Lys Val Ser
690                 695                 700

His Ser Glu Asp Asp Cys Leu Ala Phe Lys Val His Gln Tyr Phe Asn
705                 710                 715                 720

Val Glu Leu Ile Gln Pro Gly Ala Val Lys Val Tyr Ala Tyr Tyr Asn
                725                 730                 735

Leu Glu Glu Ser Cys Thr Arg Phe Tyr His Pro Glu Lys Glu Asp Gly
            740                 745                 750

Lys Leu Asn Lys Leu Cys Arg Asp Glu Leu Cys Arg Cys Ala Glu Glu
            755                 760                 765

Asn Cys Phe Ile Gln Lys Ser Asp Lys Val Thr Leu Glu Glu Arg
        770                 775                 780

Leu Asp Lys Ala Cys Glu Pro Gly Val Asp Tyr Val Tyr Lys Thr Arg
785                 790                 795                 800

Leu Val Lys Val Gln Leu Ser Asn Asp Phe Asp Glu Tyr Ile Met Ala
                805                 810                 815

Ile Glu Gln Thr Ile Lys Ser Gly Ser Asp Glu Val Gln Val Gly Gln
            820                 825                 830

Gln Arg Thr Phe Ile Ser Pro Ile Lys Cys Arg Glu Ala Leu Lys Leu
            835                 840                 845

Glu Glu Lys Lys His Tyr Leu Met Trp Gly Leu Ser Ser Asp Phe Trp
850                 855                 860

Gly Glu Lys Pro Asn Leu Ser Tyr Ile Ile Gly Lys Asp Thr Trp Val
865                 870                 875                 880

Glu His Trp Pro Glu Glu Asp Glu Cys Gln Asp Glu Glu Asn Gln Lys
                885                 890                 895

Gln Cys Gln Asp Leu Gly Ala Phe Thr Glu Ser Met Val Val Phe Gly
            900                 905                 910

Cys Pro Asn
        915

<210> SEQ ID NO 14
<211> LENGTH: 72
<212> TYPE: DNA
<213> ORGANISM: Artificial Sequence
<220> FEATURE:
<223> OTHER INFORMATION: Synthetic DNA sequence of cDNA encoding human
      CD5 signal peptide

<400> SEQUENCE: 14
atgcccatgg ggtctctgca accgctggcc accttgtacc tgctggggat gctggtcgct     60
tcctgcctcg ga                                                         72

<210> SEQ ID NO 15
<211> LENGTH: 21
<212> TYPE: PRT
<213> ORGANISM: Artificial Sequence
<220> FEATURE:
<223> OTHER INFORMATION: Synthetic polypeptide sequence of human CD5
      signal peptide
```

-continued

```
<400> SEQUENCE: 15

Met Pro Met Gly Ser Leu Gln Pro Leu Ala Thr Leu Tyr Leu Leu Gly
1               5                   10                  15

Met Leu Val Ala Ser
            20

<210> SEQ ID NO 16
<211> LENGTH: 51
<212> TYPE: DNA
<213> ORGANISM: Artificial Sequence
<220> FEATURE:
<223> OTHER INFORMATION: Synthetic DNA sequence of cDNA encoding human
      CR2 signal peptide, short version

<400> SEQUENCE: 16
atgggcgccg cgggcctgct cggggttttc ttggctctcg tcgcaccggg g             51

<210> SEQ ID NO 17
<211> LENGTH: 17
<212> TYPE: PRT
<213> ORGANISM: Artificial Sequence
<220> FEATURE:
<223> OTHER INFORMATION: Synthetic polypeptide sequence of human CR2
      signal peptide, long version

<400> SEQUENCE: 17

Met Gly Ala Ala Gly Leu Leu Gly Val Phe Leu Ala Leu Val Ala Pro
1               5                   10                  15

Gly

<210> SEQ ID NO 18
<211> LENGTH: 60
<212> TYPE: DNA
<213> ORGANISM: Artificial Sequence
<220> FEATURE:
<223> OTHER INFORMATION: Synthetic DNA sequence of cDNA encoding human
      CR2 signal peptide, long version

<400> SEQUENCE: 18
atgggagccg ctggtctgct cggcgtgttc ctcgccttgg tggcacctgg cgtcctgggc    60

<210> SEQ ID NO 19
<211> LENGTH: 20
<212> TYPE: PRT
<213> ORGANISM: Artificial Sequence
<220> FEATURE:
<223> OTHER INFORMATION: Synthetic polypeptide sequence of human CR2
      signal peptide, long version

<400> SEQUENCE: 19

Met Gly Ala Ala Gly Leu Leu Gly Val Phe Leu Ala Leu Val Ala Pro
1               5                   10                  15

Gly Val Leu Gly
            20

<210> SEQ ID NO 20
<211> LENGTH: 436
<212> TYPE: PRT
<213> ORGANISM: Staphylococcus aureus

<400> SEQUENCE: 20

Met Lys Asn Lys Tyr Ile Ser Lys Leu Leu Val Gly Ala Ala Thr Ile
1               5                   10                  15

Thr Leu Ala Thr Met Ile Ser Asn Gly Glu Ala Lys Ala Ser Glu Asn
```

```
            20                  25                  30
Thr Gln Gln Thr Ser Thr Lys His Gln Thr Thr Gln Asn Asn Tyr Val
            35                  40                  45
Thr Asp Gln Gln Lys Ala Phe Tyr Gln Val Leu His Leu Lys Gly Ile
    50                  55                  60
Thr Glu Glu Gln Arg Asn Gln Tyr Ile Lys Thr Leu Arg Glu His Pro
65                  70                  75                  80
Glu Arg Ala Gln Glu Val Phe Ser Glu Ser Leu Lys Asp Ser Lys Asn
                85                  90                  95
Pro Asp Arg Arg Val Ala Gln Gln Asn Ala Phe Tyr Asn Val Leu Lys
            100                 105                 110
Asn Asp Asn Leu Thr Glu Gln Glu Lys Asn Asn Tyr Ile Ala Gln Ile
            115                 120                 125
Lys Glu Asn Pro Asp Arg Ser Gln Gln Val Trp Val Glu Ser Val Gln
            130                 135                 140
Ser Ser Lys Ala Lys Glu Arg Gln Asn Ile Glu Asn Ala Asp Lys Ala
145                 150                 155                 160
Ile Lys Asp Phe Gln Asp Asn Lys Ala Pro His Asp Lys Ser Ala Ala
                165                 170                 175
Tyr Glu Ala Asn Ser Lys Leu Pro Lys Asp Leu Arg Asp Lys Asn Asn
            180                 185                 190
Arg Phe Val Glu Lys Val Ser Ile Glu Lys Ala Ile Val Arg His Asp
            195                 200                 205
Glu Arg Val Lys Ser Ala Asn Asp Ala Ile Ser Lys Leu Asn Glu Lys
            210                 215                 220
Asp Ser Ile Glu Asn Arg Arg Leu Ala Gln Arg Glu Val Asn Lys Ala
225                 230                 235                 240
Pro Met Asp Val Lys Glu His Leu Gln Lys Gln Leu Asp Ala Leu Val
                245                 250                 255
Ala Gln Lys Asp Ala Glu Lys Lys Val Ala Pro Lys Val Glu Ala Pro
            260                 265                 270
Gln Ile Gln Ser Pro Gln Ile Glu Lys Pro Lys Ala Glu Ser Pro Lys
            275                 280                 285
Val Glu Val Pro Gln Ile Gln Ser Pro Lys Val Glu Val Pro Gln Ser
            290                 295                 300
Lys Leu Leu Gly Tyr Tyr Gln Ser Leu Lys Asp Ser Phe Asn Tyr Gly
305                 310                 315                 320
Tyr Lys Tyr Leu Thr Asp Thr Tyr Lys Ser Tyr Lys Glu Lys Tyr Asp
                325                 330                 335
Thr Ala Lys Tyr Tyr Asn Thr Tyr Tyr Lys Tyr Lys Gly Ala Ile
            340                 345                 350
Asp Gln Thr Val Leu Thr Val Leu Gly Ser Gly Ser Lys Ser Tyr Ile
            355                 360                 365
Gln Pro Leu Lys Val Asp Asp Lys Asn Gly Tyr Leu Ala Lys Ser Tyr
            370                 375                 380
Ala Gln Val Arg Asn Tyr Val Thr Glu Ser Ile Asn Thr Gly Lys Val
385                 390                 395                 400
Leu Tyr Thr Phe Tyr Gln Asn Pro Thr Leu Val Lys Thr Ala Ile Lys
                405                 410                 415
Ala Gln Glu Thr Ala Ser Ser Ile Lys Asn Thr Leu Ser Asn Leu Leu
            420                 425                 430
Ser Phe Trp Lys
            435
```

<210> SEQ ID NO 21
<211> LENGTH: 239
<212> TYPE: PRT
<213> ORGANISM: Artificial Sequence
<220> FEATURE:
<223> OTHER INFORMATION: Synthetic polypeptide sequence of a fragment of
      S. aureus N315 Sbi protein comprising the first four N-terminal
      domains (Sbi-I-II-III-IV) of the full-length Sbi protein

<400> SEQUENCE: 21

Lys Ala Ser Glu Asn Thr Gln Gln Thr Ser Thr Lys His Gln Thr Thr
1               5                   10                  15

Gln Asn Asn Tyr Val Thr Asp Gln Gln Lys Ala Phe Tyr Gln Val Leu
            20                  25                  30

His Leu Lys Gly Ile Thr Glu Glu Gln Arg Asn Gln Tyr Ile Lys Thr
        35                  40                  45

Leu Arg Glu His Pro Glu Arg Ala Gln Glu Val Phe Ser Glu Ser Leu
    50                  55                  60

Lys Asp Ser Lys Asn Pro Asp Arg Arg Val Ala Gln Asn Ala Phe
65                  70                  75                  80

Tyr Asn Val Leu Lys Asn Asp Asn Leu Thr Glu Gln Glu Lys Asn Asn
                85                  90                  95

Tyr Ile Ala Gln Ile Lys Glu Asn Pro Asp Arg Ser Gln Gln Val Trp
            100                 105                 110

Val Glu Ser Val Gln Ser Ser Lys Ala Lys Glu Arg Gln Asn Ile Glu
        115                 120                 125

Asn Ala Asp Lys Ala Ile Lys Asp Phe Gln Asp Asn Lys Ala Pro His
    130                 135                 140

Asp Lys Ser Ala Ala Tyr Glu Ala Asn Ser Lys Leu Pro Lys Asp Leu
145                 150                 155                 160

Arg Asp Lys Asn Asn Arg Phe Val Glu Lys Val Ser Ile Glu Lys Ala
                165                 170                 175

Ile Val Arg His Asp Glu Arg Val Lys Ser Ala Asn Asp Ala Ile Ser
            180                 185                 190

Lys Leu Asn Glu Lys Asp Ser Ile Glu Asn Arg Arg Leu Ala Gln Arg
        195                 200                 205

Glu Val Asn Lys Ala Pro Met Asp Val Lys Glu His Leu Gln Lys Gln
    210                 215                 220

Leu Asp Ala Leu Val Ala Gln Lys Asp Ala Glu Lys Lys Val Ala
225                 230                 235

<210> SEQ ID NO 22
<211> LENGTH: 117
<212> TYPE: PRT
<213> ORGANISM: Artificial Sequence
<220> FEATURE:
<223> OTHER INFORMATION: Synthetic polypeptide sequence of a fragment of
      S. aureus N315 Sbi protein comprising the third and fourth
      N-terminal domains (Sbi-III-IV) of the full length Sbi protein

<400> SEQUENCE: 22

Glu Arg Gln Asn Ile Glu Asn Ala Asp Lys Ala Ile Lys Asp Phe Gln
1               5                   10                  15

Asp Asn Lys Ala Pro His Asp Lys Ser Ala Ala Tyr Glu Ala Asn Ser
            20                  25                  30

Lys Leu Pro Lys Asp Leu Arg Asp Lys Asn Asn Arg Phe Val Glu Lys
        35                  40                  45

```
Val Ser Ile Glu Lys Ala Ile Val Arg His Asp Glu Arg Val Lys Ser
    50                  55                  60

Ala Asn Asp Ala Ile Ser Lys Leu Asn Glu Lys Asp Ser Ile Glu Asn
 65                  70                  75                  80

Arg Arg Leu Ala Gln Arg Glu Val Asn Lys Ala Pro Met Asp Val Lys
                 85                  90                  95

Glu His Leu Gln Lys Gln Leu Asp Ala Leu Val Ala Gln Lys Asp Ala
            100                 105                 110

Glu Lys Lys Val Ala
            115

<210> SEQ ID NO 23
<211> LENGTH: 481
<212> TYPE: PRT
<213> ORGANISM: Artificial Sequence
<220> FEATURE:
<223> OTHER INFORMATION: Synthetic polypeptide sequence of a fragment of
      S. aureus N315 Sbi protein comprising the first four N-terminal
      domains (Sbi-I-II-III-IV) fused to the Fc domain of mouse IgG1

<400> SEQUENCE: 23

Lys Ala Ser Glu Asn Thr Gln Gln Thr Ser Thr Lys His Gln Thr Thr
  1               5                  10                  15

Gln Asn Asn Tyr Val Thr Asp Gln Gln Lys Ala Phe Tyr Gln Val Leu
                 20                  25                  30

His Leu Lys Gly Ile Thr Glu Glu Arg Asn Gln Tyr Ile Lys Thr
             35                  40                  45

Leu Arg Glu His Pro Glu Arg Ala Gln Glu Val Phe Ser Glu Ser Leu
 50                  55                  60

Lys Asp Ser Lys Asn Pro Asp Arg Arg Val Ala Gln Gln Asn Ala Phe
 65                  70                  75                  80

Tyr Asn Val Leu Lys Asn Asp Asn Leu Thr Glu Gln Glu Lys Asn Asn
                 85                  90                  95

Tyr Ile Ala Gln Ile Lys Glu Asn Pro Asp Arg Ser Gln Gln Val Trp
            100                 105                 110

Val Glu Ser Val Gln Ser Ser Lys Ala Lys Glu Arg Gln Asn Ile Glu
            115                 120                 125

Asn Ala Asp Lys Ala Ile Lys Asp Phe Gln Asp Asn Lys Ala Pro His
130                 135                 140

Asp Lys Ser Ala Ala Tyr Glu Ala Asn Ser Lys Leu Pro Lys Asp Leu
145                 150                 155                 160

Arg Asp Lys Asn Asn Arg Phe Val Glu Lys Val Ser Ile Glu Lys Ala
                165                 170                 175

Ile Val Arg His Asp Glu Arg Val Lys Ser Ala Asn Asp Ala Ile Ser
            180                 185                 190

Lys Leu Asn Glu Lys Asp Ser Ile Glu Asn Arg Arg Leu Ala Gln Arg
        195                 200                 205

Glu Val Asn Lys Ala Pro Met Asp Val Lys Glu His Leu Gln Lys Gln
210                 215                 220

Leu Asp Ala Leu Val Ala Gln Lys Asp Ala Glu Lys Lys Val Ala Gly
225                 230                 235                 240

Ser Ile Glu Gly Arg Gly Gly Ser Glu Leu Ala Asp Pro Glu Val Pro
                245                 250                 255

Arg Asp Cys Gly Cys Lys Pro Cys Ile Cys Thr Val Pro Glu Val Ser
            260                 265                 270

Ser Val Phe Ile Phe Pro Pro Lys Pro Lys Asp Val Leu Thr Ile Thr
```

```
                275                 280                 285
Leu Thr Pro Lys Val Thr Cys Val Val Asp Ile Ser Lys Asp Asp
290                 295                 300

Pro Glu Val Gln Phe Ser Trp Phe Val Asp Asp Val Glu Val His Thr
305                 310                 315                 320

Ala Gln Thr Gln Pro Arg Glu Glu Gln Phe Asn Ser Thr Phe Arg Ser
                325                 330                 335

Val Ser Glu Leu Pro Ile Met His Gln Asp Trp Leu Asn Gly Lys Glu
            340                 345                 350

Phe Lys Cys Arg Val Asn Ser Ala Ala Phe Pro Ala Pro Ile Glu Lys
        355                 360                 365

Thr Ile Ser Lys Thr Lys Gly Arg Pro Lys Ala Pro Gln Leu Tyr Thr
    370                 375                 380

Ile Pro Pro Pro Lys Glu Gln Met Ala Lys Asp Lys Val Ser Leu Thr
385                 390                 395                 400

Cys Met Ile Thr Asp Phe Phe Pro Glu Asp Leu Thr Val Glu Trp Gln
                405                 410                 415

Trp Asn Gly Gln Pro Ala Glu Asn Tyr Lys Asn Thr Gln Pro Ile Met
            420                 425                 430

Asn Thr Asn Glu Ser Tyr Phe Val Tyr Ser Lys Leu Asn Val Gln Lys
        435                 440                 445

Ser Asn Trp Glu Ala Gly Asn Thr Phe Thr Cys Ser Val Leu His Glu
    450                 455                 460

Gly Leu His Asn His His Thr Glu Lys Ser Leu Ser His Ser Pro Gly
465                 470                 475                 480

Lys

<210> SEQ ID NO 24
<211> LENGTH: 242
<212> TYPE: PRT
<213> ORGANISM: Artificial Sequence
<220> FEATURE:
<223> OTHER INFORMATION: Synthetic polypeptide sequence of Fc fragment
      of mouse IgG1

<400> SEQUENCE: 24

Gly Ser Ile Glu Gly Arg Gly Gly Ser Glu Leu Ala Asp Pro Glu Val
1               5                   10                  15

Pro Arg Asp Cys Gly Cys Lys Pro Cys Ile Cys Thr Val Pro Glu Val
                20                  25                  30

Ser Ser Val Phe Ile Phe Pro Pro Lys Pro Lys Asp Val Leu Thr Ile
            35                  40                  45

Thr Leu Thr Pro Lys Val Thr Cys Val Val Asp Ile Ser Lys Asp
        50                  55                  60

Asp Pro Glu Val Gln Phe Ser Trp Phe Val Asp Asp Val Glu Val His
65                  70                  75                  80

Thr Ala Gln Thr Gln Pro Arg Glu Glu Gln Phe Asn Ser Thr Phe Arg
                85                  90                  95

Ser Val Ser Glu Leu Pro Ile Met His Gln Asp Trp Leu Asn Gly Lys
            100                 105                 110

Glu Phe Lys Cys Arg Val Asn Ser Ala Ala Phe Pro Ala Pro Ile Glu
        115                 120                 125

Lys Thr Ile Ser Lys Thr Lys Gly Arg Pro Lys Ala Pro Gln Leu Tyr
    130                 135                 140

Thr Ile Pro Pro Pro Lys Glu Gln Met Ala Lys Asp Lys Val Ser Leu
```

```
               145                 150                 155                 160
Thr Cys Met Ile Thr Asp Phe Phe Pro Glu Asp Ile Thr Val Glu Trp
                    165                 170                 175

Gln Trp Asn Gly Gln Pro Ala Glu Asn Tyr Lys Asn Thr Gln Pro Ile
                180                 185                 190

Met Asn Thr Asn Glu Ser Tyr Phe Val Tyr Ser Lys Leu Asn Val Gln
            195                 200                 205

Lys Ser Asn Trp Glu Ala Gly Asn Thr Phe Thr Cys Ser Val Leu His
        210                 215                 220

Glu Gly Leu His Asn His His Thr Gly Lys Ser Leu Ser His Ser Pro
225                 230                 235                 240

Gly Lys

<210> SEQ ID NO 25
<211> LENGTH: 1744
<212> TYPE: PRT
<213> ORGANISM: Homo sapiens

<400> SEQUENCE: 25

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His Leu
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
                100                 105                 110

His Ser Pro Trp Leu Lys Asp Ser Leu Ser Arg Thr Thr Asn Ile Gln
            115                 120                 125

Gly Ile Asn Leu Leu Phe Ser Ser Arg Arg Gly His Leu Phe Leu Gln
        130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
```

```
                 275                 280                 285
Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
                500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
            610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
                660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
690                 695                 700
```

```
Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
        740                 745                 750

Gly Leu Gln Arg Ala Leu Glu Ile Leu Gln Glu Glu Asp Leu Ile Asp
    755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
        835                 840                 845

Leu Glu Leu Arg Pro Val Leu Tyr Asn Tyr Leu Asp Lys Asn Leu Thr
    850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
        915                 920                 925

Lys Val Leu Gln Ile Glu Lys Glu Gly Ala Ile His Arg Glu Glu Leu
    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
        995                 1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Asp Ser Ser Thr Trp Leu Thr Ala Phe Val Leu
    1070                1075                1080

Lys Val Leu Ser Leu Ala Gln Glu Gln Val Gly Gly Ser Pro Glu
    1085                1090                1095

Lys Leu Gln Glu Thr Ser Asn Trp Leu Leu Ser Gln Gln Gln Ala
    1100                1105                1110
```

Asp Gly Ser Phe Gln Asp Pro Cys Pro Val Leu Asp Arg Ser Met
1115                1120                1125

Gln Gly Gly Leu Val Gly Asn Asp Glu Thr Val Ala Leu Thr Ala
1130                1135                1140

Phe Val Thr Ile Ala Leu His His Gly Leu Ala Val Phe Gln Asp
1145                1150                1155

Glu Gly Ala Glu Pro Leu Lys Gln Arg Val Glu Ala Ser Ile Ser
1160                1165                1170

Lys Ala Asn Ser Phe Leu Gly Glu Lys Ala Ser Ala Gly Leu Leu
1175                1180                1185

Gly Ala His Ala Ala Ile Thr Ala Tyr Ala Leu Ser Leu Thr
1190                1195                1200

Lys Ala Pro Val Asp Leu Leu Gly Val Ala His Asn Asn Leu Met
1205                1210                1215

Ala Met Ala Gln Glu Thr Gly Asp Asn Leu Tyr Trp Gly Ser Val
1220                1225                1230

Thr Gly Ser Gln Ser Asn Ala Val Ser Pro Thr Pro Ala Pro Arg
1235                1240                1245

Asn Pro Ser Asp Pro Met Pro Gln Ala Pro Ala Leu Trp Ile Glu
1250                1255                1260

Thr Thr Ala Tyr Ala Leu Leu His Leu Leu His Glu Gly Lys
1265                1270                1275

Ala Glu Met Ala Asp Gln Ala Ser Ala Trp Leu Thr Arg Gln Gly
1280                1285                1290

Ser Phe Gln Gly Gly Phe Arg Ser Thr Gln Asp Thr Val Ile Ala
1295                1300                1305

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Asp Tyr Glu Tyr Asp Glu Leu Pro Ala Lys
1415                1420                1425

Asp Asp Pro Asp Ala Pro Leu Gln Pro Val Thr Pro Leu Gln Leu
1430                1435                1440

Phe Glu Gly Arg Arg Asn Arg Arg Arg Glu Ala Pro Lys Val
1445                1450                1455

Val Glu Glu Gln Glu Ser Arg Val His Tyr Thr Val Cys Ile Trp
1460                1465                1470

Arg Asn Gly Lys Val Gly Leu Ser Gly Met Ala Ile Ala Asp Val
1475                1480                1485

Thr Leu Leu Ser Gly Phe His Ala Leu Arg Ala Asp Leu Glu Lys
1490                1495                1500

Leu Thr Ser Leu Ser Asp Arg Tyr Val Ser His Phe Glu Thr Glu

```
                 1505                1510                1515
Gly Pro His Val Leu Leu Tyr Phe Asp Ser Val Pro Thr Ser Arg
        1520                1525                1530
Glu Cys Val Gly Phe Glu Ala Val Gln Glu Val Pro Val Gly Leu
    1535                1540                1545
Val Gln Pro Ala Ser Ala Thr Leu Tyr Asp Tyr Tyr Asn Pro Glu
    1550                1555                1560
Arg Arg Cys Ser Val Phe Tyr Gly Ala Pro Ser Lys Ser Arg Leu
    1565                1570                1575
Leu Ala Thr Leu Cys Ser Ala Glu Val Cys Gln Cys Ala Glu Gly
    1580                1585                1590
Lys Cys Pro Arg Gln Arg Arg Ala Leu Glu Arg Gly Leu Gln Asp
    1595                1600                1605
Glu Asp Gly Tyr Arg Met Lys Phe Ala Cys Tyr Tyr Pro Arg Val
    1610                1615                1620
Glu Tyr Gly Phe Gln Val Lys Val Leu Arg Glu Asp Ser Arg Ala
    1625                1630                1635
Ala Phe Arg Leu Phe Glu Thr Lys Ile Thr Gln Val Leu His Phe
    1640                1645                1650
Thr Lys Asp Val Lys Ala Ala Asn Gln Met Arg Asn Phe Leu
    1655                1660                1665
Val Arg Ala Ser Cys Arg Leu Arg Leu Glu Pro Gly Lys Glu Tyr
    1670                1675                1680
Leu Ile Met Gly Leu Asp Gly Ala Thr Tyr Asp Leu Glu Gly His
    1685                1690                1695
Pro Gln Tyr Leu Leu Asp Ser Asn Ser Trp Ile Glu Glu Met Pro
    1700                1705                1710
Ser Glu Arg Leu Cys Arg Ser Thr Arg Gln Arg Ala Ala Cys Ala
    1715                1720                1725
Gln Leu Asn Asp Phe Leu Gln Glu Tyr Gly Thr Gln Gly Cys Gln
    1730                1735                1740
Val

<210> SEQ ID NO 26
<211> LENGTH: 690
<212> TYPE: PRT
<213> ORGANISM: Homo sapiens

<400> SEQUENCE: 26

Ala Leu Glu Ile Leu Gln Glu Glu Asp Leu Ile Asp Glu Asp Ile
1               5                   10                  15
Pro Val Arg Ser Phe Phe Pro Glu Asn Trp Leu Trp Arg Val Glu Thr
            20                  25                  30
Val Asp Arg Phe Gln Ile Leu Thr Leu Trp Leu Pro Asp Ser Leu Thr
        35                  40                  45
Thr Trp Glu Ile His Gly Leu Ser Leu Ser Lys Thr Lys Gly Leu Cys
    50                  55                  60
Val Ala Thr Pro Val Gln Leu Arg Val Phe Arg Glu Phe His Leu His
65                  70                  75                  80
Leu Arg Leu Pro Met Ser Val Arg Arg Phe Glu Gln Leu Glu Leu Arg
                85                  90                  95
Pro Val Leu Tyr Asn Tyr Leu Asp Lys Asn Leu Thr Val Ser Val His
                100                 105                 110
Val Ser Pro Val Glu Gly Leu Cys Leu Ala Gly Gly Gly Gly Leu Ala
```

-continued

```
            115                 120                 125
Gln Gln Val Leu Val Pro Ala Gly Ser Ala Arg Pro Val Ala Phe Ser
        130                 135                 140
Val Val Pro Thr Ala Ala Ala Val Ser Leu Lys Val Val Ala Arg
145                 150                 155                 160
Gly Ser Phe Glu Phe Pro Val Gly Asp Ala Val Ser Lys Val Leu Gln
                165                 170                 175
Ile Glu Lys Glu Gly Ala Ile His Arg Glu Glu Leu Val Tyr Glu Leu
            180                 185                 190
Asn Pro Leu Asp His Arg Gly Arg Thr Leu Glu Ile Pro Gly Asn Ser
                195                 200                 205
Asp Pro Asn Met Ile Pro Asp Gly Asp Phe Asn Ser Tyr Val Arg Val
210                 215                 220
Thr Ala Ser Asp Pro Leu Asp Thr Leu Gly Ser Glu Gly Ala Leu Ser
225                 230                 235                 240
Pro Gly Gly Val Ala Ser Leu Leu Arg Leu Pro Arg Gly Cys Gly Glu
                245                 250                 255
Gln Thr Met Ile Tyr Leu Ala Pro Thr Leu Ala Ala Ser Arg Tyr Leu
            260                 265                 270
Asp Lys Thr Glu Gln Trp Ser Thr Leu Pro Pro Glu Thr Lys Asp His
                275                 280                 285
Ala Val Asp Leu Ile Gln Lys Gly Tyr Met Arg Ile Gln Gln Phe Arg
            290                 295                 300
Lys Ala Asp Gly Ser Tyr Ala Ala Trp Leu Ser Arg Asp Ser Ser Thr
305                 310                 315                 320
Trp Leu Thr Ala Phe Val Leu Lys Val Leu Ser Leu Ala Gln Glu Gln
                325                 330                 335
Val Gly Gly Ser Pro Glu Lys Leu Gln Glu Thr Ser Asn Trp Leu Leu
                340                 345                 350
Ser Gln Gln Gln Ala Asp Gly Ser Phe Gln Asp Pro Cys Pro Val Leu
            355                 360                 365
Asp Arg Ser Met Gln Gly Gly Leu Val Gly Asn Asp Glu Thr Val Ala
        370                 375                 380
Leu Thr Ala Phe Val Thr Ile Ala Leu His His Gly Leu Ala Val Phe
385                 390                 395                 400
Gln Asp Glu Gly Ala Glu Pro Leu Lys Gln Arg Val Glu Ala Ser Ile
                405                 410                 415
Ser Lys Ala Asn Ser Phe Leu Gly Glu Lys Ala Ser Ala Gly Leu Leu
                420                 425                 430
Gly Ala His Ala Ala Ala Ile Thr Ala Tyr Ala Leu Ser Leu Thr Lys
            435                 440                 445
Ala Pro Val Asp Leu Leu Gly Val Ala His Asn Asn Leu Met Ala Met
        450                 455                 460
Ala Gln Glu Thr Gly Asp Asn Leu Tyr Trp Gly Ser Val Thr Gly Ser
465                 470                 475                 480
Gln Ser Asn Ala Val Ser Pro Thr Pro Ala Pro Arg Asn Pro Ser Asp
                485                 490                 495
Pro Met Pro Gln Ala Pro Ala Leu Trp Ile Glu Thr Thr Ala Tyr Ala
            500                 505                 510
Leu Leu His Leu Leu Leu His Glu Gly Lys Ala Glu Met Ala Asp Gln
                515                 520                 525
Ala Ser Ala Trp Leu Thr Arg Gln Gly Ser Phe Gln Gly Gly Phe Arg
            530                 535                 540
```

Ser Thr Gln Asp Thr Val Ile Ala Leu Asp Ala Leu Ser Ala Tyr Trp
545                 550                 555                 560

Ile Ala Ser His Thr Thr Glu Glu Arg Gly Leu Asn Val Thr Leu Ser
            565                 570                 575

Ser Thr Gly Arg Asn Gly Phe Lys Ser His Ala Leu Gln Leu Asn Asn
        580                 585                 590

Arg Gln Ile Arg Gly Leu Glu Glu Leu Gln Phe Ser Leu Gly Ser
    595                 600                 605

Lys Ile Asn Val Lys Val Gly Asn Ser Lys Gly Thr Leu Lys Val
610                 615                 620

Leu Arg Thr Tyr Asn Val Leu Asp Met Lys Asn Thr Thr Cys Gln Asp
625                 630                 635                 640

Leu Gln Ile Glu Val Thr Val Lys Gly His Val Glu Tyr Thr Met Glu
                645                 650                 655

Ala Asn Glu Asp Tyr Glu Asp Tyr Glu Tyr Asp Glu Leu Pro Ala Lys
                660                 665                 670

Asp Asp Pro Asp Ala Pro Leu Gln Pro Val Thr Pro Leu Gln Leu Phe
        675                 680                 685

Glu Gly
    690

<210> SEQ ID NO 27
<211> LENGTH: 380
<212> TYPE: PRT
<213> ORGANISM: Homo sapiens

<400> SEQUENCE: 27

Thr Leu Glu Ile Pro Gly Asn Ser Asp Pro Asn Met Ile Pro Asp Gly
1               5                   10                  15

Asp Phe Asn Ser Tyr Val Arg Val Thr Ala Ser Asp Pro Leu Asp Thr
                20                  25                  30

Leu Gly Ser Glu Gly Ala Leu Ser Pro Gly Gly Val Ala Ser Leu Leu
            35                  40                  45

Arg Leu Pro Arg Gly Cys Gly Glu Gln Thr Met Ile Tyr Leu Ala Pro
50                  55                  60

Thr Leu Ala Ala Ser Arg Tyr Leu Asp Lys Thr Glu Gln Trp Ser Thr
65                  70                  75                  80

Leu Pro Pro Glu Thr Lys Asp His Ala Val Asp Leu Ile Gln Lys Gly
                85                  90                  95

Tyr Met Arg Ile Gln Gln Phe Arg Lys Ala Asp Gly Ser Tyr Ala Ala
                100                 105                 110

Trp Leu Ser Arg Asp Ser Ser Thr Trp Leu Thr Ala Phe Val Leu Lys
            115                 120                 125

Val Leu Ser Leu Ala Gln Glu Gln Val Gly Gly Ser Pro Glu Lys Leu
130                 135                 140

Gln Glu Thr Ser Asn Trp Leu Leu Ser Gln Gln Ala Asp Gly Ser
145                 150                 155                 160

Phe Gln Asp Pro Cys Pro Val Leu Asp Arg Ser Met Gln Gly Gly Leu
                165                 170                 175

Val Gly Asn Asp Glu Thr Val Ala Leu Thr Ala Phe Val Thr Ile Ala
            180                 185                 190

Leu His His Gly Leu Ala Val Phe Gln Asp Glu Gly Ala Glu Pro Leu
            195                 200                 205

Lys Gln Arg Val Glu Ala Ser Ile Ser Lys Ala Asn Ser Phe Leu Gly

```
            210                 215                 220
Glu Lys Ala Ser Ala Gly Leu Leu Gly Ala His Ala Ala Ile Thr
225                 230                 235                 240

Ala Tyr Ala Leu Ser Leu Thr Lys Ala Pro Val Asp Leu Leu Gly Val
                245                 250                 255

Ala His Asn Asn Leu Met Ala Met Ala Gln Glu Thr Gly Asp Asn Leu
                260                 265                 270

Tyr Trp Gly Ser Val Thr Gly Ser Gln Ser Asn Ala Val Ser Pro Thr
            275                 280                 285

Pro Ala Pro Arg Asn Pro Ser Asp Pro Met Pro Gln Ala Pro Ala Leu
            290                 295                 300

Trp Ile Glu Thr Thr Ala Tyr Ala Leu Leu His Leu Leu His Glu
305                 310                 315                 320

Gly Lys Ala Glu Met Ala Asp Gln Ala Ser Ala Trp Leu Thr Arg Gln
                325                 330                 335

Gly Ser Phe Gln Gly Gly Phe Arg Ser Thr Gln Asp Thr Val Ile Ala
                340                 345                 350

Leu Asp Ala Leu Ser Ala Tyr Trp Ile Ala Ser His Thr Thr Glu Glu
            355                 360                 365

Arg Gly Leu Asn Val Thr Leu Ser Ser Thr Gly Arg
            370                 375                 380

<210> SEQ ID NO 28
<211> LENGTH: 2039
<212> TYPE: PRT
<213> ORGANISM: Homo sapiens

<400> SEQUENCE: 28

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
                20                  25                  30

Leu Leu Ala Leu Pro Val Ala Trp Gly Gln Cys Asn Ala Pro Glu Trp
            35                  40                  45

Leu Pro Phe Ala Arg Pro Thr Asn Leu Thr Asp Glu Phe Glu Phe Pro
50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
                100                 105                 110

Gly Met Val His Val Ile Lys Gly Ile Gln Phe Gly Ser Gln Ile Lys
            115                 120                 125

Tyr Ser Cys Thr Lys Gly Tyr Arg Leu Ile Gly Ser Ser Ser Ala Thr
130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
            195                 200                 205
```

-continued

Gly Glu Pro Ser Ile Tyr Cys Thr Ser Asn Asp Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
        355                 360                 365

Arg Val Leu Phe Pro Val Asn Leu Gln Leu Gly Ala Lys Val Asp Phe
    370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Pro Val Ile Pro Asn Gly Arg His
            420                 425                 430

Thr Gly Lys Pro Leu Glu Val Phe Pro Phe Gly Lys Ala Val Asn Tyr
        435                 440                 445

Thr Cys Asp Pro His Pro Asp Arg Gly Thr Ser Phe Asp Leu Ile Gly
450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
610                 615                 620

Gly Asp Phe Ile Ser Thr Asn Arg Glu Asn Phe His Tyr Gly Ser Val

-continued

```
625                 630                 635                 640
Val Thr Tyr Arg Cys Asn Pro Gly Ser Gly Arg Lys Val Phe Glu
                645                 650                 655

Leu Val Gly Glu Pro Ser Ile Tyr Cys Thr Ser Asn Asp Asp Gln Val
                660                 665                 670

Gly Ile Trp Ser Gly Pro Ala Pro Gln Cys Ile Ile Pro Asn Lys Cys
                675                 680                 685

Thr Pro Pro Asn Val Glu Asn Gly Ile Leu Val Ser Asp Asn Arg Ser
690                 695                 700

Leu Phe Ser Leu Asn Glu Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Asp
                740                 745                 750

Val Leu His Ala Glu Arg Thr Gln Arg Asp Lys Asp Asn Phe Ser Pro
                755                 760                 765

Gly Gln Glu Val Phe Tyr Ser Cys Glu Pro Gly Tyr Asp Leu Arg Gly
                770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
                805                 810                 815

Asn Gly Arg Val Leu Phe Pro Val Asn Leu Gln Leu Gly Ala Lys Val
                820                 825                 830

Asp Phe Val Cys Asp Glu Gly Phe Gln Leu Lys Gly Ser Ser Ala Ser
                835                 840                 845

Tyr Cys Val Leu Ala Gly Met Glu Ser Leu Trp Asn Ser Ser Val Pro
                850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
                885                 890                 895

Asn Tyr Thr Cys Asp Pro His Pro Asp Arg Gly Thr Ser Phe Asp Leu
                900                 905                 910

Ile Gly Glu Ser Thr Ile Arg Cys Thr Ser Asp Pro Gln Gly Asn Gly
                915                 920                 925

Val Trp Ser Ser Pro Ala Pro Arg Cys Gly Ile Leu Gly His Cys Gln
930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
                980                 985                 990

Ser Ser Pro Lys Asp Val Cys Lys Arg Lys Ser Cys Lys Thr Pro Pro
                995                 1000                1005

Asp Pro Val Asn Gly Met Val His Val Ile Thr Asp Ile Gln Val
                1010                1015                1020

Gly Ser Arg Ile Asn Tyr Ser Cys Thr Thr Gly His Arg Leu Ile
                1025                1030                1035

Gly His Ser Ser Ala Glu Cys Ile Leu Ser Gly Asn Thr Ala His
                1040                1045                1050
```

-continued

```
Trp Ser Thr Lys Pro Pro Ile Cys Gln Arg Ile Pro Cys Gly Leu
1055                1060                1065

Pro Pro Thr Ile Ala Asn Gly Asp Phe Ile Ser Thr Asn Arg Glu
1070                1075                1080

Asn Phe His Tyr Gly Ser Val Val Thr Tyr Arg Cys Asn Leu Gly
1085                1090                1095

Ser Arg Gly Arg Lys Val Phe Glu Leu Val Gly Glu Pro Ser Ile
1100                1105                1110

Tyr Cys Thr Ser Asn Asp Asp Gln Val Gly Ile Trp Ser Gly Pro
1115                1120                1125

Ala Pro Gln Cys Ile Ile Pro Asn Lys Cys Thr Pro Pro Asn Val
1130                1135                1140

Glu Asn Gly Ile Leu Val Ser Asp Asn Arg Ser Leu Phe Ser Leu
1145                1150                1155

Asn Glu Val Val Glu Phe Arg Cys Gln Pro Gly Phe Val Met Lys
1160                1165                1170

Gly Pro Arg Arg Val Lys Cys Gln Ala Leu Asn Lys Trp Glu Pro
1175                1180                1185

Glu Leu Pro Ser Cys Ser Arg Val Cys Gln Pro Pro Glu Ile
1190                1195                1200

Leu His Gly Glu His Thr Pro Ser His Gln Asp Asn Phe Ser Pro
1205                1210                1215

Gly Gln Glu Val Phe Tyr Ser Cys Glu Pro Gly Tyr Asp Leu Arg
1220                1225                1230

Gly Ala Ala Ser Leu His Cys Thr Pro Gln Gly Asp Trp Ser Pro
1235                1240                1245

Glu Ala Pro Arg Cys Ala Val Lys Ser Cys Asp Asp Phe Leu Gly
1250                1255                1260

Gln Leu Pro His Gly Arg Val Leu Phe Pro Leu Asn Leu Gln Leu
1265                1270                1275

Gly Ala Lys Val Ser Phe Val Cys Asp Glu Gly Phe Arg Leu Lys
1280                1285                1290

Gly Ser Ser Val Ser His Cys Val Leu Val Gly Met Arg Ser Leu
1295                1300                1305

Trp Asn Asn Ser Val Pro Val Cys Glu His Ile Phe Cys Pro Asn
1310                1315                1320

Pro Pro Ala Ile Leu Asn Gly Arg His Thr Gly Thr Pro Ser Gly
1325                1330                1335

Asp Ile Pro Tyr Gly Lys Glu Ile Ser Tyr Thr Cys Asp Pro His
1340                1345                1350

Pro Asp Arg Gly Met Thr Phe Asn Leu Ile Gly Glu Ser Thr Ile
1355                1360                1365

Arg Cys Thr Ser Asp Pro His Gly Asn Gly Val Trp Ser Ser Pro
1370                1375                1380

Ala Pro Arg Cys Glu Leu Ser Val Arg Ala Gly His Cys Lys Thr
1385                1390                1395

Pro Glu Gln Phe Pro Phe Ala Ser Pro Thr Ile Pro Ile Asn Asp
1400                1405                1410

Phe Glu Phe Pro Val Gly Thr Ser Leu Asn Tyr Glu Cys Arg Pro
1415                1420                1425

Gly Tyr Phe Gly Lys Met Phe Ser Ile Ser Cys Leu Glu Asn Leu
1430                1435                1440
```

```
Val Trp Ser Ser Val Glu Asp Asn Cys Arg Arg Lys Ser Cys Gly
1445                1450                1455

Pro Pro Pro Glu Pro Phe Asn Gly Met Val His Ile Asn Thr Asp
1460                1465                1470

Thr Gln Phe Gly Ser Thr Val Asn Tyr Ser Cys Asn Glu Gly Phe
1475                1480                1485

Arg Leu Ile Gly Ser Pro Ser Thr Thr Cys Leu Val Ser Gly Asn
1490                1495                1500

Asn Val Thr Trp Asp Lys Lys Ala Pro Ile Cys Glu Ile Ile Ser
1505                1510                1515

Cys Glu Pro Pro Pro Thr Ile Ser Asn Gly Asp Phe Tyr Ser Asn
1520                1525                1530

Asn Arg Thr Ser Phe His Asn Gly Thr Val Val Thr Tyr Gln Cys
1535                1540                1545

His Thr Gly Pro Asp Gly Glu Gln Leu Phe Glu Leu Val Gly Glu
1550                1555                1560

Arg Ser Ile Tyr Cys Thr Ser Lys Asp Asp Gln Val Gly Val Trp
1565                1570                1575

Ser Ser Pro Pro Pro Arg Cys Ile Ser Thr Asn Lys Cys Thr Ala
1580                1585                1590

Pro Glu Val Glu Asn Ala Ile Arg Val Pro Gly Asn Arg Ser Phe
1595                1600                1605

Phe Ser Leu Thr Glu Ile Ile Arg Phe Arg Cys Gln Pro Gly Phe
1610                1615                1620

Val Met Val Gly Ser His Thr Val Gln Cys Gln Thr Asn Gly Arg
1625                1630                1635

Trp Gly Pro Lys Leu Pro His Cys Ser Arg Val Cys Gln Pro Pro
1640                1645                1650

Pro Glu Ile Leu His Gly Glu His Thr Leu Ser His Gln Asp Asn
1655                1660                1665

Phe Ser Pro Gly Gln Glu Val Phe Tyr Ser Cys Glu Pro Ser Tyr
1670                1675                1680

Asp Leu Arg Gly Ala Ala Ser Leu His Cys Thr Pro Gln Gly Asp
1685                1690                1695

Trp Ser Pro Glu Ala Pro Arg Cys Thr Val Lys Ser Cys Asp Asp
1700                1705                1710

Phe Leu Gly Gln Leu Pro His Gly Arg Val Leu Leu Pro Leu Asn
1715                1720                1725

Leu Gln Leu Gly Ala Lys Val Ser Phe Val Cys Asp Glu Gly Phe
1730                1735                1740

Arg Leu Lys Gly Arg Ser Ala Ser His Cys Val Leu Ala Gly Met
1745                1750                1755

Lys Ala Leu Trp Asn Ser Ser Val Pro Val Cys Glu Gln Ile Phe
1760                1765                1770

Cys Pro Asn Pro Pro Ala Ile Leu Asn Gly Arg His Thr Gly Thr
1775                1780                1785

Pro Phe Gly Asp Ile Pro Tyr Gly Lys Glu Ile Ser Tyr Ala Cys
1790                1795                1800

Asp Thr His Pro Asp Arg Gly Met Thr Phe Asn Leu Ile Gly Glu
1805                1810                1815

Ser Ser Ile Arg Cys Thr Ser Asp Pro Gln Gly Asn Gly Val Trp
1820                1825                1830

Ser Ser Pro Ala Pro Arg Cys Glu Leu Ser Val Pro Ala Ala Cys
```

```
                       1835                1840                1845

Pro His  Pro Pro Lys  Ile Gln  Asn Gly His Tyr Ile  Gly Gly His
    1850              1855                1860

Val Ser  Leu Tyr Leu  Pro Gly  Met Thr Ile Ser Tyr  Thr Cys Asp
    1865              1870                1875

Pro Gly  Tyr Leu Leu  Val Gly  Lys Gly Phe Ile Phe  Cys Thr Asp
    1880              1885                1890

Gln Gly  Ile Trp Ser  Gln Leu  Asp His Tyr Cys Lys  Glu Val Asn
    1895              1900                1905

Cys Ser  Phe Pro Leu  Phe Met  Asn Gly Ile Ser Lys  Glu Leu Glu
    1910              1915                1920

Met Lys  Lys Val Tyr  His Tyr  Gly Asp Tyr Val Thr  Leu Lys Cys
    1925              1930                1935

Glu Asp  Gly Tyr Thr  Leu Glu  Gly Ser Pro Trp Ser  Gln Cys Gln
    1940              1945                1950

Ala Asp  Asp Arg Trp  Asp Pro  Pro Leu Ala Lys Cys  Thr Ser Arg
    1955              1960                1965

Ala His  Asp Ala Leu  Ile Val  Gly Thr Leu Ser Gly  Thr Ile Phe
    1970              1975                1980

Phe Ile  Leu Leu Ile  Ile Phe  Leu Ser Trp Ile Ile  Leu Lys His
    1985              1990                1995

Arg Lys  Gly Asn Asn  Ala His  Glu Asn Pro Lys Glu  Val Ala Ile
    2000              2005                2010

His Leu  His Ser Gln  Gly Gly  Ser Ser Val His Pro  Arg Thr Leu
    2015              2020                2025

Gln Thr  Asn Glu Glu  Asn Ser  Arg Val Leu Pro
    2030              2035

<210> SEQ ID NO 29
<211> LENGTH: 597
<212> TYPE: PRT
<213> ORGANISM: Homo sapiens

<400> SEQUENCE: 29

Met His  Pro Pro Lys  Thr Pro  Ser Gly Ala Leu His  Arg Lys Arg Lys
1                 5                  10                  15

Met Ala  Ala Trp Pro  Phe Ser  Arg Leu Trp Lys Val  Ser Asp Pro Ile
                 20                  25                  30

Leu Phe  Gln Met Thr  Leu Ile  Ala Ala Leu Leu Pro  Ala Val Leu Gly
         35                  40                  45

Asn Cys  Gly Pro Pro  Pro Thr  Leu Ser Phe Ala Ala  Pro Met Asp Ile
    50                  55                  60

Thr Leu  Thr Glu Thr  Arg Phe  Lys Thr Gly Thr Leu  Lys Tyr Thr
65                  70                  75                  80

Cys Leu  Pro Gly Tyr  Val Arg  Ser His Ser Thr Gln  Thr Leu Thr Cys
                 85                  90                  95

Asn Ser  Asp Gly Glu  Trp Val  Tyr Asn Thr Phe Cys  Ile Tyr Lys Arg
                100                 105                 110

Cys Arg  His Pro Gly  Glu Leu  Arg Asn Gly Gln Val  Glu Ile Lys Thr
         115                 120                 125

Asp Leu  Ser Phe Gly  Ser Gln  Ile Glu Phe Ser Cys  Ser Glu Gly Phe
   130                 135                 140

Phe Leu  Ile Gly Ser  Thr Thr  Ser Arg Cys Glu Val  Gln Asp Arg Gly
145                 150                 155                 160
```

```
Val Gly Trp Ser His Pro Leu Pro Gln Cys Glu Ile Val Lys Cys Lys
            165                 170                 175

Pro Pro Pro Asp Ile Arg Asn Gly Arg His Ser Gly Glu Glu Asn Phe
        180                 185                 190

Tyr Ala Tyr Gly Phe Ser Val Thr Tyr Ser Cys Asp Pro Arg Phe Ser
        195                 200                 205

Leu Leu Gly His Ala Ser Ile Ser Cys Thr Val Glu Asn Glu Thr Ile
        210                 215                 220

Gly Val Trp Arg Pro Ser Pro Thr Cys Glu Lys Ile Thr Cys Arg
225                 230                 235                 240

Lys Pro Asp Val Ser His Gly Glu Met Val Ser Gly Phe Gly Pro Ile
                245                 250                 255

Tyr Asn Tyr Lys Asp Thr Ile Val Phe Lys Cys Gln Lys Gly Phe Val
        260                 265                 270

Leu Arg Gly Ser Ser Val Ile His Cys Asp Ala Asp Ser Lys Trp Asn
        275                 280                 285

Pro Ser Pro Pro Ala Cys Glu Pro Asn Ser Cys Ile Asn Leu Pro Asp
        290                 295                 300

Ile Pro His Ala Ser Trp Glu Thr Tyr Pro Arg Pro Thr Lys Glu Asp
305                 310                 315                 320

Val Tyr Val Val Gly Thr Val Leu Arg Tyr Arg Cys His Pro Gly Tyr
                325                 330                 335

Lys Pro Thr Thr Asp Glu Pro Thr Thr Val Ile Cys Gln Lys Asn Leu
                340                 345                 350

Arg Trp Thr Pro Tyr Gln Gly Cys Glu Ala Leu Cys Cys Pro Glu Pro
        355                 360                 365

Lys Leu Asn Asn Gly Glu Ile Thr Gln His Arg Lys Ser Arg Pro Ala
        370                 375                 380

Asn His Cys Val Tyr Phe Tyr Gly Asp Glu Ile Ser Phe Ser Cys His
385                 390                 395                 400

Glu Thr Ser Arg Phe Ser Ala Ile Cys Gln Gly Asp Gly Thr Trp Ser
                405                 410                 415

Pro Arg Thr Pro Ser Cys Gly Asp Ile Cys Asn Phe Pro Pro Lys Ile
                420                 425                 430

Ala His Gly His Tyr Lys Gln Ser Ser Ser Tyr Ser Phe Phe Lys Glu
        435                 440                 445

Glu Ile Ile Tyr Glu Cys Asp Lys Gly Tyr Ile Leu Val Gly Gln Ala
        450                 455                 460

Lys Leu Ser Cys Ser Tyr Ser His Trp Ser Ala Pro Ala Pro Gln Cys
465                 470                 475                 480

Lys Ala Leu Cys Arg Lys Pro Glu Leu Val Asn Gly Arg Leu Ser Val
                485                 490                 495

Asp Lys Asp Gln Tyr Val Glu Pro Glu Asn Val Thr Ile Gln Cys Asp
                500                 505                 510

Ser Gly Tyr Gly Val Val Gly Pro Gln Ser Ile Thr Cys Ser Gly Asn
        515                 520                 525

Arg Thr Trp Tyr Pro Glu Val Pro Lys Cys Glu Trp Glu Thr Pro Glu
        530                 535                 540

Gly Cys Glu Gln Val Leu Thr Gly Lys Arg Leu Met Gln Cys Leu Pro
545                 550                 555                 560

Asn Pro Glu Asp Val Lys Met Ala Leu Glu Val Tyr Lys Leu Ser Leu
                565                 570                 575

Glu Ile Glu Gln Leu Glu Leu Gln Arg Asp Ser Ala Arg Gln Ser Thr
```

-continued

```
                  580                 585                 590
Leu Asp Lys Glu Leu
        595

<210> SEQ ID NO 30
<211> LENGTH: 252
<212> TYPE: PRT
<213> ORGANISM: Homo sapiens

<400> SEQUENCE: 30

Met Phe Phe Trp Cys Ala Cys Cys Leu Met Val Ala Trp Arg Val Ser
1               5                   10                  15

Ala Ser Asp Ala Glu His Cys Pro Glu Leu Pro Pro Val Asp Asn Ser
                20                  25                  30

Ile Phe Val Ala Lys Glu Val Glu Gly Gln Ile Leu Gly Thr Tyr Val
            35                  40                  45

Cys Ile Lys Gly Tyr His Leu Val Gly Lys Lys Thr Leu Phe Cys Asn
    50                  55                  60

Ala Ser Lys Glu Trp Asp Asn Thr Thr Thr Glu Cys Arg Leu Gly His
65                  70                  75                  80

Cys Pro Asp Pro Val Leu Val Asn Gly Glu Phe Ser Ser Ser Gly Pro
                85                  90                  95

Val Asn Val Ser Asp Lys Ile Thr Phe Met Cys Asn Asp His Tyr Ile
                100                 105                 110

Leu Lys Gly Ser Asn Arg Ser Gln Cys Leu Glu Asp His Thr Trp Ala
            115                 120                 125

Pro Pro Phe Pro Ile Cys Lys Ser Arg Asp Cys Asp Pro Pro Gly Asn
130                 135                 140

Pro Val His Gly Tyr Phe Glu Gly Asn Asn Phe Thr Leu Gly Ser Thr
145                 150                 155                 160

Ile Ser Tyr Tyr Cys Glu Asp Arg Tyr Tyr Leu Val Gly Val Gln Glu
                165                 170                 175

Gln Gln Cys Val Asp Gly Glu Trp Ser Ser Ala Leu Pro Val Cys Lys
            180                 185                 190

Leu Ile Gln Glu Ala Pro Lys Pro Glu Cys Glu Lys Ala Leu Leu Ala
        195                 200                 205

Phe Gln Glu Ser Lys Asn Leu Cys Glu Ala Met Glu Asn Phe Met Gln
    210                 215                 220

Gln Leu Lys Glu Ser Gly Met Thr Met Glu Glu Leu Lys Tyr Ser Leu
225                 230                 235                 240

Glu Leu Lys Lys Ala Glu Leu Lys Ala Lys Leu Leu
                245                 250
```

NON-INVASIVE DETECTION OF COMPLEMENT-MEDIATED INFLAMMATION USING CR2-TARGETED NANOPARTICLES

CROSS-REFERENCES TO RELATED APPLICATIONS

This application is a National Stage filing of International Application No. PCT/US2010/023201, filed Feb. 4, 2010, and claims the benefit of U.S. Provisional Application No. 61/149,975, filed Feb. 4, 2009, each of which is incorporated herein by reference in its entirety and for all purposes.

STATEMENT AS TO RIGHTS TO INVENTIONS MADE UNDER FEDERALLY SPONSORED RESEARCH OR DEVELOPMENT

This invention was made with government support under grant number R01 CA53615 awarded by the National Institutes of Health. The Government has certain rights in the invention.

BACKGROUND OF THE INVENTION

This application pertains to methods and compositions for non-invasive detection of complement-mediated inflammation using CR2-targeted nanoparticles.

Complement is the collective term for a series of blood proteins that constitute a major effector mechanism of the immune system. Complement plays an important role in the pathology of many autoimmune, inflammatory, and ischemic diseases. Inappropriate complement activation and its deposition on host cells can lead to complement-mediated cell lysis of target structures, as well as tissue destruction due to the generation of powerful mediators of inflammation.

Complement can be activated by one of the three pathways, the classical, lectin, and alternative pathways. The classical pathway is activated through the binding of the complement system protein C1q to antigen-antibody complexes, pentraxins, or apoptotic cells. The pentraxins include C-reactive protein and serum amyloid P component. The lectin pathway is initiated by binding of microbial saccharides to the mannose-binding lectin. The alternative pathway is activated on surfaces of pathogens that have neutral or positive charge characteristics and do not express or contain complement inhibitors. This results from the process termed "tickover" of C3 that occurs spontaneously, involving the interaction of conformationally altered C3 with factor B, and results in the fixation of active C3b on pathogens or other surfaces. The alternative pathway can also be initiated when certain antibodies block endogenous regulatory mechanisms, by IgA-containing immune complexes, or when expression of complement regulatory proteins is decreased. In addition, the alternative pathway is activated by a mechanism called the "amplification loop" when C3b that is deposited onto targets via the classical or lectin pathway then binds factor B. See e.g., H. J. Müller-Eberhard, 1988, *Ann. Rev. Biochem.* 57:321. For example, Holers and colleagues have shown that the alternative pathway is amplified at sites of local injury when inflammatory cells are recruited following initial complement activation. See e.g., Girardi et al., 2003, *J. Clin. Invest.* 112:1644. Dramatic complement amplification through the alternative pathway then occurs through a mechanism that involves either the additional generation of injured cells that fix complement, local synthesis of alternative pathway components, or more likely because infiltrating inflammatory cells that carry preformed C3, and properdin greatly increase activation specifically at that site.

Alternative pathway activation is initiated when circulating factor B binds to activated C3. This complex is then cleaved by circulating factor D to yield an enzymatically active fragment, C3bBb. C3bBb cleaves C3 generating C3b, which drives inflammation and also further amplifies the activation process, generating a positive feedback loop. Factor H is a key regulator (inhibitor) of the alternative complement pathway that competes with factor B for binding to C3b. Binding of C3b to Factor H also leads to degradation of C3b by factor I to the inactive form C3bi (also designated iC3b), thus exerting a further check on complement activation. Factor H regulates complement in the fluid phase, circulating at a plasma concentration of approximately 500 µg/ml, but its binding to cells is a regulated phenomenon enhanced by the presence of a negatively charged surface as well as fixed C3b, iC3b, or C3d. See e.g., Jozsi et al., 2004, *Histopathol.* 19:251-258.

Complement activation and complement-mediated inflammation are involved in the etiology and progression of numerous diseases. The down-regulation of complement activation has been shown to be effective in treating several diseases in animal models and in ex vivo studies, including, for example, systemic lupus erythematosus and glomerulonephritis (Y. Wang et al., 1996, *Proc. Nat'l Acad. Sci. USA* 93:8563-8568), rheumatoid arthritis (Y. Wang et al., 1995, *Proc. Nat'l Acad. Sci. USA* 92:8955-8959), cardiopulmonary bypass and hemodialysis (C. S. Rinder, 1995, *J. Clin. Invest.* 96:1564-1572), hyperacute rejection in organ transplantation (T. J. Kroshus et al., 1995, *Transplantation* 60:1194-1202), myocardial infarction (J. W. Homeister et al., 1993, *J. Immunol.* 150:1055-1064; H. F. Weisman et al., 1990, *Science* 249:146-151), ischemia/reperfusion injury (E. A. Amsterdam et al., 1995, *Am. J. Physiol.* 268:H448-H457), antibody-mediated allograft rejection, for example, in the kidneys (J. B. Colvin, 2007, *J. Am. Soc. Nephrol.* 18(4):1046-56), and adult respiratory distress syndrome (R. Rabinovici et al., 1992, *J. Immunol.* 149:1744-1750). Moreover, other inflammatory conditions and autoimmune/immune complex diseases are also closely associated with complement activation (B. P. Morgan. 1994, *Eur. J. Clin. Invest.* 24:219-228), including, but not limited to, thermal injury, severe asthma, anaphylactic shock, bowel inflammation, urticaria, angioedema, vasculitis, multiple sclerosis, myasthenia gravis, myocarditis, membranoproliferative glomerulonephritis, atypical hemolytic uremic syndrome, Sjögren's syndrome, renal and pulmonary ischemia/reperfusion, and other organ-specific inflammatory disorders.

A variety of disorders are associated with inflammation, however, so definitive diagnosis of complement-mediated inflammation typically requires confirmation via immunostaining or other in vitro analysis performed on tissue samples retrieved by biopsy. While biopsies are in many respects routine, they have their limitations and are not risk-free. Because commonly used needle or punch biopsies sample only a small portion of the target organ, there is a risk of sample error leading to an incorrect diagnosis. Furthermore, although biopsy is a generally safe procedure, major complications such as internal bleeding may occur in a significant number of cases.

In some cases, because of the difficulties in diagnosing disease or monitoring disease progression, for example, in patients with systemic lupus erythematosus or lupus nephritis, repeat renal biopsies are therefore frequently necessary to assess the response to therapy or to diagnose disease relapse. See e.g., S. Bajaj et al., 2000, *J. Rheumatol.* 27:2822-2826.

Although renal biopsy is generally a safe procedure, complications may occur in 6% or more of biopsies and intra-renal bleeding and hematuria are common. Patients requiring repeat biopsies are at concomitantly greater risk of complications. See e.g., W. L. Whittier et al., 2004, *J. Am. Soc. Nephrol.* 15:142-147; D. C. Mendelssohn et al., 1995, *Am. J. Kidney Dis.* 26:580-585. Thus, a non-invasive method of detecting or accurately assessing the presence, degree and/or extent of complement-mediated inflammation would be of significant value in diagnosing disease, formulating treatment strategies and monitoring their efficacy for many inflammatory diseases, including lupus nephritis.

The disclosures of all publications, patents, patent applications and published patent applications referred to herein are hereby incorporated herein by reference in their entirety.

BRIEF SUMMARY OF THE INVENTION

In one aspect, provided herein are methods of detecting complement-mediated inflammation in an individual comprising: (a) administering to the individual an effective amount a composition comprising an effective amount of CR2-targeted ultrasmall superparamagnetic iron oxide ("USPIO") nanoparticles or aggregates thereof; and (b) taking a magnetic resonance image of the individual. In certain embodiments, the CR2-targeted USPIO nanoparticles comprise a targeting moiety comprising an antibody or fragment thereof directed to C3 or a portion thereof, for example but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. In certain embodiments, the individual is a mammal. In certain embodiments, the mammal is a human, a mouse, or a rat. In certain embodiments, the composition is administered by injection. In certain embodiments, the injection is parenteral, intravenous, subcutaneous, or intramuscular.

In certain embodiments, the composition comprises an effective amount of CR2-targeted USPIO nanoparticle aggregates, and the USPIO nanoparticle aggregates are coated with dextran or encapsulated with phospholipid. In certain embodiments, the CR2-targeted USPIO nanoparticle aggregates are between about 50 nm and about 150 nm in diameter, and the USPIO nanoparticle aggregates are coated with dextran or encapsulated with phospholipid. In certain embodiments, the CR2-targeted USPIO nanoparticle aggregates are between about 65 nm and about 85 nm in diameter, and the USPIO nanoparticle aggregates are coated with dextran or encapsulated with phospholipid. In certain embodiments, the CR2-targeted USPIO nanoparticle aggregates are about 75 nm in diameter, and the USPIO nanoparticle aggregates are coated with dextran or encapsulated with phospholipid. In certain embodiments, the CR2-targeted USPIO nanoparticle aggregates are about 150 nm in diameter, and the USPIO nanoparticle aggregates are coated with dextran or encapsulated with phospholipid. In certain embodiments, the phospholipid is PEGylated. In certain embodiments, the PEGylated phospholipid is amine-functionalized. In certain embodiments, the PEGylated, amine-functionalized phospholipid is 1,2-distearoyl-sn-glycero-3-phosphoethanolamine-PEG2000.

In certain embodiments, the phospholipid-encapsulated CR2-targeted USPIO nanoparticle aggregates comprise a targeting moiety comprising an antibody or fragment thereof directed to C3 or a portion thereof, for example C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. In certain embodiments, the phospholipid-encapsulated CR2-targeted USPIO nanoparticle aggregates further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

In certain embodiments, the dextran-coated CR2-targeted USPIO nanoparticle aggregates further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

In any of the embodiments described herein, the complement-mediated inflammation is associated with tissue damage resulting from ischemia reperfusion injury, inflammatory disorders, transplant rejection, pregnancy-related diseases, adverse drug reactions, cancer and autoimmune or immune complex disorders. In any of the embodiments described herein, the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In any of the embodiments described herein, the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In any of the embodiments described herein, the transplant rejection is hyperacute xenograft rejection. In any of the embodiments described herein, the pregnancy-related disease is selected from the group consisting of recurrent fetal loss and pre-eclampsia. In any of the embodiments described herein, the adverse drug reaction is selected from the group consisting of drug allergy and IL-2 induced vascular leakage syndrome. In any of the embodiments described herein, the autoimmune or immune complex disorder is selected from the group consisting of myasthenia gravis, Alzheimer's disease, multiple sclerosis, rheumatoid arthritis, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndromes, Graves' disease, Guillain-Barré syndrome, Hashimoto's disease, idiopathic thrombocytopenic purpura, pemphigus, Sjögren's syndrome, Takayasu's arteritis, autoimmune glomerulonephritis, membranoproliferative glomerulonephritis type II, hemolytic uremic syndrome, and atypical hemolytic uremic syndrome. In any of the embodiments described herein, the autoimmune glomerulonephritis is selected from the group consisting of immunoglobulin A nephropathy and membranoproliferative glomerulonephritis type I.

Also provided herein are compositions for detecting complement-mediated inflammation in an individual, the compositions comprising an effective amount of CR2-targeted ultrasmall super paramagnetic iron oxide ("USPIO") nanoparticles or aggregates thereof. In certain embodiments, the individual is a mammal. In certain embodiments, the mammal is a human, mouse, or rat. In certain embodiments, the compositions comprise an effective amount of CR2-targeted USPIO nanoparticle aggregates, and the USPIO nanoparticle aggregates are coated with dextran or encapsulated with phospholipid. In certain embodiments, the CR2-targeted USPIO nanoparticle aggregates are between about 50 nm and about 150 nm in diameter, and the USPIO nanoparticle aggregates are coated with dextran or encapsulated with phospholipid. In certain embodiments, the CR2-targeted USPIO nanoparticle aggregates are between about 65 nm and about 85 nm in diameter, and the USPIO nanoparticle aggregates are coated with dextran or encapsulated with phospholipid. In certain embodiments, the CR2-targeted USPIO nanoparticle aggregates are about 75 nm in diameter, and the USPIO nanoparticle aggregates are coated with dextran or encapsulated with phospholipid. In certain embodiments, the CR2-targeted USPIO nanoparticle aggregates are about 150 nm in diameter, and the USPIO nanoparticle aggregates are coated with dextran or encapsulated with phospholipid. In certain embodiments, the phospholipid is PEGylated. In certain embodiments, the PEGylated phospholipid is amine-functionalized. In certain embodiments, the PEGylated, amine-functionalized phospholipid is 1,2-distearoyl-sn-glycero-3-phosphoethanolamine-PEG2000.

In certain embodiments, the phospholipid-encapsulated CR2-targeted USPIO nanoparticle aggregates further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

In certain embodiments, the dextran-coated CR2-targeted USPIO nanoparticles further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

In certain embodiments, the dextran-coated CR2-targeted USPIO nanoparticles further comprise a targeting moiety comprising an antibody or fragment thereof directed to C3 or a portion thereof, for example but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d.

In another aspect, provided herein are compositions for detecting complement-mediated inflammation in an individual, the composition comprising an effective amount of CR2-targeted ultrasmall superparamagnetic iron oxide ("USPIO") nanoparticles or aggregates thereof, wherein the USPIO nanoparticles or aggregates thereof are coated with dextran or encapsulated with phospholipid. In some embodiments, the composition comprises an antibody or fragment thereof directed to C3 or a portion thereof, for example but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. In some embodiments, the compositions further comprise a targeting moiety comprising a fusion protein comprising an antibody or fragment thereof fused to CR2 or a biologically-active fragment thereof. In certain embodiments, the individual is a mammal. In certain embodiments, the mammal is a human, mouse, or rat. In certain embodiments, the composition comprises an effective amount of CR2-targeted USPIO nanoparticle aggregates. In certain embodiments, the CR2-targeted USPIO nanoparticle aggregates are between about 50 nm and about 150 nm in diameter. In certain embodiments, the CR2-targeted USPIO nanoparticle aggregates are between about 65 nm and about 85 nm in diameter. In certain embodiments, the CR2-targeted USPIO nanoparticle aggregates are about 75 nm in diameter. In certain embodiments, the CR2-targeted USPIO nanoparticle aggregates are about 150 nm in diameter.

In certain embodiments, the phospholipid is PEGylated. In certain embodiments, the PEGylated phospholipid is amine-functionalized. In certain embodiments, the PEGylated, amine-functionalized phospholipid is 1,2-distearoyl-sn-glycero-3-phosphoethanolamine-PEG2000. In certain embodiments, the CR2-targeted USPIO nanoparticle aggregates are phospholipid-encapsulated and further comprise a targeting moiety comprising a fusion protein comprising an antibody or fragment thereof fused to CR2 or a biologically-active fragment thereof. In certain embodiments, the CR2-targeted USPIO nanoparticles are dextran-coated and further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

In another aspect, provided herein is the use of any of the compositions as described herein in connection with the methods as described herein, unless otherwise noted or as is clear from the specific context. Any of the compositions as described herein may also be used in the preparation of a medicament for use in the methods as described herein.

In another aspect, provided herein are articles of manufacture or kits containing pharmaceutical compositions comprising an effective amount of any of the bacterial-, CR2-, or C4-targeted USPIO nanoparticles or aggregates thereof described herein, and instructions for their use in the non-invasive imaging methods described herein. Thus, in certain embodiments, the article of manufacture comprises instructions for the use of pharmaceutical compositions comprising an effective amount of bacterial-, CR2-, or C4-targeted USPIO nanoparticles or aggregates thereof in any of the methods of detecting complement-mediated inflammation in an individual as described herein. In certain embodiments, the composition comprises an effective amount of CR2-targeted ultrasmall superparamagnetic iron oxide ("USPIO") nanoparticles or aggregates thereof, wherein the USPIO nanoparticles or aggregates thereof are coated with dextran or encapsulated with phospholipid and further comprise a targeting moiety comprising a fusion protein comprising an antibody or fragment thereof fused to CR2 or a biologically-active fragment thereof. In certain embodiments, the USPIO nanoparticles or aggregates thereof are coated with dextran or encapsulated with phospholipid and further comprise an antibody or fragment thereof directed to C3 or a portion thereof, for example but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. In certain embodiments, the individual is a mammal. In certain embodiments, the mammal is a human, mouse or rat. In certain embodiments, the composition comprises an effective amount of CR2-targeted USPIO nanoparticle aggregates. In certain embodiments, the CR2-targeted USPIO nanoparticle aggregates are between about 50 nm and about 150 nm in diameter. In certain embodiments, the CR2-targeted USPIO nanoparticle aggregates are between about 65 nm and about 85 nm in diameter. In certain embodiments, the CR2-targeted USPIO nanoparticle aggregates are about 75 nm in diameter. In certain embodiments, the CR2-targeted USPIO nanoparticle aggregates are about 150 nm in diameter.

In certain embodiments, the phospholipid is PEGylated. In certain embodiments, the PEGylated phospholipid is amine-functionalized. In certain embodiments, the PEGylated, amine-functionalized phospholipid is 1,2-distearoyl-sn-glycero-3-phosphoethanolamine-PEG2000. In certain embodiments, the CR2-targeted USPIO nanoparticle aggregates are phospholipid-encapsulated and further comprise a targeting moiety comprising a fusion protein comprising an antibody or fragment thereof fused to CR2 or a biologically-active fragment thereof. In certain embodiments, the CR2-targeted USPIO nanoparticles are dextran-coated and further comprise a targeting moiety comprising a fusion protein comprising an antibody or fragment thereof fused to CR2 or a biologically-active fragment thereof. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$. In certain embodiments, the targeting moiety comprises a fusion protein comprising an antibody fragment fused to a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the fusion protein comprises the extracellular domain of CR2 fused to the Fc-domain of mouse immunoglobulin isotype $G_1$ ($IgG_1$), SCRs 1 to 8 of CR2 fused to the Fc-domain of mouse $IgG_1$, or SCRs 1 and 2 of CR2 fused to the Fc-domain of mouse $IgG_1$. In certain embodiments, the fusion protein comprises SCRs 1 and 2 of CR2 fused to the Fc-domain of mouse $IgG_1$.

BRIEF DESCRIPTION OF THE DRAWINGS

FIG. 1A shows a transmission electron micrograph demonstrating the appearance of the as-synthesized USPIO nanoparticles. FIG. 1B shows the size distribution by volume percentage of the phospholipid-encapsulated USPIO nanoparticle aggregates measured by dynamic light scattering. The distribution peak is 74.52 nm with a polydispersity index of 0.034.

FIG. 2A shows fluorescence-activated cell sorting (FACS) analysis using a monoclonal antibody to the C3d binding region of CR2 confirming successful conjugation of the protein to the nanoparticle surface (solid line). No staining was seen on unconjugated particles (dashed line). FIG. 2B shows FACS analysis demonstrating that incubation of CHO cells with 10% mouse serum (solid line) opsonized the cells with C3, whereas no C3 was detectable on unmanipulated cells (dashed line). FIG. 2C shows CR2-targeted USPIO nanoparticles bound to opsonized CHO cells (solid line) compared to binding to untargeted USPIO nanoparticles (striped curve) which was similar to isotype staining of CHO cells (dotted line).

FIGS. 3E-I also show immunofluorescence microscopy staining for complement protein C3 in 16-week old MRL/lpr mice demonstrating deposition of C3 in glomeruli (FIG. 3D), in tubules of the outer medulla (FIG. 3E), and in the inner medulla (FIG. 3F). Sparse deposits of C3 were present in the glomeruli (FIG. 3G), outer medulla (FIG. 3H) and inner medulla (FIG. 3I) of wild-type mice. Original magnification ×400.

FIG. 4A shows proton density (PD)-weighted rapid acquisition with relaxation enhancement (RARE) images, and FIG. 4B shows $T_2$-weighted multiple slice multiple echo (MSME) images demonstrating systemic pathology in the MRL/lpr mice, including significant lymphadenopathy (arrows) and enlarged kidneys (arrowheads). At baseline, the kidneys of MRL/lpr mice display higher $T_2$-weighted signal intensity than in wild-type controls. See also Table 1.

DETAILED DESCRIPTION OF THE INVENTION

Figure 1A:
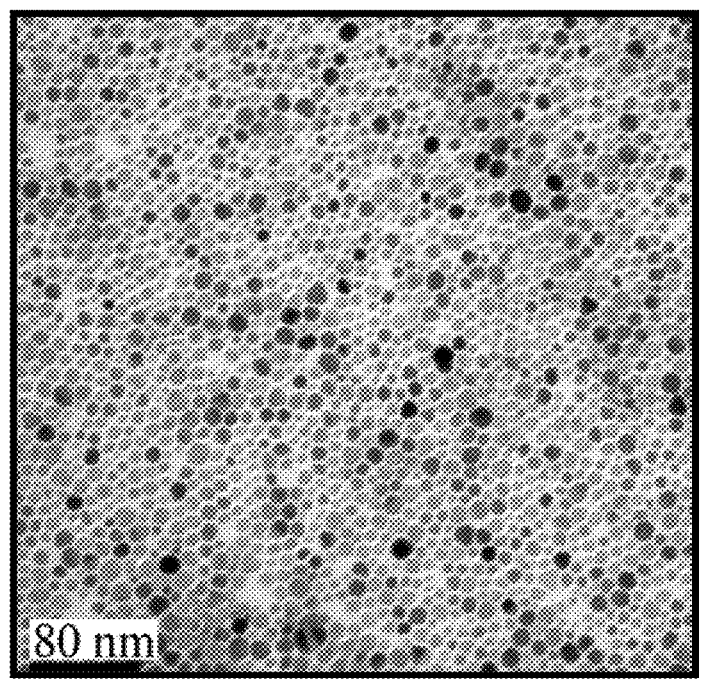
FIGS. 1A-1B depict the appearance and size distribution of ultrasmall superparamagnetic ("USPIO") nanoparticles generated as described in the Materials and Methods section of Example 1.

The complement system is activated in a number of inflammatory and autoimmune diseases. See e.g., M. J. Walport, 2001, *N. Engl. J. Med.* 344:1058-1066; M. J. Walport, 2001, *N. Engl. J. Med.* 344:1140-1144. Complement activation is central to the pathogenesis of many diseases, contributing to tissue injury in numerous inflammatory and autoimmune disorders. Moreover, products of complement activation also serve as robust markers of ongoing tissue inflammation, since activation of the complement system leads to rapid deposition of C3b on cell surfaces. Classical pathway activation by immunoglobulin, for example, can deposit more than 240 molecules of C3b to the surface for every molecule of C1q engaged by the antibody. See e.g., M. W. Ollert et al., 1994, *J. Immunol.* 153:2213-2221. Other markers of classical pathway activation include cell-bound C4b, iC4d, and C4d, indirect markers of an antibody response. The complement protein C4 is also cleaved during classical pathway activation. Like C3, C4 undergoes several proteolytic steps generating fragments (C4b, iC4b, and C4d) that remain covalently bound to tissue. The detection of C4 fragments such as C4d demonstrates that the complement activation involves the classical pathway. This is useful for diagnosing some antibody-mediated diseases, such as antibody mediated transplant rejection. Immuno-staining for deposited C3 and C4 is central to the diagnosis of autoimmune disease, and is routinely performed on kidney biopsy samples when autoimmune disease is suspected. For example, the presence of glomerular C3 deposits helps support the diagnosis of glomerulonephritis. Thus, identification of C3 and/or C4 deposits is integral to the diagnosis and assessment of autoimmune and inflammatory diseases.

Complement protein C3 is a zymogen. Intact C3 circulates at high concentrations (1-2 mg/ml). See e.g., M. Janzi et al., 2005, *Mol. Cell. Proteomics* 4(12):1942-1947. During complement activation, whole C3 is cleaved to form C3b which becomes covalently bound to target surfaces. Endogenous complement regulatory proteins inactivate tissue-bound C3b to form iC3b and eventually the 35 kilodalton ("kD") C3d fragment. The C3d fragment remains fixed to tissues and serves as a durable marker of complement-mediated inflammation. See e.g., I. Leivo et al., 1986, *J. Cell. Biol.* 103:1091-1100.

CR2 (CD21) is a ~145 kD transmembrane protein expressed on B cells, T cells, and dendritic cells. See e.g., J. Hannan et al., 2002, *Biochem. Soc. Trans.* 30:983-989; K. A. Young et al., 2007, *J. Biol. Chem.* 282(50):36614-36625. CR2 protein does not bind intact C3 protein, but binds its breakdown products, including the C3b, iC3b, and C3d cleavage fragments, via a binding site located within the first two amino-terminal short consensus repeats ("SCRs 1 and 2") of the CR2 protein. Consequently, the SCR1-2 domain of CR2 discriminates between cleaved (i.e., activated) forms of C3 and intact circulating C3. As a targeting group, SCRs 1 and 2 of CR2 are therefore able to discriminate between circulating C3 and the C3 fragments generated during complement activation. Although the affinity of CR2 for C3d is only 620-658 nM (J. Hannan et al., 2002, *Biochem. Soc. Trans.* 30:983-989; J. M. Guthridge et al., 2001, *Biochem.* 40:5931-5941), the avidity of CR2 for clustered C3d makes it an effective method of targeting molecules to sites of complement activation.

As shown in the Examples, in the murine MRL/lpr model of lupus nephritis, injection of mice with the CR2-targeted USPIO nanoparticle aggregates caused a significant reduction in $T_2$-weighted MRI signal in nephritic kidneys, while injection of the CR2-targeted USPIO nanoparticle aggregates into healthy control mice did not change the MRI signal of the kidneys. Moreover, injection of untargeted USPIO nanoparticle aggregates did not alter the $T_2$-weighted signal of the kidneys in MRL/lpr mice.

Thus, CR2-targeted nanoparticle aggregates can be used as a contrast agent specifically targeted to sites of complement activation, and provide a novel reagent useful in non-invasive methods of detecting active inflammation in immune-complex glomerulonephritis, lupus nephritis, cancer and other diseases characterized by complement-mediated inflammation. Furthermore, the methods described herein provide a more comprehensive assessment of disease activity than that afforded by biopsy. Magnetic resonance images obtained after injection with CR2-conjugated USPIO nanoparticle aggregates can specifically detect complement activation throughout both kidneys and distinguish renal C3 activation from that occurring at extra-renal locations. In patients known to have lupus nephritis whose clinical parameters have changed, this technique enables the clinician to distinguish active inflammation from increases in proteinuria or decreases in renal function caused by scarring. Currently distinguishing active inflammation from damage caused by scarring requires a biopsy. Moreover, non-invasive assessment of disease etiology and progression by the methods described herein can offer important insight into the rate at which active inflammatory disease responds to therapy and resolves.

Definitions

General reference to "the composition" or "compositions" includes and is applicable to compositions of the invention.

As used herein, the singular form of the articles "a", "an", and "the" includes plural references unless indicated otherwise. For example, "a" biologically-active CR2 fragment includes one or more biologically-active CR2 fragments.

Reference to "about" a value or parameter herein includes (and describes) embodiments that are directed to that value or parameter per se. For example, description referring to "about X" includes description of "X."

It is understood that aspects and embodiments of the invention described herein include "consisting" and/or "consisting essentially of" aspects and embodiments.

As used herein, the term "individual" refers to a vertebrate, preferably a mammal, more preferably a human. Mammals include, but are not limited to, farm animals, sport animals, pets, primates, mice and rats. In some embodiments, the individual is human. In some embodiments, the individual is an individual other than a human. In some embodiments, the individual is an animal model for the study of a disease in which the alternative complement pathway is implicated. Individuals amenable to non-invasive imaging via the methods described herein include those who are suffering from a disease characterized by complement-mediated inflammation, and those who are suffering from a disease characterized by alternative complement-mediated inflammation.

As used herein, the term "cancer" refers to all types of cancer, neoplasm or malignant tumors found in mammals, including leukemia, carcinomas and sarcomas. Exemplary cancers include, but are not limited to, cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

Provided herein are compositions (such as pharmaceutical compositions) comprising CR2-targeted nanoparticles or aggregates thereof and non-invasive methods of detecting complement-mediated inflammation using such compositions. The CR2-targeting portion is responsible for delivering the nanoparticles to the sites of complement activation and complement-mediated inflammation, and the nanoparticle portion is responsible for enhancing contrast in a non-invasive image (such as a magnetic resonance image) of the site of inflammation.

Targeted Nanoparticle Compositions for Imaging Applications

Delivery of ultrasmall superparamagnetic iron oxide ("USPIO") nanoparticles, USPIO nanoparticle aggregates, superparamagnetic iron oxide ("SPIO") nanoparticles, SPIO nanoparticle aggregates or other nanoparticle contrast agents to the sites of active inflammation via CR2-targeting to sites of complement activation permits non-invasive magnetic resonance imaging of such inflammation, enabling the specific detection of complement activation throughout the body, and distinguishing complement-mediated inflammation from other types of inflammation. Accordingly, in one aspect, the invention provides compositions comprising CR2-targeted nanoparticle contrast agents for non-invasive medical or diagnostic imaging applications. In certain embodiments, the CR2-targeted nanoparticle contrast agent compositions comprise USPIO nanoparticles or aggregates thereof. In certain embodiments, the CR2-targeted nanoparticle contrast agent compositions comprise CR2-targeted liposomes or other CR2-targeted delivery vehicles containing Gadolinium chelate ("Gd-chelate") molecules.

At least two physicochemical characteristics of ultrasmall superparamagnetic iron oxide ("USPIO") nanoparticles or aggregates thereof vary with the size of the individual nanoparticles or nanoparticle aggregates. First, the ability of USPIO nanoparticle preparations to enhance contrast in MRI imaging and the degree of contrast enhancement both vary with nanoparticle diameter, because the magnetic moment of individual USPIO nanoparticles also varies with particle diameter. Iron oxide nanoparticles with diameters up to approximately 15 nm remain superparamagnetic, but larger iron oxide nanoparticles lose their superparamagnetic properties. Thus, there is an upper limit to the diameter of USPIO nanoparticles suitable for use as MRI contrast reagents. This limitation can be overcome by use of multiparticle aggregates of smaller individual USPIO nanoparticles. Such USPIO nanoparticle aggregates effectively enhance MRI contrast because the magnetic moments of the individual nanoparticles within each nanoparticle aggregate are additive. Unlike individual iron oxide nanoparticles, aggregates of ultrasmall super paramagnetic iron oxide nanoparticles do not lose their paramagnetic properties with increased size.

Second, the in vivo half-life (e.g., circulating plasma or blood half-life and tissue half-life) and biodistribution of USPIO nanoparticles or aggregates thereof varies with nanoparticle or aggregate size. For example, USPIO nanoparticles ~10 nm or less in diameter have a circulating blood half-life of ~81 minutes (R. Weissleder et al., 1990, *Radiol.* 175(2): 489-493), USPIO nanoparticles ~50 nm in diameter have a circulating half-life of ~30 minutes (D. Pouliquen et al., 1991, *Magnet. Resonance Imag.* 9(3):275-283), USPIO nanoparticles ~150 nm in diameter are thought to have a circulating half-life of less than ~30 minutes, and USPIO nanoparticles ~80 nm in diameter have a tissue half-life on the order of one to several days (e.g., 1, 2, 3, 4, 5, 6, 7, 8, 9, or more days) and a whole body half-life of ~45 days (R. Weissleder et al., 1989, *Am. J. Roentgenol.* 152(1):167-173). Effective targeted MRI contrast-enhancing reagents must circulate in the vasculature long enough to recognize and bind the desired target (e.g., renal deposits of C3 breakdown products) while still being cleared quickly enough to minimize any potential toxicity. Optimal USPIO nanoparticle or nanoparticle aggregate sizes for generating clinically useful magnetic resonance images vary depending on the organ (e.g., the kidney), tissue, and/or physiological phenomenon (e.g., complement-mediated inflammation) to be imaged.

The circulating half-life of USPIO nanoparticles or nanoparticle aggregates can also be altered (i.e., reduced or extended) by coating them with different materials. For instance, USPIO nanoparticles or nanoparticle aggregates can be coated with natural or synthetic polymers, surfactants, or phospholipids, among other materials, any of which may be modified or derivatized to permit attachment of targeting groups, either directly or indirectly via different types of linkers, including peptides, polypeptides, proteins, or other chemical groups. In some cases, the coatings may be further modified to incorporate synthetic polymers, natural polymers or other molecules (e.g., polyvinylpyrrolidone ("PVP"), poly (lactic-co-glycolic acid) ("PLGA"), polyethylene glycol ("PEG"), polyvinyl alcohol ("PVA"), polyacrylic acid, and the like) suitable for stabilizing the aggregates or minimizing their susceptibility to extravasation, opsonization, phagocytosis, endocytosis or other modes of physiological clearance. As with USPIO nanoparticle or nanoparticle aggregate size, the particular coating, modification or derivatization suitable for targeting the nanoparticles or nanoparticle aggregates to a desired organ (e.g., the kidney), tissue, and/or physiological phenomenon (e.g., complement-mediated inflammation) may be determined empirically. The present inventors have identified an optimal USPIO nanoparticle aggregate size range and coating type suitable for production of stable targeted USPIO nanoparticle aggregates with a circulating half-life long enough that the aggregates reach their targets, permitting detection of complement-mediated inflammation in particular tissues, while not being cleared so quickly that they cannot find and bind to their targets.

In certain embodiments, the USPIO nanoparticles or aggregates thereof are between about 1 nm and about 1000 nm in diameter. In certain embodiments, the USPIO nanoparticles or aggregates thereof are between about 5 nm and about 500 nm in diameter. In certain embodiments, the USPIO nanoparticles or aggregates thereof are between about 10 nm and about 100 nm in diameter. In certain embodiments, the USPIO nanoparticles or aggregates thereof are between about 50 nm and about 150 nm in diameter. In certain embodiments, the USPIO nanoparticles or aggregates thereof are between about 65 nm and about 85 nm in diameter. In certain embodiments, the USPIO nanoparticles or aggregates thereof are about 75 nm in diameter. In certain embodiments, the USPIO nanoparticles or aggregates thereof are about 150 nm in diameter. In certain embodiments, the USPIO nanoparticles or aggregates thereof are between about 1 nm and about 1000 nm in diameter and phospholipid-encapsulated. In certain embodiments, the USPIO nanoparticles or aggregates thereof are between about 5 nm and about 500 nm in diameter and phospholipid-encapsulated. In certain embodiments, the USPIO nanoparticles or aggregates thereof are between about 10 nm and about 100 nm in diameter and phospholipid-encapsulated. In certain embodiments, the USPIO nanoparticles or aggregates thereof are between about 50 nm and about 150 nm in diameter and phospholipid-encapsulated. In certain embodiments, the USPIO nanoparticles or aggregates thereof are between about 65 nm and about 85 nm in diameter and phospholipid-encapsulated. In certain embodiments, the USPIO nanoparticles or aggregates thereof are about 75 nm in diameter and phospholipid-encapsulated. In certain embodiments, the USPIO nanoparticles or aggregates thereof are about 150 nm in diameter and phospholipid-encapsulated. In any of the embodiments described herein, the phospholipid comprises 1,2-distearoyl-sn-glycero-3-phosphoethanolamine ("DSPE"). In any of the embodiments described herein, the phospholipid is PEGylated. The term "PEGylated" refers in the customary sense to conjugation with polyethylene glycol (PEG). In certain embodiments described herein, the PEGylated phospholipid further comprises a functional group suitable for cross-linking with a CR2- or bacterial-targeting group. In certain embodiments described herein, the PEGylated phospholipid further comprises a functional group suitable for cross-linking an antibody directed to C3 or fragment thereof, including but not limited to C3b, iC3b, C3dg, C3d and the like. In certain embodiments described herein, the functional group is an amine. In any of the embodiments described herein, the functional group is maleimide. In any of the embodiments described herein, the functional group is a thiol. In any of the embodiments described herein, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In any of the embodiments described herein, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In any of the embodiments described herein, the phospholipid comprises DSPE-PEG2000. In any of the embodiments described herein, the phospholipid comprises amine-functionalized DSPE-PEG2000. In any of the embodiments described herein, the phospholipid comprises amine-functionalized DSPE-PEG2000. In any of the embodiments described herein, the phospholipid comprises maleimide-functionalized DSPE-PEG2000. In any of the embodiments described herein, the USPIO nanoparticle aggregates are CR2-targeted, phospholipid-encapsulated, have a circulating plasma half-life of between about 20 minutes and about 40 minutes, and have a tissue half life of one to several days (e.g., 1, 2, 3, 4, 5, 6, 7, 8, 9, or more days).

In certain embodiments, the USPIO nanoparticles or aggregates thereof are between about 1 nm and about 1000 nm in diameter and coated with dextran. In certain embodiments, the USPIO nanoparticles or aggregates thereof are between about 5 nm and about 500 nm in diameter and coated with dextran. In certain embodiments, the USPIO nanoparticles or aggregates thereof are between about 10 nm and about 100 nm in diameter and coated with dextran. In certain embodiments, the USPIO nanoparticles or aggregates thereof are between about 50 nm and about 150 nm in diameter and coated with dextran. In certain embodiments, the USPIO nanoparticles or aggregates thereof are between about 65 nm and about 85 nm in diameter and coated with dextran. In certain embodiments, the USPIO nanoparticles or aggregates thereof are about 75 nm in diameter and coated with dextran. In certain embodiments, the USPIO nanoparticles or aggregates thereof are about 150 nm in diameter and coated with dextran.

As used herein, the terms "CR2-targeting group," "CR2-targeted group" and the like refer to a chemical moiety such as a peptide, polypeptide, or protein, attached to a superparamagnetic nanoparticle or aggregates thereof, or to the coating of a superparamagnetic nanoparticle or aggregates thereof that selectively binds to or specifically binds to another molecule of interest, such as, for example, a cell-bound breakdown product of complement protein C3 that serves as a durable marker of complement-mediated inflammation, such as, for example, C3b (SEQ ID NO:13), iC3b (SEQ ID NO:12), C3dg (SEQ ID NO:11), and C3d (SEQ ID NO:10). Exemplary targeting groups may be, for example but not limited to, a full-length CR2 protein or biologically-active fragment thereof. In some embodiments, the CR2-targeting group is an antibody directed to C3 or a portion thereof, for example but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. Accordingly, in some embodiments, the CR2-targeted ultrasmall superparamagnetic iron oxide nanoparticles contemplated herein comprise an antibody or fragment thereof directed to C3 or a portion thereof, for example but not limited to C3b, iC3b, C3dg, C3d and the like. In some embodiments, the antibody or antibody fragment is a polyclonal antibody. In some embodiments, the antibody or antibody fragment is a monoclonal antibody. In some embodiments, the antibody or antibody fragment is covalently linked to the nanoparticle. In other embodiments, the antibody or antibody fragment is non-covalently linked (e.g. via biotin-streptavidin functional groups or equivalents thereof).

As used herein, the term "bacterial-targeting group" refers to a chemical moiety such as a peptide, polypeptide, or protein derived from a bacterial source, attached to a superparamagnetic nanoparticle or aggregate thereof or to the coating of a superparamagnetic nanoparticle or aggregate thereof that selectively binds to or specifically binds to another molecule of interest such as, for example, a cell-bound breakdown product of complement protein C3 that serves as a durable marker of complement-mediated inflammation such as, for example, C3b (SEQ ID NO:13), iC3b (SEQ ID NO:12), C3dg (SEQ ID NO:11), and C3d (SEQ ID NO:10), or a cell-bound breakdown product of complement protein C4 that serves as a marker of an antibody response such as, for example, C4d (SEQ ID NO:27). Exemplary bacterial targeting groups may be, for example, full-length *Staphylococcus aureus* immune subversion protein or biologically-active fragments thereof, or any other bacterium-derived protein that binds to cell-bound breakdown products of complement protein C3, such as, for example, C3b (SEQ ID NO:13), iC3b (SEQ ID NO:12), C3dg (SEQ ID NO:11), and C3d (SEQ ID NO:10).

*S. aureus* is a common commensal bacterium found in humans that can cause illnesses ranging from superficial skin infections to serious invasive infections such as septic arthritis, osteomyelitis, and endocarditis. See e.g., A. Upadhyay et al., 2008, *J. Biol. Chem.* 283(32):22113-22120. The broad spectrum of diseases caused by *S. aureus* reflects the bacterium's ability to circumvent various components of the immune system, including the complement cascade. The immune subversion protein (Sbi) is a secreted 436-amino acid protein (SEQ ID NO:20) found in many *S. aureus* strains that comprises four small N-terminal domains extending up to amino acid residue 266, followed by eight copies of a PXXXX repeat motif (where "X" specifies any naturally-occurring amino acid) with a high concentration of glutamine, lysine, aspartate, valine, and isoleucine, followed by a C-terminal tyrosine-rich domain of 130-amino acids. The first two N-terminal domains of Sbi (Sbi-I and Sbi-II) specifically or selectively bind to IgG, while the second two N-terminal domains (Sbi-III and Sbi-IV) specifically or selectively bind to proteolytic fragments of complement protein C3, including C3dg and C3a. Id. Thus, biologically-active Sbi fragments comprising Sbi-I-II-III-IV (amino acids 28-266; SEQ ID NO:21) and Sbi-III-IV (amino acids 150-266; SEQ ID NO:22) bind proteolytic fragments of complement protein C3, and are useful for targeted delivery of superparamagnetic nanoparticles to sites of complement-mediated inflammation.

As used herein, the term "C4-targeting group" refers to a chemical moiety such as a peptide, polypeptide, or protein, attached to a superparamagnetic nanoparticle or aggregates thereof, or to the coating of a superparamagnetic nanoparticle or aggregates thereof that selectively binds to or specifically binds to another molecule of interest, such as, for example, a cell-bound breakdown product of complement protein C4 that serves as a durable marker of antibody-mediated inflammation, such as, for example, C4b (SEQ ID NO:26), iC4b (SEQ ID NO:25), and C4d (SEQ ID NO:27). Exemplary targeting groups may be, for example, a full-length CR1 protein (SEQ ID NO:28) or biologically-active fragment thereof, or a full-length C4b-binding protein (C4 bp) (SEQ ID NOS:29 and 30) or biologically-active fragment thereof.

As used herein, the term "complement receptor 1," "CR1," or "CD35" refers to a human gene encoding a protein of 2039 amino acids, with a predicted molecular weight of 220 kilodaltons ("kD"), including homologues and fragments thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60 to 99 percent. The 30 SCR domains are further grouped into four longer regions termed long homologous repeats ("LHRs"), each encoding approximately 45 kD segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1 to 4 comprising amino acids 42-295, a C3b-binding site with lower affinity for C4b in SCRs 8 to 11 comprising amino acids 490-745, a C3b-binding site with lower affinity for C4b in SCRs 15-18 comprising amino acids 940-1196, and a C1q-binding site in SCRs 22-28 comprising amino acids 1394-1842.

SEQ ID NO:28 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain. In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCR5, amino acids 356-418 correspond to SCR6, amino acids 419-489 correspond to SCR7, amino acids 491-551 correspond to SCR8, amino acids 552-613 correspond to SCR9, amino acids 614-684 correspond to SCR10, amino acids 686-745 correspond to SCR11, amino acids 745-805 correspond to SCR12, amino acids 806-868 correspond to SCR13, amino acids 869-939 correspond to SCR14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically-active fragments thereof encompasses all species and strain variations. As used herein, the term "biologically-active" fragment of CR1 protein refers to refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein, and retaining the ability to bind C4, C4b, iC4b, or C4d.

As used herein, the term "C4b-binding protein, alpha chain," "C4 bp-alpha," or "C4 bp-α" refers to a human gene encoding a protein of 597 amino acids, with a predicted molecular weight of 67 kilodaltons ("kD"), including homologues thereof. SEQ ID NO:29 represents the full-length human C4 bp-alpha amino acid sequence (see, e.g., UniProtKB/Swiss-Prot. Accession No. P04003). Amino acids 1-48 correspond to the signal peptide, amino acids 49-597 correspond to the mature protein, comprising amino acids 49-110, corresponding to SCR 1, amino acids 111-172, corresponding to SCR2, amino acids 173-236, corresponding to SCR3, amino acids 237-296, corresponding to SCR4, amino acids 297-362, corresponding to SCR5, amino acids 363-424, corresponding to SCR5, amino acids 425-482, corresponding to SCR7, and amino acids 483-540, corresponding to SCR8. As used herein, the term "C4b-binding protein, beta chain," "C4 bp-beta," or "C4 bp-β" refers to a human gene encoding a protein of 252 amino acids, with a predicted molecular weight of 28 kilodaltons ("kD"), including homologues thereof. SEQ ID NO:30 represents the full-length human C4 bp-beta amino acid sequence (see, e.g., UniProtKB/Swiss-Prot. Accession No. P20851). Amino acids 1-17 correspond to the signal peptide, amino acids 18-252 correspond to the mature protein, comprising amino acids 21-78, corresponding to SCR 1, amino acids 79-136, corresponding to SCR2, and amino acids 137-193, corresponding to SCR3. As used herein, the term "C4-binding protein" or "C4 bp" refers to one of three disulfide-linked complexes comprising one or more C4 bp-alpha and/or one or more C4 bp-beta polypeptides: a 570 kD complex of seven C4 bp-alpha polypeptides and one C4 bp-beta polypeptide, a 530 kD complex of seven C4 bp-alpha polypeptides, or a 500 kD complex of six C4 bp-alpha polypeptides and one C4 bp-beta polypeptide. Each C4b polypeptide comprises a binding site for C4b.

As used herein, the term "biologically-active" fragment of C4 bp-alpha protein refers to refers to any soluble fragment of C4 bp-alpha, including fragments comprising, consisting essentially of or consisting of 1, 2, 3, 4, 5, 6, 7, or 8 SCR domains, including any fragments of the full-length C4 bp-alpha protein having some or all the complement inhibitory activity of the full-length C4 bp-alpha protein. As used herein, the term "biologically-active" fragment of C4 bp-beta protein refers to refers to any soluble fragment of C4 bp-beta, including fragments comprising, consisting essentially of or consisting of 1, 2, or 3 SCR domains, including any fragments of the full-length C4 bp-beta protein having some or all the complement inhibitory activity of the full-length C4 bp-beta protein. As used herein, the term "biologically active" fragment of C4 bp refers to any soluble fragment of either C4 bp-alpha or C4 bp-beta having some or all of the complement inhibitory activity of the full-length C4 bp-alpha or C4 bp-beta protein and retaining the ability to bind C4, C4b, iC4b, or C4d.

In certain embodiments, the phospholipid-encapsulated CR2-targeted USPIO nanoparticles or aggregates thereof are between about 1 nm and about 1000 nm in diameter and comprise a CR2-targeting group attached to the phospholipid coating. In certain embodiments, the phospholipid-encapsulated CR2-targeted USPIO nanoparticles or aggregates thereof are between about 5 nm and about 500 nm in diameter and comprise a CR2-targeting group attached to the phospholipid coating. In certain embodiments, the phospholipid-encapsulated CR2-targeted USPIO nanoparticles or aggregates thereof are between about 10 nm and about 100 nm in diameter and comprise a CR2-targeting group attached to the phospholipid coating. In certain embodiments, the phospholipid-encapsulated CR2-targeted USPIO nanoparticles or aggregates thereof are between about 50 nm and about 150 nm in diameter and comprise a CR2-targeting group attached to the phospholipid coating. In certain embodiments, the phospholipid-encapsulated CR2-targeted USPIO nanoparticles or aggregates thereof are between about 65 nm and about 85 nm in diameter and comprise a CR2-targeting group attached to the phospholipid coating. In certain embodiments, the phospholipid-encapsulated CR2-targeted USPIO nanoparticles or aggregates thereof are about 75 nm in diameter and comprise a CR2-targeting group attached to the phospholipid coating. In certain embodiments, the phospholipid-encapsulated CR2-targeted USPIO nanoparticles or aggregates thereof are about 150 nm in diameter and comprise a CR2-targeting group attached to the phospholipid coating. In any of the embodiments described herein, the phospholipid comprises 1,2-distearoyl-sn-glycero-3-phosphoethanolamine ("DSPE"). In any of the embodiments described herein, the phospholipid is PEGylated. In any of the embodiments described herein, the PEGylated phospholipid further comprises a functional group suitable for cross-linking with a CR2-targeting group. In any of the embodiments described herein, the functional group is an amine. In any of the embodiments described herein, the functional group is maleimide. In any of the embodiments described herein, the functional group is a thiol. In any of the embodiments described herein, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In any of the embodiments described herein, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In any of the embodiments described herein, the phospholipid comprises DSPE-PEG2000. In any of the embodiments described herein, the phospholipid comprises amine-functionalized DSPE-PEG2000. In any of the embodiments described herein, the phospholipid comprises amine-functionalized DSPE-PEG2000. In any of the embodiments described herein, the phospholipid comprises maleimide-functionalized DSPE-PEG2000.

In certain embodiments, the CR2-targeted USPIO nanoparticle aggregates are between about 50 nm and about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the CR2-targeted USPIO nanoparticle aggregates are between about 65 nm and about 85 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the CR2-targeted USPIO nanoparticle aggregates are about 75 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the CR2-targeted USPIO nanoparticle aggregates are about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In any of the embodiments described herein, the CR2-targeted USPIO nanoparticle aggregates have a circulating plasma half-life of between about 20 minutes and about 40 minutes, and have a tissue half life of one to several days (e.g., 1, 2, 3, 4, 5, 6, 7, 8, 9, or more days).

In certain embodiments, the dextran-coated CR2-targeted USPIO nanoparticles or aggregates thereof are between about 1 nm and about 1000 nm in diameter and comprise a CR2-targeting group attached to the dextran coating. In certain embodiments, the dextran-coated CR2-targeted USPIO nanoparticles or aggregates thereof are between about 5 nm and about 500 nm in diameter and comprise a CR2-targeting group attached to the dextran coating. In certain embodiments, the dextran-coated CR2-targeted USPIO nanoparticles or aggregates thereof are between about 10 nm and about 100 nm in diameter and comprise a CR2-targeting group attached to the dextran coating. In certain embodiments, the dextran-coated CR2-targeted USPIO nanoparticles or aggregates thereof are between about 50 nm and about 150 nm in diameter and comprise a CR2-targeting group attached to the dextran coating. In certain embodiments, the dextran-coated CR2-targeted USPIO nanoparticles or aggregates thereof are between about 65 nm and about 85 nm in diameter and comprise a CR2-targeting group attached to the dextran coating. In certain embodiments, the dextran-coated CR2-targeted USPIO nanoparticles or aggregates thereof are about 75 nm in diameter and comprise a CR2-targeting group attached to the dextran coating. In certain embodiments, the dextran-coated CR2-targeted USPIO nanoparticles or aggregates thereof are about 150 nm in diameter and comprise a CR2-targeting group attached to the dextran coating.

In certain embodiments, the phospholipid-encapsulated bacterial-targeted USPIO nanoparticles or aggregates thereof are between about 1 nm and about 1000 nm in diameter and comprise a bacterial-targeting group attached to the phospholipid coating. In certain embodiments, the phospholipid-encapsulated bacterial-targeted USPIO nanoparticles or aggregates thereof are between about 5 nm and about 500 nm in diameter and comprise a bacterial-targeting group attached to the phospholipid coating. In certain embodiments, the phospholipid-encapsulated bacterial-targeted USPIO nanoparticles or aggregates thereof are between about 10 nm and about 100 nm in diameter and comprise a bacterial-targeting group attached to the phospholipid coating. In certain embodiments, the phospholipid-encapsulated bacterial-targeted USPIO nanoparticles or aggregates thereof are between about 50 nm and about 150 nm in diameter and comprise a bacterial-targeting group attached to the phospholipid coating. In certain embodiments, the phospholipid-encapsulated bacterial-targeted USPIO nanoparticles or aggregates thereof are between about 65 nm and about 85 nm in diameter and comprise a bacterial-targeting group attached to the phospholipid coating. In certain embodiments, the phospholipid-encapsulated bacterial-targeted USPIO nanoparticles or aggregates thereof are about 75 nm in diameter and comprise a bacterial-targeting group attached to the phospholipid coating. In certain embodiments, the phospholipid-encapsulated bacterial-targeted USPIO nanoparticles or aggregates thereof are about 150 nm in diameter and comprise a bacterial-targeting group attached to the phospholipid coating. In any of the embodiments described herein, the phospholipid comprises 1,2-distearoyl-sn-glycero-3-phosphoethanolamine ("DSPE"). In any of the embodiments described herein, the phospholipid is PEGylated. In any of the embodiments described herein, the PEGylated phospholipid further comprises a functional group suitable for cross-linking with a bacterial-targeting group. In any of the embodiments described herein, the functional group is an amine. In any of the embodiments described herein, the functional group is maleimide. In any of the embodiments described herein, the functional group is a thiol. In any of the embodiments described herein, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In any of the embodiments described herein, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In any of the embodiments described herein, the phospholipid comprises DSPE-PEG2000. In any of the embodiments described herein, the phospholipid comprises amine-functionalized DSPE-PEG2000. In any of the embodiments described herein, the phospholipid comprises amine-functionalized DSPE-PEG2000. In any of the embodiments described herein, the phospholipid comprises maleimide-functionalized DSPE-PEG2000. In any of the embodiments described herein, the USPIO nanoparticle aggregates are bacterial-targeted, phospholipid-encapsulated, have a circulating plasma half-life of between about 20 minutes and about 40 minutes, and have a tissue half life of one to several days (e.g., 1, 2, 3, 4, 5, 6, 7, 8, 9, or more days).

In certain embodiments, the dextran-coated bacterial-targeted USPIO nanoparticles or aggregates thereof are between about 1 nm and about 1000 nm in diameter and comprise a bacterial-targeting group attached to the dextran coating. In certain embodiments, the dextran-coated bacterial-targeted USPIO nanoparticles or aggregates thereof are between about 5 nm and about 500 nm in diameter and comprise a bacterial-targeting group attached to the dextran coating. In certain embodiments, the dextran-coated bacterial-targeted USPIO nanoparticles or aggregates thereof are between about 10 nm and about 100 nm in diameter and comprise a bacterial-targeting group attached to the dextran coating. In certain embodiments, the dextran-coated bacterial-targeted USPIO nanoparticles or aggregates thereof are between about 50 nm and about 150 nm in diameter and comprise a bacterial-targeting group attached to the dextran coating. In certain embodiments, the dextran-coated bacterial-targeted USPIO nanoparticles or aggregates thereof are between about 65 nm and about 85 nm in diameter and comprise a bacterial-targeting group attached to the dextran coating. In certain embodiments, the dextran-coated bacterial-targeted USPIO nanoparticles or aggregates thereof are about 75 nm in diameter and comprise a bacterial-targeting group attached to the dextran coating. In certain embodiments, the dextran-coated bacterial-targeted USPIO nanoparticles or aggregates thereof are about 150 nm in diameter and comprise a bacterial-targeting group attached to the dextran coating. In any of the embodiments described herein, the bacterial-targeting group is *S.*

*aureus* N315 Sbi protein. In any of the embodiments described herein, the bacterial-targeting group is a biologically-active fragment of *S. aureus* N315 Sbi protein comprising the first four N-terminal domains (Sbi-I-II-III-IV) of the full-length Sbi protein or comprising the third and fourth N-terminal domains (Sbi-III-IV) of the full-length Sbi protein.

In certain embodiments, the phospholipid-encapsulated C4-targeted USPIO nanoparticles or aggregates thereof are between about 1 nm and about 1000 nm in diameter and comprise a C4-targeting group attached to the phospholipid coating. In certain embodiments, the phospholipid-encapsulated C4-targeted USPIO nanoparticles or aggregates thereof are between about 5 nm and about 500 nm in diameter and comprise a C4-targeting group attached to the phospholipid coating. In certain embodiments, the phospholipid-encapsulated C4-targeted USPIO nanoparticles or aggregates thereof are between about 10 nm and about 100 nm in diameter and comprise a C4-targeting group attached to the phospholipid coating. In certain embodiments, the phospholipid-encapsulated C4-targeted USPIO nanoparticles or aggregates thereof are between about 50 nm and about 150 nm in diameter and comprise a C4-targeting group attached to the phospholipid coating. In certain embodiments, the phospholipid-encapsulated C4-targeted USPIO nanoparticles or aggregates thereof are between about 65 nm and about 85 nm in diameter and comprise a C4-targeting group attached to the phospholipid coating. In certain embodiments, the phospholipid-encapsulated C4-targeted USPIO nanoparticles or aggregates thereof are about 75 nm in diameter and comprise a C4-targeting group attached to the phospholipid coating. In certain embodiments, the phospholipid-encapsulated C4-targeted USPIO nanoparticles or aggregates thereof are about 150 nm in diameter and comprise a C4-targeting group attached to the phospholipid coating. In any of the embodiments described herein, the phospholipid comprises 1,2-distearoyl-sn-glycero-3-phosphoethanolamine ("DSPE"). In any of the embodiments described herein, the phospholipid is PEGylated. In any of the embodiments described herein, the PEGylated phospholipid further comprises a functional group suitable for cross-linking with a C4-targeting group. In any of the embodiments described herein, the functional group is an amine. In any of the embodiments described herein, the functional group is maleimide. In any of the embodiments described herein, the functional group is a thiol. In any of the embodiments described herein, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In any of the embodiments described herein, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In any of the embodiments described herein, the phospholipid comprises DSPE-PEG2000. In any of the embodiments described herein, the phospholipid comprises amine-functionalized DSPE-PEG2000. In any of the embodiments described herein, the phospholipid comprises amine-functionalized DSPE-PEG2000. In any of the embodiments described herein, the phospholipid comprises maleimide-functionalized DSPE-PEG2000. In any of the embodiments described herein, the USPIO nanoparticle aggregates are C4-targeted, phospholipid-encapsulated, have a circulating plasma half-life of between about 20 minutes and about 40 minutes, and have a tissue half life of one to several days (e.g., 1, 2, 3, 4, 5, 6, 7, 8, 9, or more days).

In certain embodiments, the C4-targeted USPIO nanoparticle aggregates are between about 50 nm and about 150 nm in diameter and encapsulated with phospholipid, wherein the phospholipid is amine-functionalized DSPE-PEG2000, and wherein the C4-targeting group is a fusion protein comprising CR1 or a biologically active fragment thereof fused to the Fc-domain of mouse $IgG_1$. In certain embodiments, the C4-targeted USPIO nanoparticle aggregates are between about 65 nm and about 85 nm in diameter and encapsulated with phospholipid, wherein the phospholipid is amine-functionalized DSPE-PEG2000, and wherein the C4-targeting group is a fusion protein comprising CR1 or a biologically active fragment thereof fused to the Fc-domain of mouse $IgG_1$. In certain embodiments, the C4-targeted USPIO nanoparticle aggregates are about 75 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse $IgG_1$. In certain embodiments, the C4-targeted USPIO nanoparticle aggregates are about 150 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse $IgG_1$.

In certain embodiments, the C4-targeted USPIO nanoparticle aggregates are between about 50 nm and about 150 nm in diameter and encapsulated with phospholipid, wherein the phospholipid is amine-functionalized DSPE-PEG2000, and wherein the C4-targeting group is a fusion protein comprising C4 bp or a biologically active fragment thereof fused to the Fc-domain of mouse $IgG_1$. In certain embodiments, the C4-targeted USPIO nanoparticle aggregates are between about 65 nm and about 85 nm in diameter and encapsulated with phospholipid, wherein the phospholipid is amine-functionalized DSPE-PEG2000, and wherein the C4-targeting group is a fusion protein comprising C4 bp or a biologically active fragment thereof fused to the Fc-domain of mouse $IgG_1$. In certain embodiments, the C4-targeted USPIO nanoparticle aggregates are about 75 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse $IgG_1$. In certain embodiments, the C4-targeted USPIO nanoparticle aggregates are about 150 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse $IgG_1$.

As used herein, the term "C4-targeted nanoparticle" refers to a nanoparticle, or to aggregates of nanoparticles, between about 1 nm and about 1000 nm in diameter to which C4-targeting groups such as peptides, polypeptides, or proteins that bind cell-bound breakdown fragments of complement protein C4, such as C4b (SEQ ID NO:26), iC4b (SEQ ID NO:25), and C4d (SEQ ID NO:27) have been attached, either directly or through a peptide, polypeptide, protein or other linker. Such peptides, polypeptides, or proteins include, for example, full-length CR1 protein or biologically-active fragments thereof, full-length C4 bp protein or biologically-active fragments thereof, and the like. Peptide, polypeptide, or protein linkers can include, for example, antibodies or antibody fragments, receptors or receptor fragments, and the like. The nanoparticles or aggregates thereof may be coated with a wide variety of materials, including natural or synthetic polymers, surfactants, or inorganic materials, any of which may be modified or derivatized to permit attachment of, for example, bacterial-targeting groups such as peptides, polypeptides, or proteins as discussed above, either directly or via a linker of some kind, or uncoated. Possible coatings include synthetic polymers, such as those based on poly(ethylene-co-vinyl acetate), polyvinylpyrrolidone ("PVP"), poly(lactic-co-glycolic acid) ("PLGA"), polyethylene glycol ("PEG"), polyvinyl alcohol ("PVA"), polyacrylic acid, and the like; natural polymers, such as gelatin, dextran, chitosan, pullulan, and the like; surfactants, such as sodium oleate, dodecylamine, sodium carboxymethylcellulose, and the like; inorganic materials, such as gold or silica; and biological materials, such as phospholipids. The nanoparticles may comprise contrast-enhancing agents for diagnostic or medical imaging, such as USPIO nanoparticles or aggregates thereof, or may comprise liposomes or other delivery vehicles containing smaller contrast-enhancing agents, such as gadolinium chelate ("Gd-chelates") molecules. The C4-targeted nanoparticles described herein can be formulated as pharmaceutical compositions as disclosed herein, and, when so formulated can be used in any of the methods of non-invasive imaging described herein.

As used herein, the term "bacterial-targeted nanoparticle" refers to a nanoparticle, or to aggregates of nanoparticles, between about 1 nm and about 1000 nm in diameter to which bacterial-targeting groups such as peptides, polypeptides, or proteins that bind cell-bound breakdown fragments of complement protein C3, such as C3b (SEQ ID NO:13), iC3b (SEQ ID NO:12), C3dg (SEQ ID NO:11), and C3d (SEQ ID NO:10) have been attached, either directly or through a peptide, polypeptide, protein or other linker. Such peptides, polypeptides, or proteins include, for example, full-length *S. aureus* N315 Sbi protein or biologically-active fragments thereof, and the like. As discussed herein, biologically-active fragments of Sbi protein include, for example, a fragment comprising the first four N-terminal domains (Sbi-I-II-III-IV) of the full-length Sbi protein or a fragment comprising the third and fourth N-terminal domains (Sbi-III-IV) of the full-length Sbi protein. Peptide, polypeptide, or protein linkers can include, for example, antibodies or antibody fragments, receptors or receptor fragments, and the like. The nanoparticles or aggregates thereof may be coated with a wide variety of materials, including natural or synthetic polymers, surfactants, or inorganic materials, any of which may be modified or derivatized to permit attachment of, for example, bacterial-targeting groups such as peptides, polypeptides, or proteins as discussed above, either directly or via a linker of some kind, or uncoated. Possible coatings include synthetic polymers, such as those based on poly(ethylene-co-vinyl acetate), polyvinylpyrrolidone ("PVP"), poly(lactic-co-glycolic acid) ("PLGA"), polyethylene glycol ("PEG"), polyvinyl alcohol ("PVA"), polyacrylic acid, and the like; natural polymers, such as gelatin, dextran, chitosan, pullulan, and the like; surfactants, such as sodium oleate, dodecylamine, sodium carboxymethylcellulose, and the like; inorganic materials, such as gold or silica; and biological materials, such as phospholipids. The nanoparticles may comprise contrast-enhancing agents for diagnostic or medical imaging, such as USPIO nanoparticles or aggregates thereof, or may comprise liposomes or other delivery vehicles containing smaller contrast-enhancing agents, such as gadolinium chelate ("Gd-chelates") molecules.

As used herein, the term "complement receptor 2," "CR2," "CD21," or "CR2/CD21" refers to a transmembrane protein of ~145 kilodaltons ("kD") typically expressed on B cells, follicular dendritic cells, and some T cell subtypes, or fragments thereof (e.g. biologically-active fragments thereof). See e.g., J. Hannan et al., 2002, *Biochem. Soc. Trans.* 30:983-989; K. A. Young et al., 2007, *J. Biol. Chem.* 282(50):36614-36625. CR2 is a member of the structural family of C3/C4 receptor and regulatory proteins known as the regulators of complement activation ("RCA"). Members of this family are characterized by the presence of short repeating domains of ~70 amino acids known as short consensus repeat ("SCR") modules. Each SCR contains a number of conserved amino acid residues, including four cysteines and an invariant tryptophan residue. The conserved cysteine residues form a pattern of disulfide bridges that connect Cys-1 to Cys-3 and Cys-2 to Cys-4. The modular composition of CR2 is well known, and consists of a 15- or 16-SCR extracellular domain, a 24-amino acid transmembrane domain, and a short 34-amino acid intracellular carboxy-terminal tail. Biologically-active fragments of CR2 include any fragment of CR2 capable of binding a CR2 ligand, such as, for example, the complete extracellular domain of human (SEQ ID NO:3) or mouse (SEQ ID NO:4) CR2, a fragment comprising SCRs 1 to 8 of human (SEQ ID NO:5) or mouse (SEQ ID NO:6) CR2, or a fragment comprising SCRs 1 to 2 of human (SEQ ID NO:7) or mouse (SEQ ID NO:8) CR2. All known CR2 ligands bind within the first two amino-terminal SCR domains (SCR 1 and SCR 2) at overlapping but distinguishable binding sites, although an additional glycosylation-dependent interaction with CD23 also involves SCRs 3 to 5. K. A. Young et al., 2007, *J. Biol. Chem.* 282(50):36614-36625. A "biologically active" fragment of CR2 protein retains the ability to bind one or more CR2 ligands, for example, such as iC3b, C3dg, and C3d, cell-bound breakdown fragments of complement protein C3 that bind to the two N-terminal SCR domains of CR2 (SCRs 1 and 2), EBV gp350/220, IFNα, and CD23.

As used herein, the term "CR2 ligand" refers to ligands (e.g. natural ligands) capable of binding to the extracellular domain of CR2. Natural ligands for CR2 include, for example, iC3b, C3dg, and C3d, cell-bound breakdown fragments of complement protein C3 that bind to the two N-terminal SCR domains of CR2 (SCR 1 and 2). See e.g., K. Iida et al., 1983, *J. Exp. Med.* 158:1021-1033. Cleavage of C3 results initially in the generation of C3b and the covalent attachment of this C3b to the activating cell surface. The C3b fragment is involved in the generation of enzymatic complexes that amplify the complement cascade. On a cell surface, C3b (SEQ ID NO:13) is rapidly converted to inactive iC3b (SEQ ID NO:12), particularly when deposited on a host surface containing regulators of complement activation (i.e., most host tissue). Even in the absence of membrane-bound complement regulators, substantial levels of iC3b (SEQ ID NO:12) are formed. iC3b (SEQ ID NO:12) is subsequently digested to the membrane bound fragments C3dg (SEQ ID NO:11) and then C3d (SEQ ID NO:10) by serum proteases, but this process is relatively slow. Thus, the C3 ligands for CR2 are relatively long lived once they are generated and are present in high concentrations at sites of complement activation. CR2 therefore can serve as a potent targeting vehicle for bringing molecules to sites of complement activation.

Other CR2 ligands include the Epstein-Barr Virus 350 kilodalton surface glycoprotein ("EBV gp350") or its truncated 220 kilodalton form (collectively "EBV gp350/220") (K. A. Young et al., 2007, *J. Biol. Chem.* 282(50):36614-36625), interferon alpha ("IFN-α") (R. Asokan et al., 2006, *J. Immunol.* 177(1):383-394), and CD23 (J. P. Aubry et al., 1992, *Nature* 358:505-507; and J. P. Aubry et al., 1994, *J. Immunol.* 152:5806-5813). Also known as FcεRII, CD23 is a low affinity receptor for immunoglobulin E ("IgE"), an antibody isotype involved in allergy and resistance to parasites. Unlike many of the antibody Fc receptors, CD23 is a C-type lectin found on mature B cells, activated macrophages, eosinophils, follicular dendritic cells and platelets.

As used herein, the term "specifically binds to" or "selectively binds to" refers to the specific binding of one protein to another (e.g., an antibody or antigen-binding fragment thereof to an antigen, or a receptor to a ligand), wherein the level of binding, as measured by any standard assay (e.g., an immunoassay), is statistically significantly higher than the background control for the assay. For example, when performing an immunoassay, controls typically include a reaction well or tube that contains an antibody or antigen-binding fragment thereof alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art, including, but not limited to: Western blot, immunoblot, enzyme-linked immunosorbant assay ("ELISA"), radioimmunoassay ("RIA"), immunoprecipitation, surface plasmon resonance, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS"), and flow cytometry.

As used herein, the term "CR2-targeted nanoparticle" or "CR2-targeted nanoparticle aggregate" refers to nanoparticles or aggregates thereof between about 1 nm and about 1000 nm in diameter to which CR2-targeting groups such as peptides, polypeptides, or proteins (e.g., antibodies or fragments thereof) that bind C3 or fragments thereof (e.g. functional fragments thereof or cell-bound breakdown fragments of complement protein C3, such as C3b (SEQ ID NO:13), iC3b (SEQ ID NO:12), C3dg (SEQ ID NO:11), and C3d (SEQ ID NO:10)) have been attached, either non-covalently or covalently (e.g. directly or through a peptide, polypeptide, protein or other linker). Such peptides, polypeptides, or proteins include, for example, CR2 proteins or biologically-active fragments thereof, antibodies and antibody fragments, and the like. As discussed herein, biologically-active fragments of CR2 protein include, for example, the complete extracellular domain of CR2, a fragment comprising SCRs 1 to 8 of CR2, or a fragment comprising SCRs 1 to 2 of CR2. SCRs are numbered from the amino- to the carboxy-terminus of the CR2 protein, so a CR2 fragment comprising SCRs 1 and 2 of CR2 contains the first two SCR domains at the amino-terminus of the full-length CR2 protein, while a fragment comprising SCRs 1 to 8 of CR2 contains the first eight SCR domains at the amino-terminus of the full-length CR2 protein. Peptide, polypeptide, or protein linkers can include, for example, antibodies or antibody fragments, receptors or receptor fragments, and the like. The nanoparticles may be coated with a wide variety of materials, including natural or synthetic polymers, surfactants, or inorganic materials, any of which may be modified or derivatized to permit attachment of, for example, CR2-targeting groups such as peptides, polypeptides, or proteins as discussed above, either directly or via a linker of some kind, or uncoated. Possible coatings include synthetic polymers, such as those based on poly(ethylene-co-vinyl acetate), polyvinylpyrrolidone ("PVP"), poly (lactic-co-glycolic acid) ("PLGA"), polyethylene glycol ("PEG"), polyvinyl alcohol ("PVA"), polyacrylic acid, and the like; natural polymers, such as gelatin, dextran, chitosan, pullulan, and the like; surfactants, such as sodium oleate, dodecylamine, sodium carboxymethylcellulose, and the like; inorganic materials, such as gold or silica; and biological materials, such as phospholipids. The nanoparticles may comprise contrast-enhancing agents for diagnostic or medical imaging, such as USPIO nanoparticles or aggregates thereof, or may comprise liposomes or other delivery vehicles containing smaller contrast-enhancing agents, such as gadolinium chelate ("Gd-chelates") molecules.

As used herein, the term "ultrasmall superparamagnetic iron oxide nanoparticle" or "USPIO nanoparticle" refers to superparamagnetic iron oxide particles ranging from 1 to 50 nm in diameter, more typically between 5 and 40 nm in diameter (excluding any coating applied after synthesis). USPIO nanoparticles are commonly made of maghemite ($Fe_2O_3$) or magnetite ($Fe_3O_4$) having crystal-containing regions of unpaired spins. Those magnetic domains are disordered in the absence of a magnetic field, but when a field is applied (i.e., while taking an MRI), the magnetic domains align to create a magnetic moment much greater than the sum of the individual unpaired electrons without resulting in residual magnetization of the particles. When injected into the blood stream, USPIO nanoparticles are taken up by macrophages and accumulate in inflamed tissues. Their iron moiety negatively enhances signal attenuation on $T_2$-weighted images, and their relative concentrations can be assessed by decreased $T_2$-signal intensity or, more precisely, by decreased spin-spin $T_2$-relaxation time. The decreased $T_2$-relaxation time (the transverse relaxation time) can thus be used to detect inflammation. The shortened $T_2$ relaxation time results in a darkening of the magnetic resonance image where the particles are located, thereby generating "negative contrast." This approach has been successfully utilized to detect renal inflammation in several models. In some cases, USPIO nanoparticles may be aggregated after synthesis to produce aggregates thereof (referred to herein as "ultrasmall superparamagnetic iron oxide ("USPIO") nanoparticle aggregates" or "USPIO nanoparticle aggregates") of 25 nm, 50 nm, 75 nm, 100 nm, or 150 nm, in diameter, or even larger.

The USPIO nanoparticles or aggregates thereof may be coated with a wide variety of materials, including natural or synthetic polymers, surfactants, phospholipids, or inorganic materials, any of which may be modified or derivatized to permit attachment of targeting groups, either directly or via different types of linkers, including peptides, polypeptides, proteins, or other chemical groups, or uncoated. Possible coatings include synthetic polymers, such as those based on poly(ethylene-co-vinyl acetate), polyvinylpyrrolidone ("PVP"), poly(lactic-co-glycolic acid) ("PLGA"), polyethylene glycol ("PEG"), polyvinyl alcohol ("PVA"), polyacrylic acid, and the like; natural polymers, such as gelatin, dextran, chitosan, pullulan, and the like; surfactants, such as sodium oleate, dodecylamine, sodium carboxymethylcellulose, and the like; inorganic materials, such as gold or silica; and biological materials, such as phospholipids.

The term "CR2-targeted ultrasmall superparamagnetic iron oxide nanoparticles or aggregates thereof" or "CR2-targeted USPIO nanoparticles or aggregates thereof" refers to USPIO nanoparticles or aggregates thereof to which CR2-targeting groups such as peptides, polypeptides, or proteins (e.g., antibodies or fragments thereof) that bind cell-bound breakdown fragments of complement protein C3, such as C3b (SEQ ID NO:13), iC3b (SEQ ID NO:12), C3dg (SEQ ID NO:11), and C3d (SEQ ID NO:10) have been attached, either non-covalently or covalently (e.g., directly or through a peptide, polypeptide, protein or other linker). Such peptides, polypeptides, or proteins include, for example, CR2 proteins or biologically-active fragments thereof, antibodies and antibody fragments, and the like. As discussed herein, biologically-active fragments of CR2 protein include, for example, the complete extracellular domain of CR2, a fragment comprising SCRs 1 to 8 of CR2, or a fragment comprising SCRs 1 to 2 of CR2. SCRs are numbered from the amino- to the carboxy-terminus of the CR2 protein, so a CR2 fragment comprising SCRs 1 and 2 of CR2 contains the first two SCR domains at the amino-terminus of the full-length CR2 protein, while a fragment comprising SCRs 1 to 8 of CR2 contains the first eight SCR domains at the amino-terminus of the full-length CR2 protein. Peptide, polypeptide, or protein linkers can include, for example, antibodies or antibody fragments, receptors or receptor fragments, and the like.

The term "bacterial-targeted ultrasmall superparamagnetic iron oxide nanoparticles or aggregates thereof" or "bacterial-targeted USPIO nanoparticles or aggregates thereof" refers to USPIO nanoparticles or aggregates thereof to which bacterial-targeting groups such as peptides, polypeptides, or proteins that bind cell-bound breakdown fragments of complement protein C3, such as C3b (SEQ ID NO:13), iC3b (SEQ ID NO:12), C3dg (SEQ ID NO:11), and C3d (SEQ ID NO:10) have been attached, either directly or through a peptide, polypeptide, protein or other linker. Such peptides, polypeptides, or proteins include, for example, full-length *S. aureus* N315 Sbi proteins or biologically-active fragments thereof, and the like. As discussed herein, full-length *S. aureus* N315 Sbi protein or biologically-active fragments thereof, and the like. As discussed herein, biologically-active fragments of *S. aureus* N315 Sbi protein include, for example, a fragment comprising the first four N-terminal domains (Sbi-I-II-III-IV) of the full-length Sbi protein or a fragment comprising the third and fourth N-terminal domains (Sbi-III-IV) of the full-length Sbi protein. Peptide, polypeptide, or protein linkers can include, for example, antibodies or antibody fragments, receptors or receptor fragments, and the like.

As used herein, the term "antibody" or "antibody fragment" refers to a class of proteins or fragments thereof with the ability to specifically or selectively bind particular antigens. Antibodies contain immunoglobulin (Ig) domains and are members of the Ig superfamily of proteins. Generally, an antibody molecule comprises two types of chains: a heavy or H chain, and a light or L chain. The light chain contains a variable domain ($V_L$) and a constant domain ($C_L$), while the heavy chain contains a variable domain ($V_H$) and three constant domains ($C_H1$, $C_H2$, and $C_H3$), with the $C_H1$ and $C_H2$ domains separated by a hinge region. The distinctive characteristics of each isotype are defined by sequences in the constant domain of the immunoglobulin. Each antibody molecule typically contains two H chains and two L chains. The two H chains are linked together by disulfide bonds and each H chain is linked to an L chain by a disulfide bond. There are only two types of L chains referred to as lambda (λ) and kappa (κ) chains. In contrast, there are five major H chain classes, referred to as isotypes. The five classes include IgM (μ), IgD (δ), IgG (λ), IgA (α), and IgE (or ε). Human immunoglobulin molecules comprise nine isotypes: IgM, IgD, IgE, four subclasses of IgG including IgG, ($γ_1$), IgG$_2$ ($γ_2$), IgG$_3$ ($γ_3$) and IgG$_4$ ($γ_4$), and two subclasses of IgA including IgA, ($α_1$) and IgA$_2$ ($α_2$).

Together, one H chain and one L chain form an arm of an immunoglobulin molecule having an immunoglobulin variable region. A complete immunoglobulin molecule comprises two di-sulfide linked arms. Thus, each arm of a whole immunoglobulin comprises a $V_{H+L}$ region, and a $C_{H+L}$ region. As used herein, the "variable region" or "V region" refers to a $V_{H+L}$ region (also known as an Fv fragment), a $V_L$ region, or a $V_H$ region of an Ig protein. Also as used herein, the term "constant region" or "C region" refers to a $C_{H+L}$ region, a $C_L$ region or a $C_H$ region.

Limited digestion of an Ig protein with different proteases produces a number of fragments, only some of which retain the capacity to bind antigen. The antigen-binding fragments are referred to as Fab, Fab', or F(ab')$_2$ fragments. A fragment lacking the ability to bind to antigen is referred to as an Fc fragment. An Fab fragment comprises one arm of an immunoglobulin molecule containing an L chain ($V_L+C_L$ domains) paired with the $V_H$ region and the $C_H1$ region. An Fab' fragment corresponds to an Fab fragment with part of the hinge region attached to the $C_H1$ domain. An F(ab')$_2$ fragment corresponds to two Fab' fragments that are normally covalently linked to each other through a disulfide bond, typically in the hinge region.

Antibodies or antibody fragments may also be humanized antibodies. Humanized antibodies are molecules having an antigen-binding site derived from an immunoglobulin from a non-human species, the remaining immunoglobulin-derived parts of the molecule being derived from a human immunoglobulin, in order to reduce immunogenicity of the protein. The antigen-binding site may comprise either complete variable regions fused onto human constant domains or only the complementarity determining regions (CDRs) grafted onto appropriate human framework regions in the variable domains. Humanized antibodies can be produced, for example, by modeling the antibody variable domains and producing the antibodies using genetic engineering techniques, such as CDR grafting. A description of various techniques for the production of humanized antibodies is found, for example, in Morrison et al., 1984, *Proc. Nat'l Acad. Sci. USA* 81:6851-55; Whittle et al., 1987, *Prot. Eng.* 1:499-505; Co et al., 1990, *J. Immunol.* 148:1149-1154; Co et al., 1992, *Proc. Nat'l Acad. Sci. USA* 88:2869-2873; Carter et al., 1992, *Proc. Nat'l Acad. Sci. USA* 89:4285-4289; Routledge et al., 1991, *Eur. J. Immunol.* 21:2717-2725 and PCT Patent Publication Nos. WO 91/09967; WO 91/09968 and WO 92/113831.

Whole antibodies can be polyclonal or monoclonal. Alternatively, functional equivalents of whole antibodies, such as antigen-binding fragments in which one or more antibody domains are truncated or absent (e.g., Fv, Fab, Fab', or F(ab)$_2$ fragments), as well as genetically-engineered antibodies or antigen-binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be used as targeting groups.

Methods of producing polyclonal antibodies that specifically or selectively bind to a particular antigen are known in the art. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate to precipitate the antibodies.

Methods of producing monoclonal antibodies that specifically or selectively bind to a particular antigen are known in the art. For example, monoclonal antibodies may be produced according to the methodology of Kohler and Milstein (Kohler & Milstein, 1975, *Nature* 256:495-497). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen, for example in an enzyme-linked immunosorbent assay or other routine method known in the art.

In certain embodiments described herein, the targeting group is selected from the group consisting of full-length human (SEQ ID NO:1) or mouse (SEQ ID NO:2) CR2 protein, the extracellular domain of human (SEQ ID NO:3) or mouse (SEQ ID NO:4) CR2 protein, the CR2 fragment comprising SCRs 1 to 8 of the full-length human (SEQ ID NO:5) or mouse (SEQ ID NO:6) CR2 protein, and the CR2 fragment comprising SCRs 1 and 2 of the full-length human (SEQ ID NO:7) or mouse (SEQ ID NO:8) CR2 protein. In certain embodiments described herein, the targeting group comprises (and in some embodiments consists of or consists essentially of) at least the first two amino-terminal SCR domains of human or mouse CR2, including for example at least any of the first 3, 4, 5, 6, 7, 8, 9, 10, 11, 12, 13, 14, 15, or 16 SCR domains of CR2. In certain embodiments described herein, the targeting group comprises (and in some embodiments consists of or consists essentially of) at least the first two amino-terminal SCR domains of human or mouse CR2, including for example at least any of the first 3, 4, 5, 6, 7, 8, 9, 10, 11, 12, 13, 14, 15, or 16 SCR domains of CR2, fused to the Fc domain of a human or mouse Ig protein. In certain embodiments described herein, the targeting group comprises (and in some embodiments consists of or consists essentially of) at least the first two amino-terminal SCR domains of human or mouse CR2, including for example at least any of the first 3, 4, 5, 6, 7, 8, 9, 10, 11, 12, 13, 14, 15, or 16 SCR domains of CR2, fused to the Fc domain of human or mouse $IgG_1$ protein. In certain embodiments described herein, the targeting group comprises (and in some embodiments consists of or consists essentially of) at least the first two amino-terminal SCR domains of human or mouse CR2, including for example at least any of the first 3, 4, 5, 6, 7, 8, 9, 10, 11, 12, 13, 14, 15, or 16 SCR domains of CR2, fused to the Fc domain of mouse $IgG_1$ protein. In certain embodiments described herein, the targeting group comprises an antibody directed to C3 or fragment thereof, including but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d.

As discussed above, CR2 may contain an extracellular portion having 15 or 16 repeating units known as short consensus repeats, or SCR domains. The SCR domains have a framework of highly conserved residues including four cysteines, two prolines, one tryptophan and several other partially conserved glycines and hydrophobic residues. SEQ ID NO:1 represents the full-length human CR2 protein sequence. In human CR2 protein (SEQ ID NO:1), amino acids 1-20 comprise the leader peptide, amino acids 23-82 comprise SCR1, amino acids 91-146 comprise SCR2, amino acids 154-210 comprise SCR3, amino acids 215-271 comprise SCR4. The C3d binding site is located in SCRs1 and 2 (the first two N-terminal SCR domains). The SCR domains are separated by short sequences of variable length that serve as spacers. The full-length mouse CR2 protein sequence is represented herein by SEQ ID NO:2. In mouse CR2 protein (SEQ ID NO:2), amino acids 14-73 comprise SCR1 and amino acids 82-138 comprise SCR2. Human and mouse CR2 are approximately 66% identical over the full length amino acid sequences represented by SEQ ID NO:1 and SEQ ID NO:2, and approximately 61% identical over the SCR1-SCR2 regions of SEQ ID NO:1 and SEQ ID NO:2. Both mouse and human CR2 bind to C3 in the C3d region. It is understood that species and strain variations exist for the disclosed peptides, polypeptides, and proteins, and that the CR2 protein or biologically-active fragments thereof described herein encompass all species and strain variations.

In some embodiments, the CR2 portion disclosed herein refers to a polypeptide that contains some or all of the ligand binding sites of the CR2 protein, and includes, but is not limited to, full-length CR2 proteins (such as human CR2 as shown in SEQ ID NO:1 or mouse CR2 as shown in SEQ ID NO:2), soluble CR2 proteins (such as a CR2 fragment comprising the complete extracellular domain of human (SEQ ID NO:3) or mouse (SEQ ID NO:4) CR2 protein), other biologically-active fragments of CR2 protein, such as a CR2 fragment comprising SCRs 1 to 8 of human (SEQ ID NO:5) or mouse (SEQ ID NO:6) CR2 protein, a CR2 fragment comprising SCR1 and SCR2 of human (SEQ ID NO:7) or mouse (SEQ ID NO:8) CR2 protein, or any homologue of a naturally occurring CR2 protein or biologically-active fragment thereof, as described in detail below. In some embodiments, the CR2 portion has one of the following properties of CR2: (1) binding to C3d (SEQ ID NO:10), (2) binding to iC3b (SEQ ID NO:12), (3) binding to C3dg (SEQ ID NO:11), and (4) binding to cell-bound breakdown fragment(s) of complement protein C3 that bind to the two N-terminal SCR domains of CR2 (SCRs 1 and 2).

A homologue of a CR2 protein or a fragment thereof includes proteins which differ from a naturally occurring CR2 protein (or a biologically-active fragment of a CR2 protein) in that at least one or a few amino acids have been deleted (e.g., a truncated version of the protein, such as a peptide, polypeptide or other fragment), inserted, inverted, substituted and/or derivatized (e.g., by glycosylation, phosphorylation, acetylation, myristoylation, prenylation, palmitation, amidation and/or addition of glycosylphosphatidyl inositol). In some embodiments, a CR2 homologue has an amino acid sequence that is at least about 70% identical to the amino acid sequence of a naturally occurring CR2 protein (e.g., SEQ ID NO:1 or SEQ ID NO:2), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring CR2 protein (e.g., SEQ ID NO:1, or SEQ ID NO:2). A CR2 homologue or a biologically-active fragment thereof preferably retains the ability to bind to a naturally occurring ligand of CR2 protein (e.g., C3d or other C3 fragments with CR2-binding ability). For example, the CR2 homologue (or biologically-active fragment thereof) may have a binding affinity for C3d that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of that of full-length CR2 (or a biologically-active fragment thereof).

In certain embodiments, the CR2 portion comprises at least the first two N-terminal SCR domains of a human CR2 protein (SEQ ID NO:7), such as a CR2 portion having an amino acid sequence containing at least amino acids 23 through 146 of the human CR2 protein. In certain embodiments, the CR2 portion comprises at least the first two SCR domains of human CR2 protein (SEQ ID NO:7) having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 23 through 146 of the full-length human CR2 protein (SEQ ID NO:1).

An amino acid sequence that is at least about, for example, 95% identical to a reference sequence (such as full-length human CR2 protein, i.e., SEQ ID NO:1) is identical to the reference sequence except that the amino acid sequence may include up to five point alterations per each 100 amino acids of the reference sequence. These up to five point alterations may be deletions, substitutions, or additions, and may occur anywhere in the sequence, interspersed either individually among amino acids in the reference sequence or in one or more continuous groups within the reference sequence.

In certain embodiments, the CR2 portion comprises part or all of the ligand-binding sites of the CR2 protein. In certain embodiments, the CR2 portion further comprises sequences required to maintain the three dimensional structure of the ligand-binding site. Ligand-binding sites of CR2 protein can be readily determined based on the crystal structure of CR2 protein, such as the human CR2 protein crystal structure disclosed in U.S. Pat. No. 6,820,011. For example, in certain embodiments, the CR2 portion comprises the B strand and B-C loop of SCR2 of CR2. In certain embodiments, the CR2 portion comprises a site on strand B and the B-C loop of CR2 SCR comprising the segment G98-G99-Y100-K101-I102-R103-G104-S105-T106-P107-Y108 with respect to SEQ ID NO:1. In certain embodiments, the CR2 portion comprises a site on the B strand of CR2 SCR2 comprising position K119 with respect to SEQ ID NO:1. In certain embodiments, the CR2 portion comprises a segment comprising V149-F150-P151-L152, with respect to SEQ ID NO:1. In certain embodiments, the CR2 portion comprises a segment of CR2 SCR2 comprising T120-N121-F122. In some embodiments, the targeting group has two or more of these sites. For example, in certain embodiments, the CR2 portion comprises a portion comprising G98-G99-Y100-K101-I102-R103-G104-S105-T106-P107-Y108 and K119 with respect to SEQ ID NO:1. Other combinations of these sites are also contemplated herein.

In certain embodiments described herein, the targeting group is selected from the group consisting of full-length S. aureus N315 Sbi protein (SEQ ID NO:20), a biologically-active fragment of S. aureus N315 Sbi protein comprising the first four N-terminal domains (Sbi-I-II-III-IV) of the full-length Sbi protein (SEQ ID NO:21), or a biologically-active fragment of S. aureus N315 Sbi protein comprising the third and fourth N-terminal domains (Sbi-III-IV) of the full-length Sbi protein (SEQ ID NO:22).

In certain embodiments described herein, the targeting group comprises (and in some embodiments consists of or consists essentially of) at least the first four amino-terminal domains of S. aureus N315 Sbi protein (Sbi-I-II-III-IV), including for example at least third and fourth amino-terminal domains of S. aureus N315 Sbi protein (Sbi-III-IV). In certain embodiments described herein, the targeting group comprises (and in some embodiments consists of or consists essentially of) at least the first four amino-terminal domains of S. aureus N315 Sbi protein (Sbi-I-II-III-IV), including for example at least third and fourth amino-terminal domains of S. aureus N315 Sbi protein (Sbi-III-IV), fused to the Fc domain of a human or mouse Ig protein. In certain embodiments described herein, the targeting group comprises (and in some embodiments consists of or consists essentially of) at least the first four amino-terminal domains of S. aureus N315 Sbi protein (Sbi-I-II-III-IV), including for example at least third and fourth amino-terminal domains of S. aureus N315 Sbi protein (Sbi-III-IV), fused to the Fc domain of human or mouse IgG$_1$ protein. In certain embodiments described herein, the targeting group comprises (and in some embodiments consists of or consists essentially of) at least the first four amino-terminal domains of S. aureus N315 Sbi protein (Sbi-I-II-III-IV), including for example at least third and fourth amino-terminal domains of S. aureus N315 Sbi protein (Sbi-III-IV), fused to the Fc domain of mouse IgG$_1$ protein.

As discussed above, S. aureus N315 contains an amino-terminal portion of about 266 amino acids, organized into four conserved structural domains. SEQ ID NO:20 represents the full-length S. aureus N315 Sbi protein sequence. In S. aureus N315 Sbi protein (SEQ ID NO:20), amino acids 42-94 comprise the first Sbi domain (Sbi-I), amino acids 92-156 comprise the second Sbi domain (Sbi-II), amino acids 150-205 comprise the third Sbi domain (Sbi-III), and amino acids 198-266 comprise the fourth Sbi domain (Sbi-IV). Thus, a biologically-active fragment of S. aureus N315 Sbi protein having the first four Sbi domains (Sbi-I-II-III-IV) comprises amino acids 28-266 of SEQ ID NO:20, and a biologically-active fragment of S. aureus N315 Sbi protein having the third and fourth Sbi domains (Sbi-III-IV) comprises amino acids 150-266 of SEQ ID NO:20. The Sbi-I-II fragment contains binding sites for IgG. The Sbi-III-IV fragment contains binding sites for proteolytic fragments of complement protein C3, such as, for example, C3dg and C3a. It is understood that species and strain variations exist for the disclosed peptides, polypeptides, and proteins, and that the S. aureus N315 Sbi protein or biologically-active fragments thereof described herein encompass all species and strain variations.

The S. aureus N315 Sbi portion disclosed herein refers to a polypeptide that contains some or all of the ligand binding sites of the Sbi protein, and includes, but is not limited to, full-length Sbi proteins (such as S. aureus N315 Sbi protein as shown in SEQ ID NO:20), or other biologically-active fragments of S. aureus N315 Sbi protein, such as a fragment of S. aureus N315 Sbi protein having the first four Sbi domains (Sbi-I-II-III-IV) comprising amino acids 28-266 of SEQ ID NO:20, or a fragment of S. aureus N315 Sbi protein having the third and fourth Sbi domains (Sbi-III-IV) comprising amino acids 150-266 of SEQ ID NO:20, or any homologue of a naturally-occurring S. aureus N315 Sbi protein or biologically-active fragment thereof, as described in detail herein. In some embodiments, the Sbi protein fragment has one of the following properties of CR2: (1) binding to Ig, (2) binding to C3dg, and (3) binding to C3a, and (4) binding to cell-bound breakdown fragment(s) of complement protein C3 that bind to the two N-terminal SCR domains of CR2 (SCRs 1 and 2).

A homologue of an S. aureus N315 Sbi protein or a fragment thereof includes proteins which differ from a naturally occurring Sbi protein (or a biologically-active fragment of an Sbi protein) in that at least one or a few amino acids have been deleted (e.g., a truncated version of the protein, such as a peptide, polypeptide or other fragment), inserted, inverted, substituted and/or derivatized (e.g., by glycosylation, phosphorylation, acetylation, myristoylation, prenylation, palmitation, amidation and/or addition of glycosylphosphatidyl inositol). In some embodiments, an S. aureus N315 Sbi protein homologue has an amino acid sequence that is at least about 70% identical to the amino acid sequence of a naturally occurring S. aureus N315 Sbi protein (e.g., SEQ ID NO:20), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring S. aureus N315 Sbi protein (e.g., SEQ ID NO:20). An S. aureus N315 Sbi protein homologue or a biologically-active fragment thereof preferably retains the ability to bind to a naturally occurring ligand of Sbi protein (e.g., an IgG protein or proteolytic breakdown products of complement protein C3, such as C3dg, C3a, or other C3 fragments that serve as durable markers of complement activity). For example, the CR2 homologue (or biologically-active fragment thereof) may have a binding affinity for C3dg that is at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of that of full-length S. aureus N315 Sbi protein (or a biologically-active fragment thereof).

In certain embodiments, the Sbi protein portion comprises at least the first four N-terminal domains of an S. aureus N315 Sbi protein (SEQ ID NO:20), such as an Sbi protein portion having an amino acid sequence containing at least amino acids 28 through 266 of the S. aureus N315 Sbi protein. In certain embodiments, the Sbi protein portion comprises at least the third and fourth N-terminal domains of S. aureus N315 Sbi protein (SEQ ID NO:20) having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to amino acids 150 through 266 of the full-length S. aureus N315 Sbi protein (SEQ ID NO:20).

An amino acid sequence that is at least about, for example, 95% identical to a reference sequence (such as full-length S. aureus N315 Sbi protein, i.e., SEQ ID NO:20) is identical to the reference sequence except that the amino acid sequence may include up to five point alterations per each 100 amino acids of the reference sequence. These up to five point alterations may be deletions, substitutions, or additions, and may occur anywhere in the sequence, interspersed either individually among amino acids in the reference sequence or in one or more continuous groups within the reference sequence.

In another aspect, the invention provides phospholipid-encapsulated CR2-targeted USPIO nanoparticles or aggregates thereof that incorporate a CR2-targeting group that specifically or selectively binds one or more cell-bound breakdown products of complement protein C3, such as C3b (SEQ ID NO:13), iC3b (SEQ ID NO:12), C3dg (SEQ ID NO:11), or C3d (SEQ ID NO:10). In certain embodiments, the CR2-targeting group is selected from the group consisting of full-length human (SEQ ID NO:1) or mouse (SEQ ID NO:2) CR2 protein, the extracellular domain of human (SEQ ID NO:3) or mouse (SEQ ID NO:4) CR2 protein, the CR2 fragment comprising SCRs 1 to 8 of the full-length human (SEQ ID NO:5) or mouse (SEQ ID NO:6) CR2 protein, or the CR2 fragment comprising SCRs 1 and 2 of the full-length human (SEQ ID NO:7) or mouse (SEQ ID NO:8) protein. In certain embodiments, the CR2-targeting group is an antibody directed to C3 or fragment thereof including, but not limited to, C3b, iC3b, C3dg, C3d and the like. In certain embodiments, the CR2-targeting group is modified to incorporate a lipid, glycolipid or phospholipid anchor sufficient to anchor the protein or protein fragment into a lipid mono- or bilayer. In certain embodiments, the phospholipid-encapsulated CR2-targeted USPIO nanoparticles or aggregates thereof incorporate a full-length human (SEQ ID NO:1) or mouse (SEQ ID NO:2) CR2 protein modified to incorporate a lipid, glycolipid or phospholipid anchor, an extracellular domain of human (SEQ ID NO:3) or mouse (SEQ ID NO:4) CR2 protein modified to incorporate a lipid, glycolipid or phospholipid anchor, a fragment of human (SEQ ID NO:5) or mouse (SEQ ID NO:6) CR2 protein comprising SCRs 1 to 8 of the full-length CR2 protein modified to incorporate a lipid, glycolipid or phospholipid anchor, or a fragment of human (SEQ ID NO:7) or mouse (SEQ ID NO:8) CR2 protein comprising SCRs 1 and 2 of the full-length CR2 protein modified to incorporate a lipid, glycolipid or phospholipid anchor.

In certain embodiments, the phospholipid-encapsulated CR2-targeted USPIO nanoparticles or aggregates thereof incorporate a full-length human (SEQ ID NO:1) or mouse (SEQ ID NO:2) CR2 protein fused to the Fc domain of a mouse $IgG_1$ protein and modified to incorporate a lipid, glycolipid or phospholipid anchor, an extracellular domain of human (SEQ ID NO:3) or mouse (SEQ ID NO:4) CR2 protein fused to the Fc domain of a mouse $IgG_1$ protein and modified to incorporate a lipid, glycolipid or phospholipid anchor, a fragment of human (SEQ ID NO:5) or mouse (SEQ ID NO:6) CR2 protein comprising SCRs 1 to 8 of the full-length CR2 protein fused to the Fc domain of a mouse $IgG_1$ protein and modified to incorporate a lipid, glycolipid or phospholipid anchor, or a fragment of human (SEQ ID NO:7) or mouse (SEQ ID NO:8) CR2 protein comprising SCRs 1 and 2 of the full-length CR2 protein fused to the Fc domain of a mouse $IgG_1$ protein and modified to incorporate a lipid, glycolipid or phospholipid anchor.

In another aspect, the invention provides phospholipid-encapsulated CR2-targeted USPIO nanoparticles or aggregates thereof derivatized with a CR2-targeting group that specifically binds one or more cell-bound breakdown products of complement protein C3, such as C3b (SEQ ID NO:13), iC3b (SEQ ID NO:12), C3dg (SEQ ID NO:11) or C3d (SEQ ID NO:10). In certain embodiments, the CR2-targeting group is selected from the group consisting of the full-length human (SEQ ID NO:1) or mouse (SEQ ID NO:2) CR2 protein, the extracellular domain of human (SEQ ID NO:3) or mouse (SEQ ID NO:4) CR2 protein, a fragment of human (SEQ ID NO:5) or mouse (SEQ ID NO:6) CR2 protein comprising SCRs 1 to 8 of the full-length CR2 protein, or a fragment of human (SEQ ID NO:7) or mouse (SEQ ID NO:8) CR2 protein comprising SCRs 1 and 2 of the full-length CR2 protein. In certain embodiments, the phospholipid-encapsulated CR2-targeted USPIO nanoparticles or aggregates thereof are derivatized with a CR2 fragment comprising SCRs 1 and 2 of the full-length CR2 protein.

In certain embodiments, the phospholipid-encapsulated CR2-targeted USPIO nanoparticles or aggregates thereof are derivatized with CR2 fragments comprising the extracellular domain of the full-length human CR2 protein fused to the Fc domain of a human or a mouse Ig protein. In certain embodiments, the phospholipid-encapsulated CR2-targeted USPIO nanoparticles are derivatized with CR2 fragments comprising the extracellular domain of the full-length human CR2 protein fused to the Fc domain of a human or a mouse IgG protein. In certain embodiments, the phospholipid-encapsulated CR2-targeted USPIO nanoparticles or aggregates thereof are derivatized with CR2 fragments comprising SCRs 1 and 2 of the full-length human CR2 protein fused to the Fc domain of a human or a mouse $IgG_1$ protein. In certain embodiments, the phospholipid-encapsulated CR2-targeted USPIO nanoparticles or aggregates thereof are derivatized with CR2 fragments comprising the extracellular domain of the full-length human CR2 protein fused to the Fc-domain of mouse $IgG_1$.

In certain embodiments, the phospholipid-encapsulated CR2-targeted USPIO nanoparticles or aggregates thereof are derivatized with CR2 fragments comprising SCRs 1 to 8 of the full-length human CR2 protein fused to the Fc domain of a human or a mouse Ig protein. In certain embodiments, the phospholipid-encapsulated CR2-targeted USPIO nanoparticles or aggregates thereof are derivatized with CR2 fragments comprising SCRs 1 to 8 of the full-length human CR2 protein fused to the Fc domain of a human or a mouse IgG protein. In certain embodiments, the phospholipid-encapsulated CR2-targeted USPIO nanoparticles or aggregates thereof are derivatized with CR2 fragments comprising SCRs 1 to 8 of the full-length human CR2 protein fused to the Fc domain of a human or a mouse IgG$_1$ protein. In certain embodiments, the phospholipid-encapsulated CR2-targeted USPIO nanoparticles or aggregates thereof are derivatized with CR2 fragments comprising SCRs 1 to 8 of the full-length human CR2 protein fused to the Fc-domain of mouse IgG$_1$.

In certain embodiments, the phospholipid-encapsulated CR2-targeted USPIO nanoparticles or aggregates thereof are derivatized with CR2 fragments comprising SCRs 1 and 2 of the full-length human CR2 protein fused to the Fc domain of a human or a mouse Ig protein. In certain embodiments, the phospholipid-encapsulated CR2-targeted USPIO nanoparticles or aggregates thereof are derivatized with CR2 fragments comprising SCRs 1 and 2 of the full-length human CR2 protein fused to the Fc domain of a human or a mouse IgG protein. In certain embodiments, the phospholipid-encapsulated CR2-targeted USPIO nanoparticles or aggregates thereof are derivatized with CR2 fragments comprising SCRs 1 and 2 of the full-length human CR2 protein fused to the Fc domain of a human or a mouse IgG$_1$ protein. In certain embodiments, the phospholipid-encapsulated CR2-targeted USPIO nanoparticles or aggregates thereof are derivatized with CR2 fragments comprising SCRs 1 and 2 of the full-length human CR2 protein fused to the Fc-domain of mouse IgG$_1$ (SEQ ID NO:9). In any of the embodiments described herein, the phospholipid-encapsulated CR2-targeted USPIO nanoparticles or aggregates thereof, have a circulating plasma half-life of between about 20 minutes and about 40 minutes, and have a tissue half life of one to several days (e.g., 1, 2, 3, 4, 5, 6, 7, 8, 9, or more days).

In another aspect, the invention provides dextran-coated CR2-targeted USPIO nanoparticles or aggregates thereof derivatized with a targeting group that specifically binds one or more cell-bound breakdown products of complement protein C3, such as C3b (SEQ ID NO:13), iC3b (SEQ ID NO:12), C3dg (SEQ ID NO:11), or C3d (SEQ ID NO:10). In certain embodiments, the CR2-targeting group is selected from the group consisting of the full-length human (SEQ ID NO:1) or mouse (SEQ ID NO:2) CR2 protein, the extracellular domain of human (SEQ ID NO:3) or mouse (SEQ ID NO:4) CR2 protein, a fragment of human (SEQ ID NO:5) or mouse (SEQ ID NO:6) CR2 protein comprising SCRs 1 to 8 of the full-length CR2 protein, or a fragment of human (SEQ ID NO:7) or mouse (SEQ ID NO:8) CR2 protein comprising SCRs 1 and 2 of the full-length CR2 protein. In certain embodiments, the dextran-coated CR2-targeted USPIO nanoparticles or aggregates thereof are derivatized with a CR2 fragment comprising SCRs 1 and 2 of the full-length human (SEQ ID NO:7) or mouse (SEQ ID NO:8) CR2 protein.

In certain embodiments, the dextran-coated CR2-targeted USPIO nanoparticles or aggregates thereof are derivatized with CR2 fragments comprising the extracellular domain of the full-length human CR2 protein fused to the Fc domain of a human or a mouse Ig protein. In certain embodiments, the dextran-coated CR2-targeted USPIO nanoparticles or aggregates thereof are derivatized with CR2 fragments comprising the extracellular domain of the full-length human CR2 protein fused to the Fc domain of a human or a mouse IgG protein. In certain embodiments, the dextran-coated CR2-targeted USPIO nanoparticles or aggregates thereof are derivatized with CR2 fragments comprising the extracellular domain of the full-length human CR2 protein fused to the Fc-domain of human or mouse IgG$_1$. In certain embodiments, the dextran-coated CR2-targeted USPIO nanoparticles or aggregates thereof are derivatized with CR2 fragments comprising the extracellular domain of the full-length human CR2 protein fused to the Fc-domain of mouse IgG$_1$.

In certain embodiments, the dextran-coated CR2-targeted USPIO nanoparticles or aggregates thereof are derivatized with CR2 fragments comprising SCRs 1 to 8 of the full-length human CR2 protein fused to the Fc domain of a human or a mouse Ig protein. In certain embodiments, the dextran-coated CR2-targeted USPIO nanoparticles or aggregates thereof are derivatized with CR2 fragments comprising SCRs 1 to 8 of the full-length human CR2 protein fused to the Fc domain of a human or a mouse IgG protein. In certain embodiments, the dextran-coated CR2-targeted USPIO nanoparticles or aggregates thereof are derivatized with CR2 fragments comprising SCRs 1 to 8 of the full-length human CR2 protein fused to the Fc-domain of human or mouse IgG$_1$. In certain embodiments, the dextran-coated CR2-targeted USPIO nanoparticles or aggregates thereof are derivatized with CR2 fragments comprising SCRs 1 to 8 of the full-length human CR2 protein fused to the Fc-domain of mouse IgG$_1$.

In certain embodiments, the dextran-coated CR2-targeted USPIO nanoparticles or aggregates thereof are derivatized with CR2 fragments comprising SCRs 1 and 2 of the full-length human CR2 protein fused to the Fc domain of a human or a mouse Ig protein. In certain embodiments, the dextran-coated CR2-targeted USPIO nanoparticles or aggregates thereof are derivatized with CR2 fragments comprising SCRs 1 and 2 of the full-length human CR2 protein fused to the Fc domain of a human or a mouse IgG protein. In certain embodiments, the dextran-coated CR2-targeted USPIO nanoparticles or aggregates thereof are derivatized with CR2 fragments comprising SCRs 1 and 2 of the full-length human CR2 protein fused to the Fc-domain of human or mouse IgG$_1$ (SEQ ID NO:9). In certain embodiments, the dextran-coated CR2-targeted USPIO nanoparticles or aggregates thereof are derivatized with CR2 fragments comprising SCRs 1 and 2 of the full-length human CR2 protein fused to the Fc-domain of mouse IgG$_1$ (SEQ ID NO:9).

In another aspect, the invention provides phospholipid-encapsulated bacterial-targeted USPIO nanoparticles or aggregates thereof that incorporate a bacterial-targeting group that specifically or selectively binds one or more cell-bound breakdown products of complement protein C3, such as C3b (SEQ ID NO:13), iC3b (SEQ ID NO:12), C3dg (SEQ ID NO:11), or C3d (SEQ ID NO:10). In certain embodiments, the bacterial-targeting group is selected from the group consisting of full-length S. aureus N315 Sbi protein (SEQ ID NO:20), a biologically-active fragment of full-length S. aureus N315 Sbi protein comprising the first four N-terminal domains of Sbi protein (SEQ ID NO:21), or a biologically-active fragment of full-length S. aureus N315 Sbi protein comprising the third and fourth domain of Sbi protein (SEQ ID NO:22).

In any of the embodiments described herein, the phospholipid-encapsulated bacterial-targeted USPIO nanoparticles or aggregates thereof, have a circulating plasma half-life of between about 20 minutes and about 40 minutes, and have a tissue half life of one to several days (e.g., 1, 2, 3, 4, 5, 6, 7, 8, 9, or more days).

In certain embodiments, the phospholipid-encapsulated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse Ig protein. In certain embodiments, the phospholipid-encapsulated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse IgG protein. In certain embodiments, the phospholipid-encapsulated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse IgG$_1$ protein. In certain embodiments, the phospholipid-encapsulated bacterial-targeted USPIO nanoparticles or aggregates thereof are derivatized with bacterial-targeting groups comprising full-length *S. aureus* N315 Sbi protein (SEQ ID NO:20) fused to the Fc-domain of mouse IgG$_1$.

In certain embodiments, the phospholipid-encapsulated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse Ig protein. In certain embodiments, the phospholipid-encapsulated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse IgG protein. In certain embodiments, the phospholipid-encapsulated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse IgG$_1$ protein. In certain embodiments, the phospholipid-encapsulated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc-domain of mouse IgG$_1$.

In certain embodiments, the phospholipid-encapsulated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse Ig protein. In certain embodiments, the phospholipid-encapsulated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse IgG protein. In certain embodiments, the phospholipid-encapsulated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse IgG$_1$ protein. In certain embodiments, the phospholipid-encapsulated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc-domain of mouse IgG$_1$.

In another aspect, the invention provides dextran-coated bacterial-targeted USPIO nanoparticles or aggregates thereof that incorporate a bacterial-targeting group that specifically or selectively binds one or more cell-bound breakdown products of complement protein C3, such as C3b (SEQ ID NO:13), iC3b (SEQ ID NO:12), C3dg (SEQ ID NO:11), or C3d (SEQ ID NO:10). In certain embodiments, the bacterial-targeting group is selected from the group consisting of full-length *S. aureus* N315 Sbi protein (SEQ ID NO:20), a biologically-active fragment of full-length *S. aureus* N315 Sbi protein comprising the first four N-terminal domains of Sbi protein (SEQ ID NO:21), or a biologically-active fragment of full-length *S. aureus* N315 Sbi protein comprising the third and fourth domain of Sbi protein (SEQ ID NO:22).

In certain embodiments, the dextran-coated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse Ig protein. In certain embodiments, the dextran-coated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse IgG protein. In certain embodiments, the dextran-coated bacterial-targeted USPIO nanoparticles or aggregates thereof are derivatized with bacterial-targeting groups comprising full-length *S. aureus* N315 Sbi protein (SEQ ID NO:20) fused to the Fc domain of a human or a mouse IgG$_1$ protein. In certain embodiments, the dextran-coated bacterial-targeted USPIO nanoparticles or aggregates thereof are derivatized with bacterial-targeting groups comprising full-length *S. aureus* N315 Sbi protein (SEQ ID NO:20) fused to the Fc-domain of mouse IgG$_1$.

In certain embodiments, the dextran-coated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse Ig protein. In certain embodiments, the dextran-coated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse IgG protein. In certain embodiments, the dextran-coated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc domain of a human or a mouse IgG$_1$ protein. In certain embodiments, the dextran-coated bacterial-targeted USPIO nanoparticles or aggregates thereof are derivatized with a biologically-active fragment of full-length *S. aureus* N315 Sbi protein comprising the first four N-terminal domains of Sbi protein (SEQ ID NO:21) fused to the Fc-domain of mouse IgG$_1$.

In certain embodiments, the dextran-coated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse Ig protein. In certain embodiments, the dextran-coated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse IgG protein. In certain embodiments, the dextran-coated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc domain of a human or a mouse IgG$_1$ protein. In certain embodiments, the dextran-coated bacterial-targeted USPIO nanoparticles or aggregates thereof are derivatized with a biologically-active fragment of full-length *S. aureus* N315 Sbi protein comprising the third and fourth domain of Sbi protein (SEQ ID NO:22) fused to the Fc-domain of mouse IgG$_1$.

Also encompassed are variants of the CR2-targeting and bacterial-targeting group (such as CR2 protein, *S. aureus* N315 Sbi protein or biologically-active fragments thereof). A variant of the CR2-targeting or bacterial-targeting groups described herein may be: (i) one in which one or more of the amino acid residues of the CR2 portion or the Sbi portion is substituted with a conserved or non-conserved amino acid residue (preferably a conserved amino acid residue) and such substituted amino acid residue may or may not be one encoded by the genetic code; or (ii) one in which one or more of the amino acid residues in the CR2 portion or the Sbi portion includes a substituent group, or (iii) one in which the CR2-targeting group or bacterial-targeting group (such as CR2 protein, *S. aureus* N315 Sbi protein or biologically-active fragments thereof) is fused with another compound, such as a compound to increase the half-life of the CR2-targeting or bacterial-targeting group (for example, polyethylene glycol), or (iv) one in which additional amino acids are fused to the CR2-targeting or bacterial-targeting group (such as CR2 protein, *S. aureus* N315 Sbi protein or biologically-active fragments thereof), such as a leader or secretory sequence or a sequence which is employed for purification of the CR2-targeting or Sbi-targeting group (such as CR2 protein, *S. aureus* N315 Sbi protein or biologically-active fragments thereof). Such variants are deemed to be within the scope of those skilled in the art from the teachings herein.

In certain embodiments, the variant of the CR2-targeting or bacterial-targeting group contains conservative amino acid substitutions (defined further below) made at one or more predicted, preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions in the CR2 portion or the Sbi portion of the CR2-targeting group or the bacterial-targeting group can be introduced to improve the functionality of the molecule. For example, amino acid substitutions can be introduced into the CR2 portion or the Sbi portion of the molecule to increase binding affinity of the CR2 portion or the Sbi portion to its ligand(s), increase binding specificity of the CR2 portion or the Sbi portion to its ligand(s), improve targeting of the CR2-targeted or bacterial-targeted nanoparticles to desired sites, and improve pharmacokinetics of the CR2-targeting or bacterial-targeting group.

In certain embodiments, the CR2-targeted group or bacterial-targeting group (such as CR2 protein, *S. aureus* N315 Sbi protein or biologically-active fragments thereof) is fused with another compound, such as a compound to increase the half-life of the polypeptide and/or to reduce potential immunogenicity of the polypeptide (for example, polyethylene glycol, "PEG"). The PEG can be used to impart water solubility, size, slow rate of kidney clearance, and reduced immunogenicity of the CR2-targeting group or the bacterial-targeting group. See, e.g., U.S. Pat. No. 6,214,966. In the case of PEGylations, the fusion of the CR2-targeting group or the bacterial-targeting group (such as CR2 protein, *S. aureus* N315 Sbi protein or biologically-active fragments thereof) to PEG can be accomplished by any means known to one skilled in the art. For example, PEGylation can be accomplished by first introducing a cysteine mutation into the CR2-targeting group or the bacterial-targeting group, followed by site-specific derivatization with PEG-maleimide. The cysteine can be added to the C-terminus of the CR2-targeting group or the bacterial-targeting group. See, e.g., Tsutsumi et al., 2000, *Proc. Nat'l Acad. Sci. USA* 97(15):8548-8553. Another modification which can be made to the CR2-targeting group or the bacterial-targeting group (such as CR2 protein, *S. aureus* N315 Sbi protein or biologically-active fragments thereof) involves biotinylation. In certain instances, it may be useful to have the CR2-targeting group or bacterial-targeting group (such as CR2 protein, *S. aureus* N315 Sbi protein or biologically-active fragments thereof) biotinylated so that it can readily react with streptavidin. Methods for biotinylation of proteins are well known in the art. Additionally, chondroitin sulfate can be linked with the CR2-targeting group or the bacterial-targeting group (such as CR2 protein, *S. aureus* N315 Sbi protein or biologically-active fragments thereof).

The CR2-targeting group or bacterial-targeting group (such as CR2 protein, *S. aureus* N315 Sbi protein or biologically-active fragments thereof) may include the addition of an immunologically active domain, such as an antibody epitope or other tag, to facilitate purification of the polypeptide. The use of 6×His and GST (glutathione-S-transferase) as tags is well known. Inclusion of a cleavage site at or near the fusion junction will facilitate removal of the extraneous polypeptide after purification. Other amino acid sequences that may be included in the CR2-targeting portion or the bacterial-targeting portion of the molecule include functional domains, such as active sites from enzymes such as a hydrolase, glycosylation domains, and cellular targeting signals.

Variants of the CR2-targeting group or the bacterial-targeting group (such as CR2 protein, *S. aureus* N315 Sbi protein or biologically-active fragments thereof) include polypeptides having an amino acid sequence sufficiently similar to the amino acid sequence of the CR2-targeting group or the bacterial-targeting group. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Amino acid sequence similarity can be determined in various ways, for example, using publicly available computer software such as BLAST, BLAST-2, ALIGN or MegAlign™ (DNASTAR) software. One skilled in the art can determine appropriate parameters for measuring alignment, including any algorithms needed to achieve maximal alignment over the full length of the sequences being compared.

Variants include CR2-targeting groups or bacterial-targeting groups that differ in amino acid sequence due to mutagenesis. In addition, bioequivalent analogs of the CR2-targeting groups or bacterial-targeting groups (such as CR2 protein, *S. aureus* N315 Sbi protein or biologically-active fragments thereof) may also be constructed by making various substitutions on residues or sequences in the CR2 protein, the *S. aureus* N315 Sbi protein or biologically-active fragments thereof.

The CR2-targeting groups, bacterial-targeting groups or homologues thereof described herein may be made by chemical synthesis methods, or by linkage of a polynucleotide encoding the CR2 portion, the Sbi portion and/or a polynucleotide encoding the Fc domain of a human or mouse Ig protein, IgG protein, or IgG$_1$ protein (with or without a linker sequence), and introducing the resulting polynucleotide into a vector for transfecting host cells that are capable of expressing the molecule. Chemical synthesis, especially solid phase synthesis, is preferred for short peptides or those containing unnatural or unusual amino acids such as D-Tyr, ornithine, and the like. Recombinant procedures are preferred for longer polypeptides. The CR2-targeting or bacterial-targeting groups can be isolated in vitro by standard protein purification methods known to those skilled in the art.

Recombinant DNA techniques for making a CR2-targeting group or a bacterial-targeting group involve, in simplified form, taking a CR2-targeting group-encoding polynucleotide or a bacterial-targeting group-encoding polynucleotide, inserting it into an appropriate vector, inserting the vector into an appropriate host cell, and recovering or isolating the protein produced thereby.

Provided herein are polynucleotides encoding a CR2-targeting group (i.e., a full-length human or mouse CR2 protein or biologically-active fragment thereof, such as the complete extracellular domain of human or mouse CR2 protein, a fragment of human or mouse CR2 protein comprising SCRs 1 to 8, or a fragment of human or mouse CR2 protein comprising SCRs 1 and 2) (see, e.g., SEQ ID NOS:1 to 8). Also provided herein are polynucleotides encoding a bacterial-targeting group (i.e., full-length *S. aureus* N315 Sbi protein, a fragment of *S. aureus* N315 Sbi protein comprising the first four N-terminal domains, or a fragment of *S. aureus* N315 Sbi protein comprising the third and fourth N-terminal domains) (see, e.g., SEQ ID NOS:20, 21, and 22). Such polynucleotides may also be used for expression of CR2-targeting groups or bacterial-targeting groups. For example, in certain embodiments, there are provided polynucleotides encoding human or mouse CR2 protein or biologically active fragments thereof, or encoding fusion proteins comprising a CR2 portion comprising full-length CR2 protein or a biologically-active fragment thereof and an Fc portion comprising an Fc domain from a human or mouse Ig protein, a human or mouse IgG protein, a human or mouse IgG$_1$ protein, or a mouse IgG$_1$ protein. In certain embodiments, the polynucleotide further comprises a sequence encoding a signal peptide operably linked at the 5' end of the sequence encoding the CR2-targeting group. Exemplary nucleotide sequences of signal peptides known to those skilled in the art are provided in SEQ ID NOS:14, 16, and 18; exemplary amino acid sequences of signal peptides known to those skilled in the art are provided in SEQ ID NOS:15, 17, and 19. In certain embodiments, a linker sequence is used for linking the CR2 portion and the Fc portion. In certain embodiments, the CR2 portion is attached directly to the Fc portion without a linker sequence. In certain embodiments, the polynucleotide encodes SCRs 1 and 2 of full-length human CR2 protein fused to the Fc domain of mouse IgG$_1$ having an amino acid sequence of SEQ ID NO:9. In some embodiments, the polynucleotide encodes SCRs 1 and 2 of full-length human CR2 protein fused to the Fc domain of mouse IgG$_1$ having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence SEQ ID NO:9.

In certain embodiments, there are further provided polynucleotides encoding *S. aureus* N315 Sbi protein or biologically active fragments thereof, or encoding fusion proteins comprising an Sbi protein portion comprising full-length *S. aureus* N315 protein or a biologically-active fragment thereof and an Fc portion comprising an Fc domain from a human or mouse Ig protein, a human or mouse IgG protein, a human or mouse IgG$_1$ protein, or a mouse IgG$_1$ protein. In certain embodiments, the polynucleotide further comprises a sequence encoding a signal peptide operably linked at the 5' end of the sequence encoding the bacterial-targeting group. Exemplary nucleotide sequences of signal peptides known to those skilled in the art are provided in SEQ ID NOS:14, 16, and 18; exemplary amino acid sequences of signal peptides known to those skilled in the art are provided in SEQ ID NOS:15, 17, and 19. In certain embodiments, a linker sequence is used for linking the Sbi protein portion and the Fc portion. In certain embodiments, the Sbi protein portion is attached directly to the Fc portion without a linker sequence. In certain embodiments, the polynucleotide encodes a biologically-active fragment of full-length *S. aureus* N315 Sbi protein comprising the first four N-terminal domains (Sbi-I-II-III-IV) fused to the Fc domain of mouse IgG$_1$ having an amino acid sequence of SEQ ID NO:23. In some embodiments, the polynucleotide encodes a biologically-active fragment of full-length *S. aureus* N315 Sbi protein comprising the first four N-terminal domains (Sbi-I-II-III-IV) fused to the Fc domain of mouse IgG$_1$ having an amino acid sequence that is at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence SEQ ID NO:23.

In another aspect, the invention provides expression vectors comprising any of the polynucleotides described herein for expression of the CR2-targeting or bacterial-targeting groups. The expression vector can be used to direct expression of a CR2-targeting group or a bacterial-targeting group in vitro or in vivo. The vector may include any element necessary to establish a conventional function of a vector, for example, a transcription promoter, transcription terminator, selectable marker, and origin of replication. The promoter can be constitutive or regulative, and is selected from, for example, promoters of genes for galactokinase (GAL1), uridylyltransferase (GALT), epimerase (GAL10), phosphoglycerate kinase (PGK), glyceraldehyde-3-phosphate dehydrogenase (GPD), alcohol dehydrogenase (ADH), and the like.

Many expression vectors are known to those of skill in the art. For example, *E. coli* may be transformed using pBR322, a plasmid derived from an *E. coli* species (Mandel et al., 1970, *J. Mol. Biol.* 53:154). Plasmid pBR322 contains genes for ampicillin and tetracycline resistance, and thus provides easy means for selection. Other vectors include different features such as different promoters, which are often important in expression. For example, plasmids pKK223-3 (Pharmacia Fine Chemicals, Uppsala, Sweden), pKK233-2 (Clontech, Palo Alto, Calif., USA), and pGEM1 (Promega Biotech, Madison, Wis., USA), are all commercially available. Other vectors that can be used in the present invention include, but are not limited to, pET21a (Studier et al., 1990, *Methods Enzymol.* 185: 60-89), pR1T5, and pR1T2T (Pharmacia Biotechnology), and pB0475 (Cunningham et al., 1989, *Science* 243: 1330-1336; U.S. Pat. No. 5,580,723). Mammalian expression vectors may contain non-transcribed elements such as origins of replication, transcription promoters and enhancers, and 5' or 3' nontranslated sequences such as ribosome binding sites, polyadenylation sites, splice donor and acceptor sites, and transcriptional termination sequences. Promoters for use in mammalian expression vectors usually are for example viral promoters such as polyoma, Adenovirus, HTLV, Simian Virus 40 (SV 40), and human cytomegalovirus (CMV). Vectors can also be constructed using standard techniques by combining the relevant traits of the vectors described above.

Also provided are host cells (such as isolated cells, transient cell lines, and stable cell lines) for expressing a CR2-targeting group or a bacterial-targeting group. The host cell may be prokaryotic or eukaryotic. Exemplary prokaryotic host cells include *E. coli* K12 strain 294 (ATCC No. 31446), *E. coli* B, *E. coli* X1776 (ATCC No. 31537), *E. coli* W3110 (F-, gamma-, prototrophic/ATCC No. 27325), bacilli such as *Bacillus subtilis*, and other Enterobacteriaceae, such as *Salmonella typhimurium* or *Serratia marcesans*, and various *Pseudomonas* species. One suitable prokaryotic host cell is *E. coli* BL21 (Stratagene), which is deficient in the OmpT and Lon proteases, which may interfere with isolation of intact recombinant proteins, and useful with T7 promoter-driven vectors, such as the pET vectors. Another suitable prokaryote is *E. coli* W3110 (ATCC No. 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic microbes such as filamentous fungi or yeast are suitable cloning or expression hosts for fusion-protein-encoding vectors. *Saccharomyces cerevisiae* is a commonly used lower eukaryotic host microorganism. Others include *Schizosaccharomyces pombe* (Beach & Nurse, 1981, *Nature* 290: 140; EP 139,383 published 2 May 1985); *Kluyveromyces* hosts (U.S. Pat. No. 4,943,529; Fleer et al., 1991, *Bio/Technology* 9:968-975) such as, e.g., *K. lactis* (MW98-8C, CBS683, CBS4574; Louvencourt et al., 1983, *J. Bacteriol.* 154(2):737-742), *K. fragilis* (ATCC 12,424), *K. bulgaricus* (ATCC No. 16,045), *K. wickeramii* (ATCC No. 24,178), *K. waltii* (ATCC No. 56,500), *K. drosophilarum* (ATCC No. 36,906; Van den Berg et al., 1990, *Bio/Technology* 8:135), *K. thermotolerans*, and *K. marxianus; yarrowia* (EP 402,226); *Pichia pastoris* (EP 183,070; Sreekrishna et al., 1988, *J. Basic Microbiol.* 28:265-278); *Candida; Trichoderma reesia* (EP 244,234); *Neurospora crassa* (Case et al., 1979, *Proc. Nat'l Acad. Sci. USA* 76:5259-5263); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., 1983, *Biochem. Biophys. Res. Commun.* 112:284-289; Tilburn et al., 1983, *Gene* 26:205-221; Yelton et al., 1984, *Proc. Nat'l Acad. Sci. USA* 81: 1470-1474) and *A. niger* (Kelly & Hynes, 1985, EMBO J. 4:475-479). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, THE BIOCHEMISTRY OF METHYLOTROPHS, 269 (1982). Host cells also include insect cells such as *Drosophila* S2 and *Spodoptera* Sf9, as well as plant cells.

Examples of useful mammalian host cell lines include, but are not limited to, HeLa, Chinese hamster ovary (CHO), COS-7, L cells, C127, 3T3, BHK, CHL-1, NSO, HEK293, WI38, BHK, C127 or MDCK cell lines. Another exemplary mammalian cell line is CHL-1. When CHL-1 is used hygromycin is included as a eukaryotic selection marker. CHL-1 cells are derived from RPMI 7032 melanoma cells, a readily available human cell line. Cells suitable for use in this invention are commercially available from the ATCC.

In certain embodiments, the host cell is a non-human host cell. In certain embodiments, the host cell is a CHO cell. In some embodiments, the host cell is a 293 cell.

The CR2-targeting groups or bacterial-targeting groups provided herein can be isolated by a variety of methods known in the art. In certain embodiments, when the CR2-targeting group or bacterial-targeting group comprises a secretory signal sequence so that it is secreted into the growth medium, the CR2-targeting group or bacterial-targeting group can be purified directly from the culture medium. If the CR2-targeting group or bacterial-targeting group is not secreted, it can be isolated from cell lysates. Cells can be disrupted or lysed by any conventional method, including freeze-thaw cycling, sonication, mechanical disruption, or use of cell lysing agents. The CR2-targeting groups or bacterial-targeting groups can be purified by various methods, including, but not limited to, immunoaffinity chromatography, reverse phase chromatography, cation exchange chromatography, anion exchange chromatography, hydrophobic interaction chromatography, gel filtration chromatography, and HPLC. For example, the CR2-targeting group or bacterial-targeting groups can be purified by immunoaffinity chromatography using an antibody that recognizes the CR2 portion, the Sbi portion or an antibody that recognizes the Fc portion of a human or mouse Ig protein, IgG protein, or $IgG_1$ protein, or both. In certain embodiments, an antibody recognizing the first two N-terminal SCR domains of CR2 is used for purifying the CR2-targeting group. In certain embodiments, the CR2-targeting group is purified by ion exchange chromatography. In certain embodiments, an antibody recognizing two or more of the first four N-terminal domains of *S. aureus* N315 Sbi protein is used for purifying the bacterial-targeting group. In certain embodiments, the bacterial-targeting group is purified by ion exchange chromatography.

The CR2-targeting group or bacterial-targeting group peptide may or may not be properly folded when expressed as a fusion protein. A number of factors determine whether the fusion protein must be denatured and refolded, and if so, whether these procedures are employed before or after cleavage. When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The CR2-targeting groups or bacterial-targeting groups described herein may also contain a tag (such as a cleavable tag) for purification. This tag can be fused to the C-terminus or N-terminus of the CR2 portion, the Sbi portion or the Fc portion, and can be used to facilitate protein purification.

In certain embodiments, the CR2-targeting group or the bacterial-targeting portion could be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

The CR2-targeting groups or bacterial-targeting groups can be assayed for their desired properties using in vitro or in vivo assays. For example, binding of a CR2-targeting group or a bacterial-targeting group to a CR2 ligand can be determined by surface plasmon resonance method. By way of example, kinetic analysis of the interaction of the CR2-targeting group or a bacterial-targeting group with C3d-biotin can be performed using surface plasmon resonance (SPR) measurements made on a BIAcore 3000 instrument (Biacore AB, Uppsala, Sweden). Human C3d-biotin can be bound to the surface of BIAcore streptavidin sensor chips by injecting C3d-biotin over the surface of one flow cell of the chip. Binding can be evaluated over a range of CR2-targeting group or bacterial-targeting group concentrations. Association of CR2-targeting group or bacterial-targeting group with the ligand can be monitored for a certain period of time (such as 120 seconds), after which the complex is allowed to dissociate in the presence of buffer only for an additional period of time (such as 120 seconds). Binding of CR2-targeting groups or bacterial-targeting groups to C3d-immobilized flow cells can be corrected for binding to control flow cells. Binding data can be fitted to a 1:1 Langmuir binding model using BIAevaluation Version 3.1 software (BIAcore) and evaluated for best fit. The kinetic dissociation profiles obtained can be used to calculate on and off rates ($k_a$ and $k_d$) and affinity constants ($K_D$) using the BIAevaluation Version 3.1 program. Other assay methods for ligand binding are known in the art and can also be used.

Methods of Synthesizing and Aggregating Nanoparticle Contrast Agents

USPIO nanoparticles can be synthesized by a variety of methods. In certain embodiments, USPIO nanoparticles are synthesized by coprecipitation. The coprecipitation method synthesizes either $Fe_3O_4$ or $\gamma$-$Fe_2O_3$ by co-precipitation of $Fe^{2+}$ or $Fe^{3+}$ aqueous salt solutions after addition of a strong base. Control of particle size, shape, and composition depends on the type of salts used (e.g., chlorides, sulfates, nitrates, perchlorates, and the like), the ratio of $Fe^{2+}$ to $Fe^{3+}$, reaction pH, and the ionic strength of the reaction. Typically, co-precipitation of magnetite proceeds by adding a base to an aqueous mixture of $Fe^{2+}$ and $Fe^{3+}$ chloride at a 1:2 molar ratio. The chemical reaction $Fe^{2+}+2Fe^{3+}+8OH^-\rightarrow Fe_3O_4+4H_2O$ generally produces magnetite as a black precipitate.

In certain embodiments, USPIO nanoparticles are synthesized by the reverse micelle method. The reverse micelle method enables the synthesis of USPIO nanoparticles in a narrow size range with comparatively uniform chemical and physical properties. Highly monodispersed USPIO can be synthesized using the aqueous core of aerosol-OT ("AOT")/n-hexane reverse micelles (aerosol-OT or AOT is the common name for sodium bis(2-ethylhexyl)sulfo-succinate), which have an aqueous core capable of dissolving hydrophilic compounds, including salts and the like. Thus, a deoxygenated aqueous solution of the $Fe^{3+}$ and $Fe^{2+}$ salts in a molar ratio of 2:1 is dissolved into the aqueous core of AOT/n-hexane reverse micelles, and USPIO nanoparticles (i.e., magnetite particles) are precipitated by addition of a deoxygenated solution of strong base, such as sodium hydroxide. Smaller and more uniform USPIO particles can be prepared by precipitation of magnetite from such reverse micelles at lower temperatures in the presence of nitrogen gas. Because the size of the aqueous core of the AOT/n-hexane reverse micelles is in the nanometer range, this method produces very small magnetite particles (<15 nm diameter on average) with a fairly narrow size distribution. In fact, the size of the USPIO particles produced by the reverse micelle method can be controlled by varying the size of the aqueous micelle core.

In certain embodiments, USPIO nanoparticles are synthesized by a solvothermal method as follows. Trioctylamine (98%), iron(III) acetylacetonate (Fe(Acac)$_3$) (97%), heptanoic acid (99%), anhydrous toluene (99.8%) and ethanol were purchased from Sigma-Aldrich (St. Louis, Mo.). $Fe_3O_4$ nanocrystallites can be synthesized without a secondary stabilizing agent by heating 20 ml of trioctylamine to reflux (~260° C.) under nitrogen gas in a three-necked round bottom flask. The solution is mixed using a magnetic stir bar. On reaching reflux temperature, 0.045 M Fe(Acac)$_3$ is carefully added to the solvent, turning the solution a dark, opaque brown color. The reaction is allowed to proceed for the desired time (e.g., 1, 3, 6, 12, 24, 36, 48, 72, or more hours), then quenched by addition of toluene, producing a clear brown solvent with a black precipitate. In certain embodiments, the solvothermal method is modified to start with a mixture of 18.6 ml of trioctylamine and 1.4 ml of heptanoic acid as a stabilizing agent.

In certain embodiments, the USPIO nanoparticles synthesized by the solvothermal method are further treated to form multiparticle USPIO aggregates. USPIO nanoparticles synthesized by the solvothermal method described herein using an Iron (III) Acetylacetonate precursor with trioctylamine and heptanoic acid (Sigma-Aldrich, St. Louis, Mo.) as surfactants have a diameter of ~10 nm with a hydrophobic heptanoic acid surface termination. In certain embodiments, the as-synthesized USPIO nanoparticles are resuspended in tetrahydrofuran (THF) and titrated with a 1% (v/v) solution of acetic acid until the desired level of aggregation is reached. Without wishing to be bound by a particular theory, it is thought that the acetic acid partially displaces the heptanoic acid on the USPIO nanoparticle surface, decreasing steric hindrance at the nanoparticle surface and permitting increased aggregation of USPIO nanoparticles. The aggregates of as-synthesized USPIO nanoparticles are then encapsulated using phospholipids. In certain embodiments, the USPIO nanoparticle aggregates are encapsulated by amine-functionalized, PEGylated phospholipids, such as 1,2-distearoyl-sn-glycero-3-phosphoethanolamine-N-[amino(polyethylene glycol)-2000] (ammonium salt). Phospholipids functionalized for use with any desired surface chemistry can be used, and PEGylated with any desired molecular weight of PEG. The USPIO nanoparticle aggregates and PEGylated, functionalized phospholipids are dried with nitrogen and maintained under vacuum for 24 hours. The iron-oxide/phospholipid mixture is resuspended in deionized water by bath sonication at 60° C. to yield amine-functionalized, PEGylated phospholipid-encapsulated USPIO nanoparticle aggregates for subsequent protein crosslinking.

In certain embodiments, the ultrasmall superparamagnetic nanoparticle compositions comprise liposomes or other delivery vehicles containing gadolinium chelate (Gd-chelate) molecules. Gd-chelate nanoparticles enhance MRI contrast via a $T_1$ relaxation mechanism, in contrast to superparamagnetic iron oxide nanoparticles, which enhance contrast via a $T_2$ relaxation mechanism. Gd-chelate molecules can be synthesized by a variety of methods. In certain embodiments, the Gd-chelate molecules are synthesized by reacting a solution of gadolinium citrate with a chelator such as diethylenetriaminepentaacetic acid ("DTPA"), or with DTPA derivatized with a linker containing another active group to facilitate addition of the Gd-chelate to another compound, such as a targeting group. For example, DPTA derivatized with bis (stearylamide) ("DPTA-SA") can be incorporated into low density lipoproteins. See e.g., I. R. Corbin et al., 2006, *Neoplasia* 8(6):488-498. A solution of gadolinium citrate can be prepared, for example, by adding a solution of $GdCl_3$ in HCl to an excess of sodium citrate, then adjusting the pH of the solution to 7.4 with HCl or NaOH as necessary. The presence of excess citrate prevents the formation of insoluble gadolinium hydroxides. The chelator can then be labeled with Gd(III) by mixing the gadolinium citrate solution with a solution containing DTPA or a DTPA-derivatized compound at a metal:chelator ratio of 1:1. The mixture is then incubated for one hour at room temperature under a nitrogen atmosphere with gentle stirring, filtered and concentrated to the desired volume by ultrafiltration, for example using an Amicon ultrafiltration cell using a filter with an appropriate molecular weight cutoff.

Nanoparticle size can be measured by a variety of common techniques, including scanning or transmission electron microscopy, atomic force microscopy, dynamic light scattering, x-ray photoelectron spectroscopy, powder x-ray diffraction, Fourier transform infrared spectroscopy, matrix-assisted laser desorption time-of-flight mass spectroscopy, ultraviolet-visible spectroscopy, and the like.

The various methods of synthesizing paramagnetic nanoparticle compositions for medical or diagnostic imaging applications described in detail by A. K. Gupta and M. Gupta in "Synthesis and surface engineering of iron oxide nanoparticles for biomedical applications," *Biomaterials* (2005) 26:3995-4021, are hereby incorporated herein by reference. In addition, the methods of synthesizing Gd-DPTA-SA conjugates for imaging applications described in detail by I. R. Corbin and colleagues in "Low-Density Lipoprotein Nanoparticles as Magnetic Resonance Imaging Contrast Agents," *Neoplasia* (2006) 8(6):488-498, are hereby incorporated herein by reference.

In certain embodiments, the superparamagnetic nanoparticles disclosed herein are coated with a natural or synthetic polymer or other material, or formulated with a stabilizer such as a surfactant at the time of preparation. Depending on the method by which they are produced, superparamagnetic iron oxide particles, such as the USPIO nanoparticles described herein, can have hydrophobic surfaces with a large surface area to volume ratio. Consequently, without a surface coating, colloidal suspensions of USPIO nanoparticles may agglomerate to form larger clusters, resulting in increased particle size. Such clusters have strong magnetic dipole-dipole attractions between them, and exhibit ferromagnetic behavior, further increasing their aggregation properties. Thus in some cases, for effective stabilization of USPIO nanoparticles, it is desirable to coat the particles, or to include a stabilizer, such as a surfactant, at the time of preparation. In certain embodiments, the USPIO nanoparticles or aggregates thereof disclosed herein are coated with an inorganic or a polymeric material. Polymeric coating materials may be either natural or synthetic. In certain embodiments, the USPIO nanoparticles or aggregates thereof are coated with synthetic polymer materials, such as those based on poly (ethylene-co-vinyl acetate), polyvinylpyrrolidone ("PVP"), poly(lactic-co-glycolic acid) ("PLGA"), polyethylene glycol ("PEG"), polyvinyl alcohol ("PVA"), polyacrylic acid, and the like. In certain embodiments, the USPIO nanoparticles or aggregates thereof are coated with natural polymer materials, such as gelatin, dextran, chitosan, pullulan, and the like. In certain embodiments, the USPIO nanoparticles or aggregates thereof are formulated in the presence of a surfactant, such as sodium oleate, dodecylamine, sodium carboxymethylcellulose, and the like. In certain embodiments, the USPIO nanoparticles or aggregates thereof are coated with an inorganic material, such as gold or silica. In certain embodiments, the USPIO nanoparticles or aggregates thereof are encapsulated in phospholipids. In certain embodiments, the phospholipids are derivatized to enable the covalent attachment of proteins or protein fragments to the surface of the phospholipid-encapsulated USPIO nanoparticles or aggregates thereof. In certain embodiments, the phospholipids are derivatized with thiol, carboxylate, or amine groups. In certain embodiments, the USPIO nanoparticles or aggregates thereof are coated with dextran. In certain embodiments, the dextran is derivatized to enable the covalent attachment of proteins or protein fragments to the surface of the dextran-coated USPIO nanoparticles or aggregates thereof.

As used herein, the term "phospholipid" or "phospholipids" refers to a class of compounds comprising one or more phosphate groups and one or more fatty acids covalently joined by an ester linkage to glycerol. Phospholipids are amphipathic in nature, consisting of a hydrophilic portion and a hydrophobic portion. They are found in all living cells, and are a major component of cell membranes. Exemplary phospholipids include phosphatidylcholine, phosphatidylethanolamine, phosphatidylserine, phosphatidylinositol, phosphatidylglycerol, and cardiolipin.

In certain embodiments, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a CR2- or bacterial-targeting group. In certain embodiments, the functional group is an amine. In certain embodiments, the functional group is maleimide. In certain embodiments, the functional group is a thiol. In certain embodiments, the PEGylated phospholipid comprises PEG at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises maleimide-functionalized DSPE-PEG2000.

Pharmaceutical Compositions for Imaging Applications

Also provided herein are pharmaceutical compositions comprising targeted nanoparticles and a pharmaceutically acceptable carrier. In certain embodiments, the targeted nanoparticles are CR2-targeted USPIO nanoparticles or aggregates thereof. In certain embodiments, the targeted nanoparticles are bacterial targeted USPIO nanoparticles or aggregates thereof. The pharmaceutical compositions may be suitable for a variety of modes of administration as described herein, including, for example, systemic or localized administration. The pharmaceutical compositions can be in the form of injectable solutions. The pharmaceutical compositions described herein can be packaged in single unit dosages or in multidosage forms.

In certain embodiments, the pharmaceutical compositions comprise CR2-targeted nanoparticles or aggregates thereof and a pharmaceutically acceptable carrier suitable for administration to an individual. In certain embodiments, the CR2-targeted nanoparticles or aggregates thereof are CR2-targeted USPIO nanoparticles or aggregates thereof. In certain embodiments, the CR2-targeted nanoparticles or aggregates thereof are CR2-targeted liposomes or other delivery vehicles containing Gd-chelate molecules. In certain embodiments, the pharmaceutical compositions comprise CR2-targeted nanoparticles or aggregates thereof and a pharmaceutically acceptable carrier suitable for intravenous injection into an individual. In certain embodiments, the CR2-targeted nanoparticles or aggregates thereof are CR2-targeted USPIO nanoparticles or aggregates thereof. In certain embodiments, the pharmaceutical compositions are CR2-targeted liposomes or other delivery vehicles containing Gd-chelate molecules. In certain embodiments, the pharmaceutical compositions comprise CR2-targeted nanoparticles or aggregates thereof and a pharmaceutically acceptable carrier suitable for intravenous injection into an individual. In certain embodiments, the CR2-targeted nanoparticles or aggregates thereof are CR2-targeted USPIO nanoparticles or aggregates thereof. In certain embodiments, the CR2-targeted nanoparticles or aggregates thereof are CR2-targeted liposomes or other delivery vehicles containing Gd-chelate molecules. In certain embodiments, the pharmaceutical compositions comprise CR2-targeted nanoparticles or aggregates thereof and a pharmaceutically acceptable carrier suitable for injection into the arteries (such as renal arteries). In certain embodiments, the CR2-targeted nanoparticles or aggregates thereof are CR2-targeted USPIO nanoparticles or aggregates thereof. In certain embodiments, the CR2-targeted nanoparticles or aggregates thereof are CR2-targeted liposomes or other delivery vehicles containing Gd-chelate molecules.

In certain embodiments, the pharmaceutical compositions comprise bacterial-targeted nanoparticles or aggregates thereof and a pharmaceutically acceptable carrier suitable for administration to an individual. In certain embodiments, the bacterial-targeted nanoparticles or aggregates thereof are bacterial-targeted USPIO nanoparticles or aggregates thereof. In certain embodiments, the bacterial-targeted nanoparticles or aggregates thereof are bacterial-targeted liposomes or other delivery vehicles containing Gd-chelate molecules. In certain embodiments, the pharmaceutical compositions comprise bacterial-targeted nanoparticles or aggregates thereof and a pharmaceutically acceptable carrier suitable for intravenous injection into an individual. In certain embodiments, the bacterial-targeted nanoparticles or aggregates thereof are bacterial-targeted USPIO nanoparticles or aggregates thereof. In certain embodiments, the bacterial-targeted nanoparticles or aggregates thereof are bacterial-targeted liposomes or other delivery vehicles containing Gd-chelate molecules. In certain embodiments, the pharmaceutical compositions comprise bacterial-targeted nanoparticles or aggregates thereof and a pharmaceutically acceptable carrier suitable for injection into the arteries (such as renal arteries). In certain embodiments, the bacterial-targeted nanoparticles or aggregates thereof are bacterial-targeted USPIO nanoparticles or aggregates thereof. In certain embodiments, the bacterial-targeted nanoparticles or aggregates thereof are bacterial-targeted liposomes or other delivery vehicles containing Gd-chelate molecules.

In any of the embodiments described herein, the pharmaceutical compositions can be administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg.

The compositions are generally formulated as sterile, substantially isotonic, and in full compliance with all Good Manufacturing Practice (GMP) regulations of the U.S. Food and Drug Administration. In any of the embodiments described herein, the compositions are free of pathogen. For injection, the pharmaceutical composition can be in the form of liquid solutions, for example in physiologically compatible buffers such as Hank's Balanced Salt solution ("HBSS") (e.g., 0.137 M NaCl, 5.4 mM KCl, 0.25 mM $Na_2HPO_4$, 0.44 mM $KH_2PO_4$, 1.3 mM $CaCl_2$, 1.0 mM $MgSO_4$, and 4.2 mM $NaHCO_3$), Phosphate-Buffered Saline ("PBS") (e.g., 1×PBS=137 mM NaCl, 10 mM Phosphate, 2.7 mM KCl, and a pH between 7.2 and 7.4), normal saline (e.g., 0.9% (w/v) NaCl), half normal saline (e.g., 0.45% (w/v) NaCl, sometimes also including 5% (w/v) dextrose), Ringer's solution (e.g., 130 mM $Na^+$, 109 mM $Cl^-$, 4 mM $K^+$, and 3 mM $Ca^{2+}$), or lactated Ringer's solution (e.g., 130 mM $Na^+$, 109 mM $Cl^-$, 28 mM lactate, 4 mM $K^+$, and 3 mM $Ca^{2+}$). In addition, the CR2-targeted USPIO nanoparticle or nanoparticle aggregate pharmaceutical composition may be provided in a solid form (e.g., lyophilized) and redissolved or suspended immediately prior to use.

In certain embodiments, the composition is formulated in accordance with routine procedures as a pharmaceutical composition adapted for injection. In certain embodiments, the pharmaceutical compositions provided herein are formulated for intravenous, introperitoneal, or intraocular injection. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, disodium-EDTA, sorbic acid, benzethonium chloride, and the like. Typically (but not necessarily) such preservatives are employed at a level of from 0.001% to 1.0% by weight.

Suitable buffers include boric acid, sodium and potassium bicarbonate, sodium and potassium borates, phosphate-buffered saline, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents include dextran 40, dextran 70, dextrose, glycerin, potassium chloride, propylene glycol, sodium chloride, and the like, such that the sodium chloride equivalent of the injectable solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, polyoxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

In certain embodiments, the pharmaceutical compositions comprise phospholipid-encapsulated CR2-targeted USPIO nanoparticles or aggregates thereof derivatized with CR2 fragments comprising the extracellular domain of the full-length human CR2 protein fused to the Fc domain of a human or a mouse Ig protein. In certain embodiments, the pharmaceutical compositions comprise phospholipid-encapsulated CR2-targeted USPIO nanoparticles or aggregates thereof derivatized with CR2 fragments comprising the extracellular domain of the full-length human CR2 protein fused to the Fc domain of a human or a mouse IgG protein. In certain embodiments, the pharmaceutical compositions comprise phospholipid-encapsulated CR2-targeted USPIO nanoparticles or aggregates thereof derivatized with CR2 fragments comprising the extracellular domain of the full-length human CR2 protein fused to the Fc domain of a human or a mouse $IgG_1$ protein. In certain embodiments, the pharmaceutical compositions comprise phospholipid-encapsulated CR2-targeted USPIO nanoparticles or aggregates thereof derivatized with CR2 fragments comprising the extracellular domain of the full-length human CR2 protein fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated CR2-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the pharmaceutical compositions comprise phospholipid-encapsulated CR2-targeted USPIO nanoparticles or aggregates thereof derivatized with CR2 fragments comprising SCRs 1 to 8 of the full-length human CR2 protein fused to the Fc domain of a human or a mouse Ig protein. In certain embodiments, the pharmaceutical compositions comprise phospholipid-encapsulated CR2-targeted USPIO nanoparticles or aggregates thereof derivatized with CR2 fragments comprising SCRs 1 to 8 of the full-length human CR2 protein fused to the Fc domain of a human or a mouse IgG protein. In certain embodiments, the pharmaceutical compositions comprise phospholipid-encapsulated CR2-targeted USPIO nanoparticles or aggregates thereof derivatized with CR2 fragments comprising SCRs 1 to 8 of the full-length human CR2 protein fused to the Fc domain of a human or a mouse $IgG_1$ protein. In certain embodiments, the pharmaceutical compositions comprise phospholipid-encapsulated CR2-targeted USPIO nanoparticles or aggregates thereof derivatized with CR2 fragments comprising SCRs 1 to 8 of the full-length human CR2 protein fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated CR2-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the pharmaceutical compositions comprise phospholipid-encapsulated CR2-targeted USPIO nanoparticles or aggregates thereof derivatized with CR2 fragments comprising SCRs 1 and 2 of the full-length human CR2 protein fused to the Fc domain of a human or a mouse Ig protein. In certain embodiments, the pharmaceutical compositions comprise phospholipid-encapsulated CR2-targeted USPIO nanoparticles or aggregates thereof derivatized with CR2 fragments comprising SCRs 1 and 2 of the full-length human CR2 protein fused to the Fc domain of a human or a mouse IgG protein. In certain embodiments, the pharmaceutical compositions comprise phospholipid-encapsulated CR2-targeted USPIO nanoparticles or aggregates thereof derivatized with CR2 fragments comprising SCRs 1 and 2 of the full-length human CR2 protein fused to the Fc domain of a human or a mouse $IgG_1$ protein. In certain embodiments, the pharmaceutical compositions comprise phospholipid-encapsulated CR2-targeted USPIO nanoparticles or aggregates thereof derivatized with CR2 fragments comprising SCRs 1 and 2 of the full-length human CR2 protein fused to the Fc-domain of mouse $IgG_1$ (SEQ ID NO:9). In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated CR2-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the phospholipid-encapsulated CR2-targeted USPIO nanoparticles or aggregates thereof are between about 1 nm and about 1000 nm in diameter. In certain embodiments, the phospholipid-encapsulated CR2-targeted USPIO nanoparticles or aggregates thereof are between about 5 nm and about 500 nm in diameter. In certain embodiments, the phospholipid-encapsulated CR2-targeted USPIO nanoparticles or aggregates thereof are between about 10 nm and about 100 nm in diameter. In certain embodiments, the phospholipid-encapsulated CR2-targeted USPIO nanoparticles or aggregates thereof are between about 50 nm and about 150 nm in diameter. In certain embodiments, the phospholipid-encapsulated CR2-targeted USPIO nanoparticles or aggregates thereof are between about 65 nm and about 85 nm in diameter. In certain embodiments, the phospholipid-encapsulated CR2-targeted USPIO nanoparticles or aggregates thereof are about 75 nm in diameter. In certain embodiments, the phospholipid-encapsulated CR2-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a CR2-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the pharmaceutical compositions comprise phospholipid-encapsulated C4-targeted USPIO nanoparticles or aggregates thereof derivatized with CR1 or a biologically-active fragment thereof fused to the Fc domain of a human or a mouse Ig protein. In certain embodiments, the pharmaceutical compositions comprise phospholipid-encapsulated C4-targeted USPIO nanoparticles or aggregates thereof derivatized with CR1 or a biologically-active fragment thereof fused to the Fc domain of a human or a mouse IgG protein. In certain embodiments, the pharmaceutical compositions comprise phospholipid-encapsulated C4-targeted USPIO nanoparticles or aggregates thereof derivatized with CR1 or a biologically-active fragment thereof fused to the Fc domain of a human or a mouse $IgG_1$ protein. In certain embodiments, the pharmaceutical compositions comprise phospholipid-encapsulated C4-targeted USPIO nanoparticles or aggregates thereof derivatized with CR1 or a biologically-active fragment thereof fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated C4-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the phospholipid-encapsulated C4-targeted USPIO nanoparticles or aggregates thereof are between about 1 nm and about 1000 nm in diameter. In certain embodiments, the phospholipid-encapsulated C4-targeted USPIO nanoparticles or aggregates thereof are between about 5 nm and about 500 nm in diameter. In certain embodiments, the phospholipid-encapsulated C4-targeted USPIO nanoparticles or aggregates thereof are between about 10 nm and about 100 nm in diameter. In certain embodiments, the phospholipid-encapsulated C4-targeted USPIO nanoparticles or aggregates thereof are between about 50 nm and about 150 nm in diameter. In certain embodiments, the phospholipid-encapsulated C4-targeted USPIO nanoparticles or aggregates thereof are between about 65 nm and about 85 nm in diameter. In certain embodiments, the phospholipid-encapsulated C4-targeted USPIO nanoparticles or aggregates thereof are about 75 nm in diameter. In certain embodiments, the phospholipid-encapsulated C4-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a C4-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000.

In certain embodiments, the phospholipid comprises thiol-functionalized DSPE-PEG2000. In certain embodiments, the phospholipid comprises maleimide-functionalized DSPE-PEG2000.

In certain embodiments, the pharmaceutical compositions comprise phospholipid-encapsulated C4-targeted USPIO nanoparticles or aggregates thereof derivatized with C4 bp of a biologically-active fragment thereof fused to the Fc domain of a human or a mouse Ig protein. In certain embodiments, the pharmaceutical compositions comprise phospholipid-encapsulated C4-targeted USPIO nanoparticles or aggregates thereof derivatized with C4 bp of a biologically-active fragment thereof fused to the Fc domain of a human or a mouse IgG protein. In certain embodiments, the pharmaceutical compositions comprise phospholipid-encapsulated C4-targeted USPIO nanoparticles or aggregates thereof derivatized with C4 bp of a biologically-active fragment thereof fused to the Fc domain of a human or a mouse $IgG_1$ protein. In certain embodiments, the pharmaceutical compositions comprise phospholipid-encapsulated C4-targeted USPIO nanoparticles or aggregates thereof derivatized with C4 bp of a biologically-active fragment thereof fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated C4-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the phospholipid-encapsulated C4-targeted USPIO nanoparticles or aggregates thereof are between about 1 nm and about 1000 nm in diameter. In certain embodiments, the phospholipid-encapsulated C4-targeted USPIO nanoparticles or aggregates thereof are between about 5 nm and about 500 nm in diameter. In certain embodiments, the phospholipid-encapsulated C4-targeted USPIO nanoparticles or aggregates thereof are between about 10 nm and about 100 nm in diameter. In certain embodiments, the phospholipid-encapsulated C4-targeted USPIO nanoparticles or aggregates thereof are between about 50 nm and about 150 nm in diameter. In certain embodiments, the phospholipid-encapsulated C4-targeted USPIO nanoparticles or aggregates thereof are between about 65 nm and about 85 nm in diameter. In certain embodiments, the phospholipid-encapsulated C4-targeted USPIO nanoparticles or aggregates thereof are about 75 nm in diameter. In certain embodiments, the phospholipid-encapsulated C4-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a C4-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the pharmaceutical compositions comprise dextran-coated CR2-targeted USPIO nanoparticles or aggregates thereof, wherein the CR2-targeting group is an antibody directed to C3 or fragment thereof, including but not limited to C3b, iC3b, C3dg, C3d and the like. In some embodiments, the antibody is a polyclonal antibody. In some embodiments, the antibody is a monoclonal antibody. In some embodiments, the antibody is a monoclonal antibody or fragment thereof directed to C3d. In certain embodiments, the pharmaceutical compositions comprise dextran-coated CR2-targeted USPIO nanoparticles or aggregates thereof derivatized with CR2 fragments comprising the extracellular domain of the full-length human CR2 protein fused to the Fc domain of a human or a mouse Ig protein. In certain embodiments, the pharmaceutical compositions comprise dextran-coated CR2-targeted USPIO nanoparticles or aggregates thereof derivatized with CR2 fragments comprising the extracellular domain of the full-length human CR2 protein fused to the Fc domain of a human or a mouse IgG protein. In certain embodiments, the pharmaceutical compositions comprise dextran-coated CR2-targeted USPIO nanoparticles or aggregates thereof derivatized with CR2 fragments comprising the extracellular domain of the full-length human CR2 protein attached to the Fc-domain of human or mouse $IgG_1$. In certain embodiments, the pharmaceutical compositions comprise dextran-coated CR2-targeted USPIO nanoparticles or aggregates thereof derivatized with CR2 fragments comprising the extracellular domain of the full-length human CR2 protein fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use.

In certain embodiments, the pharmaceutical compositions comprise dextran-coated CR2-targeted USPIO nanoparticles or aggregates thereof derivatized with CR2 fragments comprising SCRs 1 to 8 of the full-length human CR2 protein fused to the Fc domain of a human or a mouse Ig protein. In certain embodiments, the pharmaceutical compositions comprise dextran-coated CR2-targeted USPIO nanoparticles or aggregates thereof derivatized with CR2 fragments comprising SCRs 1 to 8 of the full-length human CR2 protein fused to the Fc domain of a human or a mouse IgG protein. In certain embodiments, the pharmaceutical compositions comprise dextran-coated CR2-targeted USPIO nanoparticles or aggregates thereof derivatized with CR2 fragments comprising SCRs 1 to 8 of the full-length human CR2 protein fused to the Fc-domain of human or mouse $IgG_1$. In certain embodiments, the pharmaceutical compositions comprise dextran-coated CR2-targeted USPIO nanoparticles or aggregates thereof derivatized with CR2 fragments comprising SCRs 1 to 8 of the full-length human CR2 protein fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use.

In certain embodiments, the pharmaceutical compositions comprise dextran-coated CR2-targeted USPIO nanoparticles or aggregates thereof derivatized with CR2 fragments comprising SCRs 1 and 2 of the full-length human CR2 protein fused to the Fc domain of a human or a mouse Ig protein. In certain embodiments, the pharmaceutical compositions comprise dextran-coated CR2-targeted USPIO nanoparticles or aggregates thereof derivatized with CR2 fragments comprising SCRs 1 and 2 of the full-length human CR2 protein fused to the Fc domain of a human or a mouse IgG protein. In certain embodiments, the pharmaceutical compositions comprise dextran-coated CR2-targeted USPIO nanoparticles or aggregates thereof derivatized with CR2 fragments comprising SCRs 1 and 2 of the full-length human CR2 protein fused to the Fc-domain of human or mouse $IgG_1$. In certain embodiments, the pharmaceutical compositions comprise dextran-coated CR2-targeted USPIO nanoparticles or aggregates thereof derivatized with CR2 fragments comprising SCRs 1 and 2 of the full-length human CR2 protein fused to the Fc-domain of mouse $IgG_1$ (SEQ ID NO:9). In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising dextran-coated CR2-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the dextran-coated CR2-targeted USPIO nanoparticles or aggregates thereof are between about 1 nm and about 1000 nm in diameter. In certain embodiments, the dextran-coated CR2-targeted USPIO nanoparticles or aggregates thereof are between about 5 nm and about 500 nm in diameter. In certain embodiments, the dextran-coated CR2-targeted USPIO nanoparticles or aggregates thereof are between about 10 nm and about 100 nm in diameter. In certain embodiments, the dextran-coated CR2-targeted USPIO nanoparticles or aggregates thereof are between about 50 nm and about 150 nm in diameter. In certain embodiments, the dextran-coated CR2-targeted USPIO nanoparticles or aggregates thereof are between about 65 nm and about 85 nm in diameter. In certain embodiments, the dextran-coated CR2-targeted USPIO nanoparticles or aggregates thereof are about 75 nm in diameter. In certain embodiments, the dextran-coated CR2-targeted USPIO nanoparticles or aggregates thereof are about 150 nm in diameter.

In certain embodiments, the pharmaceutical compositions comprise phospholipid-encapsulated bacterial-targeted USPIO nanoparticles or aggregates thereof derivatized with full-length *S. aureus* N315 Sbi protein fused to the Fc domain of a human or a mouse Ig protein. In certain embodiments, the pharmaceutical compositions comprise phospholipid-encapsulated bacterial-targeted USPIO nanoparticles or aggregates thereof derivatized with full-length *S. aureus* N315 Sbi protein fused to the Fc domain of a human or a mouse IgG protein. In certain embodiments, the pharmaceutical compositions comprise phospholipid-encapsulated bacterial-targeted USPIO nanoparticles or aggregates thereof derivatized with full-length *S. aureus* N315 Sbi protein fused to the Fc domain of a human or a mouse $IgG_1$ protein. In certain embodiments, the pharmaceutical compositions comprise phospholipid-encapsulated bacterial-targeted USPIO nanoparticles or aggregates thereof derivatized with full-length *S. aureus* N315 Sbi protein fused to the Fc-domain of mouse $IgG_1$ (SEQ ID NO:23). In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated bacterial-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein comprising the first four N-terminal domains of Sbi protein (Sbi-I-II-III-IV) fused to the Fc domain of a human or a mouse Ig protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein comprising the first four N-terminal domains of Sbi protein (Sbi-I-II-III-IV) fused to the Fc domain of a human or a mouse IgG protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein comprising the first four N-terminal domains of Sbi protein (Sbi-I-II-III-IV) fused to the Fc domain of a human or a mouse $IgG_1$ protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein (Sbi-I-II-III-IV) comprising the first four N-terminal domains of Sbi protein fused to the Fc-domain of mouse $IgG_1$ (SEQ ID NO:23). In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated bacterial-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein comprising the third and fourth N-terminal domains of Sbi protein (Sbi-III-IV) fused to the Fc domain of a human or a mouse Ig protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein (Sbi-III-IV) comprising the third and fourth N-terminal domains of Sbi protein fused to the Fc domain of a human or a mouse IgG protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein (Sbi-III-IV) comprising the third and fourth N-terminal domains of Sbi protein fused to the Fc domain of a human or a mouse $IgG_1$ protein. In certain embodiments, the pharmaceutical compositions comprise phospholipid-encapsulated bacterial-targeted USPIO nanoparticles or aggregates thereof derivatized with a biologically-active fragment of full-length *S. aureus* N315 Sbi protein comprising the third and fourth N-terminal domains of Sbi protein (Sbi-III-IV) fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising phospholipid-encapsulated bacterial-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the phospholipid-encapsulated bacterial-targeted USPIO nanoparticles or aggregates thereof are between about 1 nm and about 1000 nm in diameter. In certain embodiments, the phospholipid-encapsulated bacterial-targeted USPIO nanoparticles or aggregates thereof are between about 5 nm and about 500 nm in diameter. In certain embodiments, the phospholipid-encapsulated bacterial-targeted USPIO nanoparticles or aggregates thereof are between about 10 nm and about 100 nm in diameter. In certain embodiments, the phospholipid-encapsulated bacterial-targeted USPIO nanoparticles or aggregates thereof are between about 50 nm and about 150 nm in diameter. In certain embodiments, the phospholipid-encapsulated bacterial-targeted USPIO nanoparticles or aggregates thereof are between about 65 nm and about 85 nm in diameter. In certain embodiments, the phospholipid-encapsulated bacterial-targeted USPIO nanoparticles or aggregates thereof are about 75 nm in diameter. In certain embodiments, the phospholipid-encapsulated bacterial-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a bacterial-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the pharmaceutical compositions comprise dextran-coated bacterial-targeted USPIO nanoparticles or aggregates thereof derivatized with full-length S. aureus N315 Sbi protein fused to the Fc domain of a human or a mouse Ig protein. In certain embodiments, the pharmaceutical compositions comprise dextran-coated bacterial-targeted USPIO nanoparticles or aggregates thereof derivatized with full-length S. aureus N315 Sbi protein fused to the Fc domain of a human or a mouse IgG protein. In certain embodiments, the pharmaceutical compositions comprise dextran-coated bacterial-targeted USPIO nanoparticles or aggregates thereof derivatized with full-length S. aureus N315 Sbi protein fused to the Fc domain of a human or a mouse $IgG_1$ protein. In certain embodiments, the pharmaceutical compositions comprise dextran-coated bacterial-targeted USPIO nanoparticles or aggregates thereof derivatized with full-length S. aureus N315 Sbi protein fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use.

In certain embodiments, the pharmaceutical compositions comprise dextran-coated bacterial-targeted USPIO nanoparticles or aggregates thereof derivatized with a biologically-active fragment of full-length S. aureus N315 Sbi protein comprising the first four N-terminal domains of Sbi protein (Sbi-I-II-III-IV) fused to the Fc domain of a human or a mouse Ig protein. In certain embodiments, the pharmaceutical compositions comprise dextran-coated bacterial-targeted USPIO nanoparticles or aggregates thereof derivatized with a biologically-active fragment of full-length S. aureus N315 Sbi protein comprising the first four N-terminal domains of Sbi protein (Sbi-I-II-III-IV) fused to the Fc domain of a human or a mouse IgG protein. In certain embodiments, the pharmaceutical compositions comprise dextran-coated bacterial-targeted USPIO nanoparticles or aggregates thereof derivatized with a biologically-active fragment of full-length S. aureus N315 Sbi protein comprising the first four N-terminal domains of Sbi protein (Sbi-I-II-III-IV) fused to the Fc domain of a human or a mouse $IgG_1$ protein. In certain embodiments, the pharmaceutical compositions comprise dextran-coated bacterial-targeted USPIO nanoparticles or aggregates thereof derivatized with a biologically-active fragment of full-length S. aureus N315 Sbi protein (Sbi-I-II-III-IV) comprising the first four N-terminal domains of Sbi protein fused to the Fc-domain of mouse $IgG_1$ (SEQ ID NO:23). In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising dextran-coated bacterial-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the pharmaceutical compositions comprise dextran-coated bacterial-targeted USPIO nanoparticles or aggregates thereof derivatized with a biologically-active fragment of full-length S. aureus N315 Sbi protein comprising the third and fourth N-terminal domains of Sbi protein (Sbi-III-IV) fused to the Fc domain of a human or a mouse Ig protein. In certain embodiments, the pharmaceutical compositions comprise dextran-coated bacterial-targeted USPIO nanoparticles or aggregates thereof derivatized with a biologically-active fragment of full-length S. aureus N315 Sbi protein (Sbi-III-IV) comprising the third and fourth N-terminal domains of Sbi protein fused to the Fc domain of a human or a mouse IgG protein. In certain embodiments, the pharmaceutical compositions comprise dextran-coated bacterial-targeted USPIO nanoparticles or aggregates thereof derivatized with a biologically-active fragment of full-length S. aureus N315 Sbi protein (Sbi-III-IV) comprising the third and fourth N-terminal domains of Sbi protein fused to the Fc domain of a human or a mouse $IgG_1$ protein. In certain embodiments, the pharmaceutical compositions comprise dextran-coated bacterial-targeted USPIO nanoparticles or aggregates thereof derivatized with a biologically-active fragment of full-length S. aureus N315 Sbi protein comprising the third and fourth N-terminal domains of Sbi protein (Sbi-III-IV) fused to the Fc-domain of mouse $IgG_1$. In any of the embodiments described herein, the pharmaceutical compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the pharmaceutical compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the pharmaceutical compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the pharmaceutical compositions comprising dextran-coated bacterial-targeted USPIO nanoparticles or aggregates thereof having a circulating plasma half-life of between about 20 minutes and about 40 minutes and having a tissue half life of one to several days (e.g., 1, 2, 3, 4, 5, 6, 7, 8, 9, or more days).

In certain embodiments, the dextran-coated bacterial-targeted USPIO nanoparticles or aggregates thereof are between about 1 nm and about 1000 nm in diameter. In certain embodiments, the dextran-coated bacterial-targeted USPIO nanoparticles or aggregates thereof are between about 5 nm and about 500 nm in diameter. In certain embodiments, the dextran-coated bacterial-targeted USPIO nanoparticles or aggregates thereof are between about 10 nm and about 100 nm in diameter. In certain embodiments, the dextran-coated bacterial-targeted USPIO nanoparticles or aggregates thereof are between about 50 nm and about 100 nm in diameter. In certain embodiments, the dextran-coated bacterial-targeted USPIO nanoparticles or aggregates thereof are between about 65 nm and about 85 nm in diameter. In certain embodiments, the dextran-coated bacterial-targeted USPIO nanoparticles or aggregates thereof are about 75 nm in diameter. In certain embodiments, the dextran-coated bacterial-targeted USPIO nanoparticles or aggregates thereof are about 150 nm in diameter.

Methods of Detecting Complement-Mediated Inflammation

Also provided herein are non-invasive methods of detecting complement-mediated inflammation in an individual using the CR2-targeted USPIO nanoparticle or nanoparticle aggregate compositions or the bacterial-targeted USPIO nanoparticle or nanoparticle aggregate compositions provided herein. In certain embodiments, the invention provides non-invasive methods of detecting complement-mediated inflammation in an individual, the methods comprising: (a) administering to the individual a composition comprising an effective amount of CR2-targeted ultrasmall superparamagnetic iron oxide ("USPIO") nanoparticles or aggregates thereof; and (2) taking a magnetic resonance image of the individual. In certain embodiments, the invention provides non-invasive methods of detecting complement-mediated inflammation in an individual, the methods comprising: (a) administering to the individual a composition comprising an effective amount of bacterial-targeted ultrasmall superparamagnetic iron oxide ("USPIO") nanoparticles or aggregates thereof; and (2) taking a magnetic resonance image of the individual. In any of the embodiments described herein, the complement-mediated inflammation is alternative complement-mediated inflammation.

In any of the embodiments described herein, the composition administered to the individual is a pharmaceutical composition comprising any of the CR2-targeted USPIO nanoparticle compositions described herein. In any of the embodiments described herein, the composition administered to the individual is a pharmaceutical composition comprising any of the CR2-targeted USPIO nanoparticle aggregate compositions described herein. In any of the embodiments described herein, the composition administered to the individual is a pharmaceutical composition comprising any of the bacterial-targeted USPIO nanoparticle compositions described herein. In any of the embodiments described herein, the composition administered to the individual is a pharmaceutical composition comprising any of the bacterial-targeted USPIO nanoparticle aggregate compositions described herein. In any of the embodiments described herein, the composition administered to the individual is a pharmaceutical composition comprising any of the C4-targeted USPIO nanoparticle compositions described herein. In any of the embodiments described herein, the composition administered to the individual is a pharmaceutical composition comprising any of the C4-targeted USPIO nanoparticle aggregate compositions described herein.

As used herein, the term "magnetic resonance imaging" or "MRI" refers to a non-invasive medical imaging technique commonly used to visualize the structure and function of the body that provides detailed images of the body in any plane. MRI provides much greater contrast between the different soft tissues of the body than other non-invasive imaging methods, such as computed tomography (CT), making it especially useful in neurological, musculoskeletal, cardiovascular, and oncological (cancer) imaging. Unlike CT, it does not require ionizing radiation, instead using a powerful magnetic field to align the nuclear magnetization of hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to reconstruct an image of the body or a portion thereof.

When an individual lies in a scanner, the hydrogen nuclei (i.e., protons) found in abundance in water molecules throughout the individual's body, align with the strong main magnetic field. A second electromagnetic field, which oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different body tissues (e.g., fat vs. muscle) realign at different speeds, different body structures can be imaged. Contrast agents may be injected intravenously to enhance the appearance of blood vessels, organs, tumors or sites of inflammation.

As used herein, an "effective amount" of a CR2-targeted or bacterial-targeted ultrasmall superparamagnetic iron oxide ("USPIO") nanoparticle or nanoparticle aggregate composition (including any of the pharmaceutical compositions described herein) is an amount sufficient to produce a clinically useful magnetic resonance image of complement-mediated inflammation. A clinically useful magnetic resonance image is one containing sufficient detail to enable an experienced clinician to assess the degree and/or extent of inflammation for purposes of diagnosis, monitoring the efficacy of a therapeutic intervention, and the like.

Complement-mediated inflammation associated with many diseases in which any of the three complement pathways is implicated can be detected by the non-invasive methods of the present invention. Such diseases include, for example: (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membranous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. Complement-mediated inflammation associated with autoimmune disorders including, but not limited to, myasthenia gravis, Alzheimer's disease, multiple sclerosis, rheumatoid arthritis, systemic lupus erythematosus, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barré syndrome, Hashimoto's disease, idiopathic thrombocytopenic purpura, pemphigus, Sjögren's syndrome, and Takayasu's arteritis, may also be detected with the non-invasive methods described herein.

In certain embodiments, the complement-mediated inflammation to be detected by the non-invasive methods provided herein is associated with any of the following disorders: post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukopheresis; extracorporeal membrane oxygenation (ECMO); heparin-induced extracorporeal LDL precipitation (HELP); radiographic contrast media-induced allergic response; transplant rejection; and other inflammatory conditions and autoimmune/immune complex diseases such as multiple sclerosis, myasthenia gravis, pancreatitis, rheumatoid arthritis, Alzheimer's disease, asthma, thermal injury, anaphylactic shock, bowel inflammation, urticaria, angioedema, vasculitis, glomerulonephritis, and Sjögren's syndrome, systemic lupus erythromatosus and lupus nephritis.

Membranoproliferative glomerulonephritis type II (MPGN II) is a rare kidney disease leading to persistent proteinuria, hematuria, and nephritic syndrome. FH deficiency and dysfunction in MPGN II have been reported in several cases. For example, mutations in FH have been found in human patients with MPGN II. Pigs of the Norwegian Yorkshire breed have FH defects that are inherited in a recessive pattern. These animals develop MPGN II, show massive complement deposits in the renal glomeruli and die at an early age because of the renal failure. Furthermore, an autoantibody that recognizes FH has been described in a patient with hypocomplementemic MPGN II. Thus, evidence suggests that the alternative complement pathway is involved in the development and progression of MPGN II.

Hemolytic uremic syndrome (HUS) is a disease characterized by microangiopathic hemolytic anemia and thrombocytopenia, ultimately resulting in acute renal failure, caused by continuous platelet degradation in the periphery and platelet thrombin in the microcirculation of the kidney. See e.g., Zipfel, 2001, *Seminars in Thrombosis Hemostasis* 27(3):191-199. There is now considerable evidence that the nondiarrheal form of HUS (also known as atypical HUS, or aHUS) is associated with alternations and mutations of FH. In addition, autoantibodies to FH have been reported in aHUS patients. Thus, evidence suggests that the alternative complement pathway is involved in the development and progression of HUS and aHUS.

Rheumatoid arthritis is a chronic disease which can exhibit a variety of systemic manifestations. This disease has an unknown etiology and characteristically exhibits a persistent inflammatory synovitis which usually involves peripheral joints in a symmetric distribution. The most important feature of this incurable condition is complement-mediated inflammation which causes cartilage destruction, bone erosions and, ultimately, joint deformities that are the hallmark of the disease.

As used herein, the term "ischemia reperfusion (I/R) injury" refers to inflammatory injury to the endothelium and underlying parenchymal tissues following reperfusion of hypoxic tissues. It is a general syndrome that is responsible for both acute and chronic injury to various tissues including, for example, myocardium, central nervous system, hind limb and intestine. Ischemia reperfusion injury can result in necrosis and irreversible cell injury. The complement pathway (including the alternative complement pathway) is a major mediator of I/R injury. The non-invasive methods provided herein are thus useful for detection of complement-mediated inflammation associated with ischemia reperfusion that occurs in any organ or tissue, including, but not limited to, intestinal ischemia-reperfusion injury, renal ischemia-reperfusion injury, cardiac ischemia-reperfusion injury, ischemia-reperfusion injury of other internal organs such as the lung or liver, central nervous system ischemia-reperfusion injury, ischemia-reperfusion injury of the limbs or digits, trauma-induced hypovolemia, or ischemia-reperfusion injury of any transplanted organ or tissue. Ischemia-reperfusion injury can also occur in conjunction with a variety of other conditions including, but not limited to, stroke, spinal cord injury, trauma-induced hypovolemic shock, and autoimmune diseases such as rheumatoid arthritis (e.g., which can be greatly worsened by ischemic injury of the synovium) or a variety of other inflammatory diseases (diseases mediated by inflammation or wherein inflammation is a symptom that may result in or be associated with ischemic events and reperfusion). Other conditions and diseases in which ischemia-reperfusion injury occurs will be known to those of skill in the art.

The non-invasive methods provided herein may also be used to detect complement-mediated inflammation in drusen-associated diseases. As used herein, the term "drusen-associated disease" refers to any disease in which formation of drusen or drusen-like extracellular disease plaque takes place, and for which drusen or drusen-like extracellular disease plaque causes or contributes to thereto or represents a sign thereof. For example, age-related macular degeneration (AMD), characterized by the formation of macular drusen, is considered a drusen-associated disease. Non-ocular drusen-related diseases include, but are not limited to, amyloidosis, elastosis, dense deposit disease, and/or atherosclerosis. The term "drusen-related disease" also includes glomerulonephritis, such as MPGN II.

In certain embodiments, the invention provides non-invasive methods of detecting complement-mediated inflammation in an individual in need thereof comprising: (a) administering to the individual a composition comprising an effective amount of CR2-targeted ultrasmall superparamagnetic iron oxide ("USPIO") nanoparticles or aggregates thereof and (b) taking a magnetic resonance image of the individual. In certain embodiments, the composition is any of the pharmaceutical compositions comprising CR2-targeted USPIO nanoparticles or aggregates thereof described herein. In certain embodiments, the individual is a mammal. In certain embodiments, the mammal is a human, a mouse, or a rat. In certain embodiments, the compositions comprising CR2-targeted USPIO nanoparticles or aggregates thereof are administered by injection. In certain embodiments, the injection is parenteral, intravenous, subcutaneous, or intramuscular. In any of the embodiments described herein, the complement-mediated inflammation is alternative complement-mediated inflammation.

In any of the embodiments described herein, the compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the compositions further comprise sterile normal saline (e.g., 0.9% (w/v) NaCl). In any of the embodiments described herein, the compositions further comprise sterile half normal saline (e.g., 0.45% (w/v) NaCl, sometimes also including 5% (w/v) dextrose). In any of the embodiments described herein, the compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the compositions are administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg. In any of the embodiments described herein, the compositions have a circulating plasma half-life of between about 20 minutes and about 40 minutes and a tissue half life of one to several days (e.g., 1, 2, 3, 4, 5, 6, 7, 8, 9, or more days).

In certain embodiments, the invention provides non-invasive methods of detecting complement-mediated inflammation in an individual in need thereof comprising: (a) administering to the individual a composition comprising an effective amount of bacterial-targeted ultrasmall superparamagnetic iron oxide ("USPIO") nanoparticles or aggregates thereof; and (b) taking a magnetic resonance image of the individual. In certain embodiments, the composition is any of the pharmaceutical compositions comprising bacterial-targeted USPIO nanoparticles or aggregates thereof described herein. In certain embodiments, the individual is a mammal. In certain embodiments, the mammal is a human, a mouse, or a rat. In certain embodiments, the compositions comprising bacterial-targeted USPIO nanoparticles or aggregates thereof are administered by injection. In certain embodiments, the injection is parenteral, intravenous, subcutaneous, or intramuscular. In any of the embodiments described herein, the complement-mediated inflammation is alternative complement-mediated inflammation.

In any of the embodiments described herein, the compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the compositions further comprise sterile normal saline (e.g., 0.9% (w/v) NaCl). In any of the embodiments described herein, the pharmaceutical compositions further comprise sterile half normal saline (e.g., 0.45% (w/v) NaCl, sometimes also including 5% (w/v) dextrose). In any of the embodiments described herein, the compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the compositions are administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg. In any of the embodiments described herein, the compositions have a circulating plasma half-life of between about 20 minutes and about 40 minutes and a tissue half life of one to several days (e.g., 1, 2, 3, 4, 5, 6, 7, 8, 9, or more days).

In certain embodiments, the invention provides non-invasive methods of detecting complement-mediated inflammation in an individual in need thereof comprising: (a) administering to the individual a composition comprising an effective amount of C4-targeted ultrasmall superparamagnetic iron oxide ("USPIO") nanoparticles or aggregates thereof; and (b) taking a magnetic resonance image of the individual. In certain embodiments, the composition is any of the pharmaceutical compositions comprising C4-targeted USPIO nanoparticles or aggregates thereof described herein. In certain embodiments, the individual is a mammal. In certain embodiments, the mammal is a human, a mouse, or a rat. In certain embodiments, the compositions comprising C4-targeted USPIO nanoparticles or aggregates thereof are administered by injection. In certain embodiments, the injection is parenteral, intravenous, subcutaneous, or intramuscular. In any of the embodiments described herein, the complement-mediated inflammation is alternative complement-mediated inflammation.

In any of the embodiments described herein, the compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the compositions further comprise sterile normal saline (e.g., 0.9% (w/v) NaCl). In any of the embodiments described herein, the compositions further comprise sterile half normal saline (e.g., 0.45% (w/v) NaCl, sometimes also including 5% (w/v) dextrose). In any of the embodiments described herein, the compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the compositions are administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg. In any of the embodiments described herein, the compositions have a circulating plasma half-life of between about 20 minutes and about 40 minutes and a tissue half life of one to several days (e.g., 1, 2, 3, 4, 5, 6, 7, 8, 9, or more days).

The CR2-targeted, bacterial-targeted and C4-targeted USPIO nanoparticle or nanoparticle aggregate compositions described herein can be administered to an individual via any route, including, but not limited to, intravenous (e.g., by infusion pumps), intraperitoneal, intraocular, intraarterial, intravesicular, intramuscular, subcutaneous, intrathecal, transpleural, intraarterial, subcutaneous, intraarticular, intracisternal, intraventricular, intracranial, intraurethral, intrahepatic, and intratumoral. In certain embodiments, the CR2-targeted, bacterial-targeted or C4-targeted USPIO nanoparticle or nanoparticle aggregate compositions are administered systemically (for example, by intravenous injection). In some embodiments, the CR2-targeted, bacterial-targeted or C4-targeted USPIO nanoparticle or nanoparticle aggregate compositions are administered locally (for example, by intraarterial or intraocular injection).

In certain embodiments, the compositions are administered directly to the eye or the eye tissue. In certain embodiments, the compositions are administered by injection to the eye (intraocular injection) or to the tissues associated with the eye. The CR2-targeted, bacterial-targeted, or C4-targeted USPIO nanoparticle or nanoparticle aggregate compositions can be administered, for example, by intraocular injection, periocular injection, subretinal injection, intravitreal injection, transseptal injection, subscleral injection, intrachoroidal injection, intracameral injection, subconjunctival injection, subtenon injection, retrobulbar injection, or peribulbar injection. These methods are known in the art. For example, exemplary periocular routes for retinal drug delivery are disclosed in "Periocular routes for retinal drug delivery," Raghava et al., 2004, *Exp. Opin. Drug Deliv.* 1(1):99-114. The CR2-targeted, bacterial-targeted, or C4-targeted USPIO nanoparticle or nanoparticle aggregate compositions may be administered, for example, to the vitreous humor, aqueous humor, sclera, conjunctiva, the area between the sclera and conjunctiva, the retina, the choroid, the macula, to any other area in or proximate to the eye of an individual.

In certain embodiments, the CR2-targeted, bacterial-targeted, or C4-targeted compositions are administered intravascularly, such as intravenously (IV) or intraarterially. In certain embodiments (for example for the treatment of renal diseases), the compositions are administered directly into arteries (such as renal arteries).

In certain embodiments, the complement-mediated inflammation is associated with tissue damage resulting from ischemia reperfusion injury, inflammatory disorders, transplant rejection, pregnancy-related diseases, adverse drug reactions, and autoimmune or immune complex disorders. In certain embodiments, the tissue damage resulting from ischemia reperfusion injury is associated with a disorder selected from the group consisting of myocardial infarction, aneurysm, stroke, hemorrhagic shock, crush injury, multiple organ failure, hypovolemic shock, intestinal ischemia, spinal cord injury and traumatic brain injury. In certain embodiments, the inflammatory disorder is selected from the group consisting of burns, endotoxemia, septic shock, adult respiratory distress syndrome, cardiopulmonary bypass, hemodialysis, anaphylactic shock, asthma, angioedema, Crohn's disease, sickle cell anemia, poststreptococcal glomerulonephritis, membranous nephritis, and pancreatitis. In certain embodiments, the transplant rejection is hyperacute xenograft rejection. In certain embodiments, the pregnancy-related disease is selected from the group consisting of recurrent fetal loss and pre-eclampsia. In certain embodiments, the adverse drug reaction is selected from the group consisting of drug allergy and IL-2 induced vascular leakage syndrome. In certain embodiments, the autoimmune or immune complex disorder is selected from the group consisting of myasthenia gravis, Alzheimer's disease, multiple sclerosis, rheumatoid arthritis, systemic lupus erythematosus, lupus nephritis, insulin-dependent diabetes mellitus, acute disseminated encephalomyelitis, Addison's disease, antiphospholipid antibody syndrome, autoimmune hepatitis, Crohn's disease, Goodpasture's syndromes, Graves' disease, Guillain-Barré syndrome, Hashimoto's disease, idiopathic thrombocytopenic purpura, pemphigus, Sjögren's syndrome, Takayasu's arteritis, autoimmune glomerulonephritis, membranoproliferative glomerulonephritis type II, hemolytic uremic syndrome, and atypical hemolytic uremic syndrome. In certain embodiments, the autoimmune glomerulonephritis is associated with immunoglobulin A nephropathy or membranoproliferative glomerulonephritis type I.

In certain embodiments, the compositions comprise CR2-targeted USPIO nanoparticles or aggregates thereof coated with dextran or encapsulated with phospholipid. In certain embodiments, the phospholipid-encapsulated CR2-targeted USPIO nanoparticles or aggregates thereof further comprise a targeting moiety selected from the group consisting of complement receptor 2 (CR2) or a biologically-active fragment thereof, and a fusion protein comprising an antibody or fragment thereof fused to CR2 or a biologically-active fragment thereof. In certain embodiments, the dextran-coated CR2-targeted USPIO nanoparticles or aggregates thereof further comprise a targeting moiety selected from the group consisting of complement receptor 2 (CR2) or a biologically-active fragment thereof and a fusion protein comprising an antibody or fragment thereof fused to CR2 or a biologically-active fragment thereof. In certain embodiments, the phospholipid-encapsulated CR2-targeted USPIO nanoparticles or aggregates thereof further comprise a targeting moiety comprising a fusion protein comprising an antibody or fragment thereof fused to CR2 or a biologically-active fragment thereof. In certain embodiments, the dextran-coated CR2-targeted USPIO nanoparticles or aggregates thereof further comprise a targeting moiety comprising a fusion protein comprising an antibody or fragment thereof fused to CR2 or a biologically-active fragment thereof.

In certain embodiments, the targeting moiety comprises a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the targeting moiety comprises a fusion protein comprising an antibody fragment fused to a biologically active fragment of CR2. In certain embodiments, the fusion protein comprises the extracellular domain of CR2 fused to the Fc-domain of mouse immunoglobulin isotype $G_1$ (Ig$G_1$), SCRs 1 to 8 of CR2 fused to the Fc-domain of mouse Ig$G_1$, or SCRs 1 and 2 of CR2 fused to the Fc-domain of mouse Ig$G_1$.

In certain embodiments, the phospholipid-encapsulated CR2-targeted USPIO nanoparticles or aggregates thereof are between about 1 nm and about 1000 nm in diameter. In certain embodiments, the phospholipid-encapsulated CR2-targeted USPIO nanoparticles or aggregates thereof are between about 5 nm and about 500 nm in diameter. In certain embodiments, the phospholipid-encapsulated CR2-targeted USPIO nanoparticles or aggregates thereof are between about 10 nm and about 100 nm in diameter. In certain embodiments, the phospholipid-encapsulated CR2-targeted USPIO nanoparticles or aggregates thereof are between about 50 nm and about 150 nm in diameter. In certain embodiments, the phospholipid-encapsulated CR2-targeted USPIO nanoparticles or aggregates thereof are between about 65 nm and about 85 nm in diameter. In certain embodiments, the phospholipid-encapsulated CR2-targeted USPIO nanoparticles or aggregates thereof are about 75 nm in diameter. In certain embodiments, the phospholipid-encapsulated CR2-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a CR2-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the composition comprises CR2-targeted USPIO nanoparticle aggregates between about 1 nm and about 1000 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates between about 5 nm and about 500 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates between about 10 nm and about 100 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates between about 50 nm and about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates between about 65 nm and about 85 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates about 75 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$.

In certain embodiments, the compositions comprise C4-targeted USPIO nanoparticles or aggregates thereof encapsulated with phospholipid. In certain embodiments, the phospholipid-encapsulated C4-targeted USPIO nanoparticles or aggregates thereof further comprise a targeting moiety selected from the group consisting of CR1 or a biologically-active fragment thereof, a fusion protein comprising an antibody or fragment thereof fused to CR1 or a biologically-active fragment thereof, C4 bp or a biologically-active fragment thereof, and a fusion protein comprising an antibody or fragment thereof fused to C4 bp or a biologically-active fragment thereof. In certain embodiments, the phospholipid-encapsulated C4-targeted USPIO nanoparticles or aggregates thereof further comprise a targeting moiety comprising a fusion protein comprising an antibody or fragment thereof fused to CR1 or a biologically-active fragment thereof. In certain embodiments, the phospholipid-encapsulated C4-targeted USPIO nanoparticles or aggregates thereof further comprise a targeting moiety comprising a fusion protein comprising an antibody or fragment thereof fused to C4 bp or a biologically-active fragment thereof.

In certain embodiments, the composition comprises C4-targeted USPIO nanoparticle aggregates between about 1 nm and about 1000 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates between about 5 nm and about 500 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates between about 10 nm and about 100 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates between about 50 nm and about 150 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates between about 65 nm and about 85 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates about 75 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$. In certain embodiments, the composition comprises C4-targeted USPIO nanoparticle aggregates about 150 nm in diameter and encapsulated with phospholipid, wherein the phospholipid is amine-functionalized DSPE-PEG2000, and wherein the C4-targeting group is a fusion protein comprising CR1 or a biologically-active fragment thereof fused to the Fc-domain of mouse IgG$_1$.

In certain embodiments, the composition comprises C4-targeted USPIO nanoparticle aggregates between about 1 nm and about 1000 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates between about 5 nm and about 500 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates between about 10 nm and about 100 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates between about 50 nm and about 150 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates between about 65 nm and about 85 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates about 75 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$. In certain embodiments, the composition comprises C4-targeted USPIO nanoparticle aggregates about 150 nm in diameter and encapsulated with phospholipid, wherein the phospholipid is amine-functionalized DSPE-PEG2000, and wherein the C4-targeting group is a fusion protein comprising C4 bp or a biologically-active fragment thereof fused to the Fc-domain of mouse IgG$_1$.

In certain embodiments, the dextran-coated CR2-targeted USPIO nanoparticles or aggregates thereof are between about 1 nm and about 1000 nm in diameter. In certain embodiments, the dextran-coated CR2-targeted USPIO nanoparticles or aggregates thereof are between about 5 nm and about 500 nm in diameter. In certain embodiments, the dextran-coated CR2-targeted USPIO nanoparticles or aggregates thereof are between about 10 nm and about 100 nm in diameter. In certain embodiments, the dextran-coated CR2-targeted USPIO nanoparticles or aggregates thereof are between about 50 nm and about 150 nm in diameter. In certain embodiments, the dextran-coated CR2-targeted USPIO nanoparticles or aggregates thereof are between about 65 nm and about 85 nm in diameter. In certain embodiments, the dextran-coated CR2-targeted USPIO nanoparticles or aggregates thereof are about 75 nm in diameter. In certain embodiments, the dextran-coated CR2-targeted USPIO nanoparticles or aggregates thereof are about 150 nm in diameter.

In certain embodiments, the compositions comprise bacterial-targeted USPIO nanoparticles or aggregates thereof coated with dextran or encapsulated with phospholipid. In certain embodiments, the phospholipid-encapsulated bacterial-targeted USPIO nanoparticles or aggregates thereof further comprise a targeting moiety selected from the group consisting of full-length *S. aureus* N315 Sbi protein or a biologically-active fragment thereof, and a fusion protein comprising an antibody or fragment thereof fused to full-length *S. aureus* N315 Sbi protein or a biologically-active fragment thereof. In certain embodiments, the dextran-coated bacterial-targeted USPIO nanoparticles or aggregates thereof further comprise a targeting moiety selected from the group consisting of full-length *S. aureus* N315 Sbi protein or a biologically-active fragment thereof and a fusion protein comprising an antibody or fragment thereof fused to full-length *S. aureus* N315 Sbi protein or a biologically-active fragment thereof. In certain embodiments, the phospholipid-encapsulated bacterial-targeted USPIO nanoparticles or aggregates thereof further comprise a targeting moiety comprising a fusion protein comprising an antibody or fragment thereof fused to full-length *S. aureus* N315 Sbi protein or a biologically-active fragment thereof. In certain embodiments, the dextran-coated bacterial-targeted USPIO nanoparticles or aggregates thereof further comprise a targeting moiety comprising a fusion protein comprising an antibody or fragment thereof fused to full-length *S. aureus* N315 Sbi protein or a biologically-active fragment thereof.

In certain embodiments, the targeting moiety comprises a biologically active fragment of full-length *S. aureus* N315 Sbi protein. In certain embodiments, the biologically-active fragment of full-length *S. aureus* N315 Sbi protein comprises the first four N-terminal domains of Sbi protein (Sbi-I-II-III-IV) or the third and fourth N-terminal domains of Sbi protein (Sbi-III-IV). In certain embodiments, the targeting moiety comprises a fusion protein comprising an antibody fragment fused to a biologically active fragment of full-length *S. aureus* N315 Sbi protein. In certain embodiments, the fusion protein comprises the first four N-terminal domains of Sbi protein (Sbi-I-II-III-IV) fused to the Fc-domain of mouse immunoglobulin isotype G$_1$ (IgG$_1$) or the third and fourth N-terminal domains of Sbi protein (Sbi-III-IV) fused to the Fc-domain of mouse IgG$_1$.

In certain embodiments, the phospholipid-encapsulated bacterial-targeted USPIO nanoparticles or aggregates thereof are between about 1 nm and about 1000 nm in diameter. In certain embodiments, the phospholipid-encapsulated bacterial-targeted USPIO nanoparticles or aggregates thereof are between about 5 nm and about 500 nm in diameter. In certain embodiments, the phospholipid-encapsulated bacterial-targeted USPIO nanoparticles or aggregates thereof are between about 10 nm and about 100 nm in diameter. In certain embodiments, the phospholipid-encapsulated bacterial-targeted USPIO nanoparticles or aggregates thereof are between about 50 nm and about 150 nm in diameter. In certain embodiments, the phospholipid-encapsulated bacterial-targeted USPIO nanoparticles or aggregates thereof are between about 65 nm and about 85 nm in diameter. In certain embodiments, the phospholipid-encapsulated bacterial-targeted USPIO nanoparticles or aggregates thereof are about 150 nm in diameter. In certain embodiments, the phospholipid-encapsulated bacterial-targeted USPIO nanoparticles or aggregates thereof are about 75 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a bacterial-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the dextran-coated bacterial-targeted USPIO nanoparticles or aggregates thereof are between about 1 nm and about 1000 nm in diameter. In certain embodiments, the dextran-coated bacterial-targeted USPIO nanoparticles or aggregates thereof are between about 5 nm and about 500 nm in diameter. In certain embodiments, the dextran-coated bacterial-targeted USPIO nanoparticles or aggregates thereof are between about 10 nm and about 100 nm in diameter. In certain embodiments, the dextran-coated bacterial-targeted USPIO nanoparticles or aggregates thereof are between about 50 nm and about 150 nm in diameter. In certain embodiments, the dextran-coated bacterial-targeted USPIO nanoparticles or aggregates thereof are between about 65 nm and about 85 nm in diameter. In certain embodiments, the dextran-coated bacterial-targeted USPIO nanoparticles or aggregates thereof are about 75 nm in diameter. In certain embodiments, the dextran-coated bacterial-targeted USPIO nanoparticles or aggregates thereof are about 150 nm in diameter.

Methods of Detecting Complement-Mediated Renal Inflammation Associated with Systemic Lupus Erythematosus Also provided herein are non-invasive methods of detecting complement-mediated inflammation associated with systemic lupus erythematosus (SLE), membranous glomerulonephritis, or lupus nephritis in an individual in need thereof using the CR2-targeted USPIO nanoparticle or nanoparticle aggregate compositions provided herein. In certain embodiments, the complement-mediated inflammation is alternative complement-mediated inflammation.

As used herein, the term "systemic lupus erythematosus" or "lupus" or "SLE" refers to a chronic, occasionally fatal, autoimmune disease. As with other autoimmune diseases, in SLE, the immune system attacks the body's cells and tissue, resulting in inflammation and tissue damage. SLE can affect any part of the body, but most often harms the heart, joints, skin, lungs, blood vessels, liver, kidneys, and nervous system. The course of the disease is unpredictable, with periods of illness, or flares, alternating with periods of remission. Diagnosis can be elusive, with patients sometimes suffering unexplained symptoms and untreated SLE for years. Common initial and chronic complaints are fever, malaise, joint pains, myalgias, fatigue and temporary loss of cognitive abilities. In some cases, the disease is accompanied by chronic renal dysfunction, including the development of lupus nephritis.

As used herein, the term "membranous glomerulonephritis" or "lupus nephritis" refers to an inflammation of the kidney caused by the chronic autoimmune disease SLE. Those afflicted with lupus nephritis may or may not have renal symptoms, but the disease can manifest itself through weight gain, high blood pressure, darker foamy urine or swelling around the eyes, legs, ankles or fingers.

SLE is a complex autoimmune disease with pleiotropic clinical manifestations. Up to 80% of patients with lupus develop renal abnormalities, but the renal prognosis varies greatly within this population. C. Parikh et al., (2006) "The Long Term Outcome of Glomerular Diseases, in DISEASES OF THE KIDNEY AND Urinary TRACT: CLINICOPATHOLOGIC FOUNDATIONS OF MEDICINE (R. W. Schrier ed., $8^{th}$ ed., Lippincott Williams & Wilkins, Philadelphia, Pa.). Furthermore, in individual patients the disease may transform from one pattern to another. In some cases, the only renal manifestation of the disease is painless hematuria or proteinuria, but in some cases patients develop lupus nephritis, leading to acute or end-stage renal failure. Patients with active proliferative nephritis are usually treated with steroids in combination with cytotoxic agents or mycophenolate mofetil. Waldman, M. et al., 2006, Kidney Int. 70:1403-1412. Because of the significant morbidity associated with these agents, however, careful consideration is necessary to identify patients who require aggressive therapy. The duration and intensity of therapy are also frequently adjusted according to how well a patient is responding. Thus, one of the great challenges to treating SLE patients with lupus nephritis is assessing the activity of the disease, and tailoring pharmacologic therapy to achieve remission while minimizing toxicity.

The most commonly used system for classifying the different histologic patterns of lupus nephritis was originally developed by the World Health Organization ("WHO"), and is based upon the appearance of glomeruli by light microscopy. J. J. Weening et al., 2004, J. Am. Soc. Nephrol. 15:241-250. Proliferative lupus nephritis (WHO class III or IV) has the worst prognosis and most large clinical trials have focused on the response of these patients to therapy. The histologic pattern of disease may change over time or in response to treatment, however, and clinical parameters do not correlate well with disease activity. Serologic studies, such as measurement of perturbations in circulating levels of C3 and C4, are also poor markers of disease activity and are not specific to renal disease activity.

Histologically, a hallmark of SLE is membranous glomerulonephritis (also referred to as "lupus nephritis") with "wire loop" abnormalities, comprising a glomerular capillary loop with a circumferential, subendothelial immune complex deposit around the loop. The wire loop lesion results from immune complex deposition along the glomerular basement membrane, which leads to a characteristic granular appearance in immunofluorescence images. Thus, the diagnosis of active lupus nephritis is founded upon the presence of mesangial, subendothelial, and/or subepithelial immune-complexes. Complement activation is an essential prerequisite to active immune complex disease such as lupus nephritis.

Because effective treatment of proliferative lupus nephritis often requires treatment with potent immunosuppressive agents such as cyclophosphamide or mycophenolate mofetil, treatment is usually guided by examination of a renal biopsy.

Definitive diagnosis of glomerular diseases such as active lupus nephritis is based upon the examination of renal biopsy tissue by light microscopy, electron microscopy, and immunofluorescence staining for clinical markers of inflammation, including, but not limited to, IgM, IgA, IgG, C3, C4, and C1q.

Percutaneous renal biopsy is the gold standard for the definitive diagnosis of lupus nephritis and for monitoring the course of disease. As discussed herein, however, renal biopsies have their limitations and risks. Because a needle biopsy samples only a small portion of the kidney, there is a risk of sample error leading to an incorrect diagnosis. Furthermore, although biopsy is a generally safe procedure, major complications may occur in a significant percentage of biopsies and intra-renal bleeding and hematuria are common. W. L. Whittier et al., 2004, *J. Am. Soc. Nephrol.* 15:142-147; D. C. Mendelssohn et al., 1995, *Am. J. Kidney Disease* 26:580-585. Therefore, there is a need to develop accurate, safe, and non-invasive methods to image and diagnose renal inflammation, including lupus nephritis associated with SLE.

MRI can be used to non-invasively acquire tissue images with high resolution. USPIO nanoparticles or aggregates thereof enhance signal attenuation on T2-weighted magnetic resonance images, and conjugation of such nanoparticles to binding ligands permits the detection of specific molecules at the cellular level. For example, MRI with nanoparticle detection agents can image cell migration (J. W. Bulte et al., 2001, *Nat. Biotechnol.* 19:1141-1147), apoptosis (M. Zhao et al., 2001, *Nat. Med.* 7:1241-1244), and can detect small foci of cancer. See e.g., Y. W. Jun et al., 2005, *J. Am. Chem. Soc.* 127:5732-5733; Y. M. Huh et al., 2005, *J. Am. Chem. Soc.* 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, *NMR Biomed.* 17:484-499.

Because complement (e.g., the alternative complement pathway) is known to be involved in etiology and progression of renal inflammation and lupus nephritis associated with SLE, a ligand capable of targeting components of the complement pathway (e.g., the alternative complement pathway) would be useful in targeted delivery of USPIO nanoparticles or aggregates thereof to sites of renal inflammation in SLE patients. For example, a fragment comprising SCRs 1 and 2 of complement receptor 2 ("CR2") binds the C3b, iC3b, and C3d cleavage products of alternative complement protein C3. Phospholipid-encapsulated or dextran-coated USPIO nanoparticles or aggregates thereof can be covalently conjugated to a protein ligand such as the extracellular domain of CR2, SCRs 1 to 8 of CR2, or SCRs 1 and 2 of CR2 by linkage to thiol, amine, or carboxyl groups, either directly or through an antibody or antibody fragment. The labeled protein can then be used to target the USPIO nanoparticles or aggregates thereof to sites of complement-mediated (e.g., alternative complement-mediated) inflammation.

Thus, in certain embodiments, the invention provides non-invasive methods of detecting complement-mediated inflammation associated with systemic lupus erythematosus (SLE), membranous glomerulonephritis, or lupus nephritis in an individual in need thereof, the methods comprising: (a) administering to the individual a composition comprising an effective amount of CR2-targeted USPIO nanoparticles or aggregates thereof; and (2) taking a magnetic resonance image of the individual. In certain embodiments, the complement-mediated inflammation is alternative complement-mediated inflammation. In certain embodiments, the individual is a mammal. In certain embodiments, the mammal is a human, a mouse, or a rat. In certain embodiments, the compositions comprising CR2-targeted USPIO nanoparticles or aggregates thereof are administered by injection. In certain embodiments, the injection is parenteral, intravenous, subcutaneous, or intramuscular.

In any of the embodiments described herein, the compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the compositions further comprise sterile normal saline (e.g., 0.9% (w/v) NaCl). In any of the embodiments described herein, the compositions further comprise sterile half normal saline (e.g., 0.45% (w/v) NaCl, sometimes also including 5% (w/v) dextrose). In any of the embodiments described herein, the compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the compositions are administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg. In any of the embodiments described herein, the compositions have a circulating plasma half-life of between about 20 minutes and about 40 minutes and a tissue half life of one to several days (e.g., 1, 2, 3, 4, 5, 6, 7, 8, 9, or more days).

In certain embodiments, the compositions administered as part of the methods described herein comprise CR2-targeted USPIO nanoparticles or aggregates thereof coated with dextran or encapsulated with phospholipid. In certain embodiments, the phospholipid-encapsulated CR2-targeted USPIO nanoparticles or aggregates thereof further comprise a targeting moiety selected from the group consisting of complement receptor 2 (CR2) or a biologically-active fragment thereof, and a fusion protein comprising an antibody or fragment thereof fused to CR2 or a biologically-active fragment thereof. In certain embodiments, the dextran-coated CR2-targeted USPIO nanoparticles or aggregates thereof further comprise a targeting moiety selected from the group consisting of complement receptor 2 (CR2) or a biologically-active fragment thereof, and a fusion protein comprising an antibody or fragment thereof fused to CR2 or a biologically-active fragment thereof. In certain embodiments, the phospholipid-encapsulated CR2-targeted USPIO nanoparticles or aggregates thereof further comprise a targeting moiety comprising a fusion protein comprising an antibody or fragment thereof fused to CR2 or a biologically-active fragment thereof. In certain embodiments, the dextran-coated CR2-targeted USPIO nanoparticles or aggregates thereof further comprise a targeting moiety comprising a fusion protein comprising an antibody or fragment thereof fused to CR2 or a biologically-active fragment thereof.

In certain embodiments, the targeting moiety comprises a biologically active fragment of CR2. In certain embodiments, the biologically-active fragment of CR2 comprises the extracellular domain of CR2, short consensus repeat sequences (SCRs) 1 to 8 of CR2, or SCRs 1 and 2 of CR2. In certain embodiments, the targeting moiety comprises a fusion protein comprising an antibody fragment fused to a biologically active fragment of CR2. In certain embodiments, the fusion protein comprises the extracellular domain of CR2 fused to the Fc-domain of mouse immunoglobulin isotype $G_1$ (IgG$_1$), SCRs 1 to 8 of CR2 fused to the Fc-domain of mouse IgG$_1$, or SCRs 1 and 2 of CR2 fused to the Fc-domain of mouse IgG$_1$.

In certain embodiments, the phospholipid-encapsulated CR2-targeted USPIO nanoparticles or aggregates thereof are between about 1 nm and about 1000 nm in diameter. In certain embodiments, the phospholipid-encapsulated CR2-targeted USPIO nanoparticles or aggregates thereof are between about 5 nm and about 500 nm in diameter. In certain embodiments, the phospholipid-encapsulated CR2-targeted USPIO nanoparticles or aggregates thereof are between about 10 nm and about 100 nm in diameter. In certain embodiments, the phospholipid-encapsulated CR2-targeted USPIO nanoparticles or aggregates thereof are between about 50 nm and about 150 nm in diameter. In certain embodiments, the phospholipid-encapsulated CR2-targeted USPIO nanoparticles or aggregates thereof are between about 65 nm and about 85 nm in diameter. In certain embodiments, the phospholipid-encapsulated CR2-targeted USPIO nanoparticles or aggregates thereof are about 75 nm in diameter. In certain embodiments, the phospholipid-encapsulated CR2-targeted USPIO nanoparticles or aggregates thereof are about 150 nm in diameter. In any of the embodiments described herein, the phospholipid comprises 1,2-distearoyl-sn-glycero-3-phosphoethanolamine ("DSPE"). In certain embodiments, the phospholipid is PEGylated. In certain embodiments, the PEGylated phospholipid further comprises a functional group suitable for cross-linking with a CR2-targeting group. In certain embodiments, the functional group is an amine. In certain embodiments, the functional group is maleimide. In certain embodiments, the functional group is a thiol. In certain embodiments, the PEGylated phospholipid comprises polyethylene glycol ("PEG") at a molecular weight ranging from PEG100 to PEG5000, from PEG 500 to PEG5000, from PEG1000 to PEG5000, or from PEG2000 to PEG4000. In certain embodiments, the PEGylated phospholipid comprises PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000. In certain embodiments, the phospholipid comprises DSPE-PEG2000. In certain embodiments, the phospholipid comprises amine-functionalized DSPE-PEG2000. In certain embodiments, the phospholipid comprises thiol-functionalized DSPE-PEG2000. In certain embodiments, the phospholipid comprises maleimide-functionalized DSPE-PEG2000.

In certain embodiments, the compositions administered as part of the methods described herein comprise CR2-targeted USPIO nanoparticle aggregates between about 50 nm and about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates between about 65 nm and about 85 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates about 75 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$. In certain embodiments, the composition comprises CR2-targeted USPIO nanoparticle aggregates about 150 nm in diameter and encapsulated with phospholipid, wherein the phospholipid is amine-functionalized DSPE-PEG2000, and wherein the CR2-targeting group is a fusion protein comprising SCRs 1 and 2 of CR2 fused to the Fc-domain of mouse IgG$_1$.

In certain embodiments, the compositions administered as part of the methods described herein comprise dextran-coated CR2-targeted USPIO nanoparticles or aggregates thereof are between about 1 nm and about 1000 nm in diameter. In certain embodiments, the dextran-coated CR2-targeted USPIO nanoparticles or aggregates thereof are between about 5 nm and about 500 nm in diameter. In certain embodiments, the dextran-coated CR2-targeted USPIO nanoparticles or aggregates thereof are between about 10 nm and about 100 nm in diameter. In certain embodiments, the dextran-coated CR2-targeted USPIO nanoparticles or aggregates thereof are between about 50 nm and about 150 nm in diameter. In certain embodiments, the dextran-coated CR2-targeted USPIO nanoparticles or aggregates thereof are between about 65 nm and about 85 nm in diameter. In certain embodiments, the dextran-coated CR2-targeted USPIO nanoparticles or aggregates thereof are about 75 nm in diameter. In certain embodiments, the dextran-coated CR2-targeted USPIO nanoparticles or aggregates thereof are about 150 nm in diameter.

In any of the embodiments described herein, the compositions further comprise sterile phosphate-buffered saline ("PBS") (e.g., 1×PBS=137 mM NaCl, 10 mM Phosphate, 2.7 mM KCl, and a pH between 7.2 and 7.4). In any of the embodiments described herein, the compositions further comprise sterile normal saline (e.g., 0.9% (w/v) NaCl). In any of the embodiments described herein, the compositions further comprise sterile half normal saline (e.g., 0.45% (w/v) NaCl, sometimes also including 5% (w/v) dextrose). In any of the embodiments described herein, the compositions are provided as lyophilized compositions, and are resuspended in phosphate-buffered saline ("PBS") (e.g., 1×PBS=137 mM NaCl, 10 mM Phosphate, 2.7 mM KCl, and a pH between 7.2 and 7.4), sterile normal saline (e.g., 0.9% (w/v) NaCl), or sterile half normal saline (e.g., 0.45% (w/v) NaCl, sometimes also including 5% (w/v) dextrose) before use. In any of the embodiments described herein, the compositions are administered to provide a dose between about 1 mg/kg and about 1000 mg/kg, between about 100 mg/kg and about 1000 mg/kg, between about 250 mg/kg and about 750 mg/kg, and between about 400 mg/kg and 600 mg/kg, or a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg and about 100 mg/kg. In any of the embodiments described herein, the compositions have a circulating plasma half-life of between about 20 minutes and about 40 minutes and a tissue half life of one to several days (e.g., 1, 2, 3, 4, 5, 6, 7, 8, 9, or more days).

Articles of Manufacture Comprising CR2-Targeted Nanoparticles or Aggregates Thereof Also provided herein are articles of manufacture (e.g., kits) containing pharmaceutical compositions comprising an effective amount of bacterial-, CR2-, or C4-targeted USPIO nanoparticles or aggregates thereof as described herein, and instructions for their use in the non-invasive imaging methods described herein. Thus, in certain embodiments, the article of manufacture comprises instructions for the use of pharmaceutical compositions comprising an effective amount of bacterial-, CR2-, or C4-targeted USPIO nanoparticles or aggregates thereof in any of the methods of detecting complement-mediated inflammation in an individual as described herein. In certain embodiments, the article of manufacture comprises a lyophilized preparation of any of the pharmaceutical compositions comprising bacterial-, CR2-, or C4-targeted USPIO nanoparticles or aggregates thereof. In certain embodiments, the individual is a mammal. In certain embodiments, the mammal is a human, mouse or rat.

The article of manufacture further comprises one or more containers. Suitable containers include, for example, bottles, vials (e.g., dual chamber vials), syringes (such as single or dual chamber syringes) and test tubes. The containers may be formed from a variety of materials such as glass or plastic. In certain embodiments, the containers hold a lyophilized preparation of any of the pharmaceutical compositions comprising bacterial-, CR2-, or C4-targeted USPIO nanoparticles or aggregates thereof and optionally sterile solutions or diluents for resuspending or reconstituting a lyophilized pharmaceutical composition to a desired concentration. In certain embodiments, the article of manufacture comprises a single container comprising a frozen preparation of any of the pharmaceutical compositions comprising bacterial-, CR2-, or C4-targeted USPIO nanoparticles or aggregates thereof. The label, which is on or associated with the container, may indicate directions for resuspending, reconstituting and/or using the pharmaceutical composition. The label may further indicate that the lyophilized or frozen preparations comprising pharmaceutical composition comprising bacterial-, CR2-, or C4-targeted USPIO nanoparticles or aggregates thereof are useful or intended for subcutaneous or any other mode of administration disclosed herein. The container holding the formulation may be a single-use vial or a multi-use vial. A multi-use vial allows for repeat administrations (e.g. from 2-6 administrations) of the reconstituted pharmaceutical composition. Upon mixing the sterile solution or diluent with the lyophilized pharmaceutical composition, the final concentration of bacterial-, CR2-, or C4-targeted USPIO nanoparticles or aggregates thereof in the resuspended or reconstituted pharmaceutical composition will generally be between at least 0.1 mg/ml and at least 20 mg/ml. The kit may further include other materials desirable from a commercial, therapeutic, and user standpoint, including other buffers, diluents, filters, needles, syringes, and package inserts with instructions for use.

EXAMPLES

Example 1

Non-Invasive Detection of Alternative Complement-Mediated Inflammation in MRL/lpr Mice, an Animal Model of Lupus Nephritis Associated with Systemic Lupus Erythematosus Materials and Methods Synthesis of iron oxide nanoparticles. Ultrasmall superparamagnetic iron oxide nanoparticles were generated and functionalized for conjugation to proteins as previously described. See e.g., A. J. Barker et al., 2005, *J. Appl. Physics* 98:063528; B. A. Larsen et al., 2008, *Nanotechnol.* 19:265102. Briefly, USPIO were synthesized by a solvothermal method using an Iron (III) Acetylacetonate precursor with trioctylamine and heptanoic acid (Sigma-Aldrich, St. Louis, Mo.) as surfactants, yielding ~10 nm magnetite nanoparticles (FIG. 1A) with a hydrophobic heptanoic acid surface termination. The as-synthesized USPIO nanoparticles were resuspended in tetrahydrofuran (THF) and titrated with a 1% (v/v) solution of acetic acid until the desired level of aggregation (~75 nm) was reached. The acetic acid partially displaces the heptanoic acid on the USPIO nanoparticle surface, decreasing steric hindrance at the nanoparticle surface and permitting increased aggregation of USPIO. The aggregates of as-synthesized particles were then encapsulated using amine-functionalized phospholipids (1,2-distearoyl-sn-glycero-3-phosphoethanolamine-N-[amino(polyethylene glycol)-2000] (ammonium salt):

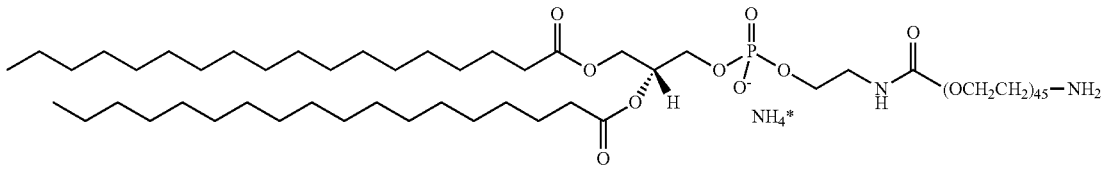

Figure 1B:
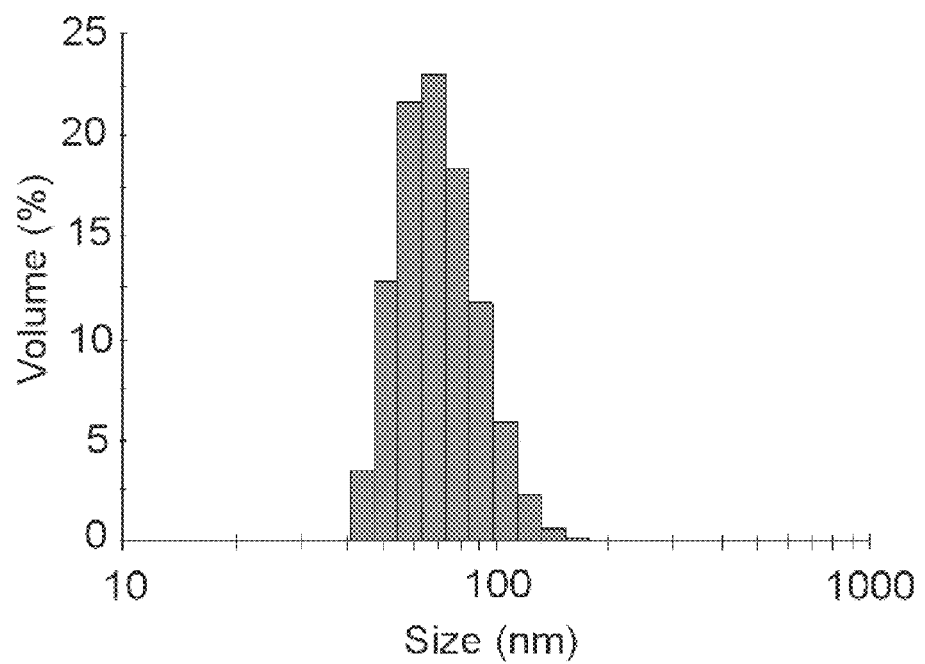

(DSPE-PEG2000-Amine) (Avanti Polar Lipids, Alabaster, Ala.). The resulting micellar USPIO nanoparticle aggregates were ~75 nm in diameter, as measured by dynamic light scattering (FIG. 1B). The USPIO aggregates and phospholipids were dried with nitrogen and maintained under vacuum for 24 hours. The iron-oxide/phospholipid mixture was resuspended in deionized water by bath sonication at 60° C. to yield amine-functionalized, phospholipid-encapsulated USPIO aggregates for subsequent protein crosslinking. The measured particle diameter was 9.7±2 nm (1151 particles measured by ImageJ particle analysis).

A recombinant protein containing the first two SCRs of CR2 linked to the Fc portion of a mouse $IgG_1$ was generated as previously described. See e.g., H. E. Gilbert et al., 2006, *J. Mol. Biol.* 356:397-412. To conjugate CR2-Fc to the USPIO nanoparticle aggregates, 1 mg of the recombinant protein (6.7 nmol) was mixed with 10 mg (1.5 nmol) of the phospholipid-encapsulated USPIO nanoparticle aggregates. Two mg of 1-ethyl-3-(3-dimethylaminopropyl)carbodiimide hydrochloride (Pierce Biotechnology, Rockford, Ill.) and 0.2 mg of N-hydroxysulfosuccinimide (Sulfo-NHS) (Pierce Biotechnology, Rockford, Ill.) were added, and the mixture was left at room temperature for two hours while vortexing every 15 minutes. The mixture was then pelleted by centrifugation at 1500 rpm, washed, and resuspended in PBS. The resulting preparation of USPIO nanoparticle aggregates contained CR2-Fc targeting groups attached to the PEGylated head group of the phospholipid via an amide linkage.

Flow cytometry. To confirm conjugation of CR2-Fc to the surface of the USPIO nanoparticle aggregates, 10 μg of conjugated or unconjugated particles were incubated with 1 μg of Cy3-labeled anti-mouse IgG (Jackson ImmunoResearch Laboratories, Inc., West Grove, Pa.) or with biotinylated mouse anti-CR2 (mAb 171; J. M. Guthridge et al., 2001, *J. Immunol.* 167:5758-5766) for 40 minutes on ice. The biotinylated antibody was then detected with FITC-streptavidin. The particles were washed in PBS and resuspended in 0.5 ml of PBS. Surface staining was detected with a BD Biosciences FACSCalibur™ machine and analyzed with BD Biosciences CellQuest™ Pro software (BD Biosciences, San Jose, Calif.). To test whether the conjugated particles bound to C3 opsonized cells, Chinese hamster ovary cells (CHO cells; ATCC, Manassas, Va.) were incubated with 10% normal mouse serum for 1 hour at room temperature. Surface deposition of C3 was confirmed by staining with a FITC-conjugated goat anti-mouse C3 antibody (Cappel/ICN, now MP Biomedicals, Solon, Ohio) and detection by flow cytometry. The binding of CR2-Fc conjugated USPIO nanoparticle aggregates to CHO cells was performed by incubating opsonized or unmanipulated CHO cells with conjugated USPIO nanoparticle aggregates for 40 minutes at 4° C. Cy3 conjugated anti-mouse IgG was used to detect the conjugated USPIO, and forward and side scatter were used to identify the CHO cells. Binding of the USPIO nanoparticle aggregates to CHO cells was then identified by examining Cy3 staining in the CHO cell population.

MRI image acquisition and imaging parameters. To evaluate in vivo anatomical and molecular abnormalities, 16 week-old MRL/lpr mice (n=5; Jackson Laboratories, Bar Harbor, Me.) and C57BL/6 wild-type animals (n=6; Jackson Laboratories, Bar Harbor, Me.) were assessed by MRI. The proton density weighted MRI (for anatomical assessment) and series of T2-weighted MRI (for molecular assessment based on T2 values) scans were performed at baseline and 4, 24, 48 and 72 hours after USPIO nanoparticle aggregate injection (untargeted as well as CR2-Fc conjugated). The baseline MRI was performed in the morning prior to the USPIO nanoparticle aggregate injection. The mice were injected with 0.4 mg (10-16 mg/kg) of CR2-Fc conjugated or non-targeted USPIO nanoparticle aggregates via the tail vein in a volume of less than 200 μl. At each time point, animals were weighed, anesthetized by isoflurane (4% for induction, followed by 2-2.5% isoflurane during the scan) and placed into a mouse animal bed. Anesthetized animals were then inserted into a 4.7 Tesla Bruker PharmaScan® MRI scanner (Bruker BioSpin Inc., Fremont, Calif.). A Bruker volume coil (38 mm diameter) tuned to the $^1$H frequency of 200 MHz was used for radiofrequency (RF) transmission and reception. First, a fast spin echo Rapid Acquisition with Relaxation Enhancement (RARE) tri-pilot scan was performed for anatomical localization for all three dimensions (axial, coronal and sagittal). Then high-resolution RARE proton density (PD)-weighted images were acquired: field of view (FOV)=4.00 cm; slice thickness 1.0 mm; inter-slice distance 1.0 mm (no gap allowed); echo time/repetition time (TE/TR)=31.9/3,000 ms; slice orientation axial; number of slices 16; number of averages 2; matrix size 256×256; total acquisition time 4 min 16 sec. Subsequently, a series of multiple slice multiple echo (MSME) T2-weighted pulses with 16 various echo times was applied for precise T2 mapping and calculation of T2 relaxation times. The scan parameters were as followed: FOV=4.00 cm; slice thickness 1.50 mm; inter-slice distance 1.80 mm; TR=2,650 ms; TE1=10 ms; TE2=20 ms (followed by 30, 40, 50, 60, 70, 80, 90, 100, 110, 120, 130, 140, 150, 160 ms); slice orientation axial; number of slices 16; number of averages 2; matrix size 128×256; total acquisition time 11 min. After 1 min of pre-contrast images, 0.1 mmol/kg OMNISCAN® was injected using the tail vein catheter. T1-weighted gadolinium-enhanced MRI scans were continuously taken for another 14 minutes.

MRI imaging data analysis. All images were processed using Bruker ParaVision® software (version PV3.0.2; Bruker BioSpin Inc., Fremont, Calif.). For PD-weighted MRI, only visualization of abnormal lymphadenopathy and kidney size was taken into consideration. For the series of T2-weighted images with 16 various echo-time, a low-volume region of interest (ROI) was placed onto muscle, fat, spleen, left and right kidney cortex, left and right outer medulla and left and right inner medulla on a corresponding slice for each set of TE series. From the basic physics of magnetic resonance (MR), the signal intensity of an MR image is proportional to tissue $T_1$ and $T_2$ relaxation times, as well as applied repetition and echo times. Thus, for the series of 16 echo times in our MR protocol, a Bruker-based t2vtr-fitting function based on the equations below was applied in order to calculate $T_2$ relaxation time as a function of signal intensity and TE values of each image: (1) $S=M_0(1-e^{-TR/T1})e^{-TE/T2}$; and (2) $S=C_2(e^{-TE/T2})$, where $C_2=M_0(1-e^{-TR/T1})$ is a constant (which gets fitted). All calculated $T_2$ times are given in milliseconds (ms).

Immunofluorescence microscopy and histology. For immunofluorescence, sagittal sections of the kidneys were snap-frozen in OCT compound (Sakura Finetek, Torrance, Calif.). Four μm sections were cut with a cryostat and stored at −70° C. The slides were later fixed with acetone and stained with FITC-conjugated anti-mouse C3 (ICN/Cappel, now MP Biomedicals, Solon, Ohio), mouse IgG (Jackson ImmunoResearch Laboratories, Inc., West Grove, Pa.). Sections were counterstained with hematoxylin (Vector Laboratories, Inc., Burlingame, Calif.). For iron staining, sagittal sections were fixed, embedded in paraffin, and four μm sections were cut and stained with periodic acid-Schiff stain or Perl's Prussian Blue.

Statistical analysis. All numerical data for T2 values are presented as mean±standard deviation from the replicate experiments. One-way analysis of variance (ANOVA) method was used to determine differences between groups (wild-type vs. lupus mice at a defined time point, as well as differences between various time points in the same group). Tukey's test was used as a post-hoc test in combination with ANOVA to test for significances between groups. The significance level was set at $p<0.05$ for all tests (SigmaPlot®-version 9.01, Systat Software, Point Richmond, Calif. and SPSS version 14.0, SPSS Inc., Chicago, Ill.).

Results

Figure 2A:
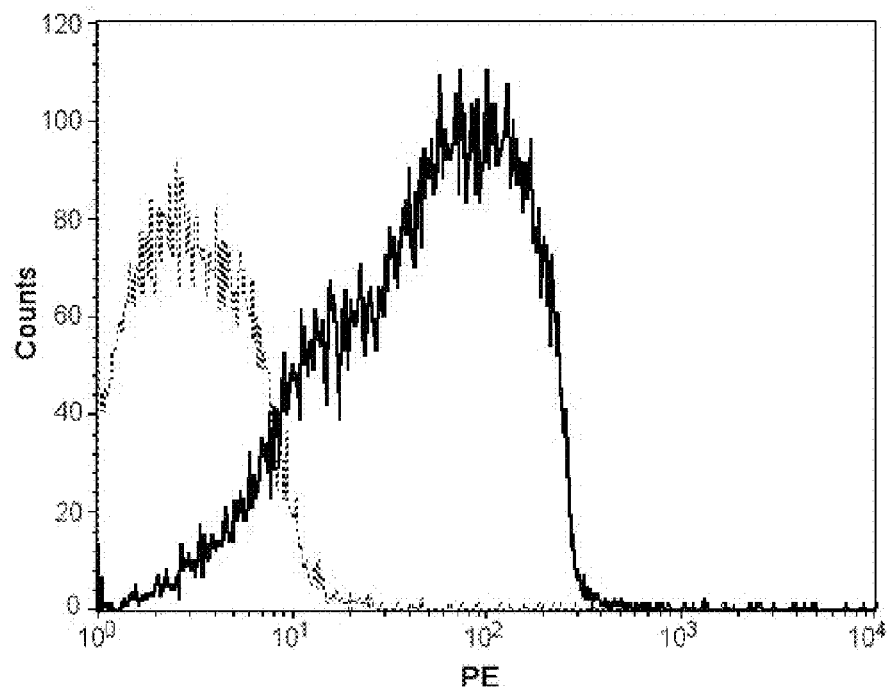
FIGS. 2A-2C depict data which confirms the successful conjugation of CR2-Fc to the surface of USPIO nanoparticles.
Figure 2B:
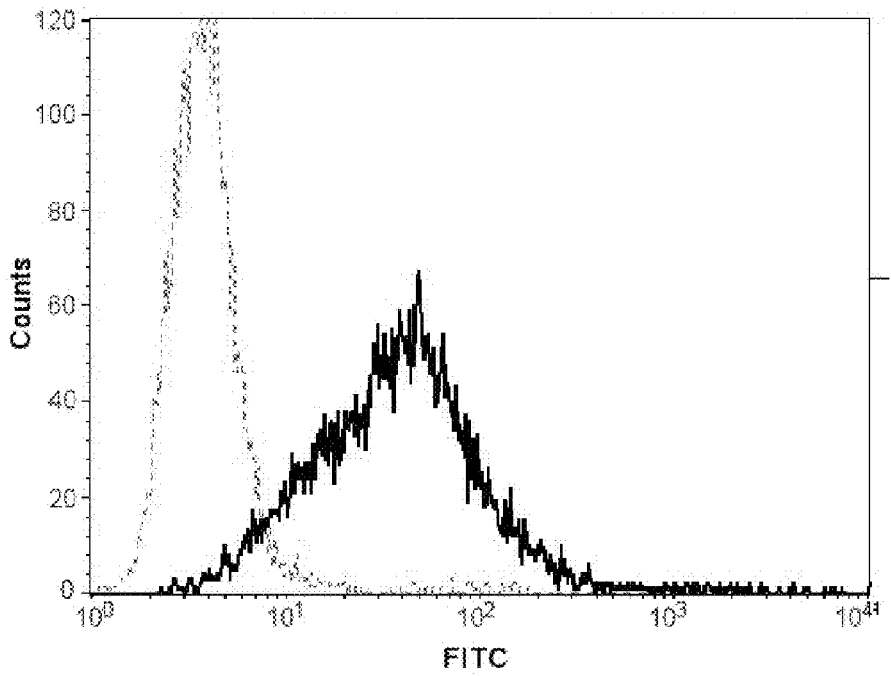
Figure 2C:
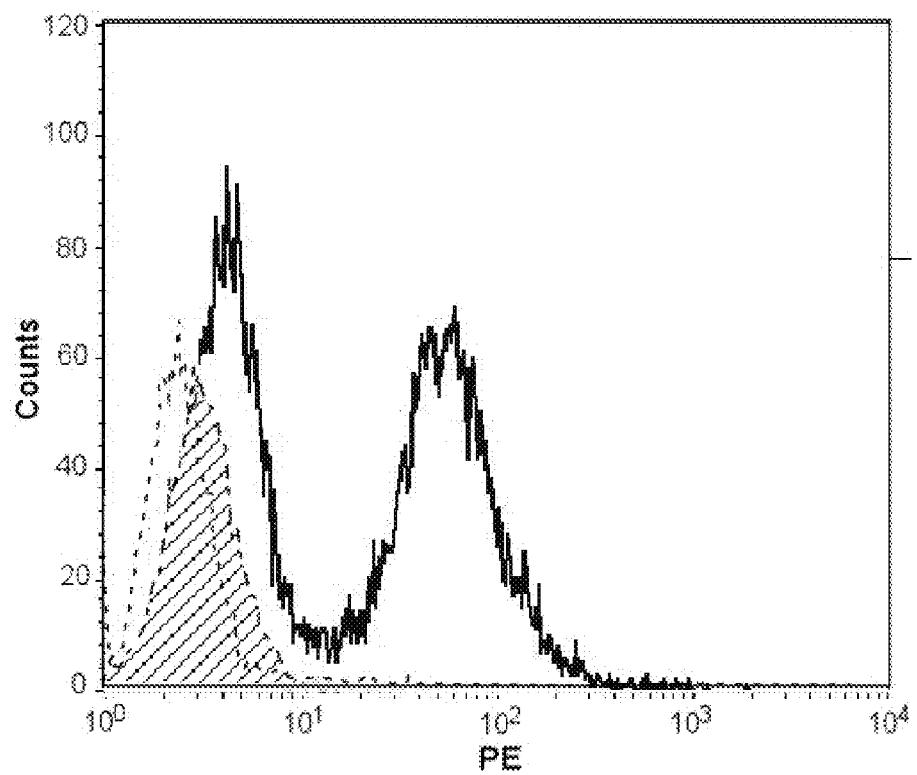

CR2-conjugated iron oxide nanoparticle aggregates bind to cell-bound C3. Ultrasmall superparamagnetic iron oxide (USPIO) nanoparticles and USPIO nanoparticle aggregates were generated as described above (FIGS. 1A-B). A recombinant protein comprising the first two SCRs of human CR2, containing the C3d binding domain, linked to the Fc region of a mouse $IgG_1$ molecule ("CR2-Fc") (H. E. Gilbert et al., 2006, *J. Mol. Biol.* 356:397-412) was conjugated to the surface of the lipid-encapsulated USPIO nanoparticle aggregates by cross-linking the carboxyl-terminus of the Fc region to surface amines on the lipid coating. The presence of CR2-Fc on the surface of the USPIO nanoparticle aggregates was confirmed by flow cytometry (FIG. 2A). Chinese hamster ovary (CHO) cells were next incubated with normal mouse serum in order to opsonize them with C3 activation fragments (FIG. 2B). When CR2-Fc conjugated USPIO nanoparticle aggregates and unconjugated USPIO nanoparticle aggregates were incubated with C3 opsonized CHO cells, the CR2-Fc conjugated USPIO nanoparticle aggregates bound to the CHO cells, but the unconjugated USPIO nanoparticle aggregates did not (FIG. 2C). Furthermore, CR2-Fc conjugated USPIO nanoparticle aggregates did not bind to CHO cells that had not been treated with serum. These experiments confirmed that the CR2-Fc conjugated to the surface of the USPIO nanoparticle aggregates mediated binding of those aggregates to cell-bound breakdown fragments of complement protein C3.

Stability of CR2-targeted USPIO nanoparticle aggregates was tested as follows. CR2-Fc conjugated USPIO nanoparticle aggregates were incubated in normal serum for up to one month. Aliquots were removed at various intervals for analysis by forward and side scatter and flow cytometry as described herein. After one week, the CR2-targeted USPIO nanoparticle aggregates were stable and the surface CR2 was intact. After one month, the appearance of the particles by forward and side scatter remained the same, though the surface CR2 appeared degraded. Thus, the USPIO nanoparticle aggregates were stable for up to one month in normal serum, while the CR2-targeting group was susceptible to degradation, presumably by serum proteases.

Figure 3:
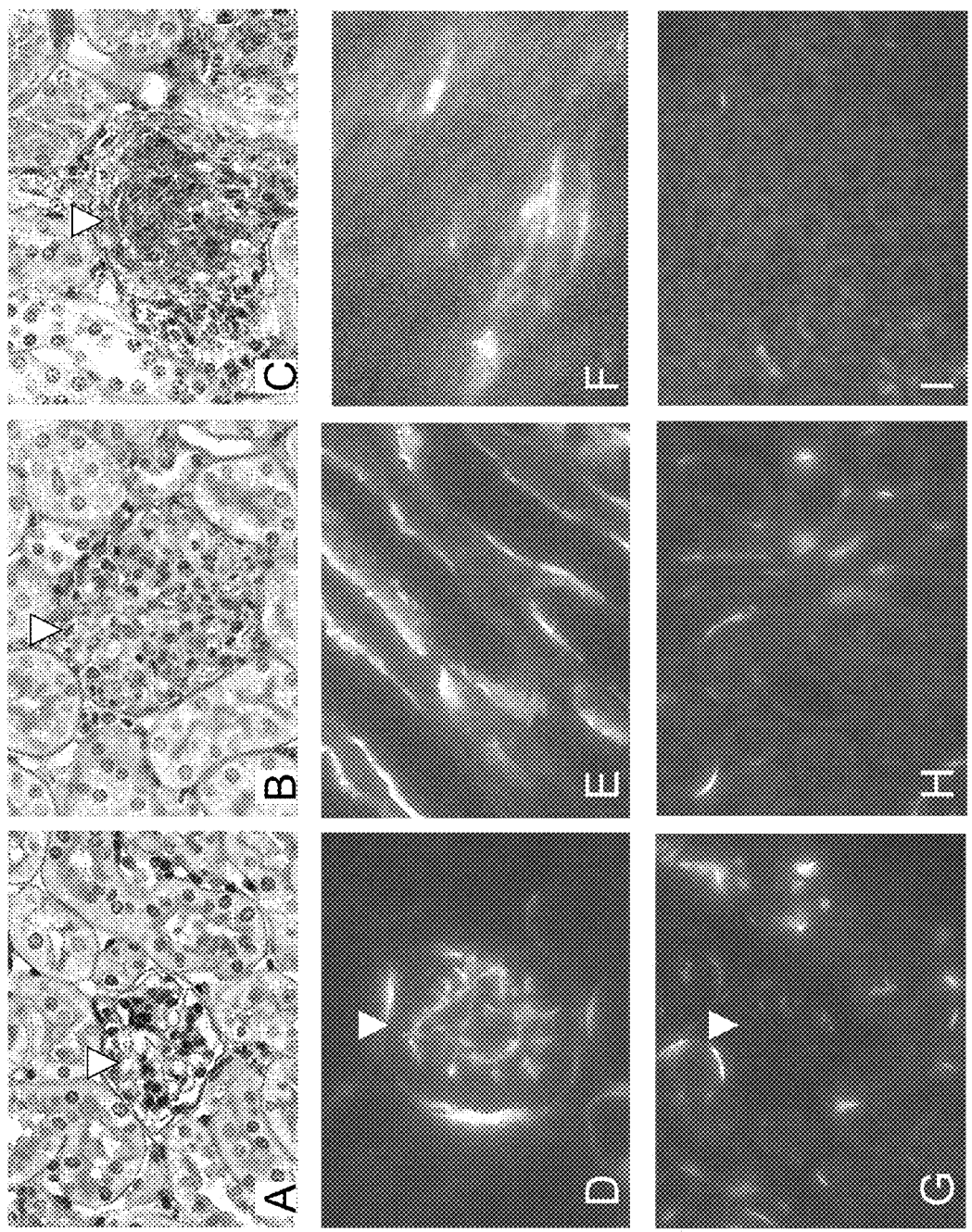
FIGS. 3A-3I depict periodic acid-Schiff (PAS) staining demonstrating the normal glomerulus (arrowhead) of a wild-type mouse (FIG. 3A), proliferative changes in a 16-week old MRL/lpr mouse (FIG. 3B), and glomerulosclerosis in an 18-week old MRL/lpr mouse (FIG. 3C).

Immune complexes deposit in the glomeruli of MRL/lpr mice and activate complement. The MRL/lpr strain of mice is homozygous for the lpr (lymphoproliferation) mutation in the gene for the Fas antigen. See e.g., M. Adachi et al., 1993, *Proc. Nat'l Acad. Sci. USA* 90:1756-1760; R. Watanabe-Fukunaga et al., 1992, *Nature* 356:314-317. MRL/lpr mice spontaneously develop lupus-like renal disease characterized by glomerular immune-complex deposition and complement activation. See e.g., M. H. Foster, 1999, *Semin. Nephrol.* 19:12-24. This model has been widely utilized to examine the role of complement activation in the pathogenesis of lupus-like renal disease. See e.g., C. Atkinson et al., 2008, *J. Immunol.* 180:1231-1238; L. Bao et al., 2002, *J. Immunol.* 168:3601-3607; S. Einav et al., 2002, *J. Immunol.* 168:1036-1041; M. K. Elliott et al., 2004, *Kidney Int.* 65:129-138; H. Sekine et al., 2001, *J. Immunol.* 166:6444-6451; H. Watanabe et al., 2000, *J. Immunol.* 164:786-794. Examination of the kidneys of 16 week-old mice confirmed that proliferative changes were present in the glomeruli but were not present in wild-type mice (FIGS. 3A-B). By 18-20 weeks glomerulosclerosis and tubulointerstitial fibrosis were apparent (FIG. 3C). Immunofluorescence microscopy confirmed the presence of C3 in the glomeruli of 16 week-old MRL/lpr mice (FIG. 3D). In the MRL/lpr mice, C3 was also deposited along the tubular basement membrane in the outer medulla (FIG. 3E) and in the inner medulla (FIG. 3F). As has been described elsewhere (J. M. Thurman et al., 2003, *J. Immunol.* 170:1517-1523), small C3 deposits are present along Bowman's capsule and the tubular basement membrane of unmanipulated wild-type mice (FIGS. 3G, 3H, and 3I).

Figure 4A:
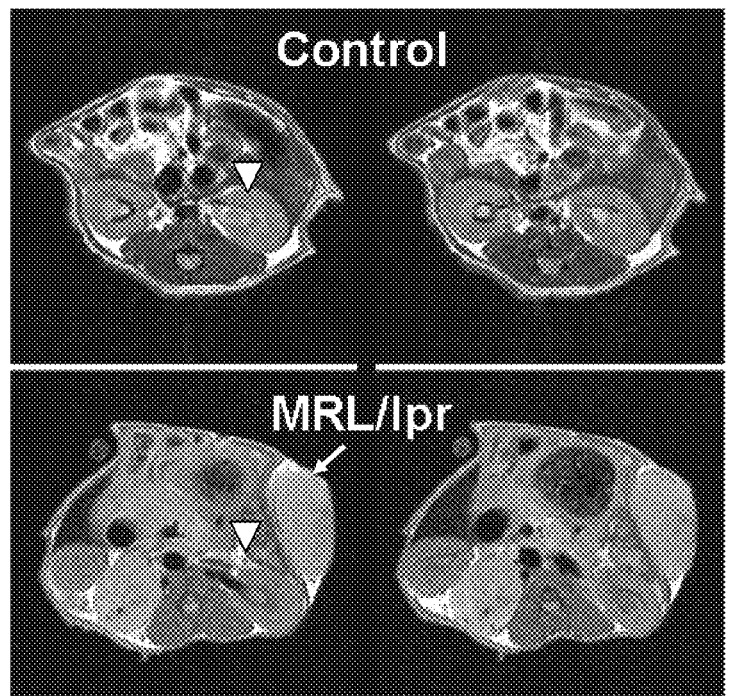
FIGS. 4A-4B depict abdominal MRI analyses of MRL/lpr mice used as a model system for lupus nephritis (lower panels) and wild-type mice (upper panels).
Figure 4B:
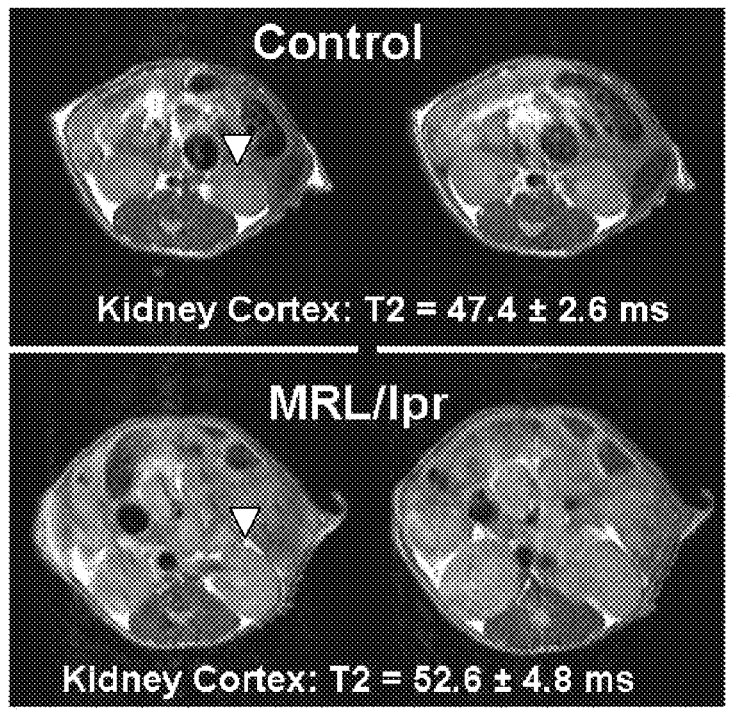

Kidneys of MRL/lpr mice have higher baseline T2-values than those of wild-type mice. Various anatomic and morphological abnormalities were present in MR images of 16 week-old MRL/lpr mice. The body weights of MRL/lpr mice (35.1±2.3 g) were higher than those of the wild-type mice (27.6±2.9 g; P=0.006; Table 1). Proton-density-weighted rapid acquisition with relaxation enhancement (RARE) MRI images in the MRL/lpr mice demonstrated multiple areas of lymphadenopathy and hyperplasia of the lymphoid organs (FIG. 4A). Multiple slice multiple echo (MSME) T2-weighted MRI series (FIG. 4B) showed similar T2 relaxation time values in the muscle, fat and spleens of both groups (Table 1). T2-weighted signal intensity and corresponding T2 relaxation time values in the renal cortex of MRL/lpr mice were significantly higher than in wild-type animals (Table 1). The higher T2 values in the kidneys of MRL/lpr mice likely represent higher water content, possibly the result of tissue inflammation.

TABLE 1

T2 relaxation time values in various organs at baseline and 4, 24, 48 and 72 hours after injection of CR2-targeted USPIO nanoparticles.

| | Baseline | | 4 hrs post | | 24 hrs post | | 48 hrs post | | 72 hrs post | |
|---|---|---|---|---|---|---|---|---|---|---|
| Organ | MRL/lpr | WT | MRL/lpr | WT | MRL/lpr | WT | MRL/lpr | WT | MRL/lpr | WT |
| Cortex | $52.6 \pm 4.8^A$ | $47.4 \pm 2.6$ | $47.1 \pm 3.6^B$ | $47.6 \pm 4.8$ | $46.0 \pm 3.3^C$ | $49.2 \pm 4.1$ | $47.5 \pm 3.5^C$ | $50.7 \pm 3.7$ | $49.8 \pm 5.32$ | $50.0 \pm 3.4$ |
| O-Medu | $68.8 \pm 8.4^A$ | $61.3 \pm 4.9$ | $57.4 \pm 3.4^B$ | $63.3 \pm 5.8$ | $55.5 \pm 3.4^C$ | $68.9 \pm 10.0$ | $54.9 \pm 3.2^C$ | $64.2 \pm 4.9$ | $56.4 \pm 6.5^C$ | $62.5 \pm 6.3$ |
| I-Medu | $93.3 \pm 10.3$ | $89.7 \pm 3.0$ | $77.7 \pm 8.3^B$ | $91.1 \pm 8.2$ | $66.3 \pm 6.4^C$ | $92.7 \pm 7.4$ | $67.6 \pm 7.1^C$ | $91.9 \pm 6.0$ | $77.6 \pm 9.6^C$ | $92.2 \pm 6.3$ |
| Spleen | $41.8 \pm 1.0$ | $38.8 \pm 4.0$ | $41.5 \pm 5.4$ | $40.2 \pm 7.3$ | $43.2 \pm 4.1$ | $38.6 \pm 4.2$ | $44.5 \pm 2.9$ | $34.5 \pm 4.8$ | $44.4 \pm 6.5$ | $38.2 \pm 7.1$ |
| Muscle | $33.1 \pm 0.8$ | $32.8 \pm 2.6$ | $31.0 \pm 3.1$ | $37.0 \pm 1.4$ | $32.7 \pm 3.1$ | $33.0 \pm 0.3$ | $35.5 \pm 2.8$ | $33.0 \pm 1.3$ | $35.4 \pm 1.3$ | $33.0 \pm 0.4$ |
| Fat | $103.0 \pm 5.1$ | $100.4 \pm 7.8$ | $102.0 \pm 3.0$ | $100.0 \pm 4.1$ | $99.4 \pm 6.4$ | $100.2 \pm 2.8$ | $102.3 \pm 3.1$ | $97.8 \pm 3.3$ | $101.7 \pm 3.5$ | $98.7 \pm 3.9$ |
| Body Wt. (g) | $35.1 \pm 2.3^B$ | $27.6 \pm 2.9$ | $35.1 \pm 6.3$ | $27.6 \pm 3.1$ | $34.4 \pm 2.8$ | $25.5 \pm 2.3$ | $34.8 \pm 2.2$ | $26.4 \pm 2.2$ | $34.6 \pm 2.4$ | $26.8 \pm 2.6$ |

Figure 5:
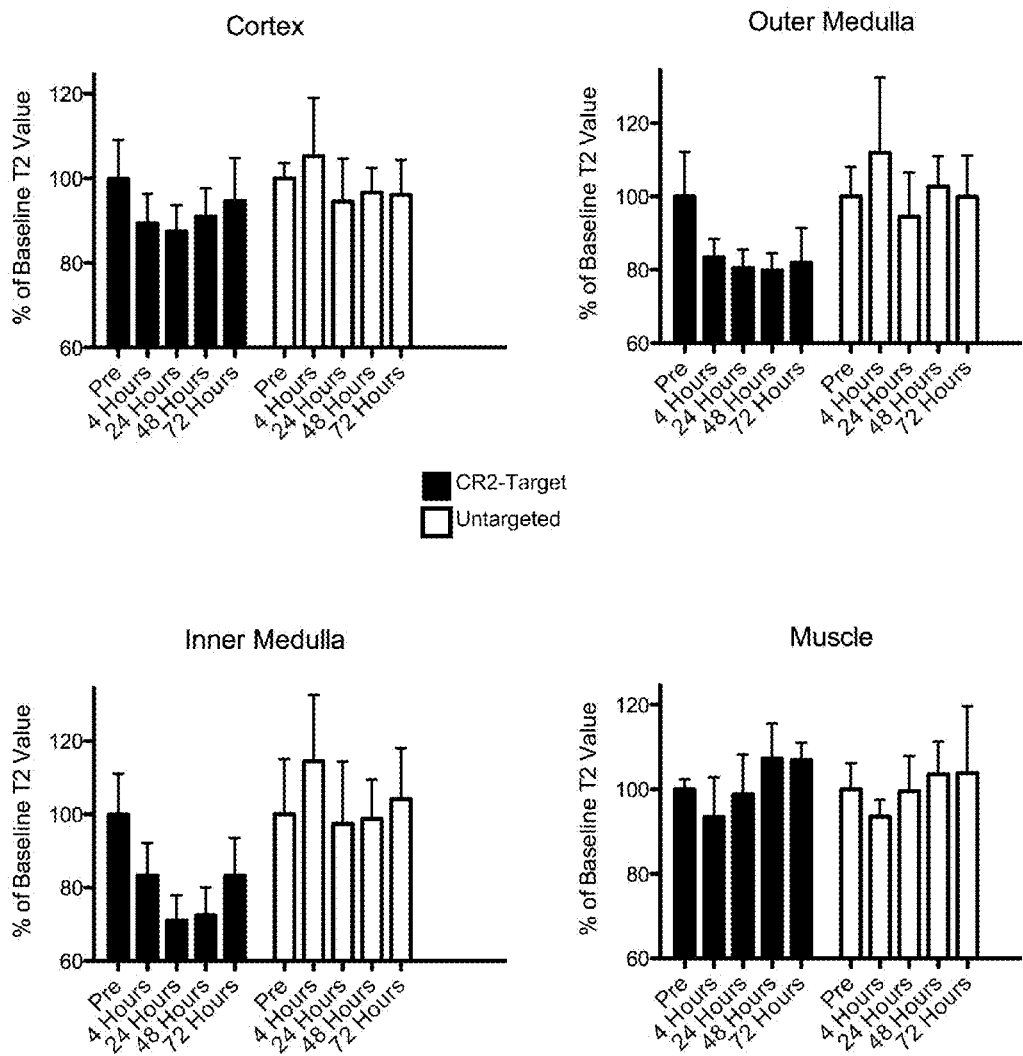
FIG. 5 depicts relative changes in $T_2$ values after injection with CR2-targeted and untargeted USPIO nanoparticles in MRL/lpr mice. $T_2$-weighted signal intensity was measured at various time-points in the cortex, inner and outer medulla as well as in the muscle (as an unchanged comparison) of MRL/lpr mice. After injection with untargeted USPIO nanoparticles, no changes in $T_2$-signal intensity were seen in the cortex, outer or inner medulla or in the muscle. In contrast, after injection of CR2-targeted USPIO nanoparticles, significant decreases in the $T_2$-relaxation time were seen in the cortex, outer and inner medulla. The changes were observed as early as 4 hrs after injection and persisted up to 72 hours after injection. Data are given as mean±S.D. (n=5). For evaluation of kidneys, 10 repetitions were performed since both the left and right kidneys of each animal were evaluated. *$P<0.05$ versus pre-injection baseline.

Abbreviations: I-Medu, inner medulla; O-Medu, outer medulla; WT, wild-type.
Data are given as means ± S.D. n = 5 for MRL/lpr and n = 3 for wild-type mice for examination of spleen, muscle and fat.
For evaluation of kidneys the number of repetitions were n = 10 and n = 6, respectively, since left and right kidneys of each animal were evaluated.
[A] $p < 0.05$ MRL/lpr versus wild-type at baseline;
[B] $p < 0.01$ MRL/lpr versus wild-type at baseline;
[C] $p < 0.05$ post-USPIO injection versus baseline values Untargeted USPIO nanoparticle aggregates do not alter the T2-weighted signal in the kidneys of MRL/lpr mice. MRL/lpr mice and wild-type mice were injected intravenously with unconjugated USPIO nanoparticle aggregates, and $T_2$-weighted images were obtained 4, 24, 48, and 72 hours post injection. $T_2$-relaxation times in the cortex, outer medulla, and inner medulla of the kidneys were determined, and $T_2$ values in the kidneys of MRL/lpr mice did not significantly decrease after injection of unconjugated USPIO nanoparticle aggregates (FIG. 5). In wild-type mice, a small decrease in the signal in the outer medulla of the kidney was observed 48 hours after injection with the unconjugated USPIO nanoparticle aggregates (data not shown). The spleens of wild-type mice also demonstrated slightly decreased T2 values 48 hours after injection of the USPIO nanoparticle aggregates, but decreased T2 values were not seen in the spleens of MRL/lpr mice. No significant decreases in the T2-weighted signal intensity in muscle and fat were observed in either MRL/lpr or wild-type animals at any time-point. No changes in body weights were observed after injection of unconjugated USPIO nanoparticle aggregates at any time point.

USPIOs conjugated to CR2-Fc reduce T2 relaxation times in the kidneys of MRL/lpr mice. After one week the same mice were injected with CR2-targeted USPIO nanoparticle aggregates and $T_2$-weighted images were again obtained after 4, 24, 48, and 72 hours. $T_2$-MRI series were then used for precise calculations of the $T_2$-relaxation times. Unmanipulated wild-type mice have deposited C3 on Bowman's capsule and in the tubulointerstitium (FIGS. 3G-I). Injection of wild-type mice with the CR2-conjugated USPIO nanoparticle aggregates, however, did not cause a significant reduction in the $T_2$-weighted signal in any region of the kidneys (Table 1). Signal in the spleen, muscle, and fat of wild-type mice also did not change after injection with CR2-conjugated USPIO nanoparticle aggregates.

Figure 6:
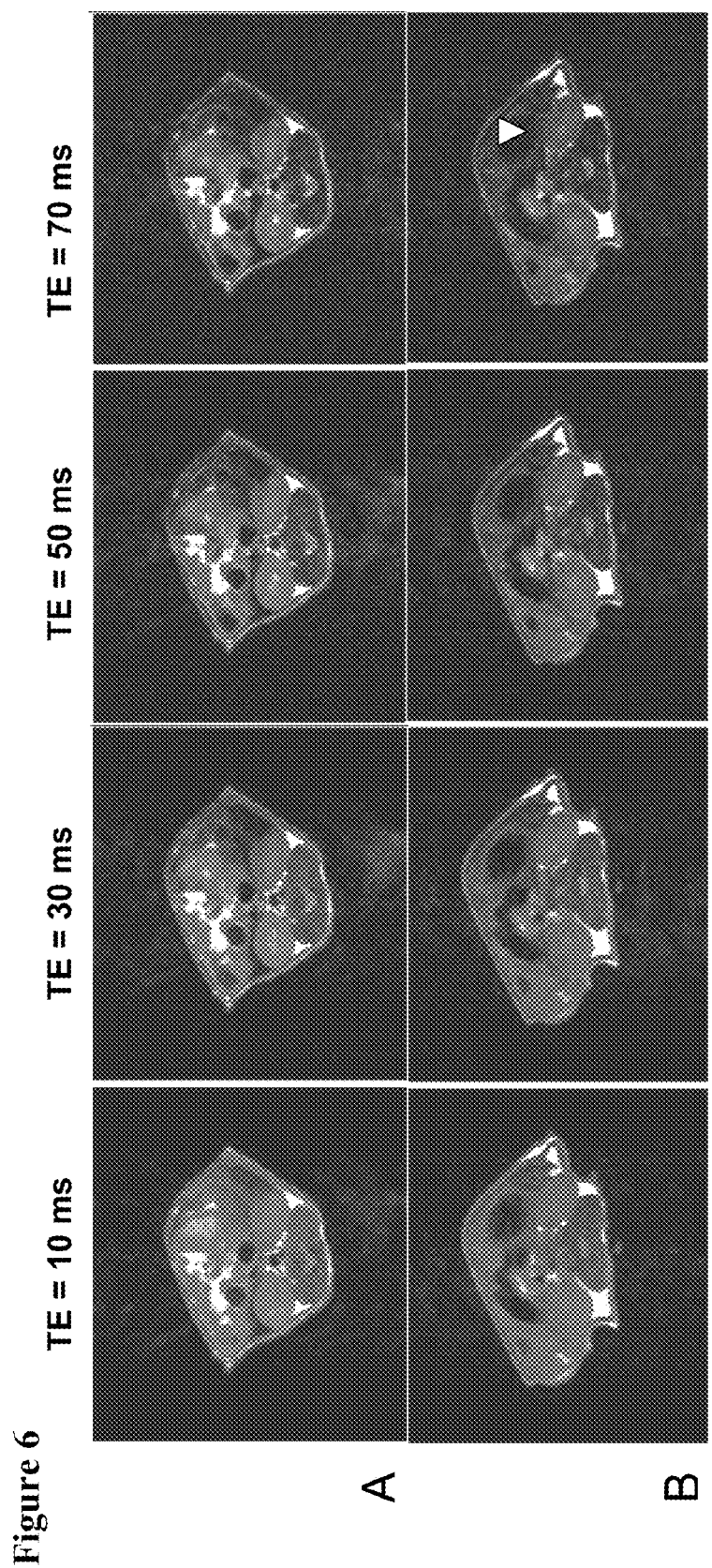
FIGS. 6A-6B depict $T_2$-weighted MSME MR images (TR=2,650 ms) of a wild-type (FIG. 6A) and an MRL/lpr mouse (FIG. 6B) 48 hours after injection of CR2-conjugated SPIOs. Images at echo times (TE) of 10, 30, 50, and 70 ms are shown. A decrease in $T_2$ signal intensity in the kidney of the MRL/lpr mouse is visible in all regions of the kidney, particularly at TE=70 ms (arrowhead).
Figure 7:
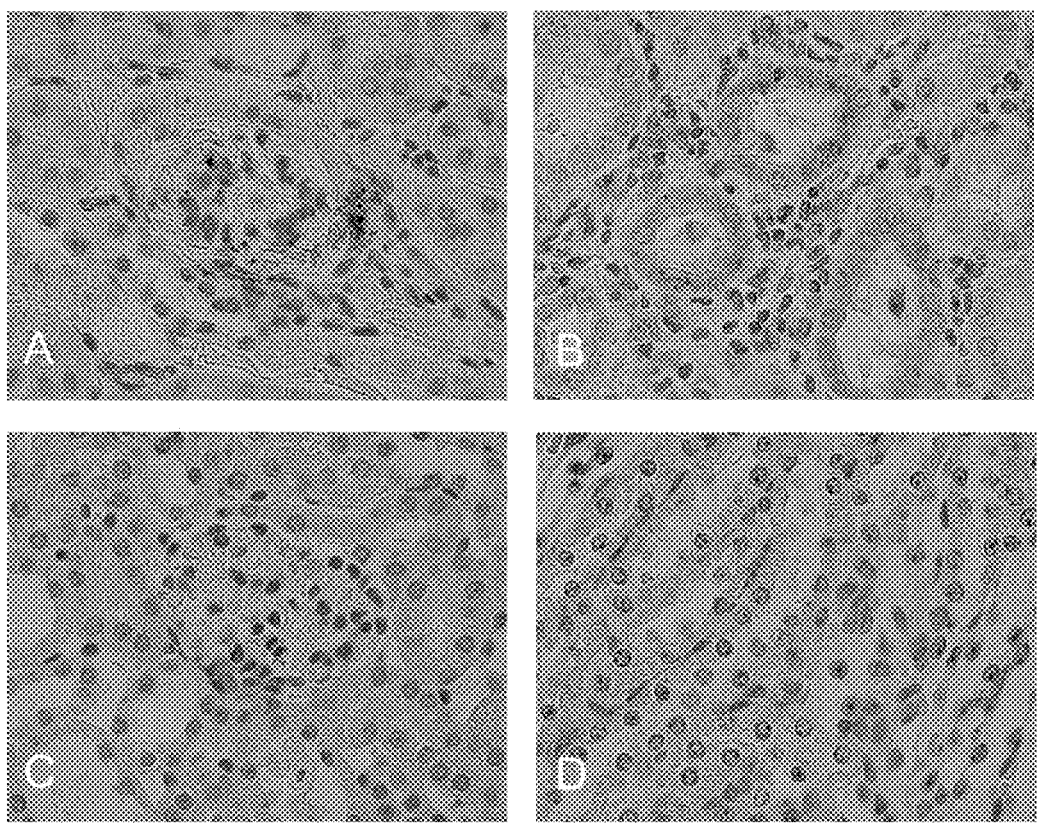
FIGS. 7A-7D show that iron can be detected in the glomeruli and renal tubules of MRL/lpr mice injected with CR2-targeted USPIO nanoparticles. MRL/lpr and wild-type mice were sacrificed at the completion of the study. Kidney sections were stained with Perl's Prussian Blue to detect iron deposits in the tissue. In the MRL/lpr mice, iron could be detected in the glomeruli (FIG. 7A) and in renal tubules (FIG. 7B). In wild-type mice, iron was not seen in any glomeruli (FIG. 7C) or renal tubules (FIG. 7D). Original magnification ×400.

In marked contrast, injection of CR2-targeted USPIO nanoparticle aggregates into MRL/lpr mice caused a significant decrease in the $T_2$-weighted signal in the kidneys (FIG. 5; Table 1). Signal in the cortex was reduced from 4 to 48 hours after injection, and signal in the outer and inner medulla was reduced from 4 to 72 hours after injection (FIG. 5). No significant reduction in signal was seen in muscle, fat or spleen tissue of MRL/lpr mice (Table 1). Although the baseline (pre-enhanced) $T_2$-relaxation times in the cortex were higher in MRL/lpr mice than in wild-type controls, injection of the CR2-targeted USPIO nanoparticle aggregates caused a reduction in the $T_2$-relaxation times in the kidneys of MRL/lpr below the values of the control mice (Table 1). Darkening in the MRL/lpr kidneys is clearly visible on the $T_2$-MRI series with increasing echo times (FIG. 6B). No changes were seen in the $T_2$-relaxation times of kidneys in wild-type mice after injection with the CR2-targeted USPIO nanoparticle aggregates, confirming the specificity of this method.

Location of iron and macrophages in the kidneys of mice injected with CR2-targeted USPIO nanoparticles. Kidneys were obtained from the mice at the end of the study, and stained for iron with Perl's Prussian Blue (FIGS. 7A-D). Iron was still detectable in some glomeruli and in tubules of MRL/lpr mice injected with the targeted USPIO nanoparticle aggregates, but was not seen in the kidneys of control mice.

Discussion

USPIO nanoparticles and aggregates thereof have been used as a contrast agent for MR imaging. The experiments described herein used a recombinant form of CR2 protein to target such particles to sites of complement activation. In vitro assays confirmed that CR2 linked to the surface of the aggregates mediated binding to cells that were opsonized with C3 activation fragments, and that the particles did not bind to cells in that were not opsonized with C3 fragments.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

DESCRIPTION OF SEQUENCES
SEQ ID NO: 1 [amino acid sequence of full-length human CR2 protein]:
MGAAGLLGVFLALVAPGVLGISCGSPPPILNGRISYYSTPIAVGTVIRYS

CSGTFRLIGEKSLLCITKDKVDGTWDKPAPKCEYFNKYSSCPEPIVPGGY

KIRGSTPYRHGDSVTFACKTNFSMNGNKSVWCQANNMWGPTRLPTCVSVF

PLECPALPMIHNGHHTSENVGSIAPGLSVTYSCESGYLLVGEKIINCLSS

-continued

GKWSAVPPTCEEARCKSLGRFPNGKVKEPPILRVGVTANFFCDEGYRLQG

PPSSRCVIAGQGVAWTKMPVCEEIFCPSPPPILNGRHIGNSLANVSYGSI

VTYTCDPDPEEGVNFILIGESTLRCTVDSQKTGTWSGPAPRCELSTSAVQ

CPHPQILRGRMVSGQKDRYTYNDTVIFACMFGFTLKGSKQIRCNAQGTWE

PSAPVCEKECQAPPNILNGQKEDRHMVRFDPGTSIKYSCNPGYVLVGEES

IQCTSEGVWTPPVPQCKVAACEATGRQLLTKPQHQFVRPDVNSSCGEGYK

LSGSVYQECQGTIPWFMEIRLCKEITCPPPPVIYNGAHTGSSLEDFPYGT

TVTYTCNPGPERGVEFSLIGESTIRCTSNDQERGTWSGPAPLCKLSLLAV

QCSHVHIANGYKISGKEAPYFYNDTVTFKCYSGFTLKGSSQIRCKRDNTW

DPEIPVCEKGCQPPPGLHHGRHTGGNTVFFVSGMTVDYTCDPGYLLVGNK

SIHCMPSGNWSPSAPRCEETCQHVRQSLQELPAGSRVELVNTSCQDGYQL

TGHAYQMCQDAENGIWFKKIPLCKVIHCHPPPVIVNGKHTGMMAENFLYG

NEVSYECDQGFYLLGEKNCSAEVILKAW1LERAFPQCLRSLCPNPEVKHG

YKLNKTHSAYSHNDIVYVDCNPGFIMNGSRVIRCHTDNTWVPGVPTCIKK

AFIGCPPPPKTPNGNHTGGNIARFSPGMSILYSCDQGYLVVGEPLLLCTH

EGTWSQPAPHCKEVNCSSPADMDGIQKGLEPRKMYQYGAVVTLECEDGYM

LEGSPQSQCQSDHQWNPPLAVCRSRSLAPVLCGIAAGLILLTFLIVITLY

VISKHRERNYYTDTSQKEAFHLEAREVYSVDPYNPAS.

SEQ ID NO: 2 [amino acid sequence of full-length mouse CR2 protein]:
MLTWFLFYFSEISCDPPPEVKNARKPYYSLPIVPGTVLRYTCSPSYRLIG

EKAIFCISENQVHATWDKAPPICESVNKTISCSDPIVPGGFMNKGSKAPF

RHGDSVTFTCKANFTMKGSKTVWCQANEMWGPTALPVCESDFPLECPSLP

TIHNGHHTGQHVDQFVAGLSVTYSCEPGYLLTGKKTIKCLSSGDWDGVIP

TCKEAQCEHPGKFPNGQVKEPLSLQVGTTVYFSCNEGYQLQGQPSSQCVI

VEQKAIWTKKPVCKEILCPPPPPVRNGSHTGSFSENVPYGSTVTYTCDPS

PEKGVSFTLIGEKTINCTTGSQKTGIWSGPAPYCVLSTSAVLCLQPKIKR

GQILSILKDSYSYNDTVAFSCEPGFTLKGNRSIRCNAHGTWEPPVPVCEK

GCQAPPKIINGQKEDSYLLNFDPGTSIRYSCDPGYLLVGEDTIHCTPEGK

WTPITPQCTVAECKPVGPHLFKRPQNQFIRTAVNSSCDEGFQLSESAYQL

CQGTIPWFIEIRLCKEITCPPPPVIHNGTHTWSSSEDVPYGTVVTYMCYP

GPEEGVKFKLIGEQTIHCTSDSRGRGSWSSPAPLCKLSLPAVQCTDVHVE

NGVKLTDNKAPYFYNDSVMFKCDDGYILSGSSQIRCKANNTWDPEKPLCK

KEGCEPMRVHGLPDDSHIKLVKRTCQNGYQLTGYTYEKCQNAENGTWFKK

IEVCTVILCQPPPKIANGGHTGMMAKHFLYGNEVSYECDEGFYLLGEKSL

QCVNDSKGHGSWSGPPPQCLQSSPLTHCPDPEVKHGYKLNKTHSAFSHND

IVHFVCNQGFIMNGSHLIRCHTNNTWLPGVPTCIRKASLGCQSPSTIPNG

NHTGGSIARFPPGMSVMYSCYQGFLMAGEARLICTHEGTWSQPPPFCKEV

NCSFPEDTNGIQKGFQPGKTYRFGATVTLECEDGYTLEGSPQSQCQDDSQ

WNPPLALCKYRRWSTIPLICGISVGSALIILMSVGFCMILKHRESNYYTK

TRPKEGALHLETREVYSIDPYNPAS.

SEQ ID NO: 3 [amino acid sequence of the extracellular domain of human CR2 protein]:
ISCGSPPPILNGRISYYSTPIAVGTVIRYSCSGTFRLIGEKSLLCITKDK
VDGTWDKPAPKCEYFNKYSSCPEPIVPGGYKIRGSTPYRHGDSVTFACKT
NFSMNGNKSVWCQANNMWGPTRLPTCVSVFPLECPALPMIHNGHHTSENV
GSIAPGLSVTYSCESGYLLVGEKIINCLSSGKWSAVPPTCEEARCKSLGR
FPNGKVKEPPILRVGVTANFFCDEGYRLQGPPSSRCVIAGQGVAWTKMPV
CEEIFCPSPPPILNGRHIGNSLANVSYGSIVTYTCDPDPEEGVNFILIGE
STLRCTVDSQKTGTWSGPAPRCELSTSAVQCPHPQILRGRMVSGQKDRYT
YNDTVIFACMFGFTLKGSKQIRCNAQGTWEPSAPVCEKECQAPPNILNGQ
KEDRHMVRFDPGTSIKYSCNPGYVLVGEESIQCTSEGVWTPPVPQCKVAA
CEATGRQLLTKPQHQFVRPDVNSSCGEGYKLSGSVYQECQGTIPWFMEIR
LCKEITCPPPPVIYNGAHTGSSLEDFPYGTTVTYTCNPGPERGVEFSLIG
ESTIRCTSNDQERGTWSGPAPLCKLSLLAVQCSHVHIANGYKISGKEAPY
FYNDTVTFKCYSGFTLKGSSQIRCKADNTWDPEIPVCEKETCQHVRQSLQ
ELPAGSRVELVNTSCQDGYQLTGHAYQMCQDAENGIWFKKIPLCKVIHCH
PPPVIVNGKHTGMMAENFLYGNEVSYECDQGFYLLGEKKLQCRSDSKGHG
SWSGPSPQCLRSPPVTRCPNPEVKHGYKLNKTHSAYSHNDIVYVDCNPGF
IMNGSRVIRCHTDNTWVPGVPTCIKKAFIGCPPPPKTPNGNHTGGNIARF
SPGMSILYSCDQGYLLVGEALLLCTHEGTWSQPAPHCKEVNCSSPADMDG
IQKGLEPRKMYQYGAVVTLECEDGYMLEGSPQSQCQSDHQWNPPLAVCRS
R.

SEQ ID NO: 4 [amino acid sequence of the extracellular domain of mouse CR2 protein]:
ISCDPPPEVKNARKPYYSLPIVPGTVLRYTCSPSYRLIGEKAIFCISENQ
VHATWDKAPPICESVNKTISCSDPIVPGGFMNKGSKAPFRHGDSVTFTCK
ANFTMKGSKTVWCQANEMWGPTALPVCESDFPLECPSLPTIHNGHHTGQH
VDQFVAGLSVTYSCEPGYLLTGKKTIKCLSSGDWDGVIPTCKEAQCEHPG
KFPNGQVKEPLSLQVGTTVYFSCNEGYQLQGQPSSQCVIVEQKAIWTKKP
VCKEILCPPPPPVRNGSHTGSFSENVPYGSTVTYTCDPSPEKGVSFTLIG
EKTINCTTGSQKTGIWSGPAPYCVLSTSAVLCLQPKIKRGQILSILKDSY
SYNDTVAFSCEPGFTLKGNRSIRCNAHGTWEPPVPVCEKGCQAPPKIING
QKEDSYLLNFDPGTSIRYSCDPGYLLVGEDTIHCTPEGKWTPITPQCTVA
ECKPVGPHLFKRPQNQFIRTAVNSSCDEGFQLSESAYQLCQGTIPWFIEI
RLCKEITCPPPPVIHNGTHTWSSSEDVPYGTVVTYMCYPGPEEGVKFKLI
GEQTIHCTSDSRGRGSWSSPAPLCKLSLPAVQCTDVHVENGVKLTDNKAP
YFYNDSVMFKCDDGYILSGSSQIRCKANNTWDPEKPLCKKEGCEPMRVHG
LPDDSHIKLVKRTCQNGYQLTGYTYEKCQNAENGTWFKKIEVCTVILCQP
PPKIANGGHTGMMAKHFLYGNEVSYECEDGFYLLGEKSLQCVNDSKGHGS
WSGPPPQCLQSSPLTHCPDPEVKHGYKLNKTHSAFSHNDIVHFVCNQGFI
MNGSHLIRCHTNNTWLPGVPTCIRKASLGCQSPSTIPNGNHTGGSIARFP
PGMSVMYSCYQGFLMAGEARLICTHEGTWSQPPPFCKEVNCSFPEDTNGI

QKGFQPGKTYRFGATVTLECEDGYTLEGSPQSQCQDDSQWNPPLALCKYR
RW.

SEQ ID NO: 5 [amino acid sequence of SCRs 1 to 8 of human CR2 protein]:
ISCGSPPPILNGRISYYSTPIAVGTVIRYSCSGTFRLIGEKSLLCITKDK
VDGTWDKPAPKCEYFNKYSSCPEPIVPGGYKIRGSTPYRHGDSVTFACKT
NFSMNGNKSVWCQANNMWGPTRLPTCVSVFPLECPALPMIHNGHHTSENV
GSIAPGLSVTYSCESGYLLVGEKIINCLSSGKWSAVPPTCEEARCKSLGR
FPNGKVKEPPILRVGVTANFFCDEGYRLQGPPSSRCVIAGQGVAWTKMPV
CEEIFCPSPPPILNGRHIGNSLANVSYGSIVTYTCDPDPEEGVNFILIGE
STLRCTVDSQKTGTWSGPAPRCELSTSAVQCPHPQILRGRMVSGQKDRYT
YNDTVIFACMFGFTLKGSKQIRCNAQGTWEPSAPVCEKECQAPPNILNGQ
KEDRHMVRFDPGTSIKYSCNPGYVLVGEESIQCTSEGVWTPPVPQCKVAA
CEATGRQLLTKPQHQFVRPDVNSSCGEGYKLSGSVYQECQGTIPWFMEIR
LCKE.

SEQ ID NO: 6 [amino acid sequence of SCRs 1 to 8 of mouse CR2 protein]:
ISCDPPPEVKNARKPYYSLPIVPGTVLRYTCSPSYRLIGEKAIFCISENQ
VHATWDKAPPICESVNKTISCSDPIVPGGFMNKGSKAPFRHGDSVTFTCK
ANFTMKGSKTVWCQANEMWGPTALPVCESDFPLECPSLPTIHNGHHTGQH
VDQFVAGLSVTYSCEPGYLLTGKKTIKCLSSGDWDGVIPTCKEAQCEHPG
KFPNGQVKEPLSLQVGTTVYFSCNEGYQLQGQPSSQCVIVEQKAIWTKKP
VCKEILCPPPPPVRNGSHTGSFSENVPYGSTVTYTCDPSPEKGVSFTLIG
EKTINCTTGSQKTGIWSGPAPYCVLSTSAVLCLQPKIKRGQILSILKDSY
SYNDTVAFSCEPGFTLKGNRSIRCNAHGTWEPPVPVCEKGCQAPPKIING
QKEDSYLLNFDPGTSIRYSCDPGYLLVGEDTIHCTPEGKWTPITPQCTVA
ECKPVGPHLFKRPQNQFIRTAVNSSCDEGFQLSESAYQLCQGTIPWFIEI
RLCKE.

SEQ ID NO: 7 [amino acid sequence of SCRs 1 and 2 of human CR2 protein]:
ISCGSPPPILNGRISYYSTPIAVGTVIRYSCSGTFRLIGEKSLLCITKDK
VDGTWDKPAPKCEYFNKYSSCPEPIVPGGYKIRGSTPYRHGDSVTFACKT
NFSMNGNKSVWCQANNMWGPTRLPTCVS.

SEQ ID NO: 8 [amino acid sequence of SCRs 1 and 2 of mouse CR2 protein]:
ISCDPPPEVKNARKPYYSLPIVPGTVLRYTCSPSYRLIGEKAIFCISENQ
VHATWDKAPPICESVNKTISCSDPIVPGGFMNKGSKAPFRHGDSVTFTCK
ANFTMKGSKTVWCQANEMWGPTALPVCES.

SEQ ID NO: 9 [amino acid sequence of SCRs 1 and 2 of human CR2 protein fused to the Fc domain of mouse IgGi (CR2 sequences are underlined)]:
<u>ISCGSPPPILNGRISYYSTPIAVGTVIRYSCSGTFRLIGEKSLLCITKDK</u>
<u>VDGTWDKPAPKCEYFNKYSSCPEPIVPGGYKIRGSTPYRHGDSVTFACKT</u>
<u>NFSMNGNKSVWCQANNMWGPTRLPTCVSVFPLEG</u>SIEGRGGSELADPEVP
RDCGCKPCICTVPEVSSVFIFPPKPKDVLTITLTPKVTCVVVDISKDDPE
VQFSWFVDDVEVHTAQTQPREEQFNSTFRSVSELPIMHQDWLNGKEFKCR

```
VNSAAFPAPIEKTISKTKGRPKAPQLYTIPPPKEQMAKDKVSLTCMITDF
FPEDITVEWQWNGQPAENYKNTQPIMNTNESYFVYSKLNVQKSNWEAGNT
FTCSVLHEGLHNHHTEKSLSHSPGK.

SEQ ID NO: 10 [amino acid sequence of human C3d
protein]:
HLIVTPSGCGEQNMIGMTPTVIAVHYLDETEQWEKFGLEKRQGALELIKK
GYTQQLAFRQPSSAFAAFVKRAPSTWLTAYVVKVFSLAVNLIAIDSQVLC
GAVKWLILEKQKPDGVFQEDAPVIHQEMIGGLRNNNEKDMALTAFVLISL
QEAKDICEEQVNSLPGSITKAGDFLEANYMNLQRSYTVAIAGYALAQMGR
LKGPLLNKFLTTAKDKNRWEDPGKQLYNVEATSYALLALLQLKDFDFVPP
VVRWLNEQRYYGGGYGSTQATFMVFQALAQYQKDAPDHQELNLDVSLQLP
SR.

SEQ ID NO: 11 [amino acid sequence of human C3dg
protein]:
EGVQKEDIPPADLSDQVPDTESETRILLQGTPVAQMTEDAVDAERLKHLI
VTPSGCGEQNMIGMTPTVIAVHYLDETEQWEKFGLEKRQGALELIKKGYT
QQLAFRQPSSAFAAFVKRAPSTWLTAYVVKVFSLAVNLIAIDSQVLCGAV
KWLILEKQKPDGVFQEDAPVIHQEMIGGLRNNNEKDMALTAFVLISLQEA
KDICEEQVNSLPGSITKAGDFLEANYMNLQRSYTVAIAGYALAQMGRLKG
PLLNKFLTTAKDKNRWEDPGKQLYNVEATSYALLALLQLKDFDFVPPVVR
WLNEQRYYGGGYGSTQATFMVFQALAQYQKDAPDHQELNLDVSLQLPSR.

SEQ ID NO: 12 [amino acid sequence of human iC3b
protein]:
EGVQKEDIPPADLSDQVPDTESETRILLQGTPVAQMTEDAVDAERLKHLI
VTPSGCGEQNMIGMTPTVIAVHYLDETEQWEKFGLEKRQGALELIKKGYT
QQLAFRQPSSAFAAFVKRAPSTWLTAYVVKVFSLAVNLIAIDSQVLCGAV
KWLILEKQKPDGVFQEDAPVIHQEMIGGLRNNNEKDMALTAFVLISLQEA
KDICEEQVNSLPGSITKAGDFLEANYMNLQRSYTVAIAGYALAQMGRLKG
PLLNKFLTTAKDKNRWEDPGKQLYNVEATSYALLALLQLKDFDFVPPVVR
WLNEQRYYGGGYGSTQATFMVFQALAQYQKDAPDHQELNLDVSLQLPSR.

SEQ ID NO: 13 [amino acid sequence of human C3b
protein]:
SNLDEDIIAEENIVSRSEFPESWLWNVEDLKEPPKNGISTKLMNIFLKDS
ITTWEILAVSMSDKKGICVADPFEVTVMQDFFIDLRLPYSVVRNEQVEIR
AVLYNYRQNQELKVRVELLHNPAFCSLATTKRRHQQTVTIPPKSSLSVPY
VIVPLKTGLQEVEVKAAVYHHFISDGVRKSLKVVPEGIRMNKTVAVRTLD
PERLGREGVQKEDIPPADLSDQVPDTESETRILLQGTPVAQMTEDAVDAE
RLKHLIVTPSGCGEQNMIGMTPTVIAVHYLDETEQWEKFGLEKRQGALEL
IKKGYTQQLAFRQPSSAFAAFVKRAPSTWLTAYVVKVFSLAVNLIAIDSQ
VLCGAVKWLILEKQKPDGVFQEDAPVIHQEMIGGLRNNNEKDMALTAFVL
ISLQEAKDICEEQVNSLPGSITKAGDFLEANYMNLQRSYTVAIAGYALAQ
MGRLKGPLLNKFLTTAKDKNRWEDPGKQLYNVEATSYALLALLQLKDFDF
VPPVVRWLNEQRYYGGGYGSTQATFMVFQALAQYQKDAPDHQELNLDVSL
QLPSRSSKITHRIHWESASLLRSEETKENEGFTVTAEGKGQGTLSVVTMY
HAKAKDQLTCNKFDLKVTIKPAPETEKRPQDAKNTMILEICTRYRGDQDA TMSILDISMMTGFAPDTDDLKQLANGVDRYISKYELDKAFSDRNTLIIYL
DKVSHSEDDCLAFKVHQYFNVELIQPGAVKVYAYYNLEESCTRFYHPEKE
DGKLNKLCRDELCRCAEENCFIQKSDDKVTLEERLDKACEPGVDYVYKTR
LVKVQLSNDFDEYIMAIEQTIKSGSDEVQVGQQRTFISPIKCREALKLEE
KKHYLMWGLSSDFWGEKPNLSYIIGKDTWVEHWPEEDECQDEENQKQCQD
LGAFTESMVVFGCPN.

SEQ ID NO: 14 [cDNA sequence of human CD5 signal
peptide]:
ATGCCCATGGGGTCTCTGCAACCGCTGGCCACCTTGTACCTGCTGGGGAT
GCTGGTCGCTTCCTGCCTCGGA.

SEQ ID NO: 15 [amino acid sequence of human CD5
signal peptide]:
MPMGSLQPLATLYLLGMLVAS.

SEQ ID NO: 16 [cDNA sequence of human CR2 signal
peptide, short version]:
ATGGGCGCCGCGGGCCTGCTCGGGGTTTTCTTGGCTCTCGTCGCACCGGG
G.

SEQ ID NO: 17 [amino acid sequence of human CR2
signal peptide, long version]:
MGAAGLLGVFLALVAPG.

SEQ ID NO: 18
[cDNA sequence of human CR2 signal peptide, long
version]:
ATGGGAGCCGCTGGTCTGCTCGGCGTGTTCCTCGCCTTGGTGGCACCTGG
CGTCCTGGGC.

SEQ ID NO: 19 [amino acid sequence of human CR2
signal peptide, long version]:
MGAAGLLGVFLALVAPGVLG.

SEQ ID NO: 20 [amino acid sequence of full-length
S. aureus N315 immune subversion protein (Sbi)]:
MKNKYISKLLVGAATITLATMISNGEAKASENTQQTSTKHQTTQNNYVTD
QQKAFYQVLHLKGITEEQRNQYIKTLREHPERAQEVFSESLKDSKNPDRR
VAQQNAFYNVLKNDNLTEQEKNNYIAQIKENPDRSQQVWVESVQSSKAKE
RQNIENADKAIKDFQDNKAPHDKSAAYEANSKLPKDLRDKNNRFVEKVSI
EKAIVRHDERVKSANDAISKLNEKDSIENRRLAQREVNKAPMDVKEHLQK
QLDALVAQKDAEKKVAPKVEAPQIQSPQIEKPKAESPKVEVPQIQSPKVE
VPQSKLLGYYQSLKDSFNYGYKYLTDTYKSYKEKYDTAKYYYNTYYKYKG
AIDQTVLTVLGSGSKSYIQPLKVDDKNGYLAKSYAQVRNYVTESINTGKV
LYTFYQNPTLVKTAIKAQETASSIKNTLSNLLSFWK.

SEQ ID NO: 21 [amino acid sequence of a fragment
of S. aureus N315 Sbi protein comprising the first
four N-terminal domains (Sbi-I-II-III-IV) of the
full-length Sbi protein]:
KASENTQQTSTKHQTTQNNYVTDQQKAFYQVLHLKGITEEQRNQYIKTLR
EHPERAQEVFSESLKDSKNPDRRVAQQNAFYNVLKNDNLTEQEKNNYIAQ
IKENPDRSQQVWVESVQSSKAKERQNIENADKAIKDFQDNKAPHDKSAAY
EANSKLPKDLRDKNNRFVEKVSIEKAIVRHDERVKSANDAISKLNEKDSI
ENRRLAQREVNKAPMDVKEHLQKQLDALVAQKDAEKKVA.
```

SEQ ID NO: 22 [amino acid sequence of a fragment of S. aureus N315 Sbi protein comprising the third and fourth N-terminal domains (Sbi-III-IV) of the full length Sbi protein]:
ERQNIENADKAIKDFQDNKAPHDKSAAYEANSKLPKDLRDKNNRFVEKVS

IEKAIVRHDERVKSANDAISKLNEKDSIENRRLAQREVNKAPMDVKEHLQ

KQLDALVAQKDAEKKVA.

SEQ ID NO: 23 [amino acid sequence of a fragment of S. aureus N315 Sbi protein comprising the first four N-terminal domains (Sbi-I-II-III-IV) fused to the Fc domain of mouse IgGi (Sbi protein sequences are underlined)]:
KASENTQQTSTKHQTTQNNYVTDQQKAFYQVLHLKGITEEQRNQYIKTLR

EHPERAQEVFSESLKDSKNPDRRVAQQNAFYNVLKNDNLTEQEKNNYIAQ

IKENPDRSQQVWVESVQSSKAKERQNIENADKAIKDFQDNKAPHDKSAAY

EANSKLPKDLRDKNNRFVEKVSIEKAIVRHDERVKSANDAISKLNEKDSI

ENRRLAQREVNKAPMDVKEHLQKQLDALVAQKDAEKKVAGSIEGRGGSEL

ADPEVPRDCGCKPCICTVPEVSSVFIFPPKPKDVLTITLTPKVTCVVVDI

SKDDPEVQFSWFVDDVEVHTAQTQPREEQFNSTFRSVSELPIMHQDWLNG

KEFKCRVNSAAFPAPIEKTISKTKGRPKAPQLYTIPPPKEQMAKDKVSLT

CMITDFFPEDITVEWQWNGQPAENYKNTQPIMNTNESYFVYSKLNVQKSN

WEAGNTFTCSVLHEGLHNHHTEKSLSHSPGK.

SEQ ID NO: 24 [amino acid sequence of Fc fragment of mouse IgGi]:
GSIEGRGGSELADPEVPRDCGCKPCICTVPEVSSVFIFPPKPKDVLTITL

TPKVTCVVVDISKDDPEVQFSWFVDDVEVHTAQTQPREEQFNSTFRSVSE

LPIMHQDWLNGKEFKCRVNSAAFPAPIEKTISKTKGRPKAPQLYTIPPPK

EQMAKDKVSLTCMITDFFPEDITVEWQWNGQPAENYKNTQPIMNTNESYF

VYSKLNVQKSNWEAGNTFTCSVLHEGLHNHHTEKSLSHSPGK.

SEQ ID NO: 25 [amino acid sequence of human C4 protein]:
MRLLWGLIWASSFFTLSLQKPRLLLFSPSVVHLGVPLSVGVQLQDVPRGQ

VVKGSVFLRNPSRNNVPCSPKVDFTLSSERDFALLSLQVPLKDAKSCGLH

QLLRGPEVQLVAHSPWLKDSLSRTTNIQGINLLFSSRRGHLFLQTDQPIY

NPGQRVRYRVFALDQKMRPSTDTITVMVENSHGLRVRKKEVYMPSSIFQD

DFVIPDISEPGTWKISARFSDGLESNSSTQFEVKKYVLPNFEVKITPGKP

YILTVPGHLDEMQLDIQARYIYGKPVQGVAYVRFGLLDEDGKKTFFRGLE

SQTKLVNGQSHISLSKAEFQDALEKLNMGITDLQGLRLYVAAAIIESPGG

EMEEAELTSWYFVSSPFSLDLSKTKRHLVPGAPFLLQALVREMSGSPASG

IPVKVSATVSSPGSVPEVQDIQQNTDGSGQVSIPIIIPQTISELQLSVSA

GSPHPAIARLTVAAPPSGGPGFLSIERPDSRPPRVGDTLNLNLRAVGSGA

TFSHYYYMILSRGQIVFMNREPKRTLTSVSVFVDHHLAPSFYFVAFYYHG

DHPVANSLRVDVQAGACEGKLELSVDGAKQYRNGESVKLHLETDSLALVA

LGALDTALYAAGSKSHKPLNMGKVFEAMNSYDLGCGPGGGDSALQVFQAA

GLAFSDGDQWTLSRKRLSCPKEKTTRKKRNVNFQKAINEKLGQYASPTAK

RCCQDGVTRLPMMRSCEQRAARVQQPDCREPFLSCCQFAESLRKKSRDKG

QAGLQRALEILQEEDLIDEDDIPVRSFFPENWLWRVETVDRFQILTLWLP

DSLTTWEIHGLSLSKTKGLCVATPVQLRVFREFHLHLRLPMSVRRFEQLE

LRPVLYNYLDKNLTVSVHVSPVEGLCLAGGGGLAQQVLVPAGSARPVAFS

VVPTAAAAVSLKVVARGSFEFPVGDAVSKVLQIEKEGAIHREELVYELNP

LDHRGRTLEIPGNSDPNMIPDGDFNSYVRVTASDPLDTLGSEGALSPGGV

ASLLRLPRGCGEQTMIYLAPTLAASRYLDKTEQWSTLPPETKDHAVDLIQ

KGYMRIQQFRKADGSYAAWLSRDSSTWLTAFVLKVLSLAQEQVGGSPEKL

QETSNWLLSQQQADGSFQDPCPVLDRSMQGGLVGNDETVALTAFVTIALH

HGLAVFQDEGAEPLKQRVEASISKANSFLGEKASAGLLGAHAAAITAYAL

SLTKAPVDLLGVAHNNLMAMAQETGDNLYWGSVTGSQSNAVSPTPAPRNP

SDPMPQAPALWIETTAYALLHLLLHEGKAEMADQASAWLTRQGSFQGGFR

STQDTVIALDALSAYWIASHTTEERGLNVTLSSTGRNGFKSHALQLNNRQ

IRGLEEELQFSLGSKINVKVGGNSKGTLKVLRTYNVLDMKNTTCQDLQIE

VTVKGHVEYTMEANEDYEDYEYDELPAKDDPDAPLQPVTPLQLFEGRRNR

RRREAPKVVEEQESRVHYTVCIWRNGKVGLSGMAIADVTLLSGFHALRAD

LEKLTSLSDRYVSHFETEGPHVLLYFDSVPTSRECVGFEAVQEVPVGLVQ

PASATLYDYYNPERRCSVFYGAPSKSRLLATLCSAEVCQCAEGKCPRQRR

ALERGLQDEDGYRMKFACYYPRVEYGFQVKVLREDSRAAFRLFETKITQV

LHFTKDVKAAANQMRNFLVRASCRLRLEPGKEYLIMGLDGATYDLEGHPQ

YLLDSNSWIEEMPSERLCRSTRQRAACAQLNDFLQEYGTQGCQV.

SEQ ID NO: 26 [amino acid sequence of human C4b protein]:
ALEILQEEDLIDEDDIPVRSFFPENWLWRVETVDRFQILTLWLPDSLTTW

EIHGLSLSKTKGLCVATPVQLRVFREFHLHLRLPMSVRRFEQLELRPVLY

NYLDKNLTVSVHVSPVEGLCLAGGGGLAQQVLVPAGSARPVAFSVVPTAA

AAVSLKVVARGSFEFPVGDAVSKVLQIEKEGAIHREELVYELNPLDHRGR

TLEIPGNSDPNMIPDGDFNSYVRVTASDPLDTLGSEGALSPGGVASLLRL

PRGCGEQTMIYLAPTLAASRYLDKTEQWSTLPPETKDHAVDLIQKGYMRI

QQFRKADGSYAAWLSRDSSTWLTAFVLKVLSLAQEQVGGSPEKLQETSNW

LLSQQQADGSFQDPCPVLDRSMQGGLVGNDETVALTAFVTIALHHGLAVF

QDEGAEPLKQRVEASISKANSFLGEKASAGLLGAHAAAITAYALSLTKAP

VDLLGVAHNNLMAMAQETGDNLYWGSVTGSQSNAVSPTPAPRNPSDPMPQ

APALWIETTAYALLHLLLHEGKAEMADQASAWLTRQGSFQGGFRSTQDTV

IALDALSAYWIASHTTEERGLNVTLSSTGRNGFKSHALQLNNRQIRGLEE

ELQFSLGSKINVKVGGNSKGTLKVLRTYNVLDMKNTTCQDLQIEVTVKGH

VEYTMEANEDYEDYEYDELPAKDDPDAPLQPVTPLQLFEG.

SEQ ID NO: 27 [amino acid sequence of human C4d protein]:
TLEIPGNSDPNMIPDGDFNSYVRVTASDPLDTLGSEGALSPGGVASLLRL

PRGCGEQTMIYLAPTLAASRYLDKTEQWSTLPPETKDHAVDLIQKGYMRI

QQFRKADGSYAAWLSRDSSTWLTAFVLKVLSLAQEQVGGSPEKLQETSNW

LLSQQQADGSFQDPCPVLDRSMQGGLVGNDETVALTAFVTIALHHGLAVF

QDEGAEPLKQRVEASISKANSFLGEKASAGLLGAHAAAITAYALSLTKAP

PVDLLGVAHNNLMAMAQETGDNLYWGSVTGSQSNAVSPTPAPRNPSDPMP
QAPALWIETTAYALLHLLLHEGKAEMADQASAWLTRQGSFQGGFRSTQDT
VIALDALSAYWIASHTTEERGLNVTLSSTGR.

SEQ ID NO: 28 [amino acid sequence of human
complement receptor 1 protein (CR1)]:
MGASSPRSPEPVGPPAPGLPFCCGGSLLAVVVLLALPVAWGQCNAPEWLP
FARPTNLTDEFEFPIGTYLNYECRPGYSGRPFSIICLKNSVWTGAKDRCR
RKSCRNPPDPVNGMVHVIKGIQFGSQIKYSCTKGYRLIGSSSATCIISGD
TVIWDNETPICDRIPCGLPPTITNGDFISTNRENFHYGSVVTYRCNPGSG
GRKVFELVGEPSIYCTSNDDQVGIWSGPAPQCIIPNKCTPPNVENGILVS
DNRSLFSLNEVVEFRCQPGFVMKGPRRVKCQALNKWEPELPSCSRVCQPP
PDVLHAERTQRDKDNFSPGQEVFYSCEPGYDLRGAASMRCTPQGDWSPAA
PTCEVKSCDDFMGQLLNGRVLFPVNLQLGAKVDFVCDEGFQLKGSSASYC
VLAGMESLWNSSVPVCEQIFCPSPPVIPNGRHTGKPLEVFPFGKAVNYTC
DPHPDRGTSFDLIGESTIRCTSDPQGNGVWSSPAPRCGILGHCQAPDHFL
FAKLKTQTNASDFPIGTSLKYECRPEYYGRPFSITCLDNLVWSSPKDVCK
RKSCKTPPDPVNGMVHVITDIQVGSRINYSCTTGHRLIGHSSAECILSGN
AAHWSTKPPICQRIPCGLPPTIANGDFISTNRENFHYGSVVTYRCNPGSG
GRKVFELVGEPSIYCTSNDDQVGIWSGPAPQCIIPNKCTPPNVENGILVS
DNRSLFSLNEVVEFRCQPGFVMKGPRRVKCQALNKWEPELPSCSRVCQPP
PDVLHAERTQRDKDNFSPGQEVFYSCEPGYDLRGAASMRCTPQGDWSPAA
PTCEVKSCDDFMGQLLNGRVLFPVNLQLGAKVDFVCDEGFQLKGSSASYC
VLAGMESLWNSSVPVCEQIFCPSPPVIPNGRHTGKPLEVFPFGKAVNYTC
DPHPDRGTSFDLIGESTIRCTSDPQGNGVWSSPAPRCGILGHCQAPDHFL
FAKLKTQTNASDFPIGTSLKYECRPEYYGRPFSITCLDNLVWSSPKDVCK
RKSCKTPPDPVNGMVHVITDIQVGSRINYSCTTGHRLIGHSSAECILSGN
TAHWSTKPPICQRIPCGLPPTIANGDFISTNRENFHYGSVVTYRCNLGSR
GRKVFELVGEPSIYCTSNDDQVGIWSGPAPQCIIPNKCTPPNVENGILVS
DNRSLFSLNEVVEFRCQPGFVMKGPRRVKCQALNKWEPELPSCSRVCQPP
PEILHGEHTPSHDNFSPGQEVFYSCEPGYDLRGAASLHCTPQGDWSPEA
PRCAVKSCDDFLGQLPHGRVLFPLNLQLGAKVSFVCDEGFRLKGSSVSHC
VLVGMRSLWNNSVPVCEHIFCPNPPAILNGRHTGTPSGDIPYGKEISYTC
DPHPDRGMTFNLIGESTIRCTSDPHGNGVWSSPAPRCELSVRAGHCKTPE
QFPFASPTIPINDFEFPVGTSLNYECRPGYFGKMFSISCLENLVWSSVED NCRRKSCGPPPEPFNGMVHINTDTQFGSTVNYSCNEGFRLIGSPSTTCLV
SGNNVTWDKKAPICEIISCEPPPTISNGDFYSNNRTSFHNGTVVTYQCHT
GPDGEQLFELVGERSIYCTSKDDQVGVWSSPPPRCISTNKCTAPEVENAI
RVPGNRSFFSLTEIIRFRCQPGFVMVGSHTVQCQTNGRWGPKLPHCSRVC
QPPPEILHGEHTLSHQDNFSPGQEVFYSCEPSYDLRGAASLHCTPQGDWS
PEAPRCTVKSCDDFLGQLPHGRVLLPLNLQLGAKVSFVCDEGFRLKGRSA
SHCVLAGMKALWNSSVPVCEQIFCPNPPAILNGRHTGTPFGDIPYGKEIS
YACDTHPDRGMTFNLIGESSIRCTSDPQGNGVWSSPAPRCELSVPAACPH
PPKIQNGHYIGGHVSLYLPGMTISYTCDPGYLLVGKGFIFCTDQGIWSQL
DHYCKEVNCSFPLFMNGISKELEMKKVYHYGDYVTLKCEDGYTLEGSPWS
QCQADDRWDPPLAKCTSRHDALIVGTLSGTIFFILLIIFLSWIILKHRKG
ANNAHENPKEVAIHLHSQGGSSVHPRTLQTNEENSRVLP.

SEQ ID NO: 29 [amino acid sequence of human
C4b-binding protein (C4bp), alpha chain]:
MHPPKTPSGALHRKRKMAAWPFSRLWKVSDPILFQMTLIAALLPAVLGNC
GPPPTLSFAAPMDITLTETRFKTGTTLKYTCLPGYVRSHSTQTLTCNSDG
EWVYNTFCIYKRCRHPGELRNGQVEIKTDLSFGSQIEFSCSEGFFLIGST
TSRCEVQDRGVGWSHPLPQCEIVKCKPPPDIRNGRHSGEENFYAYGFSVT
YSCDPRFSLLGHASISCTVENETIGVWRPSPPTCEKITCRKPDVSHGEMV
SGFGPIYNYKDTIVFKCQKGFVLRGSSVIHCDADSKWNPSPPACEPNSCI
NLPDIPHASWETYPRPTKEDVYVVGTVLRYRCHPGYKPTTDEPTTVICQK
NLRWTPYQGCEALCCPEPKLNNGEITQHRKSRPANHCVYFYGDEISFSCH
ETSRFSAICQGDGTWSPRTPSCGDICNFPPPKIAHGHYKQSSSYSFFKEEI
IYECDKGYILVGQAKLSCSYSHWSAPAPQCKALCRKPELVNGRLSVDKDQ
YVEPENVTIQCDSGYGVVGPQSITCSGNRTWYPEVPKCEWETPEGCEQVL
TGKRLMQCLPNPEDVKMALEVYKLSLEIEQLELQRDSARQSTLDKEL.

SEQ ID NO: 30 [amino acid sequence of human
C4b-binding protein (C4bp), beta chain]:
MFFWCACCLMVAWRVSASDAEHCPELPPVDNSIFVAKEVEGQILGTYVCI
KGYHLVGKKTLFCNASKEWDNTTTECRLGHCPDPVLVNGEFSSSGPVNVS
DKITFMCNDHYILKGSNRSQCLEDHTWAPPFPICKSRDCDPPGNPVHGYF
EGNNFTLGSTISYYCEDRYYLVGVQEQQCVDGEWSSALPVCKLIQEAPKP
ECEKALLAFQESKNLCEAMENFMQQLKESGMTMEELKYSLELKKAELKAK
LL.

What is claimed is:

1. A composition for detecting complement-mediated inflammation in an individual, the composition comprising an effective amount of CR2-targeted ultrasmall superparamagnetic iron oxide ("USPIO") nanoparticles or aggregates thereof, wherein the USPIO nanoparticles or aggregates thereof are coated with dextran or encapsulated with phospholipid and further comprise a targeting moiety comprising a fusion protein comprising an antibody Fc region or fragment thereof fused to CR2 or a biologically-active fragment thereof which comprises SCR 1 and SCR 2 of CR2.

2. The composition of claim 1, wherein the individual is a mammal.

3. The composition of claim 2, wherein the mammal is a human, mouse, or rat.

4. The composition of claim 1, wherein said USPIO nanoparticles or aggregates thereof further comprise a plurality of said fusion proteins.

5. The composition of claim 1, wherein said fusion protein is covalently attached to said USPIO nanoparticle or aggregate thereof.

6. The composition of claim 1, wherein said USPIO nanoparticles or aggregates thereof are encapsulated with phospholipid.

7. The composition of claim 6, where said fusion protein is attached to said phospholipid via an amide linkage.

* * * * *